US010450581B2

(12) United States Patent
Vossen et al.

(10) Patent No.: US 10,450,581 B2
(45) Date of Patent: *Oct. 22, 2019

(54) **CLONING AND EXPLOITATION OF A FUNCTIONAL R-GENE FROM *SOLANUM CHACOENSE***

(71) Applicant: WAGENINGEN UNIVERSITEIT, Wageningen (NL)

(72) Inventors: Jacobus Hubertus Vossen, Wageningen (NL); Maarten Nijenhuis, Arnhem (NL); Marion Johanna Barbara Arens-De Reuver, Bennekom (NL); Edwin Andries Gerard Van Der Vossen, Utrecht (NL); Evert Jacobsen, Wageningen (NL); Richard Gerardus Franciscus Visser, Bennekom (NL)

(73) Assignee: WAGENINGEN UNIVERSITEIT, Wageningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/294,220

(22) Filed: Oct. 14, 2016

(65) Prior Publication Data

US 2017/0145437 A1 May 25, 2017

Related U.S. Application Data

(63) Continuation of application No. 13/496,845, filed as application No. PCT/NL2010/050612 on Sep. 20, 2010, now Pat. No. 9,551,007.

(30) Foreign Application Priority Data

Sep. 18, 2009 (EP) .................................. 09170769

(51) Int. Cl.
*A01H 5/08* (2018.01)
*A01H 1/00* (2006.01)
*C12N 15/82* (2006.01)
*C07K 14/415* (2006.01)

(52) U.S. Cl.
CPC .......... *C12N 15/8282* (2013.01); *A01H 1/00* (2013.01); *C07K 14/415* (2013.01); *A01H 5/08* (2013.01)

(58) Field of Classification Search
None
See application file for complete search history.

(56) References Cited

U.S. PATENT DOCUMENTS 7,485,773 B2  2/2009  Allefs et al.

FOREIGN PATENT DOCUMENTS

WO   WO-2009/013468   1/2009

OTHER PUBLICATIONS

Bradeen et al., "Concomitant reiterative BAC walking and fine genetic mapping enable physical map development for the broad-spectrum late blight resistance region, RB," Mol. Gen. Genomics (2003) 269:603-611.
Durr et al., "A monoclonal antibody induces opening of a coiled coil. Global protection of amide protons from H/D exchange decreased by up to 1000-fold in antibody-bound triple-stranded coiled coil," Eur. J. Biochem. (1997) 249:325-329.
International Search Report for PCT/NL2010/050612, dated Mar. 2, 2011, 6 pages.
Jiang et al., "Amplification generates modular diversity at an avirulence locus in the pathogen Phytophthora," Genome Res. (2006) 16:827-840.
Nelson, "Late Blight of Tomato (Phytophthora infestans)," CES CTAHR, Plant Disease (2008) PD-45, p. 1-10.
Oberhagemann et al., "A genetic analysis of quantitative resistance to late blight in potato: towards marker-assisted selection," Molecular Breeding (1999) 5:399-415.
Song et al., "Gene RB cloned from Solanum bulbocastanum confers broad spectrum resistance to potato late blight," PNAS (2003) 100(16):9128-9133.
Van Der Vossen et al., "An ancient R gene from the wild potato species *Solanum bulbocastanum* confers broad-spectrum resistance to Phytophthora infestans in cultivated potato and tomato," The Plant Journal (2003) 36:867-882.
Veilleux and Miller, "Hybrid Breakdown in the $F_1$ between Solanum chacoense and *S. phureja* and Gene Transfer for Leptine Biosynthesis," J. Amer. Soc. Hort. Sci. (1998) 123(5):854-858.

*Primary Examiner* — Phuong T Bui
(74) *Attorney, Agent, or Firm* — Morrison & Foerster LLP

(57) ABSTRACT

The invention relates to a resistance gene and functional homologs or fragments thereof isolated from *S. chacoense, S. berthaultii, S. sucrense* or *S. tarijense*. Moreover, the invention relates to the use of said resistance gene, for example the use of said resistance gene in a method to increase or confer at least partial resistance in a plant to an oomycete infection.
The invention provides an isolated or recombinant nucleic acid sequence comprising a nucleic acid sequence encoding one of the amino acid sequences of FIG. 4 or a functional fragment or a functional homolog thereof such as those presented in FIG. 13.

12 Claims, 89 Drawing Sheets

Figure 1A:
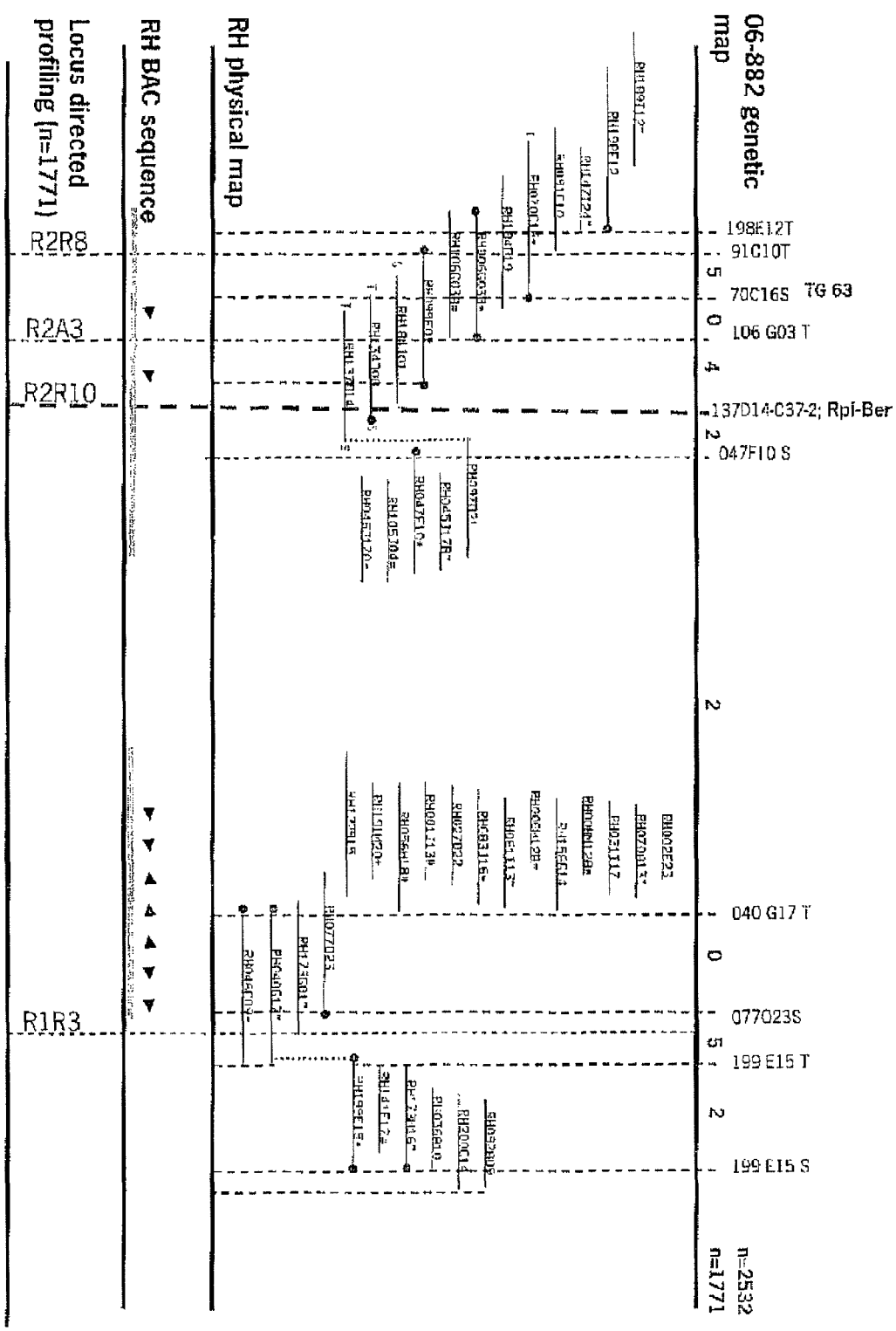

Specification includes a Sequence Listing.

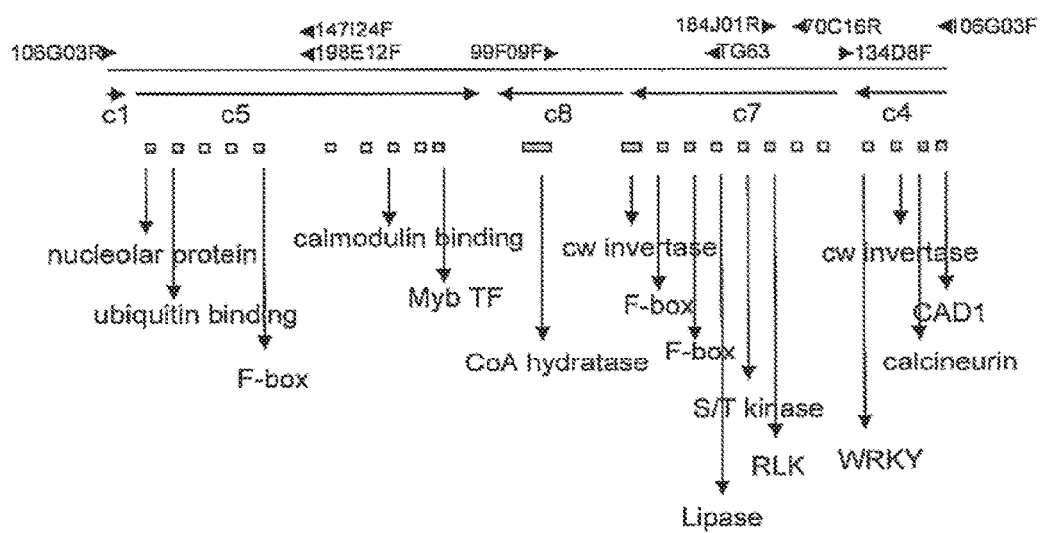
FIG. 2A: RH106G03, 131kb

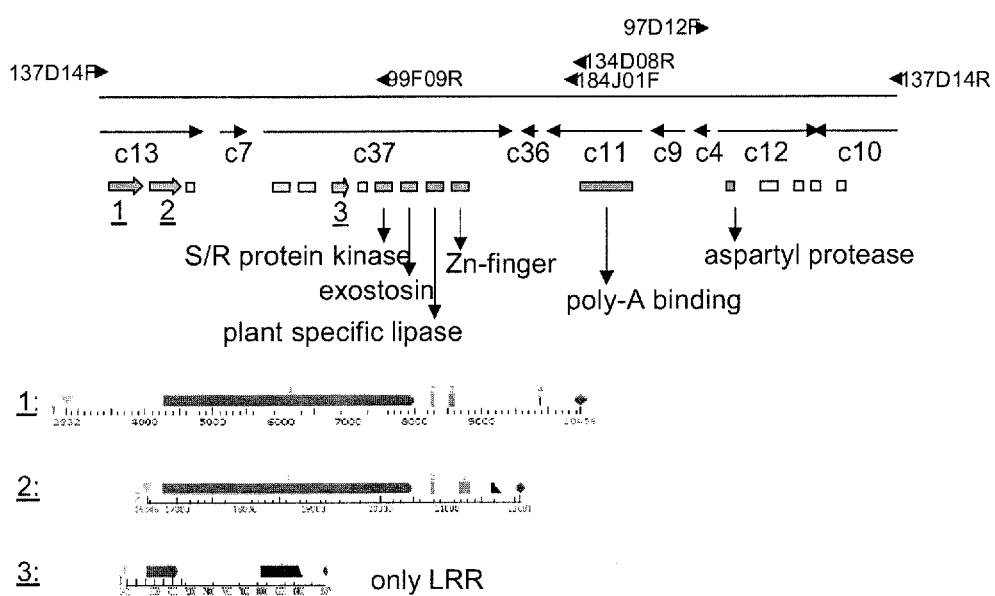

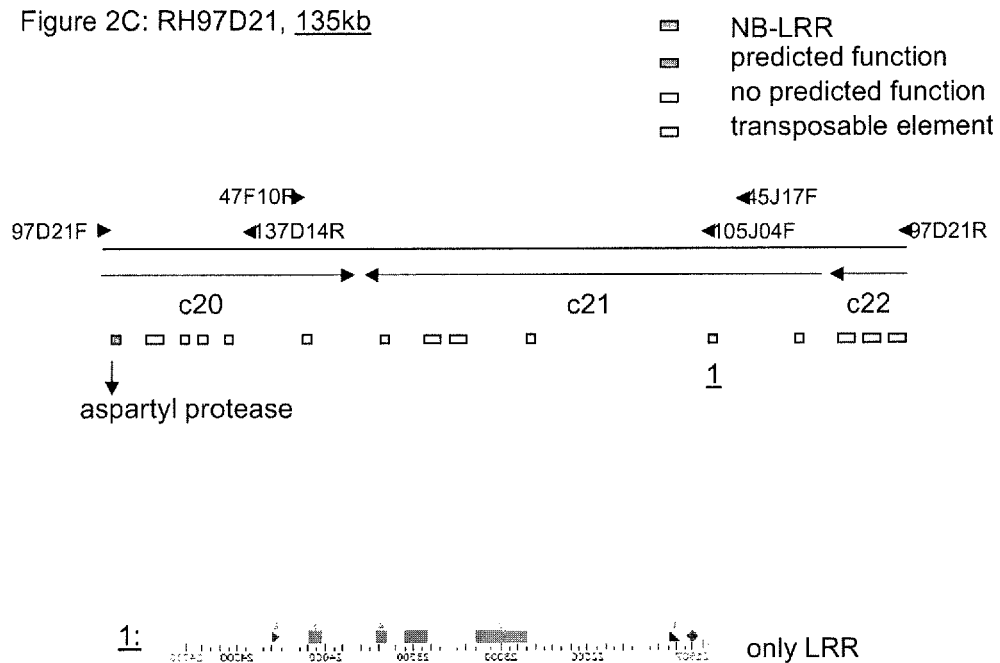
Figure 2C: RH97D21, 135kb

Figure 2D: RH122B15, 44kb
▭ NB-LRR
▭ predicted function
▭ no predicted function
▭ transposable element
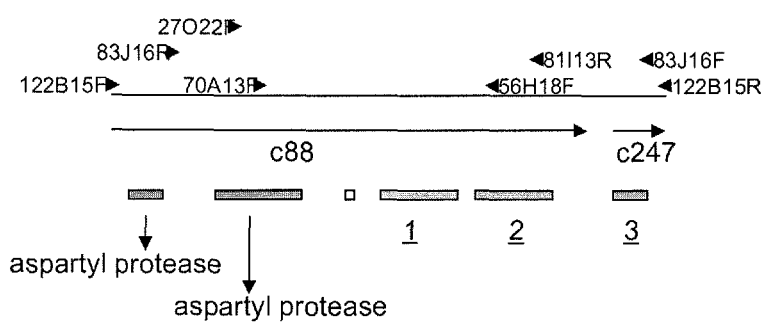
 only LRR

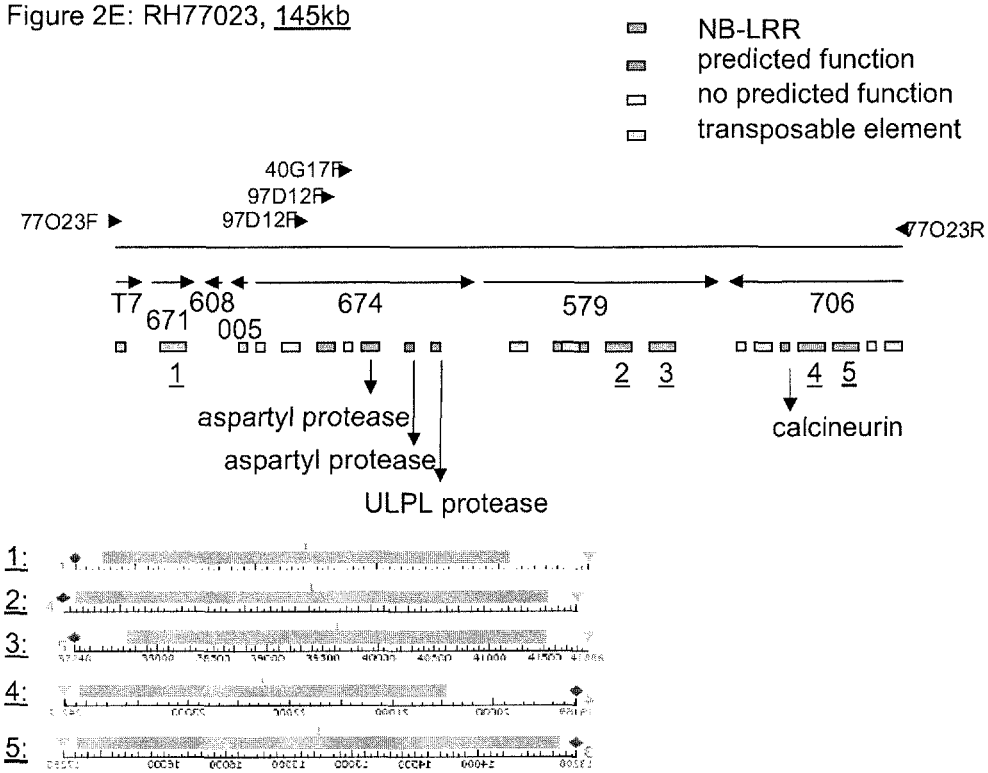
Figure 2E: RH77023, 145kb

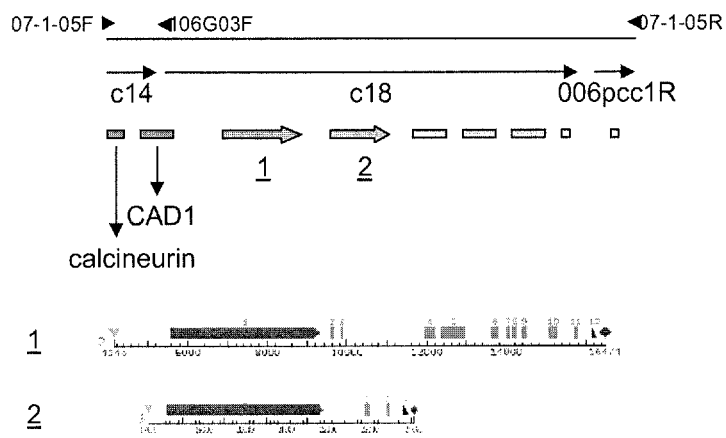
Figure 2F: CHC B1 (B07-1-05), 87kb

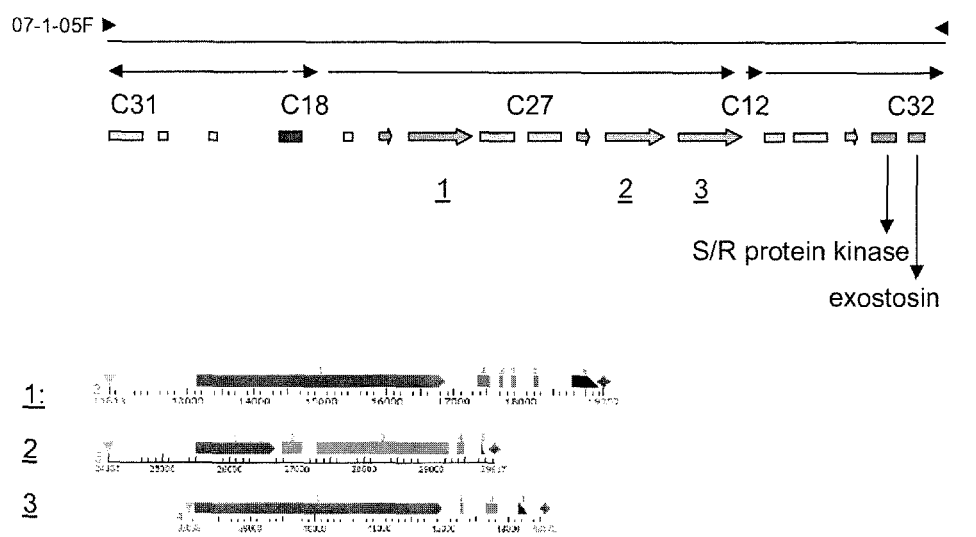
Figure 2G: CHC B2 (2-D06_3-D21), 120kb

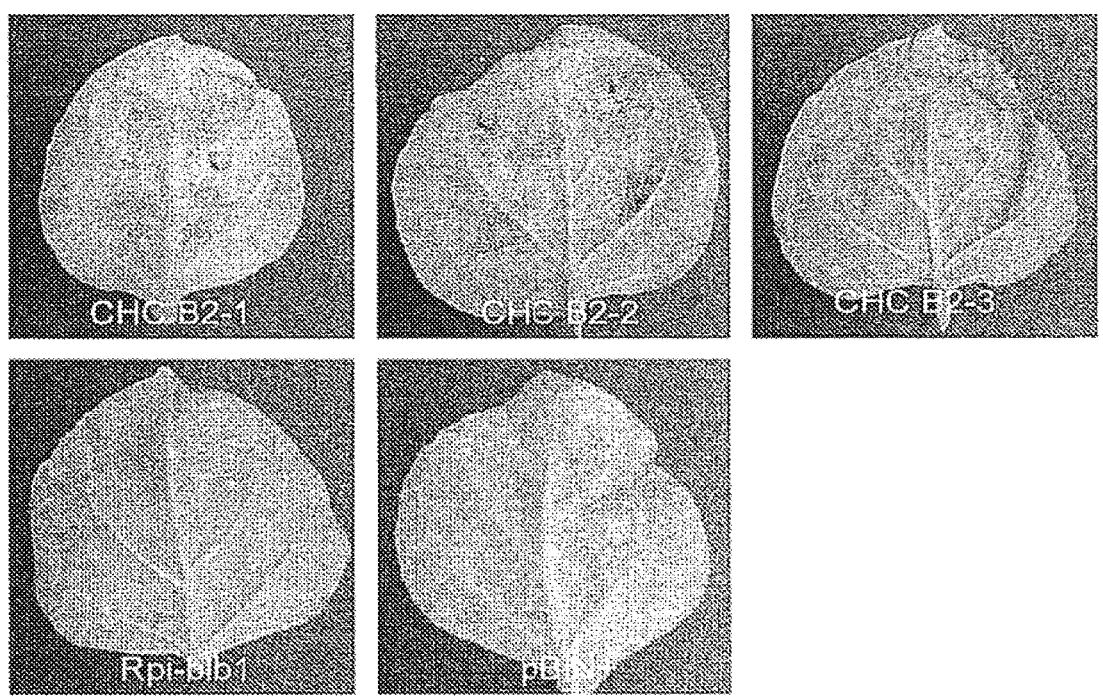
Figure 3: Complementation analysis in *N. benthamiana*

```
1    MNYCLPSSTLQTTTKRALTLRRLCC                    VIGATVQVLLE   60
61   KLISLTI                    IQAFTRDVETP                    120
121                  KTKVVRSPLKKVSGFFSHTAF                     180
181  LQSLMVPSRKILPIRETDSFVVASDIVG                              231

232  TIP                KRIYNDEHMKQIFEKRIWLCLPEMSETKSFLEQILESLIERKIE  291
292  VERRDIIVKKLQDELG            CVDSTSWHEFIDTLRGINTSK        RK   351
352  QVASTVATDLMILGKLTEDHCNSIFKQKAPVDGRVPEELASMGMKTVKM           SVL  411
412  GGLLHNKEXHEWQAILDGNLLVAGEDDNGENSIKKILKLSYDYLPSPHLKK              471
472  KDYMFEKDQLIQLWMAEGFLRPSQEIPVMEDVGHRFFQILLQNSLLQDVLLDENMNITHC  531
532  K            AGDILKSRLFDPKGDN                                 556

557      GEK  SQ  RY  GCESPTQQIDK                               578
579      YEPEB CT  FWRSNYTSKDM                                  598
599      LN  KF  RV  D SSGIKELSAK                                621
622      GK  IY  RY  D SNTEITALPMS                               644
645      CK  YN  DT  R IMCFS QELPYE                              668
669      MRNMIS  RH  YYTSVDETSGHWGGWCLAMEHFQIPLNMGQ              708
709      TS  QT  KP  K GLEXGRQIEELGHLKN                         736
737      RGELT  MG  Q VCDKEZAQTAYLADKPN                         765
766      CK  AY  WSHDESEGCE KDEHVLDG                            791
792      QPHPN  KT  N VDYLGTKFPSWFGEES                          819
820         PN  VK  K GSKRCKEIPS                                839
840      GQ  KS  RM  E TGFHE KC GPAFYSVEMRNIGSNGI                877
878      QV  PS  KK  V KDMKS IBWKGDEVG                          904
905      RMSPQ  ER  R TDCPL KSIPRQ                              928
929         EI  RQ  K TGVDSEMPLLNLCSN                           952
953         TG  VH  R YDMKE TCLPDEM                             974
975      RSNVS  QQ  I FNCGE RELPQS                              998
999      YN  HS  RD  D YRCTN SELPVPNG                           1024
1025     UNY  TS  EP  C HNCKG LSIPIG                            1048
1049     MLDQCK  VT  N SCCNN VSFPVH                             1072
1073     WEMFS  SY  L SECPR ISVPKVG                             1097
1098     HR  TG  VH  G PFSEMVDFDAFQLIPNG                        1127
1128     QQ  LS  RD  E YGRGHWDSLPYQ                             1151
1152     MQ  SD  RE  T ADFGIEALPPT                              1174
1175     DN  TS  ES  T VRCKQ QHLMF                              1197
1198     SDAMPK  RL  W RDCFI EALSDG                             1221
1222     GN  VS  EE  V HDCEK EHLFSRDA                           1247
1248     MRR  TR  WNMK  KGCFN EESFTNYSQ                         1274
1275     WSK  SH  SN  E GGWRRTAISLGFSFTF                        1302 lxxlxxlxxlxlxxCxxlxxxP
```

Figure 5: Protein domain organisation in Rpi-chc1.

The N-terminal CC-domain comprises amino acids 1-231. The amino acids depicted in green shading are predicted to fold into a coiled coil structure using the "coil" algorithm with window size 14. The central domain NB-ARC domain comprises amino acids 232-557. Aminoacids in red shading show similarity to the previously described Kinase 1a, Kinase 2, kinase 3a, GLPL, RNBS-D and MHD domains, respectively. The C-terminal LRR-domain consists of 29 imperfect leucine rich repeats. Conserved hydrophobic aminoacids (A, V, L, and F) are marked by pink shading. The consensus is shown at the bottom.

FIG. 7A

FIG. 7B

Figure 8
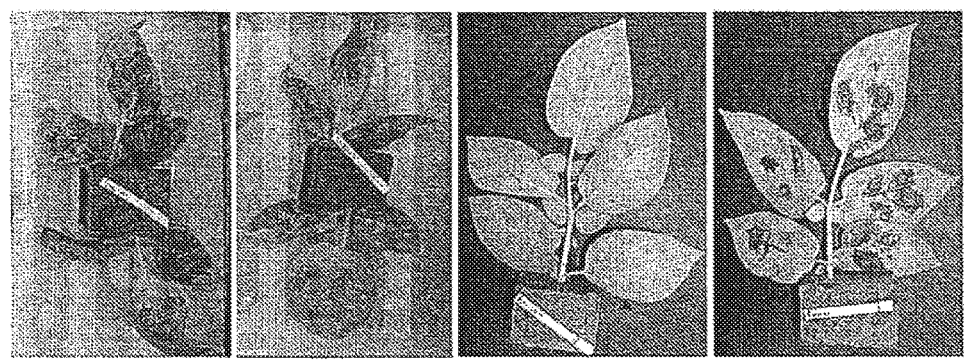
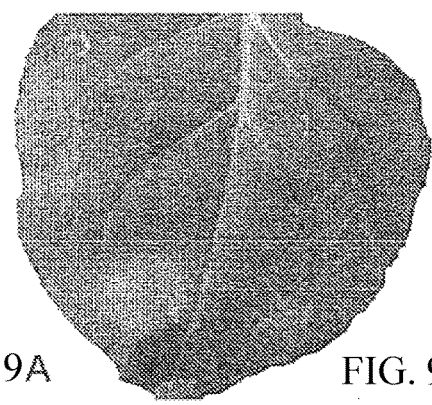
FIG. 9A
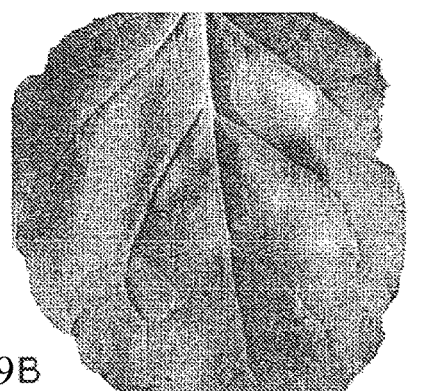
FIG. 9B
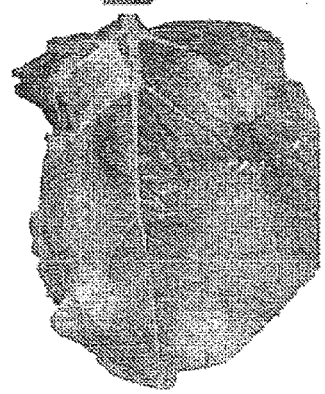
FIG. 9C
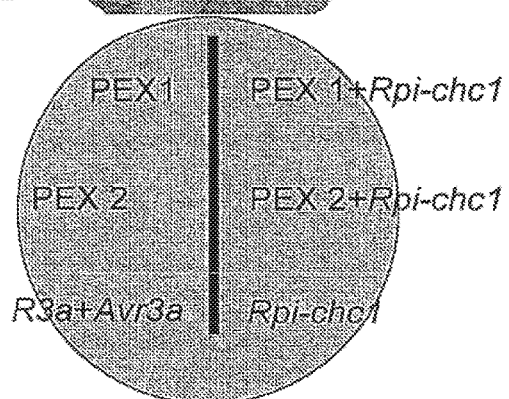

Figure 10
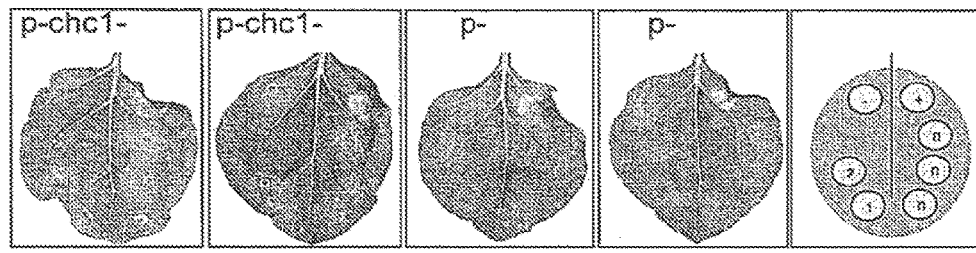
FIG. 11A
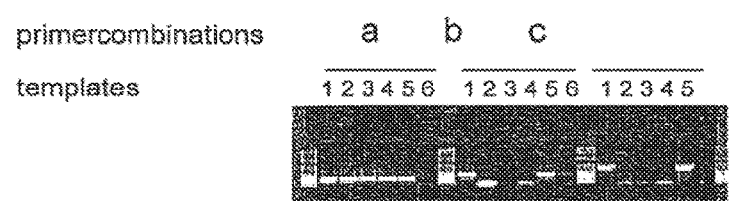
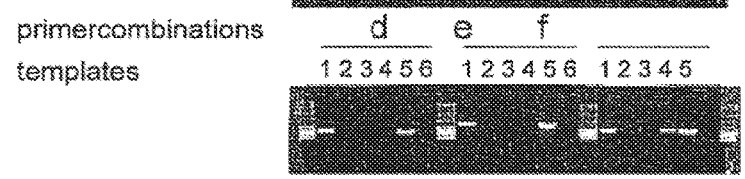
FIG. 11B
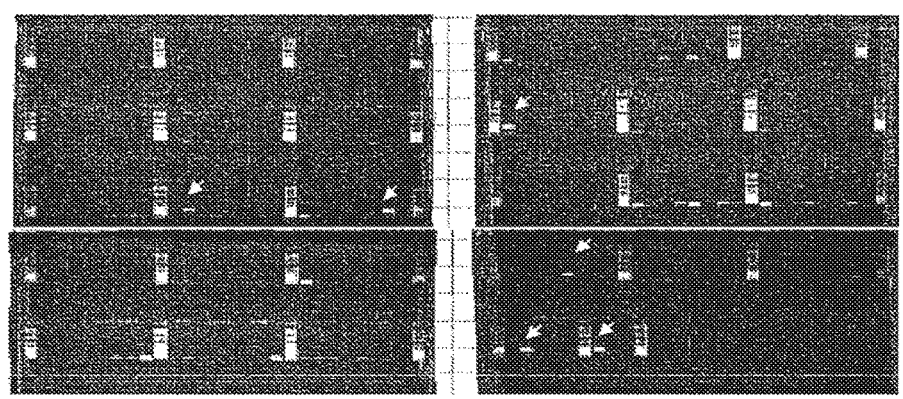

Figure 12

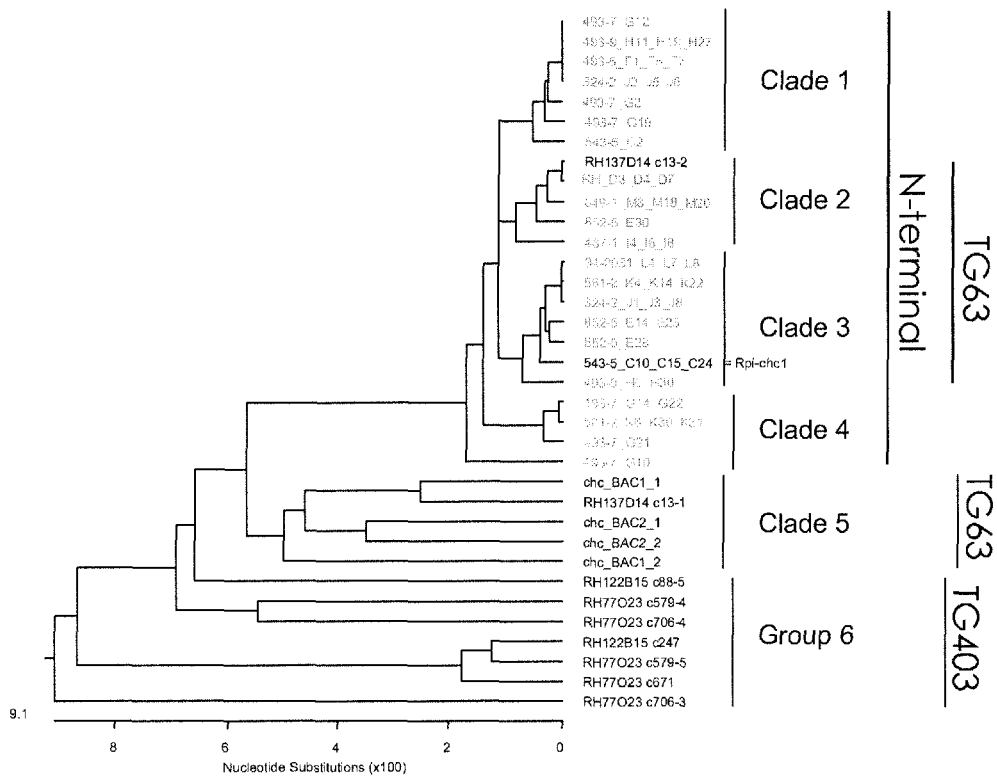

```
Figure 13:
>493-7_G12
ATGAATTATTGTCTTCCTTCGAGTACTCTACAAACAACTACCAAACGAAGACTTACTTTGAGAAGACTTTGTTGCA
AACAGCTCAGGAAGAAGACTTTGGTGCAGATTGCAGAGGAAGAGGAAGCAAACACAACTATGGCCGATGCTGTAAT
TGGTGCTACTGTTCAAGTTTTGCTTGAAAAGTTGATTTCTCTCACTATCGAGGAGGTCAACAGCTCAAGGGATTTC
AACAAAGATCTCGAAATGTTGACACAAAATGTATCTTTAATCCAAGCTTTCATTCATGATGTTGAAACACCACAAG
AGAAACAACAGTCTGTCGAACACTGGCTCAACAGGCTTGAGAGAGTTGCTGAAGATGCTGAAAATGTGTTTGATCG
ATTCAGATATGAATCTCTCAAACAAAAGTGGTGAGGAGCCCATTGAAAAAGGTCAGTGGTTTCTTTTCTCATACT
GCTTTTAAGAGAAAAATGTCTCAAAAAATCAACAACATCAATAAAGAGTTGACGGCTATCAATAAGGTAGCCAAAG
ACCTCGGTCTACAATCACTCATGGTACCTTCTCGGAAAATACTACCAATTCGAGAAACAGATTCCTTCGTAGGTGC
TTCTGATGTTGTTGGTAGAGATTTAGATGTTGCTGAGATAAAGGAGAAGATTTTGAAGATGAGAGGAGGATGTT
GTTCTGTCCACCATTCCCATAGTAGGTATGGGAGGTTTAGGGAAAACAACTGTGGCTAAGAGGATTTACAATGATG
AACACATCAAGCAAATCTTTAAAGAGAATTTGGTTGTGTATACCTGAAATGTCTGAAACGAAGAGCTTTCTTGA
ACAAATCCTCGAATCGTTGATAGAGAGGAAATTGAGGTTGAAAGGAGAGATATAATAGTCAAGAAGCTACAAGAT
GAATTGGGAGGAAAAAAATATTTGCTAGTCCTGGATGATTTGTGGCGTGTTGACTCTACATCGTGGCATGAGTTCG
TCGACACCCTGAGAGGAATAAATACATCCAGAGGAAACTGCATTCTTGTGACTACTCGTATGAAGCGGGTGGCATC
CACAGTAGCAACAGATCTTCATATCTTGGGAAGTTAACAGAAGATCATTGTTGGTCTATTTTCAAACAAAAAGCA
TTTGTTGATGGCAGGGTTCCAGAGGAATTAGCGAGCATGGGCAACAATATTGTTAAAATGTGCCAAGGTCTACCGT
TGGCTGCAAGTGCATTGGGAGGGCTCTTACACAACAAAGAAAAACATGAATGGCAAGCAATTCTTGATGGCAACCT
CCTTGTTGCAGGTGAAGATGATAATGGAGAAAATAGCATAAAGAAAATCCTAAAACTCAGCTATGATTATCTACCA
TCTCCACATCTGAAACAATGCTTTGCTTACTTTGCAATGTTTCCAAAAGATTATATGTTTGAAAAGGACCAACTAA
TCCAACTCTGGATGGCAGAAGGGTTTCTTCGTCCAAGTCAAGAGATCCCTGTGATGGAAGACGTTGGGCACAGGTT
TTTTCAAATCTTGTTGCAgAATTCCTTGCTACAAGATGTTGTGTTAgATGAACACAACAATATAACACACTGTAAG
ATGCACGATCTTGTGCATGATTTGGCTGGAGATATCTTAAAATCTAGACTATTTGATCCGAAGGGCGACAATGGAG
AAAAACTTTCTCAAGTTCGATACTTTGGATGTGAGTCACCAAAGGATCAAATAGATAAGATATATGAGCCAGAACG
TTTGTGCACACTGTTTTGGAGAAGCAATTATACATCTAAAGATATGCTGTTGAACTTTAAGTTCTTGAGAGTTTTA
GATTTGTCCAGTTCAGGAATCAAGGAGTTGTCAGCCAAAATCGGGAAGCTGATATACTTGAGATATCTTGATCTCT
CGAACACTGAGATCACAGCCTTGCCCAACTCCATTTGCGAGCTCTATAATTTGCAAACATTTAGAGTCATCAACTG
CTTTTCACTCCAGGGACTTCCATATGAGATGAGAAAATATGATAAGTTTGAGACACATATATTACACTTCTATTGAC
GAAACAAGTGGGCATTGGGGAGGATGGTGTCTTCACAATGAACATTTTCAGATTCCACTTAATATGGGCGAATTGA
CTAGTCTTCAAACCCTCAAGTTTTTCAAGGTAGGTTTAGAGAAAGGTCGTCAAATAGAAGAATTAGGTCATTTGAA
AAACCTAGGAGGTGAATTGACAATCAATGGTCTCCAATTGGTCTGTGATAAAGAAGAGGCTCGAACAGCATATTTA
CACGATAAACCAAACATCTGCAAGCTGGCATATTTATGGTCCCATGATGAATCAGAAGGCTGTGTGATCAATGATG
AGCATGTGTTGGATGGTCTTCAACCGCATCCTAACTTGAAAACCCTTAGCAGTAGTGGACTATTTAGGGACTAAATT
```

```
CTTTTCACTCCAGGGACTTCCATATGAGATGAGAAATATGATAAGTTTGAGACACATATATTACACTTCTATTGAC
GAAACAAGTGGGCATTGGGGAGGATGGTGTCTTCACAATGAACATTTTCAGRATCCACTRAATATGGGCAATTGA
CTAGTCTTCAAACCCTCAAGTTTTTCAAGGTAGGTTTAGAGAAAGGTCGTCAAATAGAAGAATTAGGTCATTTGAA
AAACCTAGGAGGTGAATTGACAATCAATGGTCTCCAATTGGTCTGTGATAAAGAAGAGGCTCGAACAGCATATTTA
CAGGATAAACCAAACATCTGCAAGCTGGGATATTTATGGTCCGATGATGAATCGAAGGCTGTGTGATCAAATGATG
AGCATGTGTTGGATGGTCTTCAACCGCATCCTAACTTGAAAACCTTAGCAGTAGTGGACTATTTAGGGACTAAATT
TCCTTCATGGTTCAGTGAAGAGTCGCTACCAAATTTGGTTAAGTTGAAATTAAGTGGTAGCAAAAGGTGCAAAGAA
ATTCCATCCCTTTGGCCAACTGAAATTCCTTCGGCATCTTGAGCTGATAGGATTCCATGACGTTGGAATGCATTTGAC
CTGCTTTATATGGTGTTGAGATTAGAAATACCGGATCAAACAGCAATATCCAAGTGTTCCCGTCATTGAAAGAACT
AGTATTGGAGGATATGCGTAGCCTTATTGAGTGGAAGGGAGATGAAGTCGGAGTAAGAATGTCTCCCGGGCTTGAG
AAGTTGCGGATTACAGACTGTCCATTGTTAAAAAGTATTCCAAATCAATTTGAAATCCTCTGTGAATTAGAAAGTTA
GAGGAGTTGACAGTGAAATGCCATTGGTTGAACTTGTGCAGCAACTTGACATCTCTCGTAAAGCTTAGTGTCTATGA
TATGAATGAGGTCACTTGTCTTCCAGCGATGAGATACTACGTAACGCCATCCGTTCTCGTTCAACAGATAACGATTTTCAAC
TGTGGAGAGTTTCGTGAATTGCCACAAAGCTTGTACAATCTCCATTCTCTTAAGAGATTAGACATTTACAACTGCA
CCAACTTCAGTTCTCTTCCTCTTTCGGAATGGAGACAACTATTTGACTTCCCTCGAATTCTTTTTCTTATATAATTG
TAATGGATTGATCAGTATACCAATTGGAATGCTAGATCAATGACGGTCTCTAGAGTTTTTGCATGTCAGCTGCTGT
AACAACTTGGTTTCATTCCCTTTACATGTGTGGGAAATGCCTTCATTTTCATTTTTGGATATAAGAGAATGTCCCA
AATTGATTAGTGTACCCAAAGTGGGCCTTCACCATCGCACGGGGTTATTGAGTTTGGGAATTGGTCCTTTCTCAGA
GATGGTGGATTTGATGCATTCCAATTGATTTTTAATGGCATTCAGCAGTTCTTGTCCCTTCGTGATCTGGAGGTG
TACGGACGTGGGCACTGGGATTCTCTGCCCTATCAGCTTATGCAACTCTCTAACCTAAGAGAGATCACAATAGCTG
ATTTCGGAATTGAGGCTCTTCCTCCTAGACTTGACAACCTTACTTCTCTTGAAAGTTTGACTCTAGACACGGTGCAA
ACGGCCTACAACATCTGGACTTCTCAGATGCCATGCCCAAATTCGGCCTTCGTGGATAAGTGATTGTCCATTGGTA
GAACCTTCGTCCGGATGGGCTCGGCAACCTTGGTTCGTTTGGAAGAATTATATTTACAGGACTCGGAAAAACTAGAGC
TTCTACCGTCCCGAGATGCCATGACAGCGCCTCACTAAATTATGGAACATGGGAATTAAAGGATGCCCAAAGTTAGA
AGAAAGTTTCACCAACTACTCCGAGTGGTCCAAAATTTCCCATATTTCAAATATTGAATTAGGTGGGTGGAGAAGG
ACAGCCATAGTCTCGGTTTCTCTTTCACTTTCTGA

>493-9_H11_H19_H27
ATGAATTATTGTCTTCCTTCGAGTACTCTACAAACAACTACCAAACGAAGACTTACTTTGAGAAGACTTTGTTGCA
AACAGCTCAGGAAGAGACTTTGGTGCAGAATTGCAGAGGAGGAGGAAGCAAACACAACTATGGCCGATGCTGTAAT
TGGTGCTACTGTTCAAGTTTTGCTGAAAAGTTGATTCTCCACTATCGGAGGCTCAACAGCTGCAAGGGGATTTC
AACAAAGATCTCGAACACTGGCACAAAATGTATCTTTAATCCAAGCTTTCATTCATGAAGGTGAAACACCACAAG
AGAAACAACAGTCTGTCGAACACTGGCTCAACAGGCTTGAGAGAGTTGCTGAAGATGCTGAAAATGTGTTTGATCG
ATTCAGATATGAATCTCTCAAAACAAAAGTGGTGAGGAGCCCATTGAAAAAGGTCAGTGGTTTCTTTCTCATACT
GCTTTTAAGAGAAAATGTCTCAAAAAATCAACAACATCAATAAAGAGTTGACGGCTATCAATAAGGTAGCCAAGG
ACCTCGGTCTACAATCACTCATGGTACCTTCTCGGAAAATACTACCAATTGAGAAACAGATCCTTCGTAGGTGC
TTCGATGTTGTTGGTAGAGATTTAGATGGTGCTGAGATAAAGGAGAAGATTTGAAGATGAGAGGAGGATGTT
GTTCTTCCACCATTCCCATAGTAGGTATGGGAGGTTTAGGGAAAACAACTGTGGCTAGGAGGATTTACAATGATG
AACACATCAAGCAAATCTTTAAAGAGAGAATTTGGTTGTGTATACCTGAAATGTCTGAAACGAAGAGCTTTCTTGA
ACAAATCCTCGAATCGTTGATGAGAAGGACGGAAAATTGAAGTGCAAAGACGAGAAAATTGAATAAGGAAGCTACAAGAT
GAATTGGGAGGAAAAATATTTGCTAGTCCTGGATGATTGTGGCGTGTTGACTCTACATCGTGGCATGAGTTCG
TGGACACCCTGAGAGGAATAAATACATCCGAGGGAAACTGCATTCTTGTGACTACTCGTATGAAGCGGGTGGCATC
CACAGTAGCAACAGATCTTCATATCTTGGGGAAGTTAACGAAGATCATTGTTGGTCTATTTCAAACAAAAGCA
TTTGTTGATGGCAGGGTTCCAGAGGAATTAGCGAGCATGGGCAACAATATTCTTAAAATGTGCAAGGTCTAGGGT
TGGCTCCAAGTGCATTGGGAGGGCTCTTACACAACAAGAAAACATGAAGGCAAGCAATTCTTGATGGCAACCT
CCTTGTTGCAGGTGAAGATGATAATGGAGAAAATAGCATAAAGAAAATCCTAAAACTCGGCTATGATTATCTACCA
TCTCCAGATCTGAAACAATGCTTTGCTTACTTTGCAATGTTTCCAAAAGATTATATGTTTGAAAAGGACCAACTAA
TCCAACTCTGGATGGCAGAAGGGTTTCTTGGTCCAAGTCAAGAGATCCCTGTGATGGAAGACGTTGGGCACAGGTT
TTTTCAAATCTTGTTGCAGGATTCCTTGCTACAAGATGTTGTGTTAGATGAACACAACAATATAACACACTGTAAG
ATGCACGACTGTTGTGCATGATTTGGCTGGAGATATCTTAAAATCTAGACTATTTGATCGAAGGCGCAATGGAG
AAAAACTTTCTCAAGTTCGATACTTTGGATGCAGTCACCAAAGGATCAAATAGATAGATATGTGAGCCAGAACG
TTTGTGCACACTGTTTTGGAGAAGCAATTATACATCTAAAGATATGCTGTTGAACTTTAAGTTCTTGAGAGTTTTA
GATTTGTCCAGTTCAGGAATCAAGGAGTTGTCAGCCAAAATCGGAAGCTCATATACTTGCATATCTTGATCTCT
CGAACACTGAGATCACAGCCCTTGCCCAACTCCATTTGCGAGCTCTATAAGTTGCAAAGATTTAGAGTCATCAACTG
CTTTTCACTCCAGGGACTTCCATATGAGATGAGAAATATGATAAGTTTGAGACACATATATTACACTTCTATTGAC
GAAACAAGTGGGCATTGGGGAGGATGGTGTCTTCACAATGAACATTTTCAGATTCCACTTAATATGGGGCAATTGA
CTAGTCTTCAAACCCTCAAGTTTTTCAAGGTAGGTTTAGAGAAAGGTCGTCAAATAGAAGAATTAGGTCATTTGAA
AAACCTAGGAGGTGAATTGACAATCAATGGTCTCCAATTGGTCTGTGATAAAGAAGAGGCTCGAACAGCATATTTA
CAGGATAAACCAAACATCTGCAAGCTGGGATATTTATGGTCCGATGAATGAATCGAAGGCTGTGTGATCAATGATG
AGCATGTGTTGGATGGTCTTCAACCGCATCCTAACTTGAAAACCTTAGCAGTAGTGGACTATTTAGGGACTAAATT
TCCTTCATGGTTCAGTGAAGAGTCGCTACCAAATTTGGTTAAGTTGAAATTAAGTGGTAGCAAAAGGTGCAAAGAA
ATTCCATCCCTTTGGCCAACTGAAATTCCTTCGGCATCTTGAGCTGATAGGATTCCATGAGTTGGAATGCATTGGAC
CTGCTTTATATGGTGTTGAGATTAGAAATACCGGATCAAACAGCAATATCCAAGTGTTCCCGTCATTGAAAGAACT
AGTATTGGAGGATATGCGTAGCCTTATTGAGTGGAAGGGAGATGAAGTCGGAGTAAGAATGTCTCCCGGGCTTGAG
```

```
TCTCCACATCTGAAAAAATGCTTTGCTTACTTTGCAATGTTTCCAAAAGATTATATGTTTGAAAAGGACCAACTAA
TCCAACTCTGGATGGCAGAAGGGTTTCTTCGTCCAAGTCAAGAGATCCCTGTGATGGAAGACGTTGGGCACAGGTT
TTTTCAAATCTTGTTGCAGAATTCCTTGCTACAAGATGTTCTGTTAGATGAACACAACAATATAACACACTGCAAG
ATGCACGATCTTGTGCATGATTTGGCTGGAGATATCTTAAAATCTAGACTATTTGATCCGAAGGGCAACAATGGAG
AAAAACTTTCTCAAGTTCGATACTTTGGATGTGAGTCACCAACGGATCAAATAGATAAGATATATGAGCCAGAACG
TTTGTGCACACTGTTTTGGAGAAGCAATTATACATCTAAAGATATGCTGTTGAACTTTAAGTTCTTGAGAGTTTTA
GATTGTCCAGTTCAGGAATCAAGGAGTTGTCAGCCAAAATCGGGAAGCTGATATACTTGAGATATCTTGATCTCT
CGACACTGAGATCACAGCCTTGCCCAACTCCATTTGCAAGCTCTATAATTTGCAAACATTTAGAGTCATCAACTG
CTTTTCACTCCAGGAACTTCCATATGAGATGAGAAAATGATAAGTTTGAGACACATATATTACACTTCTGTTGAC
GAAACAAGTGGGCATTGGGGAGGATGGTGTCTTCACGATGAACATTTTCAGATTCCACTTAATATGGGCAATTGA
CTAGTCTTCAAACCCTCAAGTTTTTCAAGGTAGTTTAGAGAAAGGTCGTCAAATAGAAGAATTAGGTCATTTGAA
AAACCTAAGAGGTGAATTGACGATCAATGGTCTCCAATTGGTCTGTGATAAAGAAGAGGCTCAAACAGCATATTTA
CACGATAAAGCAAACATCTGCAAGCTGGCATATTTATGGTCCCATGATGAATCAGAAGGCTGTGAGATCAATGATC
AGCATGTGTTGGATGGTCTTCAACCGCATCCTAACTTGAACAACCTTAGCCAGTAGTGGACTATTTAGGGACTAAATT
TCCTTCATGGTTCAGTGAACAGTCTGCTACCCAAATTTGTGCGAGTTGAAATAGTGGTAGCAAAAGGTGCAAAGAA
ATTCCATCCCTTGGCCAACTGAAATTCCTTGGCATCTTGAGCTGGTAGGATTCCATGAGTTGGAATGCATTGGAC
CTGCTTTTTATGGTGTGGAGATGAGAAATATTGGATCAACAGCATTATCCAAGTGTTCCCGTCATTGAAAAAACT
AGTATTGAAGGATATGCGTAGCCCTTATTGAGTGGAAGGGAGATGAAGTTGGAGTAAGAATGTCTCCCGGTCTTGAG
AAGTTGCGGATTACAGACTGTCCATTGTTAAAAGTATTGCGAATCAATTTGAAATCCTCCGTCAATTAAAAATTA
CAGGAGGTTGACAGTGAAATGCCATTGTTGAACTTGTGCAGCAACTTGACATCTCTCGTAAAGCTTAGAGTCTATCA
TATGAAAGAGCTCACTTGTCTTCCAGATGAGATGCTACGTAACAACGTTTCTCTTCAACAGATAATAATTTTCAAC
TGCGAGAGTTTCGTGAATTGCCACAAAGCTTGTACAATCTCCATTCTCTTAGGAGATTAGACATTTACAACTGCA
CCAATTTCAGTTCTCTTCCTGTTCCCAATGGAGGCAACTATTTGACTTCCCTCGAATCTTTTGCTATATAATTG
TAATGGATTGATCAGTATACCAATTGGAATGCTAGGACCGGCTAGTGTTTTCGAATGTCAGCTCGTAAC
AACTTGGTTTCATTCCCTGTACATGTGTGGGAAATGGCTTCACTTTCATATTGGTATATGCAGAATGTCCCAAAT
TGATTAGTGTACCCAAAGTGGGCCCTTCACCATCTCACCGGGTTAGTGAGATTGGGAATTGGTCCTTTCTCAGAGAT
GGTGGATTTGATGCATTCCAATGATTTTTAATGGCATTCAGCAGTTGTTGTCCCCTTCGTGATCTGGAGGTGTAC
GGACGTGGGCACTGGGATTCTCTGCCCTATCAGCTTATGCAACTCTCTGACCTAAGAGAGATCACAATAGCTGATT
TCGGAATTGAGGCTCTTCCTGCTACTCTTGACAACCTTACTTCTCTTGAAAGTTTGACGCTAGTGAGGTGCAAACA
GCTACAACATCTGAACTTCTCGGATGCCATGCCCAAATTACGGCTCCTGTGGATACGTGATTGTCCATTGTTAGAA
GCTCTGTCGGATGGGCTCGGCAACCTTGTTTCTTTGGAAGAATTATATTTACATGACTGGAAAAACTAGAGCATC
TACCGTCCCGAGGATGCCATGCGACGCCTCACTAAATTATGGAACATGAGAATTAAAGGATGCCCAAAGTTAGAAGA
AAGTTTCACCAACTACTCCCAGTGGTCCAAAATTTCCCATATTTCAAATATTGAATTAGGTGGGTGGAGAAGGGACA
GCCATAAGTCTCGGTTTCTCTTTCACTTTCTGA

>324-2_J3_J3_J6
atgaattactgtcttcccttcggGTACTCTACAAACAACTACCAAACGAAGACTTACTTTGAGAAGACTTTGTTGCA
AACAGCTCAGGAAGAAGACTTTGGTGCAGATTGCAGACGAAGACGAAGCAAACACAACTATGGCCGATGCTGTAAT
TGGTGCTACTCTTCAAGTTTTGCTTGAAAAGTTGATTTCTCTCACTATCGAGGAGGTCAACAGCTCAAGGGATTTC
AACAAAGATCTCGAAATGTTGACACGAAATGTATCTTTAATCCAAGCTTTCATTCAGTGTGTTGAAACACCACAAG
AGAAACAGTCTGTGGAACAATGGCTCAACAGGCTTGAGAGAGTTGCTGAAGATGCTGAAAATGTGTTTGATCG
ATTCAGATATGAATCTCTCAAACAAAAGTGGTGAGGAGCCCATTGAAAAAGGTCAGTGGTTTCTTTTTCTCAGACT
GCTTTTAAGAGAAAATGTCTCAAAAAATCAACAACATAAATAAGAAGTTGACGGCTATCAATAAGGTAGCCAAAG
ACCCTCGGTCTACAATCACTCATGGTACCTTCTTGGAAAATACTACCAATTCGAGAAACAGATTCCTTCGTAGGTGC
TTCGATGTTGTTGGTAGAGATTTGGATGTTGCTGAGATAAAGGAGAAGATTTTGAACATGAGAGAGGAGGATGTT
GTTCTGTGCCACCATTCCCATAGTAGGTATGGGAGGTTTAGGGAAAACGAACTGTTGGCTAAGAGGATTTACAATGATG
AACACATCAAGCAAATCTTTAAAGAGAGAATTGGTTGTGTATACCTGAAATGTCTGAAACGAAGAGCTTTCTTCA
ACAAATCCTGGAATCCTTGATAGAGAGGAAAAGTGAGGTTGAAAGGAGAGATATAATAGTCAAGAAGCTACAAGAT
GAATTGGAGGAAAAAATATTTGCTAGTCCTGGATGATTGTGGCGTGTTGACTCTACATCGTGGCATGAGTTCG
TCGACACCCTGAGAGGAATAAATACATCCAGAGGAAACTGCATTCTTGTGACTACTCGTAGGAAGCAGGTGGCATC
CACAGTAGCAACAGATCTTCATATCTTGGGAAGTTAACAGAAGATCATTGTTGTCTATTTCAAACAAAAGCA
TTTGTTCGATGGCAGTGTTCCAGAGGAATTAGGGAGCATGGCAACAAGATTGTTAAAGGTCATGGGTCTACCGT
TGCTGCAAGTGTGTTGGAAGGGCTCTTACACAACAAAGAAAAACAATGAGGCTGGCAAGCAATTCTTGATGGCAACCT
CCTTGTTGCAGGTGAAGATGATAATGGAGAAAATAGGATAAAGAAAATCCTAAAACTCAGCTATGATTATCTACCCA
TCTCCACATCTGAAAAAATGCTTTGCTTACTTTGCAATGTTTCCAAAAGATTATATGTTTGAAAAGGACCAACTAA
TCCAACTCTGGATGGCAGAAGGGTTTCTTCGTCCAAGTCAAGAGATCCCTGTGATGGAAGACGTTGGGCACAGGTT
TTTTCAAATCTTGTTGCAGAATTCCTTGCTACAAGATGTTCTGTTAGATGAACACAACAATATAACACACTGCAAG
ATGCACGATCTTGTGCATGATTTGGCTGGAGATATCTTAAAATCTAGACTATTTGATCCGAAGGGCAACAATGGAG
AAAAACTTTCTCAAGTTCGATACTTTGGATGTGAGTCACCAACGGATCAAATAGATAAGATATATGAGCCAGAACG
TTTGTGCACACTGTTTTGGAGAAGCAATTATACATCTAAAGATATGCTGTTGAACTTTAAGTTCTTGAGAGTTTTA
GATTGTCCAGTTCAGGAATCAAGGAGTTGTCAGCCAAAATCGGGAAGCTGATATACTTGAGATATCTTGATCTCT
CGACACTGAGATCACAGCCTTGCCCAACTCCATTTGCAAGCTCTATAATTTGCAAACATTTAGAGTCATCAACTG
CTTTTCACTCCAGGAACTTCCATATGAGATGAGAAAATGATAAGTTTGAGACACATATATTACACTTCTGTTGAC
GAAACAAGTGGGCATTGGGGAGGATGGTGTCTTCACGATGAACATTTTCAGATTCCACTTAATATGGGCAATTGA
```

```
GCTCTGTCGGATGGGCTCGGCAACCTTGTTTCTTTGGAAGAATTATATTTACATGACTGCGAAAAACTAGAGCATC
TACCGTCCGGAGATGCCATGCGACGGCTCACTAAATTATGGAACATGAGAATTAAAGGATGCCCAAAGTTAGAAGA
AAGTTTCACCAACTACTCCCAGTGGTCCAAAATTTCCCATATTTCAAATATTGAATTAGGTGGTGGAGAAGGACA
GCCATAAGTCTGGTTTCTCTTTCACTTTCTGA

>543-5_C10_C15_C24=Rp1-chc1
ATGAATTATTGTCTTCCTTCGAGTACTCTACAAACAACTACCAAACGAAGACTTACTTTGAGAAGACTTTGTTGCA
AACAGCTCAGGAAGAAGACTTTGGTGCAGACTGCAGAGGAAGAGGAAGCAAACACAACAATGGCCGATCCTGTAAT
TGGTGCTACTGTTCAAGTTTTGCTTGAAAAGTTGATTTCTCTCACTATCGAGGAAGTCAACAGCTCAAGGGATTTC
AACAAAGATCTCGAAATGTTGACACAAAATGTATCTTTAATCCAAGCTTTCATTCATGATGTTGAAACACCACAAG
AGAAACAACAGTCTGTGGAACAATGGCTCAACAGGCTTGAGAGAGTTGCTGAACAATGCTCAAAATGTGTTTGATCG
ATTCATATATGAATCTCTCAAAACAAAAGTGGTGAGGAGCCCATTGAAAAAGGTCAGTGGTTTCTTTTCTCATACT
GCTTTTAAGAGAAAAATGTCTCAAAAAATCAACAACATCAATAAAGAGTTGACGGCTATCAATAAGGTAGCCAAAG
ACCTCGGTCTACAATCACTCATGGTTCCTTCTCGGAAAATACTACCAATTCGAGAAACAGATTCCTTTGTAGTTGC
TTCTGATATTGTCGGTAGAGATTTGGATATTGCTGAGATAAAGGGACAAGAGATTTCAACAGAAGAAGAAGGATATT
GTTCTGTCCACCATTCCCATAGTACGTATGGAGGTTTAGGGAAAACAACTGTGGCTAAGGGATTTACAATGATG
AACGCATGAAGCAAATCTTTGAAAAGAGAATTTGGTTGTGTCTACCTGAAATGTCTGAACGAAGAGCTTTCTTGA
ACAAATCCTCGAATCGTTGATAGACAGGAAAATTGAGGTTGAAAGGAGAGATATAATAGTCAAGAAGCTACAAGAT
GAATTGGAGGAAAAAAATATTTGCTAGTCCTGCATGAATTTGTGGTGTGTTGACTCTACATCCTCGCATGAGTTCA
TTGACACCTTGAGAGGAATAAATACATCCAGAGGAAACTGCATTCTTGTGACTACTCGTAGGAAGCAGGTGGCATC
CACAGTAGCAACAGATCTTCATATCTTGGGGAAGTTAACAGAAGATCATTGTTGGTCTATTTCAAACAAAAAGCA
TTGTTGATGGCAGGGTTCCAGAGGAATTAGCGAGCATGGGCAACAGAGATTGTTAAAATGTGCCAAGGTCTACCGT
TGGCTGCAAGTGTGTTGGGAGGGCTCTACACAACAAGAAAAACATGAATGGCAACCAATTCTTGATGGCAACCT
CCTCGTTGCACGGTGAAGATAATGGAGAAAATAGCATAAAGAATCCTAAAACTCAGCTATGATTATCTACCA
TCTCCACATCTGAAAAAATGCTTTGCTTACTTTGCAATGTTTCCAAAAGATTATATGTTGAAAAGGACCAACTAA
TCCAACTCTGGATGGCAGAAGGGTTTCTTCGTCCAAGTCAAGAGATCCCTGTGAGGAAGACGTTGGGCACAGGTT
TTTTCAAATCTTGTTGCAGAATTCCTTGCTACAAGATGTTCTGTTGATGAACACAACAATATAACACACTGCAAG
ATGCACGATCTTGTTCATGATTTGGCTGGAGATATCTTAAAATCTAGAACTATTTGATCCGAAGGGCGACAATGGAG
AAAAACTTTCTCAAGTTCGATACTTTGCATGTGAGTCACCAACGGATCAAATAGATAAGATATATGAGCCAgAACG
TTTGTGCACACTGTTTTGGAGAAGCAATTATACATCTAAAGATATGCTGTTGAACTTTAAGTTCTTGAGAGTTTTA
GATTTGTCCAGTTCAGGAATCAAGGAGTTGTCAGCCAAAATCGGGAAGCTGATATACTTGAGATATCTTGATCTCT
CGAACACTGAGATCACGGCCTTGCCCAACTCCATTTGCAAGCTCTATAATTTGCAACACATATATTACACTTCTGTTGAC
CTTTTCACTCCAGGGACTTCCATATGAGATAGAGGAACATGATAAGTTTGAGACACACATATATTACACTTCTGTTGAC
GAAAATGGGCATTGGGAGGATGGTGTCTTCACAATGAACATTTTCAGATTCCACTTAATATGGGGCAATTGA
CTAGTCTTCAAACCCTCAAGTTTTTCAAGGTAGGTTTAGAGAAAGTCGTCAAATAGAAGAATTAGGTCATTTGAA
AAACCTAGAGGTGAATTGACGGATCAATGGTCTCCAATTGGTCTGTGATAAAGAAGAGGCTAAACAGCATATTTA
CACGATAAACCAAACATCTGCAAGCTGGCATATTTATGGTCCCATGATGAATCAGAAGGCTGTGAGATCAATGATG
AGCATGTGTTGATGGTCTTCAACCGCATCCTACTGAAAACCTTAGCAGTAGTGGACTATTTAGGGACTAAATT
TCCTTCATGGTTCAGTGAAGAGTCGCTACCAAATTTGTTCAAGTTGAAATTAAGTGGTAGCAAAAGGTGCAAAGAA
ATTCCATGCCTTGGCCAACTGAAATTCCTTCCGGCATCTTGAGCTGATAGGATTCCAAGTGTTCCCGTCATTGAAAAAACT
AGTATTGAAGGATATGCGTAGCCTTATTGAGTGGAAGGAGATGAAGTTGGAGTAAGAATGTCTCCCGGTCTTGAG
AAGTTGCCGGATTACAGACTGTCCATTGTTAAAAGTATTCCGAATCAATTTGAAATCCTCCGTCAATTAAAAATTA
CAGGAGTTGACAGTGAAATGCCATTGTTGAACTTGTGCAGCAACTTGACATCTCTCGTAAAGCTTAGAGTCTATGA
TATGAAAGAGCTCACTTGTCTTCCAGATGAGATGCTACGTAACAACGTTTCTCTTCAACAGATAATAATTTTCAAC
TGCGGAGAGTTTCGTGAATTGCCACAAAGCTTGTGCAATCTCCATTCTCTTAGGAGAATAGACATTTACAACTGCA
CCAATTTCAGTTCTCTTCCTGTTCCCAATGGAGACAACTATTTGACTTCCCTCGAATTCTTTTGCTTACATAATTG
TAATGGATTGATCAGTATACCAATTGGAATGCTAGATCAATGCCGGCTAGTGTTTTTGAATGTCAGCTGCTGTAAC
AACTTGGTTTCATTCCCTGTACATGTGTGGGAAATGCCTTCACTTTCATATTTGCTTATATCAGAATGTCCCAAAT
TGATTAGTACCCAAAGTGGGCCTTCACCATCTCACCGGTTGATGATGGGAATTGGTCCTTCTGATCGGAGTGTAC
GGACGTGGCACTGGGATTCTCTGCCCTATCAGCTTATGCAACTCTCTGACCTAAGAGAGATCAATAGCTGATT
TGGAATTGAGGCTCTTCCTCCTACTCTTGACAACCTTACTTCTCTTGAAAGTTTGACGCTAGTGAGGTGCAAACA
GCTACAACATCTGGAACTTCTCAGATGCCATGCCCAAATTACGGCTCCTGTGGATACGTGATTGTCCATTGTTAGAA
GCTCTGTCGGATGGCTCGGCAACCTTGTTTCTTTGGAAGAATTATATTTACATGACTGCGAAAAACTAGAGCATC
TACCGTCCGGAGATGCCATGCGACGGCTCACTAAATTATGGAACATGAGAATAAGGATGCCCAAAGTTAGAAGA
AAGTTTCACCAACTACTCCCAGTGGTCCAAAATTTCCCATATTTCAAATATTGAATTAGGTGGTGGAGAAGGACA
GCCATAAGTCTGGTTTCTCTTTCACTTTCTGA >493-9_H5_H30
ATGAATTATTGTCTTCCTTCGAGTACTCTACAAACAACTACCAAACGAAGACTTACTTTGAGAAGACTTTGTTGCA
AACAGCTCAGGAAGAAGACTTTGGTGCAGATTGCAGAGGAAGAGGAAGCAAACACAACAATGGCCGATCCTGTAAT
TGGTGCTACTGTTCAAGTTTTGCTTGAAAAGTTGATTTCTCTCACTATCGAGGAGGTCAACAGCTCAAGGGATTTC
AACAAAGATCTCGAAATGTTGACACAAAATGTATCTTTAATCCAAGCTTTCATTCATGATGTTGAAACACCACAAG
```

```
CTGCTTTTTAATGTGTTGAGATTAGAAATATTGGATCAAACAGCCATTATCCAAGTGTTCCCGTCATTGAAAAAACT
AGTATTGACGGATATGCGTAGCCTTATTGAGTGGAAGGGAGATGAAGTTGGAGTAAGAATGTCTCCCGGGCTTGAG
AAGTTGCGGATTACAGACTGTCCATTGTTAAAAAGTATCCCGAATCAATTTGAAATCCTCCGTCAATTAGACATTA
GAGGAGTTGACAGTGAAATACCATTGTTGAACTTGTGCAGCAACTTGACATCTCTCGTAAAGCTTAGTGTCTATGA
TATGAAAGAGCTCACTTGTCTTCCAGATGAGATGCTACGTAACAACGTTTCTCTTCAACAGATAATGATTTTCGAC
TGTCGAGAGTTTCGTGAATTGCCACAAAGCTTGTACAATCTCCATTTCTTAAGAGATTAGAAATTTACAACTGCA
CCAATTTCAGTTCTCTTCCTGTTCCCAATGGAGACAACTATTTGACTTCCCTCCAATTCTTTCAGTTATATAATTG
TGATGGATTGATCAGTTTACCAATTGGAATGCTAGATCAATGCCGGTCTCTAGAGTGTTTGTCTGTCAGCTGCTGT
AACAACTTGGTTTCATTCCCTTTACATGTGTGGGAAATGCCTTCACTTTCATATTTGGTTATATCAGAATGTCCCA
AATTGATTAGTGTACCCGAAGTGGGCCTTCACCGTCTCACTGGGTTATTGAGATTGGGAATTGGTCCTTTCTCAGA
GATGGTGGATTTTGATGCATTCCAATTGAGTTTTAATGGCATTCAGCAGCTGTTGTCCCTTAGTGATCTGGAGGTG
TATGGACATGGGCACTGGGATTCTCTGGCCTATCAGCTTATGCAACTCTCTGACCTAGCAGAGAGATCCAAATAGCTG
ATTTCGGAATTGAGGCTCTTCCACCTAGACTTGACAACCTTACTTCTCTTGAAAAGTTTGACGCTAGTGAGGTGCAA
ACGGCTACAACATCTGAACTTCTCAGATGCCATGCCCTCATTACGGCTTCTGTGGATACGTGATTGTCCATTGTTA
GAAGCTCTGTCGGATGATCTCGGCAACCTTGTTTCTTTGGAAGAATTATATATTACTTGACTGCAAAAAACTAGAGG
GTCTACCGGTCCCGAGATGCCATGCGACGCCTCACTAAATTATGGAACTTGGGAATTAAAGCCTGCCCAAAGTTAAA
AGAAACGTGGTCCAAGATTTCCCATATTCCAAGGAATTGGATTTGGTGGGATGATAATTAAGGACACATGTAAGTGT
TGGTTTCTCTTTCACTTTCTGAAC

>493-7_G10
ATGAATTATTGTCTTCCTTCGAGTACTCTACAAACAACTACCAAACGAAGACTTACTTTGAGAAGACTTTGTTGCA
AACAGCTCAGGAAGAAGACTTTGGTGCAGACTGCAGAGGAAGAGGAAGCAAACACAACTATGGCCGGATCCTGTAAT
TGGTGCTACTGTTCAAGTTTTGCTTGAAAAGTTGATTTCTCTCACTATCGAGGAGGTCAACAGCTCAAGGGATTTC
AACAAAGATCTCGAAATGTTGACACAAAATGTATCTTTAATCCAAGCTTTCATTCATGATGTTGAAACACCCAAAG
AGAAACAACAGTCTGTCGAACAATGGCTCAACAGGCTTGAGAGAGTTGCTGAAGATGCTGAAAATGTGTTTGATCG
ATTCAGATATGAATCTCTCAAAACAAAAGTGGTCGAGAGCCCATTGAAAAAGTCGGTGTTTCCTTTTCTCATATT
GCTTTTAGAGAAAATGTCTCAAAAAATCAACAACATCAATAAAGAGTTGACGGCTATCAATAAGGTAGCCAAAG
ACCTGGGTCTACAATCACTCATGGTACCTTCTCGGAAAATACTACCAATTCGAGAAACAGATTCCTTAGTAGTTGC
TTCTGATATTGTCGGTAGAGATTTGGATGTTGCTGAAGATAAAGGAAGATTTTGAAGATGAGAGGAGGATATT
GTTCTGTCCACCATTCCCATTGTAGGTATGGGAGGTTTAGGGAAACAACTGTGGCTAAGAGGATTTACAATGATG
AACACATGAAGCAAATCTTTAAAAAGAGAATTTGGTTGTGTGTACCTGAAATGTCTGAAACGAAGAGCTTCTTGA
ACAAATCCTCGAATCGTTCATAGAGAGGAAAATTGAGTGTAGAAGGAATGATATAATAGTCAAGAAGCTACAAGAT
GAATTGGGAGGGAAAAAATATTTGCTAGTCCTGGAGGATTTGTGGCGTGTTGACTCTACATCGTGGCATGAGTTCG
TGCACCCTGAGAGGAATAAATACATCGAGAGGGAAACTGCATTCTTGTGACTACTTGTAGGAAGCAGGTGGCATC
CACAGTAGCAACAGATCTTCATATCTTGGGGAAGTTAACAGAAGATCATTGTTGGTCTATTTTCAAACAAAAGCA
TTTGTTGATGGCAGGGTTCCAGAGGAATTAGGGAGCATGGGCAACAAGATTGTTAAAATGTGCCAAGGTCTACCGT
TGCCTGCAAGTGCGTTGGGAGGGGCTCTTACACAACAAAGAAAAACATGAATGGCAAGCAATTCTTGATGGCAACCT
CCTTGTTGCAGGTGAAGATGATAATGGGAAAATAGCATAAAGAAAATCCTAAAACTCAGCTATGATTATCTACCA
TCTCCACATCTGAAAAAATGCTTTGCTTACTTTGCAATGTTTCCAAAAGATTAAATGTTTGAAAAGGACCAACTAA
TCCAACTCTGGATGGCAGAAGGATTTCTTCGTCCAAGTCAAGAGATCCCTGTGATGAAGACGTTGGGCACAGGTT
TTTTCAAATCTTGTTGCAGAATTCCTTGCTACAAGATGTTGTGTTAGATGAACACAACAATATAACACACTGTAAG
ATGCACGATCTTGTGCATGATTTGGCTGAGATATCTTAAAATCTAGACTATTTGATCCGAAGGGCGACAGTGGAG
AAAAACTTTCTCAAGTTCGATACTTTGGATGTGAGTGCACCAGCAGAACGTCAAATAGATAACGATATATGAGCCAGAACG
TTTGTGCACACTGTTTTGGAGAAGGCAATTATACAGTCTGAAGATATGCTTGTGAACTTTAAGTTCTTGAGAGTTTTTA
GATTTGTCCAGTTCAGGAATCAAGGAGTTGTCAGCCAAAATCGGAAGCTGATATACTTGAGATATCTTGATCTCT
CGAACACTGAGATCACAGCCTTGCCCAACTCCATTTGCAAGCTCTATAATTTTGCAAACATTGAGGTCATCAACTG
CTTTTCACTCCAGAAACTTCCATATGAGATGGGAAATGTAAGTTTGAGACACTATATTCACACTTCTGTTTGAC
AAAAGAAATGAGCATTGGGGAGGATGGTGTATTCTCAATGAACGTTTTCAGATGCCACTTAAGATGCGACAATTAA
CTTGTCTTCAAACCCTCAAGTTTTTCAAGATAGGTTTAAAGAAAGGGTCGTCAAATAGAAGAATTGGGTCATTTGAA
AAACCTAGAGGTGAATTGACGATCAATGGTCTCCAAGTTGGTCTGTGATAAAGAAGAGGCTGAACAGCATATTGA
CACGATAAACCAAACATCTTCAAGCTGGCATTTTTATGGTCCCAGGATGAATCAGAAGGCTGTGAGATCAATGATG
AGCATGTGTTGGATGGTCTTCAACCGGCATCCTAACTTGAAAACCTTAGCAGTAGTGGACTATTTAGGGACTAAATT
TCCTTCATGGTTCAGTGAAGAGTGCGCTACCAAATTTGTTGAGTTGGAAATTAAGTGGTAGCAAAAGGTGCAAAGAA
ATTCCATCCCTTGGGCCAACTGAAATTCCTTCGGCATCTTGAGCTGATAGGGATTGAGTTGGAATGCATTGGAC
CTGCTTTATATGGTGTTGAGATTAGAAATATTGGATCAAACAGCCATTATCCAAGTGTTCCCGTCATTGAAGAACT
AGTATTGGAGGATATGCGTAGCCTTATTGAGTGAAGGAGATGAAGTTGGAGTAAGAATGTTTCTAGGCTTGAG
AAGTTGAGGATTATGGAGTGTCCATTGTTAAAAGTACTGCAAGTCAATTTGAAAGCCTGCGTGAATTAGACATTG
TCACAGTTGACAGTGAAATGCCATTGTTGAACTTGTGCAGCAACTTAACATCTCTCGTAGAGCTTAGCGTCTTTGC
TGTGAAAGAGCTCACTTGTTTACCGGATGAGATGCTACGCAACAACGTTTCTCTTCAACAGATAACGATTTCAAC
TGCGGAGAGTTTCGTGAATTGCCACAAAGCTTGTACAATCTCCATTCTCTGAGGAAATTAGGCATTTACAACTGCA
CCAATTTCAGTTCTCTTCCTGTTCCCAATGGAGACAACTATTTGACTTCCCTCCAACTCTTTTCTTATATAATTG
TAATGGATTGATCAGTATACCAATTGGAATGCTAGATCAATGCCGGTCTCTAGAGTTTTGAATGTCAGCTGCTGT
AACAACTTGGTTTCATTCCCTTTACGTGTGTGGGAAATGCCTTCATTATTATTTTGGATATAACAGAATGTCCCA
AATTGATTAGTGTACCCGAAAGTGGGCCTTCACCATCTCACTGGGTTATTGAGATTGGGAATTGGTCCTTTCTCAAA
```

FIG. 13S

GATGGTGGATTTTGATGCATTCCAATTGATTTTTAATGGCATTCAGCAGCTGTTGTCCCTTCGTGATCTGGAGGTG
TACGGACGTGGGCACTGGGATTCTCTGCCCTATCAGRTTATGCAACTATCTGACCTAAGAGAGATCACAATAGCTG
ATTTTGGAATTGAGGCTCTTCCTCCTAGACTTGACAACCTTACTTCTCTTGAAAGCTTGACTCTAGTGAGGTGCAA
ACAGCTACAACATCTGAACTTCTCAGATGCCATGCCCAAATTACGGCTCCTGTGAATACGTGATTTTCCATTGTTA
GAAGCTCTGTCAGATGGGCTCGGCAACCTTGTTCTTTGAAGAATTATATTTACATGACTGCGAAAAACTAGAGC
ATCTACCGTCCCGAGATGCCATGCGATGCCTCACTAAATTATGGAACATGGGAATTAAAGGCTGCCCAAAGTTAGA
AGAAAGTTACACCAACTACTCCCAGTGGTCCAAAATTTCCCATATTTCAAATATTGAATTAGGTGGGAGGAGAAGT
ACAGCCGTAAGTCTCGGTTTCTCTTTCACTTTCTGA

FIG. 13T

Alignment Report of 'chc_allele-mining_total_alignment_proteins18-9-9 + chc_homologs + RH_homologs-Ph2candidate.meg'

```
              Majority          --------------------
MNYCLPSSTLQTTTKRRLTLRRLCCKQLRKKTLVQIASEERANTTMADPVIGATVQVLLS
         ------------+---------+---------+---------+---------
+--------+--------+---------+
                                  10        20        30        40
50        60        70        80
         ------------+---------+
+--------+--------+---------+
94-2031_L4_L7_L8                 --------------------
MNYCLPSSTLQTTTKRRLTLRRLCCKQLRKKTLVQIASEERANTTMADAVIGATVQVLLS    178
324-2_J1_J3_J8                   --------------------
MNYCLPSSTLQTTTKRRLTLRRLCCKQLRKKTLVQIASEERANTTMADAVIGATVQVLLS    178
324-2_J2_J5_J6                   --------------------
MNYCLPSSTLQTTTKRRLTLRRLCCKQLRKKTLVQIASEERANTTMADAVIGATVQVLLS    178
407-1_I4_I6_I8                   --------------------
MNYCLPSSTLQTTTKRRLTLRRLCCKQLRKKTLVQIASEERANTTMADAVIGATVQVLLS    178
493-5_F1_F5_F7                   --------------------
MNYCLPSSTLQTTTKRRLTLRRLCCKQLRKKTLVQIASEERANTTMADAVIGATVQVLLS    178
493-7_G2                         --------------------
MNYCLPSSTLQTTTKRRLTLRRLCCKQLRKKTLVQIASEERANTTMADAVIGATVQVLLS    178
493-7_G10                        --------------------
MNYCLPSSTLQTTTKRRLTLRRLCCKQLRKKTLVQIASEERANTTMADAVIGATVQVLLS    178
493-7_G12                        --------------------
MNYCLPSSTLQTTTKRRLTLRRLCCKQLRKKTLVQIASEERANTTMADAVIGATVQVLLS    178
493-7_G14_G22                    --------------------
MNYCLPSSTLQTTTKRRLTLRRLCCKQLRKKTLVQIASEERANTTMADAVIGATVQVLLS    178
493-7_G19                        --------------------
MNYCLPSSTLQTTTKRRLTLRRLCCKQLRKKTLVQIASEERANTTMADAVIGATVQVLLS    178
493-7_G21                        --------------------
MNYCLPSSTLQTTTKRRLTLRRLCCKQLRKKTLVQIASEERANTTMADAVIGATVQVLLS    178
493-9_H5_H10                     --------------------
MNYCLPSSTLQTTTKRRLTLRRLCCKQLRKKTLVQIASEERANTTMADAVIGATVQVLLS    178
493-9_H11_H19_H27                --------------------
MNYCLPSSTLQTTTKRRLTLRRLCCKQLRKKTLVQIASEERANTTMADAVIGATVQVLLS    178
543-9_C2                         --------------------
MNYCLPSSTLQTTTKRRLTLRRLCCKQLRKKTLVQIASEERANTTMADPVIGATVQVLLS    178
561-2_K4_K14_K22                 --------------------
MNYCLPSSTLQTTTKRRLTLRRLCCKQLRKKTLVQIASEERANTTMADAVIGATVQVLLS    178
561-2_K6_K30_K31                 --------------------
MNYCLPSSTLQTTTKRRLTLRRLCCKQLRKKTLVQIASEERANTTMADAVIGATVQVLLS    178
849-1_M8_M18_M20                 --------------------
MNYCLPSSTLQTTTKRRLTLRRLCCKQLRKKTLVQIASEERANTTMADPVIGATVQVLLS    178
852-5_E14_E23                    --------------------
MNYCLPSSTLQTTTKRRLTLRRLNCKQLRKKTLVQIASEERANTTMADPVIGATVQVLLS    178
852-5_E28                        --------------------
MNYCLPSSTLQTTTKRRLTLRRLCCKQLRKKTLVQIASEERANTTMADAVIGATVQVLLS    178
852-5_E30                        --------------------
MNYCLPSSTLQTTPKRRLTLRRLNCKQLRKKTLVQIASEERANTTMADPVIGATVQVLLS    178
RH_D3_D4_D7                      --------------------
MNYCLPSSTLQTTTKRRLTLRRLCCIQLRKKTLVQIASEERANTTMADPVIGATVQVLLS    178
Rpi-chc1_ORF                     --------------------
MNYCLPSSTLQTTTKRRLTLRRLCCKQLRKKTLVQIASEERANTTMADPVIGATVQVLLS    178
chc1_BAC_B07-1C15                --------------------
---------------MADPVIGATVQVLLD           43
chc2_BAC_B07-1C15                --------------------
---------------MADPVIGATVQVLLS           43
chc_RGC1_BAC_2D06-3D21           --------------------
---------------MADPVIGATVQVLLS           43
chc_RGC2_BAC_2D06-3D21           --------------------
---------------MADPVIGATVQVLLS           43
```

FIG. 14A

```
RH122B15 c247                    ------------------------------
---------------MADPVIGATVQVVLLS      43
RH122B15 c88-5                   ------------------------------
---------------MADPVIGATVQVLLS       43
RH137D14 c13-1
MEMRXIICWTYALIKWLGTGTYLTRHGRSQSKKTFTERRHRVGHTVGMQKKTFLRRRFCEGANATMADPVTGATVQ
VLVD     238
RH137D14 c13-2                   ------------------------------
MNYCLPLSTLQTTTKRRLTLRRLCCIQLRKKTLVQIASEEKANTTMADPVIGATVQVLLS         178
RH77023 c573-6                   ------------------------------
---------------MADPVFAATVKVLLD       43
RH77023 c579-5                   ------------------------------
---------------MADPVIGATVQVVLS       43
RH77023 c671                     ------------------------------
---------------MADPVIGATVQVVLS       43
RH77023 c706-3                   ------------------------------
---------------MADPVIGATVQVVLS       43
RH77023 c706-6                   ------------------------------
---------------MADPVIGATVQVVLS       43
ph2 candidate                    ------------------------------
---------------MADPVIGATVQVLLS       15

Majority      KLISLTIEEVNSSRDFNKDLEMLTQNVSLIQAFIHDVETPQ-
EKQQSVEQNLNRLERVAEDAENVFDRFRYESLK--TKV
                  ~~~~~~~~~~~~~~~~~~~~~~~~~~~~~~~~~~~~~~~~~~~~~~~~~~~
~~~~~~~~~~~~~~~~~~~~~~~~~~~~~~~~~~~~~~~
                                   90       100       110       120       130
  140       150       160
                  ~~~~~~~~~~~~~~~~~~~~~~~~~~~~~~~~~~~~~~~~~~~~~~~~~~~
~~~~~~~~~~~~~~~~~~~~~~~~~~~~~~~
94-2931_L4_L7_L8        KLISLTIEEVNSSRDFNKDLEMLTQNVSLIQAFIHDVETPQ-
EKQQSVEQNLNRLERVAEDAENVFDRFRYESLK--TKV     409
324-2_J1_J3_J8          KLISLTIEEVNSSRDFNKDLEMLTQNVSLIQAFIHDVETPQ-
EKQQSVEQNLNRLERVAEDAENVFDRFRYESLK--TKV     409
324-2_J2_J5_J6          KLISLTIEEVNSSRDFNKDLEMLTQNVSLIQAFIHDVETPQ-
EKQQSVEQNLNRLERVAEDAENVFDRFRYESLK--TKV     409
487-1_I4_I6_I8          KLISLTIEEVNSSRDFNKDLEMLTQNVSLIQAFIHDVETPQ-
EKQQSVEQNLNRLERVAEDAENVFDRFRYESLK--TKV     409
493-5_F1_F5_F7          KLISLTIEEVNSSRDFNKDLEMLTQNVSLIQAFIHDVETPQ-
EKQQSVEQNLNRLERVAEDAENVFDRFRYESLK--TKV     409
493-7_G2                KLISLTIEEVNSSRDFNKDLEMLTQNVSLIQAFIHDVETPQ-
EKQQSVEQNLNRLERVAEDAENVFDRFRYESLK--TKV     409
493-7_G10               KLISLTIEEVNSSRDFNKDLEMLTQNVSLIQAFIHDVETPQ-
EKQQSVEQNLNRLERVAEDAENVFDRFRYESLK--TKV     409
493-7_G12               KLISLTIEEVNSSRDFNKDLEMLTQNVSLIQAFIHDVETPQ-
EKQQSVEQNLNRLERVAEDAENVFDRFRYESLK--TKV     409
493-7_G14_G22           KLISLTIEEVNSSRDFNKDLEMLTQNVSLIQAFIHDVETPQ-
EKQQSVEQNLNRLERVAEDAENVFDRFRYESLK--TKV     409
493-7_G19               KLISLTIEEVNSSRDFNKDLEMLTQNVSLIQAFIHDVETPQ-
EKQQSVEQNLNRLERVAEDAENVFDRFRYESLK--TKV     409
493-7_G31               KLISLTIEEVNSSRDFNKDLEMLTQNVSLIQAFIHDVETPQ-
EKQQSVEQNLNRLERVAEDAENVFDRFRYESLK--TKV     409
493-9_H5_H30            KLISLTIEEVNSSRDFNKDLEMLTQNVSLIQAFIHDVETPQ-
EKQQSVEQNLNRLERVAEDAENVFDRFRYESLK--TKV     409
493-9_H13_H19_H27       KLISLTIEEVNSSRDFNKDLEMLTQNVSLIQAFIHDVETPQ-
EKQQSVEQNLNRLERVAEDAENVFDRFRYESLK--TKV     409
543-5_C2                KLISLTIEEVNSSRDFNKDLEMLTQNVSLIQAFIHDVETPQ-
EKQQSVEQNLNRLERVAEDAQNVFDRFIYESLK--TKV     409
561-2_K4_K14_K23        KLISLTIEEVNSSRDFNKDLEMLTQNVSLIQAFIHDVETPQ-
EKQQSVEQNLNRLERVAEDAENVFDRFRYESLK--TKV     409
561-3_K5_K30_K31        KLISLTIEEVNSSRDFNKDLEMLTQNVSLIQAFIHDVETPQ-
EKQQSVEQNLNRLERVAEDAENVFDRFRYESLK--TKV     409
```

FIG. 14B

```
849-1_N8_M16_M30         KLISLTIEEVNSSRDFNKDLEMLTQNVSLIQAFIHDVETPQ-
EKQQSVEQWLNRLERVAEDAENVFDRFRYESLK--TKV      409
852-5_E14_E23
KLISLTIEDVNSSRDFNKDLEMLTQNVSLIQAFIHDVKTPQVEKQQSFEQWLNRLERVAEDAQNVFDRFRYESLK-
-TKV       413
852-5_E28                KLISLTIEDVNSSRDFNKDLEMLTQNVSLIQAFIHDVETPQ-
EKQQSVEQWLNRLERVAEDAENVFDRFRYESLK--TKV      409
852-5_E30
KLISLTIEDVNSSRDFNKDLEMLTQNVSLIQAFIHDVKTPQVEKQQSFEQWLNRLERVAEDAQNVFDRFRYESLK-
-TKV       413
BH_D3_04_D7              KLISLTIEEVNSSRDFNKDLEMLTQNVSLIQAFIHDVETPQ-
EKQQSVEQWLNRLERVAEDAENVFDRFRYESLK--TKV      409
Rpi-chc1_ORF             KLISLTIEEVNSSRDFNKDLEMLTQNVSLIQAFIHDVETPQ-
EKQQSVEQWLNRLERVAEDAQNVFDRFYESLK--TKV       409
chc1_BAC_B07-1C15        KLISLTIEEFSSSRDCNKDLEMLTQNVSLIQAFIHDAERRQ-
VEDKAVKLWLERLDNAAENARYVFDKFRYESLKRQVKI      280
chc2_BAC_B07-1C15        KLISLTIEEFSSSRDQNKDLRMLTQNVSMIQAFIHDGERRQ-
VEDQSVKLNFTRLERAAENAENVFDKYRYESLKRQVKI      280
chc_RGC1_BAC_2D06-3D21   KLISLTIEEFNSSRDCNKDLEMLTQRVSNIQAFIHDAERRQ-
VEDQAVKLNLRLERAAENAENVFDKFRYESLKRQVKI       280
chc_RGC2_BAC_2D06-3D21   KLISLTTEEFSSSRDCNKDLRMLTQNVSMIQAFIHDAERRQ-
VEDQSMKLNFTRLERAAENAENVFDKFRYESLKRQVKI      280
RH122B15_c247            KLLSLTIEEARNLRNCKNDLRMLSRYVTNIQAFIHDAERRQVED-
KAVEEWLKMLERIAEDAENVFDKFTYESIK----AKV       274
RH122B15_c88-5           KLISLTIEEVNSSRDFNKDLEMLT---------------
QFDKQQSVEQWLNRLERVAEDAQNVFDRFRYESLK--TKV    229
RH137D14_c13-1           KLISLTIEEFSSSRDCNKDLEMLTQNVSLIQAFIHDAERRQ-
VEDSVKVNLRSLERAAENAEYVCDKFRYESLKRQVKI       475
RH137D14_c13-2           KLISLTIEEVNSSRDFNKDLEMLTQNVSLIQAFIHDVETPQ-
EKQQSVEQNLNRLERVAEDAENVFDRFRYESLK--TKV      409
RH77023_c579-4
KLISLTIKEISSSRDFNEDLEMLTHNVSLIQAFLEDVETPQVEKQQGVEQWLERLERVAENAENVFDRFRYESLK-
-TKV       277
RH77023_c579-5           KLLSLTIEEARSLRNCKNNLRMLSRYVTNIQAFIHDAERRQ------
VEENWLKMLERIAEDAENVFDKPTYESIK--AKV          259
RH77023_c671             KLLSLTIEEARNVRNCKRNLRMLSRYVTNIQAFIHDAERRQVED-
RVEEWLKMLERIAEDAENVFDKFTYESIK--AKV          274
RH77023_c706-3           KLISLTIEEVRRLGNCKDLEMLTDNVSLIQAFIHDAERRQ-
VEDQVVEQWLKMLERVTENAENVFDRFRYESLKRQVKI      280
RH77023_c706-4
KLISLTIEEVNSSRDFNKDLEMLTQNASLIQAFIHDVETPQVEKQQSVRQWLYRLERVAEDAQNVFDRFRYESLK-
-TKV       277
ph3 candidate
KLLSLSIEEVRTLRNCKNLSKLTRHVTMIQAYTHDAETRQVEDNQAVEEWLKMLEKIAEDAENVFDKFTYVSIK-
-ARV       93

Majority   VR---
          SPLKKVSGFFSHTAFKRKMSQKINNIMKELTAINKVAKDLGLQSLMVPSRKILPIRETDSFVVASDVVGRDLDVA -----------+----------+----------+----------+----------+----------+
                                       170       180       190       200
     210       220       230       240
                                       -----------+----------+----------+----------+

+----------+----------+----------+
94-2031_L4_L7_L8         VR---
          SPLKKVSGFFSHTAFKRKMSQKINNINKELTAINKVAKDLGLQSLMVPSNKILPIRETDSFVGASDVVGRDLDVA
640
324-2_J1_J3_J8           VR---
          SPLKKVSGFFSHTAFKRKMSQKINNINKELTAINKVAKDLGLQSLMVPSNKILPIRETDSFVGASDVVGRDLDVA
640
```

FIG. 14C

```
324-2_J2_J5_J6              VR---
SPLKKVSGFFSHTAFKRKMSQKINNINKELTAINKVAKDLGLQSLMVPSRKILPIRSTDSFVGASDVVGRDLOVA
640
487-1_I4_I6_I8              VR---
SPLKKVSGFFSHTAFKRKMSQKINNINKELTAINKVAKDLGLQSLMVPSRKILPIRSTDSLVVASDIVGRDLOVA
640
493-5_F1_F5_F7              VR---
SPLKKVSGFFSHTAFKRKMSQKINNINKELTAINKVAKDLGLQSLMVPSRKILPIRETDSFVGASDVVGRDLOVA
640
493-7_G2                    VR---
SPLKKVSGFFSHTAFKRKMSQKINNINKELTAINKVAKDLGLQSLMVPSRKILPIRETDSFVGASDVVGRDLOVA
640
493-7_G10                   VR---
SPLKKVSGFFSHTAFKRKMSQKINNINKELTAINKVAKDLGLQSLMVPSRKILPIRETDSLVVASDIVGRDLOVA
640
493-7_G12                   VR---
SPLKKVSGFFSHTAFKRKMSQKINNINKELTAINKVAKDLGLQSLMVPSRKILPIRSTDSFVGASDVVGRDLOVA
640
493-7_G14_G22               VR---
SPLKKVSGFFSHTAFKRKMSQKINNINKELTAINKVAKDLGLQSLMVPSRKILPIRSTDSLVVASDIVGRDLOVA
640
493-7_G19                   VR---
SPLKKVSGFFSHTAFKRKMSQKINNINKELTAINKVAKDLGLQSLMVPSRKILPIRSTDSLVVASDIVGRDLOVA
640
493-7_G21                   VR---
SPLKKVSGFFSHTAFKRKMSQKINNINKELTAINKVAKDLGLQSLMVPSRKILPIRSTDSFVGASDVVGRDLOVA
640
493-9_H5_H30                VR---
SPLKKVSGFFSHTAFKRKMSQKINNINKELTAINKVAKDLGLQSLIVPSRKILPIRETDSIVGASDVVGRDLOVA
640
493-9_H11_H19_H27           VR---
SPLKKVSGFFSHTAFKRKMSQKINNINKELTAINKVAKDLGLQSLMVPSRKILPIRETDSFVGASDVVGRDLOVA
640
543-5_C2                    VR---
SPLKKVSGFFSHTAFKRKMSQKINNINKELTAINKVAKDLGLQSLMVPSRKILPIRSTDSFVVASDIVGRDLDIA
640
561-2_K4_K14_K23            VR---
SPLKKVSGFFSHTAFKRKMSQKINNINKELTAINKVAKDLGLQSLMVPSWKILPIRETDSFVGASDVVGRDLOVA
640
561-3_K6_K30_K31            VR---
SPLKKVGGFFSHTAFKRKMSQKINNINKELTAINKVAKDLGLQSLMVPSRKILPIRETDSLVVASDIVGRDLOVA
640
849-3_M8_M18_M20            VR---
SPLKKVSGFFSHTAFKRKMSQKINNINKELTAINKVAKDLGLQSLMVPSRKILPIRETDSLVVASDIVGRDLOVA
640
852-5_E14_E23               VR---
SPLKKVSGFFSHSAFKRKMSQNINNINKELTAINKVAKDLGLQSLMVPSRKILPIRETDSFVGASDVVGRDLOVA
643
852-5_E28                   VR---
SPLKKVSGFFSHTAFKRKMSQKINNINKELTAINKVAKDLGLQSLMVPSRKILPIRETDSFVGASDVVGRDLOVA
640
852-5_E30                   VR---
SPLKKVSGFFSHSAFKRKMSQNINNINKVAKDLGLQSLMVPSRKILPIRETDSFVGASDVVGRDLOVA
643
R51_D2_D4_D7                VR---
SPLKKVGGFFSHTAFKRKMSQKINNINKELTAINKVAKDLGLQSLMVPSRKILPIRSTDSLVVASDIVGRDLOVA
640
Rpi-chc1_ORF                VR---
SPLKKVSGFFSHTAFKRKMSQKINNINKELTAINKVAKDLGLQSLMVPSRKILPIRSTDSFVVASDIVGRDLDIA
640
chc1_BAC_807-1018           RN---
NPNRKVSDFFSHTAFKNKMSRKINNINRELKAINKVAKTLGLQALMVPPQKILPIRETDSIVVASYVVGRDNDVA
513
```

FIG. 14D

```
493-5_F1_F5_F7
EIKEKILKMREEDVVLSTIPIVGMGGLGKTTVAKRIYNDEKIKQIFKERIWLCIPEMSETKSFLEQILESLIERKI
EVER        880
493-7_G2
EIKEKILKMREEDIVLSTIPIVGMGGLGKTTVAKRIYNDEHMKQIFKKRIWLCLPEMSETKSFLEQILESLIERKI
EVER        880
493-7_G10
EIKEKILKMREEDIVLSTIPIVGMGGLGKTTVAKRIYNDEHMKQIFKKRIWLCLPEMSETKSFLEQILESLIERKI
EVER        880
493-7_G13
EIKEKILKMREEDVVLSTIPIVGMGGLGKTTVAKRIYNDEKIKQIFKERIWLCIPEMSETKSFLEQILESLIERKI
EVER        880
493-7_G14_G22
EIKEKILKMREEDVVLSTIPIVGMGGLGKTTVAKRIYNDEHMKQIFKKRIWLCLPEMSETKSFLEQILESLIERKI
EVER        880
493-7_G19
EIKEKILKMREEDVVLSTIPIVGMGGLGKTTVAKRIYNDEHMKQIFKKRIWLCLPEMSETKSFLEQILESLIERKI
EVER        880
493-7_G21
EIKEKILKMREEDVVLSTIPIVGMGGLGKTTVAKRIYNDEHMKQIFKERIWLCIPEMSETKSFLEQILESLIERKI
EVER        880
493-9_H5_H30
EIKEKILKMREEDVVLSTIPIVGMGGLGKTTVAKRIYNDEHIKQIPKERIWLCIPEMSETKSFLEQILESLIERKI
EVER        880
493-9_H11_H19_H27
EIKEKILKMREEDVVLSTIPIVGMGGLGKTTVAKRIYNDEHIKQIFKERIWLCIPEMSETKSFLEQILESLIERKI
EVER        880
543-5_C2
EIKEKILKMREEDIVLSTIPIVGMGGLGKTTVAKRIYNDEHMKQIFERRIWLCLPEMSETKSFLEQILESLIERKI
EVER        880
561-2_K4_K14_K22
EIKEKILKMREEDVLSTIPIVGMGGLGKTTVAKRIYNDEHIKQIFKERIWLCIPEMSETKSFLQQILESLIERKI
EVER        880
561-2_K6_K30_K31
EIKEKILKMREEDVLSTIPIVGMGGLGKTTVAKRIYNDEHMKQIFKKRIWLCLPEMSETKSFLEQILESLIERKI
EVER        880
849-1_M6_M18_M20
EIKEKILKMREEDIVLSTIPIVGMGGLGKTTVAKRIYNDEHMKQIFKKRIWLCLPEMSETKSFLEQILESLIERKI
EVER        880
852-5_E14_E23
EIKEKILKMREEDVVLSTIPIVGMGGLGKTTVAKRIYNDEHIKQIFKERIWLCIPEMSETKSFLEQILESLIERKI
EVER        883
852-5_E28
EIKEKILKMREEDVVLSTIPIVGMGGLGKTTVAKRIYNDEHMKQIFKKRIWLCLPEMSETKSFLEQILESLIERKI
EVER        880
852-5_E30
EIKEKILKMREEDVVLSTIPIVGMGGLGKTTVAKRIYNDEHIKQIFKERIWLCIPEMSETKSFLEQILESLIERKI
EVER        883
RR_D3_D4_D7
EIKEKILKMREEDIVLSTIPIVGMGGLGKTTVAKRIYNDEHMKQIFKKRIWLCLPEMSETKSFLEQILESLIERKI
EVER        880
Rpi-chc1_ORF
EIKEKILKMREEDIVLSTIPIVGMGGLGKTTVAKRIYNDEHMKQIFKKRIWLCLPEMSETKSFLEQILESLIERKI
EVER        880
chc1_BAC_B07-1C15        EIKRKMLNIK-
DDVVLCTIPIVGMGGLGKTTVAKIIFNDSQIEKHFEKRVWLCLPEMSEIKSFLELILESLTERKLEVQS
748
chc2_BAC_B07-1C15        EIKEKIFTIR-
EDIDLCTIPIVGMGGLGKTTVAKRIFNDEQIEKHFEKRVWLCLPEMSEIKSFLELILESLTERKLEVQS
748
chc_RGC1_BAC_2D06-3D21   EIKEKILTIR-
EDIDLCTIPIVGMGGLGKTTVAKRIFNDEQIEKHFEKRVWLCQPEMSETKSFLKLILESLTERKVRVLS
748
```

FIG. 14F

```
chc_RGC2_BAC_2D06-3D21    EIKEKILTIR-
EDIDLCTIPIVGNGGLGKTTVAKRIFNDEQIEKHFEKRVWLCLPEMSEIKSFLELILESLTERKVEVQS
748
RH122B15 c247             EIKGKILNMR-
KDAVLCTIPIVGMGGLGKTTLAKRIFNDQHIEKHFEKRIWLCIPEMSEIKSFLELILESLTERKVEVQS
751
RH122B15 c88-5
VIKEKILNMRKEDVVLSTIPIVGMGGLGKTTMAKRIYNDEHIKQAFEKRIWLCLPEMSERTKSFLEQILESLTERKF
EVER      700
RH137D14 c13-1            EIKRKMLNIR-
DDVVLCTIPIVGMGGLGKTTVAKRIFNDEQIEKNFEKRVWLCLPEMSEIKSFLELILESLTERKLEVQS
843
RH137D14 c13-2
SIKEKILKMREEDIVLSTIPIVGMGGLGKTTVAKRIYNDEHMKQIFKKRIWLCLPEMSETKSFLEQILESLIERKI
EVEK      880
RH77O23 c679-4
SIKEKILNMREDVWKCTIPIVGMGGLGKTTVAKRIYNDEHIKQIFERRIWLCLPEMSERTKSFLEQILESLTERKV
EVQR      757
RH77O23 c679-5            SIKEKILNMR-
KDAVLCTIPIVGMGGLGKTTLAKRIFNDQHIEKHFEKRIWLCLPEMSEIKSFLELILESLTERKVEVQS
736
RH77O23 c671              VIKEKILNMR-
KDAVLCTIPIVGMGGLGKTTLAKRIFNDQHIEKHFERRIWLCLPEMSEIKNFLELILESLTERKVEVQS
751
RH77O23 c706-3            EIKEKILTMR-
DDIDLCTIPIVGMGGLGKTTVAKRVFNDEQIEKHFEKRVWLCLPEMSETKSFLELILESLTERKLEVQS
748
RH77O23 c706-4
EIKEKILKMREEDAVLCTIPIVGMGGLGKTTVAKRIYNDEHIKQIFEKRIWLCLPEMSEIKIFLEQILESLTERKV
EVQR      757
ph2 candidate             EVKEKILNMR-
RIDVVLCTIPIVGMGGLGKTTLVKRIFNDVEIEKHFVKRVWLCLPEMSDAKSFLELILHSLVNQKLELQS
350

Majority
RDIIVKKLQDELGGKKYLLVLDDLWRVDSTSWHEFVDTLRGINTSRGNCILVTTRMKQVASTVATDL--
HILGKLTEDHC 330       340       350       360
370       380       390       400

94-2031_L4_L7_L8
RDIIVKKLQDELGGKKYLLVLDDLWRVDSTSWHEFVDTLRGINTSRGNCILVTTRRKQVASTVATDL--
HILGKLTEDHC      1114
324-2_J1_J3_J8
RDIIVKKLQDELGGKKYLLVLDDLWRVDSTSWHEFVDTLRGINTSRGNCILVTTRRKQVASTVATDL--
HILGKLTEDHC      1114
324-2_J2_J5_J6
RDIIVKKLQDELGGKKYLLVLDDLWRVDSTSWHEFVDTLRGINTSRGNCILVTTRMKRVASTVATDL--
HILGKLTEDHC      1114
487-1_I4_I6_I8
RDIIVKKLQDELGGKKYLLVLDDLWSVDSTLWHEFVDTLRGINTSRGNCILVTTRRKQVASTVATDL--
HILGKLTEDHC      1114
453-5_F1_F5_F7
RDIIVKKLQDELGGKKYLLVLDDLWRVDSTSWHEFVDTLRGINTSRGNCILVTTRMKRVASTVATDL--
HILGKLTEDHC      1114
493-7_G2
RDIIVKKLQDELGGKKYLLVLDDLWRVDSTSWHEFVDTLRGINTSRGNCILVTTRMKWVASTVATDL--
HILGKLTEDHC      1114
```

FIG. 14G

FIG. 14H

```
RH122B15 c89-5
RDIIVKKLQDELGGNKYLLVLDDLNRVDFTSNHEFVDTLRGINTSRGNCILVTTRNKRVASTVATDL--
NMLGKLTDDNC        934
RH137D14 c13-1
RDIIVKKLRDELAGNKYLLVLDDLNRVDFTLNDEFVDTLRGINTSRGNFIIVTTDNELVASTVATVLGPNMLEKLS
RDNC        1163
RH137D14 c13-2
RDIIVKKLQDELGGNKYLLVLDDLNRVDSTSNHEFVDTLRRINTSRGNCILVTTRREQVASTVATDL--
NILGKLTRDNC        1114
RH77023 c579-4
RDIIVKKLQDELGGNYLLVLDDLNCVDSTSNHEFVDTLRGINTAKGNCILVTTRMKRVASTVAADL--
NMLGKLTDDNC        991
RH77023 c579-5
RDIIVKKLRDALGEKQYFLVLDDLNRVDYTLNHEFLDTLRGINTSRGNCILVTTRSKQVASIVAADL--
NKLGKLTDDQC        970
RH77023 c671
RDIIVKKLAALGEKQYLLVLDDLNRADSTSNHEFLDTLRGINTTRGNCILVTTRSKQVASTVARDL--
NKLGKLTDDNC        985
RH77023 c706-3
RDIIVKKLRDELAGNKYLLVLDDLNRVDPTLNHEFLDTLRGINTTRGNCILVTTPMKLVASTVAVGL--
NMLGKLADDNC        982
RH77023 c706-4
RDIIVKKLQDELGGNKYLLVLDDLNRLDSTSNHEFVDTLRGINTSRGNCILVTTRMKRVASTIATNL--
NILGKLTDDNC        991
ph2 candidate
RDIIVKKLQDALGEKRYLLVLDDLNRVDSTNNYEFMDTLRGINTSRGNCILVTTRMKQVASIVAADL--
NMLGKLADDNC        328

Majority
NSIFKQKAFVDGRVPEELASMGNKIVKNCQGLPLAASVLGGLLHNKEDHEWQAILDGNLLVAGEDDNGENSIKKIL
KLSY
                 .........+.........+.........+.........+.........+
                                          410       420       430       440
       450       460       470       480
.........+.........+.........+.........+
.........+.........+.........+
94-2031_L4_L7_L8
NSIFKQKAFVDGRVPEELASMGNKIVKNCQGLPLAASVLGGLLHNKEDHEWQAILDGNLLVAGEDDNGENSIKKIL
KLSY        1354
324-2_J1_J3_J8
NSIFKQKAFVDGSVPEELASMGNKIVKNCQGLPLAASVLGGLLHNKEHHEWQAILDGNLLVAGEDDNGENSIKKIL
KLSY        1354
324-2_J2_J5_J6
NSIFKQKAFVDGRVPEELASMGNNIVKNCQGLPLAASALGGLLHNKEKHEWQAILDGNLLVAGEDDNGENSIKKIL
KLSY        1354
487-1_I4_I6_I8
NSIFKQKAFVDGRVPEELASMGNKIVKNCQGLPLAASALGGLLHNKEHHEWQAILDGNLLVAGEDDNGENSIKKIL
KLSY        1354
493-9_F1_F5_F7
NSIFKQKAFVDGRVPEELASMGNNIVKNCQGLPLAASALGGLLHNKEKHEWQAILDGNLLVAGEDDNGENSIKKIL
KLSY        1354
493-7_G2
NSIFKQKAFVDGRVPEELASMGNKIVKNCQGLPLAASVLGGLLHNKEKHEWQAILDGNLLVASEDDNGENSIKKIL
KLSY        1354
493-7_G10
NSIFKQKAFVDGRVPEELASMGNKIVKNCQGLPLAASALGGLLHNKEKHEWQAILDGNLLVAGEDDNGENSIKKIL
KLSY        1354
493-7_G12
NSIFKQKAFVDGRVPEELASMGNNIVKNCQGLPLAASALGGLLHNKEKHEWQAILDGNLLVAGEDDNGENSIKKIL
KLSY        1354
```

FIG. 14I

```
493-7_G14_G22
NSIFKQKAFVDGRVPEELASMGNKIVKMCQGLPLAASVLGGLLHNKEKHEWQAILDGNLLVAGEDDNGENSIKKIL
KLSY      1354
493-7_G18
NSIFKQKAFVDGRVPEELASMGNKIVKMCQGLPLAASVLGGLLHNKEKHEWQAILDGNLLVAGEDDNGENSIKKIL
KLSY      1354
493-7_G21
NSIFKQKAFVDGRVPEELASMGNKIVKMCQGLPLAASALGGLLHNKEKHEWQAILDGNLLVAGEDDNGENSIKKIL
KLSY      1354
493-9_H5_H30
NSIFKQKAFVDGRVPEELASMGNKIVKMCQGLPLAASALGGLLHNKEKHEWQAILDGNLLVAGEDDNGENSLKKIL
KLSY      1354
493-9_H11_H19_H27
NSIFKQKAFVDGRVPEELASMGNKIVKMCQGLPLAASALGGLLHNKEKHEWQAILDGNLLVAGEDDNGENSIKKIL
KLSY      1354
543-5_C2
NSIFKQKAFVDGRVPEELASMGNKIVKMCQGLPLAASVLGGLLHNKEKHEWQAILDGNLLVAGEDDNGENSIKKIL
KLSY      1354
561-2_K4_K14_K22
NSIFKQKAFVDGRVPEELASMGNKIVKMCQGLPLAASVLGGLLHNKEKHEWQAILDGNLLVAGEDDNGENSIKKIL
KLSY      1354
561-2_K6_K30_K31
NSIFKQKAFVDGRVPEELASMGNKIVKMCQGLPLAASVLGGLLHNKEKHEWQAILDGNLLVAGEDDNGENSIKKIL
KLSY      1354
849-1_M8_M18_M30
NSIFKQKAFVDGRVPEELASMGNKIVKMCQGLPLAASALGGLLHNKEKHEWQAILDGNLLVAGEDDNGENSIKKIL
KLSY      1354
852-5_R14_R23
NSIFKQKAFVDGRVPEELASMGNKIVKMCQGLPLAASVLGGLLHNKEKHEWQAILDGNLLVAGEDDNGENSIKKIL
KLSY      1357
852-5_R28
NSIFKQKAFVDGRVPEELASMGNKIVKMCQGLPLAASVLGGLLHNKEKHEWQAILDGNLLVAGEDDNGENSIKKIL
KLSY      1354
852-5_R30
NSIFKQKAFVDGRVPEELASMGNKIVKMCQGLPLAASVLGGLLHNKEKHEWQAILDGNLLVAGEDDNGENSIKKIL
KLSY      1357
R8_D3_D4_D7
NSIFKQKAFVDGRVPEELASMGNKIVKMCQGLPLAASALGGLLHNKEKHEWQAILDGNLLVPGEDDNGENSIKKIL
KLSY      1354
Rpi-chc1_ORF
NSIFKQKAFVDGRVPEELASMGNKIVKMCQGLPLAASVLGGLLHNKEKHEWQAILDGNLLVAGEDDNGENSIKKIL
KLSY      1354
chc1_BAC_B07-1C15
NSIFKQRAFVDGKIPEEIVMEKRIVEMCQGLPLAASVLGGLLRSKEKHEWQAILDGNPLVAGENDNGEKSIKKIL
KLSY      1228
chc2_BAC_B07-1C15
NSIFKQRAFVDGKIPEEIVRMEKRIVEMCQGLPLAASVLGGLLRSKEKHEWQAILDGNPLVAGENDNGVKSIKKIL
KLSY      1228
chc_RGC1_BAC_2006-3D21
NSIFKQRAFVDGKIPEEIVSMEKRIVEMCQGLPLAASVLGGLLRSKEKHEWQAILDGNPLVAGENDNGRKSIKKIL
KLSY      1228
chc_RGC2_BAC_2006-3D21
NSIFKQRAFVDGKIPEEIVSMEKRIVEMCQGLLLAASVLGGLLRSKEKHEWQAILDGNPLAK-------------
-----     1174
RH132B19_c247
NSIFKQRAFVDGSVPEETLGVEKKIVEMCQGLPLAASVLGGLFCNKEKHEWQAILDGSSLVASE-D----
SIKNILKLSY     1210
RH122B15_c89-5
NSIFKQKAFVDGRVPEELASMGNKIVEMCQGLPLAASVLGGLLHNKEKHEWQAILDGNPLVAGEDDNGENSIKKIL
TLSY      1174
RH137B14_c13-1
NSIFKQRAFVDGKIPEEIVSMEKRIVEMCQGLPLAASVLGGLLRSKEKHEWQAILDGNPLVAGENDNGEKSIKKIL
KLSY      1423
```

FIG. 14J

```
RH137D14 c13-2
WSIFKQRAFVDGRVPERLASMGNKIVRNCQGLPLAASALGGLLHNKEKHEWQAILDGNLLVTGEDDNGENSIKKIL
KLSY        1354
RH77O23 c579-6
WSIFEQKAFVDGRVPERLASMGNKIVRMCHQLPLAASVLGGLLHNKEKHEWQAILDGSPLVAGEDDNGENSIKKIL
KLSY        1231
RH77O23 c579-5
WSIFKQRAFVDGRVPEEILSVENKIVENCQGLPLAASVLGGLFCNKEKHEWQAILDGSSLVASD-D----
SIKNILKLSY       1155
RH77O23 c671
WSIFKQRAFVDGRVPEEILSVENKIVENCQGLPLAASVLGGLFCNKEKHEWQAILDGSSLVASD-D----
SIKNILKLSY       1210
RH77O23 c706-3
WSIFKQRAFVDGRVPERMVIMENRIVETCQGLPLAACVLGGLIRNKEKHEWQAILDGSNSLVANEDDLGENSIKKIL
KLSY        1222
RH77O23 c706-4
WSIFKQRAFVDGRVPERFASMGRKIVRMCEGLPLAASVLGGLLCNKEKHEWQAILDGNPLIVGEDDNGENNIKKIL
KLSY        1231
ph2 candidate
LSIFKQRAFVDGSVPQRILSMEKKIVRLCQGLPLAASVLGCLLCNKEKHEWQAILVAGEDONGS-N----
SLKKILKLSY       403

Majority
DYLPSPHLKKCFAYFAMFPKDYMFEKDQLIQLWWARGFLRPSQEIPVMEDVGHRFFQILLQNSLLQDVVLDERRNI
TRCK
     ~~~~~~~~~~+~~~~~~~~~~+~~~~~~~~~~+~~~~~~~~~~+~~~~~~~~~~+
                                       480        500        510        520
530        540        550        560
     ~~~~~~~~~~+~~~~~~~~~~+~~~~~~~~~~+~~~~~~~~~~+~~~~~~~~~~+
94-2031_D4_D7_D8
DYLPSPHLKKCFAYFAMFPKDYMFEKDQLIQLWWARGFLRPSQEIPVMEDVGHRFFQILLQNSLLQDVVLDERRNI
TRCK        1594
324-2_J1_J3_J8
DYLPSPHLKKCFAYFAMFPKDYMFEKDQLIQLWWARGFLRPSQEIPVMEDVGHRFFQILLQNSLLQDVVLDERRNI
TRCK        1594
324-2_J2_J5_J6
DYLPSPHLKQCFAYFAMFPKDYMFEKDQLIQLWWARGFLRPSQEIPVMEDVGHRFFQILLQNSLLQDVVLDERRNI
TRCK        1594
467-1_I4_I6_I8
DYLPSPHLKKCFAYFAMFPKDYMFEKDQLIQLWWARGFLRPSQEIPVMEDVGHRFFQILLQNSLLQDVVLDERRNI
TRCK        1594
493-5_F1_F5_F7
DYLPSPHLKQCFAYFAMFPKDYMFEKDQLIQLWWARGFLRPSQEIPVMEDVGHRFFQILLQNSLLQDVVLDERRNI
TRCK        1594
493-7_G2
DYLPSPHLKQCFAYFAMFPKDYMFEKDQLIQLWWARGFLRPSQEIPVMEDVGHRFFQILLQNSLLQDVVLDERRNI
TRCK        1594
493-7_G10
DYLPSPHLKKCFAYFAMFPKDYMFEKDQLIQLWWARGFLRPSQEIPVMEDVGHRFFQILLQNSLLQDVVLDERRNI
TRCK        1594
493-7_G12
DYLPSPHLKQCFAYFAMFPKDYMFEKDQLIQLWWARGFLRPSQEIPVMEDVGHRFFQILLQNSLLQDVVLDERRNI
TRCK        1594
493-7_G14_G22
DYLPSPHLKKCFAYFAMFPKDYMFEKDQLIQLWWARGFLRPSQEIPVMEDVGHRFFQILLQDVLDERRNI
TRCK        1594
493-7_G15
DYLPSPHLKKCFAYFAMFPKDYMFEKDQLIQLWWARGFLRPSQEIPVMEDVGHRFFQILLQNSLLQDVVLDERRNI
TRCK        1594
```

FIG. 14K

```
493-7_G21
DYLPSPHLKQCFAYFAMFPKDYMFEKDQLIQLWWAEGFLRPSQEIPVMEDVGHRFFQILLQNSLLQDVVLDEHNNI
THCK        1594
493-9_H6_H30
DYLPSPHLKKCFAYFAMFPKDYMFEKDQLIQLWWAEGFLRPSQEIPVMEDVGHRFFQILLQNCLLQDDVLDEHNNI
THCK        1594
493-9_H11_H19_H27
DYLPSPHLQCFAYFAMFPKDYMFEKDQLIQLWWAEGFLRPSQEIPVMEDVGHRFFQILLQNSLLQDVVLDEHNNI
THCK        1594
843-6_C2
DYLPSPHLKKCFAYFAMFPKDYMFEKDQLIQLWWAEGFLRPSQEIPVMEDVGHRFFQILLQNSLLQDVLDEHNNI
THCK        1594
861-2_K4_K14_K22
DYLPSPHLKKCFAYFAMFPKDYMFEKDQLIQLWWAEGFLRPSQEIPVMEDVGHRFFQILLQNSLLQDVVLDEHNNI
THCK        1594
861-2_K6_K30_K31
DYLPSPHLKKCFAYFAMFPKDYMFEKDQLIQLWWAEGFLRPSQEIPVMEDVGHRFFQILLQNSLLQDDVLHEHNNI
THCK        1594
849-1_M8_M18_M20
DYLPSPHLKKCFAYFAMFPKDYMFEKDQLIQLWWAEGFLRPSQEIPVMEDVGHRFFQILLQNSLLQDVVLDEHNYI
THCK        1594
852-6_E14_E23
DYLPSPHLKKCFAYFAMFPKDYMFEKDQLIQLWWAEGFLRPSQEIPVMEDVGHRFFQILLQNSLLQDVLDEHNNI
THCK        1597
852-6_E28
DYLPSPHLKKCFAYFAMFPKDYMFEKDQLIQLWWAEGFLRPSQEIPVMEDVGHRFFQILLQNSLLQDVVLDEHNNI
THCK        1594
852-6_E30
DYLPSPHLKKCFAYFAMFPKDYMFEKDQLIQLWWAEGFLRPSQEIPVMEDVGHRFFQILLQNSLLQDVVLDEHNNI
THCK        1597
RH_D3_D4_D7
DYLPSPHLKKCFAYFAMFPKDYMFEKDQLIQLWWAEGFLRPSQEIPVMEDVGHRFFQILLQNSLLQDVVLDEHNNI
THCK        1594
Rpl-chcl_ORF
DYLPSPHLKKCFAYFAMFPKDYMFEKDQLIQLWWAEGFLRPSQEIPVMEDVGHRFFQILLQNSLLQDVLDEHNNI
THCK        1594
chcl_BAC_B07-1C15
DYLPSPQLKKCFAYFAMFPKDFSFEKDQLIQLWWAEGFLHPCQEITVMEDVGHRFFQILLQNSLLQDVELDEHDNI
THCK        1468
chc2_BAC_B07-1C15
DYLPSPQLKKCFAYFRLFPKDFSFEKDQLIQLWWAEGFLHPCQEIPVMEDVGHRFFQILLQNSLLQDVELDEHNNI
THCK        1468
chc_RGC1_BAC_2D06-3D21
DYLPSPQLKKCFAYFAMFPKDFSFEKDQLIQLWWAEGFLHPCQEITVMSDIGHRFFQILLQNSLLQDVELDEHNNI
THCK        1468
chc_RGC2_BAC_2D06-3D21                     --------------------
DFSFEKDQLIQLWWAEGFLHPCQEIPAMEDVGHWFFQILLQNSLLQDVELDEQNNITHCK      1394
RH133R15 c247
DYLPSPHLKKCFSYFAMFEKDFSFEKDQLIQLWWAEGFLRPCQETTVMEDVGHRFFQLLLQYSLLQDVNLDEYNNI
THCK        1460
RH122R15 c88-6
VYLPSVQLKKCFAYFAMFPKDSFFEKDQLIQLWWAEGFLHPCQETTVMEDVGHRFFQILLQNSLLQDIRLDELNNI
THCK        1414
RH137D14 c13-1
DYLPSPYLKKCFAYFAMFPKDFEFEKDQLIQLWWAEGFLHPCQETTVMEDVGHRFFQILLKNSLLQDVELDEHNNI
THCK        1653
RH137D14 c13-3
DYLPSPHLKKCFAYFAMFPKDYMFEKDQLIQLWWAEGFLRPSQEIPVMEDVGHRFFQILLQNSLLQDVVLDEHNNI
THCK        1594
RH77Q23 c979-4
DYLPSPHLKKCFAYFAMLFKDLMFEKAQLIQLWWAEGFLHPCQETTVMEDIGHRFFQLLLRNSLLQDVLDEHNNI
KYCK        1471
```

```
RH77023 c679-5
DYLPSPHLKKCPSYFAMFPKDPEFSKDQLIQLMMASGFLRPCQETTVMEDVGNKFFQLLLQYSLLQDVNLDEYNNI
THCK         1435
RH77023 c671
DYLPSPHLKKCFSYFAIFPKDPEFPKDQLIQLMMASGFLRPCQETPVMEDVGNKFFQLLLQYSLLQDVNLDKYNNT
THCK         1450
RH77023 c706-3
VYLPSPHLKKCFAYFAMFPKDPEFSKDQLIQLMMASGFLHPCQETIVMEDVGNKFFQILLQNSLLQDVKLDEHNYI
THGK         1462
RH77023 c706-4
DYLPSFYLKKCFAYFAMFPKDPKFSKDQLIQLMMASGFLHPCQETTVMEDIGNSFFRLLRSSLLQDVVLDEHNNI
KYCK         1471
ph3 candidate
DYLPSPHLKKCFAYFAMFPKDPEFPKDQLIQLMMASGFLRPCQETPVMEDVGIKPFQLLPQYSLLQDVKLDEYNNY
THCK         483

Majority
MHDLVHDLAGDILKSRLFDPKGDNGEKLSQVRYFGCESPTDQIDKIYEPERLCTLFWRSNYTSKDMLLNFKFLRVL
DLSS 570        580        590        600
610       620        630        640

94-2031_L4_L7_L8
MHDLVHDLAGDILKSRLFDPKGNNGEKLSQVRYFGCESPTDQIDKIYEPERLCTLFWRSNYTSKDMLLNFKFLRVL
DLSS         1834
324-2_J1_J3_J8
MHDLVHDLAGDILKSRLFDPKSNNGEKLSQVRYFGCESPTDQIDKIYEPERLCTLFWRSNYTSKDMLLNFKFLRVL
DLSS         1834
324-2_J3_J5_J6
MHDLVHDLAGDILKSRLFDPKGDNGEKLSQVRYFGCESPKDQIDKIYEPERLCTLFWRSNYTSKDMLLNFKFLRVL
DLSS         1834
487-1_I4_I5_I6
MHDLVHDLAGDILKSRLFDPKGDGEKLSQVRYFGCESPTDQIDKICEPERLCTLFWRSNYTSKDMLLNFKFLRVL
DLSS         1834
493-5_F1_F5_F7
MHDLVHDLAGDILKSRLFDPKGDNGEKLSQVRYFGCESPKDQIDKIYEPERLCTLFWRSNYTSKDMLLNFKFLRVL
DLSS         1834
493-7_G2
MHDLVHDLAGDILKSRLFDPKGDNGEKLSQVRYFGCESPKDQIDKIYEPERLCTLFWRSNYTSKDMLLNFKFLRVL
DLSS         1834
493-7_G10
MHDLVHDLAGDILKSRLFDPKGDDGEKLSQVRYFGCESPTDQIDKIYEPERLCTLFWRSNYTSKDMLLNFKFLRVL
DLSS         1834
493-7_G12
MHDLVHDLAGDILKSRLFDPKGDNGEKLSQVRYFGCESPKDQIDKIYEPERLCTLFWRSNYTSKDMLLNFKFLRVL
DLSS         1834
493-7_G14_G22
MHDLVHDLAGDILKSRLFDPKGDNGEKLSQVRYFGCESPTDQIDKIYEPERLCTLFWRSNYTSKDMLLNFKFLRVL
DLSS         1834
493-7_G19
MHDLVHDLAGDILKSRLFDPKGDNGEKLSQVRYFGCESPTDQIDKIYEPERLCTLFWRSNYTSKDMLLNFKFLRVL
DLSS         1834
493-7_G31
MHDLVHDLAGDILKSRLFDPKGDNGEKLSQVRYFGCESPKDQIDKIYEPERLCTLFWRSNYTSKDMLLNFKFLRVL
DLSS         1834
493-9_H5_H30
MHDLVHDLAGDILKSRLFDPKGDNGEKLSQVRYFGCESPTDQIDKIYEPERLCTLFWRSNYTSKDMLLNFKFLRVL
DLSS         1834
```

FIG. 14M

493-S_H11_H19_H27
MNDLVHDLAGDILKSRLFDPKGDNGEKLSQVRYFGCESPKDQIDKIYEPERLCTLFWRSNYTSKDMLLSFKFLRVL
DLSS      1834
543-S_C2
MNDLVHDLAGDILKSRLFDPKGDNGEKLSQVRYFGCESPTDQIDKIYEPERLCTLFWRSNYTSKDMLLNFKFLRVL
DLSS      1834
561-3_K4_K14_K23
MNDLVHDLAGDILKSRLFDPKGNNGEKLSQVRYFGCESPTDQIDKIYEPERLCTLFWRSNYTSKDMLLNFKFLRVL
DLSS      1834
561-2_K6_K30_K31
MNDLVHDLAGDILKSRLFDPKGDNGEKLSQVRYFGCESPADQIDKIYEPERLCTLFWRSNYTSKDMLLNFKFLRVL
DLSS      1834
848-1_N6_N18_N20
MNDLVHDLAGDILKSRLFDPKGDNGEKLSQVRYFGCESPTDQIDKIYEPERLCTLFWRSNYTSKDMLLKYKFLRVL
DLSS      1834
892-5_B14_B23
MNDLVHDLAGDILKSRLFDPKGDNGEKLSQVRYFGCESPTDQIDKIYEPERLCTLFWRSNYTSKDMLLNFKFLRVL
DLSS      1837
852-5_K28
MNDLVHDLAGDILKSRLFDPKGDNGEKLSQVRYFGCESPTDQIDKIYEPERLCTLFWRSNYTSKDMLLNFKFLRVL
DLSS      1834
852-5_K30
MNDLVHDLAGDILKSRLFDPKGDNGEKLSQVRYFGCESPTDQIDKIYEPERLCTLFWRSNYTSKDMLLKYKFLRVL
DLSS      1837
RH_D3_D4_D7
MNDLVHDLAGDILKSRLFDPKGDNGEKLSQVRYFGCESPTDQIDKIYEPERLCTLFWRSNYTSKDMLLKYKFLRVL
DLSS      1834
Rpi-chc1_ORF
MNDLVHDLAGDILKSRLFDPKGDNGEKLSQVRYFGCESPTDQIDKIYEPERLCTLFWRSNYTSKDMLLNFKFLRVL
DLSS      1834
chc1_BAC_B07-1C15
MNDLVHDLAGDILKSKLFDPKGNDGEKLSQVRYFGCESPGDQIDKIYEPERLCTLFWRSNYISEDMLLSFKLLRVL
DLSS      1708
chc2_BAC_B07-1C15
MNDLVHDLAGEILKCKLFDPKGDDGEKLSQVRYFGCESPNEQIGKIYAFERLCTLFWRDNYIWEDMLLSFKFLRVL
DLSS      1708
che_RGC1_BAC_2D06-3D21
MNDLVHDLAGDILKSKLFDPKGNDGEKLSQVRYFGCESPNDQIDKIYEPERLCTLFWRSNYIWEDMLLSFKFLRVL
DLSS      1708
che_RGC3_BAC_2D06-3D21      MNDLVHDLAGDILKSKLFDPKGDDGEKLSQVRYFG---------------
-----------------------------      1459
RH133815 c247
MNDLVHDLAHDIFKSKLFSQKSVGGENLSQVRYFGWSPSDQIDKIYEPERLCTLFWKSN-
ISDDMLLSFQPLRVLNLSG      1687
RH133815 c66-5
VHDLVHDLAGDILFKDPKGDDGEKLSQVRYFGCESPRNQIDKIYEPQRLCTLFWRSNSISEDMLLSFKFLRAL
NLSS      1654
RH137D14 c13-1
MNDLVHDLAGDILKSKLFDPKGNDGEKPSQVRYFGCESPGDQIDKIYEPERLCTLFWRSNYIWEDMLLSFKLLAVL
DLSS      1903
RH137D14 c13-2
MNDLVHDLAGDILKSRLFDPKGDNGEKLSQVRYFGCESPTDQIDKIYEPERLCTLFWRSNYTSKDMLLKYKFLRVL
DLSS      1834
RH77Q23 c579-4
MNDLVHDLAGDIFKSKLFDSKGNDGEKLSQVRYFGWDSPSDQIDKINEPQRLCTLFWRSNYISEDMLLSFKFLRVL
NLSS      1711
RH77Q23 c579-5
MNDLVHDLAGDIFKSKLFDQKSVGGENLSQVRYFGWESPSDQIDKIYEPQRLCTLFWKSN-
ISDDMLLSFQPLRVLNLSG      1672
RH77Q23 c871
MNDLVHDLAGDIFKSKLFDQKSVGGESLSQVRYFGWESPSDQIDKIYEPQRLCTLFWRSNHISEAMLLSFKFLRVL
NLSS      1690

FIG. 14N

```
RH77023 c706-3
MHDLVRDLAGDILKSKLPDRKGDVGEISSQVRYFGRDSPIDQIDKINEPGRLCALFSRSN-
IPNDVLFSFQFLRVLNLSR        1699
RH77023 c706-4
MHDLVRDLAGDILKSKLPDRKGNDGEKLSQVRYGGNDSPEDQIGKINEPGRLCTLFWREMYISEDMLLSFKPLRVL
NLSS        1711
ph2 candidate
MHDLVRDLAGDILKSKLPDKKSVEGENLSQVRYFGNDSPEDQIDKISEDGRLCTLFWESM-
ISDDMLLSFQFLRVLNLSA        962

Majority        SGIKELSAKIGKLIYLRYLDLS--------------
NTEITALPNSICKLYNLQTFRVI-NCFSLQELPYEMRNMISLRHIY
         --------+-----------+-----------+-----------+-----------+-----------+
         --------+-----------+
                                        650         660         670         680
         690         700         710         720
         --------+-----------+-----------+-----------+-----------+-----------+

94-2031_L4_L7_L8             SGIKELSAKIGKLIYLRYLDLS--------------
NTEITALPNSICKLYNLQTFRVI-NCFSLQELPYEMRNMISLRHIY        2035
324-2_J1_J3_J8               SGIKELSAKIGKLIYLRYLDLS--------------
NTEITALPNSICKLYNLQTFRVI-NCFSLQELPYEMRNMISLRHIY        2035
324-2_J2_J5_J6               SGIKELSAKIGKLIYLRYLDLS--------------
NTEITALPNSICELYNLQTFRVI-NCFSLQGLPYEMRNMISLRHIY        2035
487-1_I4_I6_I8               SGIKELSAKIGKLIYLRYLDLS--------------
NTEITALPNSICELYNLQTFRVI-NCFSLQELPYEMRMVSLRHIY        2035
493-5_F1_F5_F7               SGIKELSAKIGKLIYLRYLDLS--------------
NTEITALPNSICELYNLQTFRVI-NCFSLQGLPYEMRNMISLRHIY        2035
493-7_G2                     SGIKELSAKIGKLIYLRYLDLS--------------
NTEITALPNSICELYNLQTFRVI-NCFSLQGLPYEMRNMISLRHIY        2035
493-7_G10                    SGIKELSAKIGKLIYLRYLDLS--------------
NTEITALPNSICKLYNLQTFRVI-NCFSLQELPYEMRNMVSLRHIY        2035
493-7_G13                    SGIKELSAKIGKLIYLRYLDLS--------------
NTEITALPNSICELYNLQTFRVI-NCFSLQGLPYEMRNMISLRHIY        2035
493-7_G14_G23                SGIKELSAKIGKLIYLRYLDLS--------------
NTEITALPNSICKLYNLQTFRVI-NCFSLQELPYEMRNMISLRHIY        2035
493-7_G15                    SGIKELSAKIGKLIYLRYLDLS--------------
NTEITALPNSICELYNLQTFRVI-NCFSLQELPYEMRNMISLRHIY        2035
493-7_G21                    SGIKELSAKIGKLIYLRYLDLS--------------
NTEITALPNSICKLYNLQTFRVI-NCFSLQELPYEMRNMISLRHIY        2035
493-9_H5_H30                 SGIKELSAKIGKLIYLRYLDLS--------------
NTEITALPNSICKLYNLQTFRVI-NCFSLQELPYEMRNMISLRHIY        2035
493-9_H11_H19_H27            SGIKELSAKIGKLIYLRYLDLS--------------
NTEITALPNSICELYNLQTFRVI-NCFSLQGLPYEMRNMISLRHIY        2035
543-5_C2                     SGIKELSAKIGKLIYLRYLDLS--------------
NTEITALPNSICKLYNLQTFRVI-NCFSLQELPYEMRNMISLRHIY        2035
561-2_K4_K14_K22             SGIKELSAKIGKLIYLRYLDLS--------------
NTEITALPNSICKLYNLQTFRVI-NCFSLQELPYEMRNMISLRHIY        2035
561-2_K6_K30_K31             SGIKELSAKIGKLIYLRYLDLS--------------
NTEITALPNSICKLYNLQTFRVI-NCFSLQELPYEMRNMISLRHIY        2035
849-1_M6_M18_M20             SGIKELSTKIGKLIYLRYLDLS--------------
NTEITALPNSICKLYNLQTFRVI-NCFSLQELPYEMRNMISLRHIY        2035
852-5_E14_E23                SGIKELSAKIGKLIYLRYLDLS--------------
NTEITALPNSICKLYNLQTFRVI-NCFSLQELPYEMRNMISLRHIY        2038
852-5_E28                    SGIKELSAKIGKLIYLRYLDLS--------------
NTEITALPNSICKLYNLQTFRVI-NCFSLQELPYEMRNMISLRHIY        2035
852-5_E30                    SGIKELSTKIGKLIYLRYLDLS--------------
NTEITALPNSICELYNLQTFRVI-NCFSLQELPYEMRNMISLRHIY        2038
RH_D3_D4_D7                  SGIKELSTKIGKLIYLRYLDLS--------------
NTEITALPNSICELYNLQTFRVI-NCFSLQELPYEMRNMISLRHIY        2038
Rpi-chc1_ORF                 SGIKELSAKIGKLIYLRYLDLS--------------
NTEITALPNSICKLYNLQTFRVI-NCFSLQELPYEMRNMISLRHIY        2035
```

FIG. 14O

```
chc1_BAC_B07-1C15        SGINELSTKIGKLIYLRYLDLS--------------
NTEITALPSSICELYNLQTFRVI-NCFSLQELPYEMGMMISLRHIY        1909
chc2_BAC_B07-1C15        SGINEVSAKIGKLIYLRYLDLS--------------
NTNITALPNSICELYSLQTFRVT-NCFSLKELPYENGMMISLRHIY        1909
chc_RGC1_BAC_2006-3D21   SGIKELSAKIGKLIYLRYLDLS--------------
NTEITALPNSICKLYNLQTFRVI-NCHSLKELPYEMGMMISLRHIY        1909
chc_RGC2_BAC_2006-3D21   -----------------------------------F--
LPNSICELYNLQTFRVN-DCFSLRELPYEMGMMISLRHIY        1579
RH122B1S c247
SDIKELSASIVKLIYLRYLDLSNTKMNDRYLDLSNTEMNDLPNSICKLYNLQTLRFY-
CWYPLRKLPEEMANMISLRHIC        1924
RH122B1S c88-5           SGIKELSAKIGKLIYLRYLDLS--------------
NTEITALPNSICKLYNLQTFRVI-NCHSLKELPYEMGMMISLRHIY        1855
RH137D14 c13-1           SGINELSAKIGNLIYLRYLDLS--------------
NTEITALPNSICELYNLQTFRVI-NCFSLQELPYEMGMRSLRHIY        2104
RH137D14 c13-2           SGIKELSTKIGKLIYLRYLDLS--------------
NTEITALPNSICELYNLQTFRVI-NCFSLQELPYEMGMMISLRHIY        2035
RH77023 c579-4           SGIKELSASIGKLIYLRYLDIS--------------
STEITALPNSICKLYNLQTFRAN-CCYSLKEFPYEMGMMISLRHIY        1912
RH77023 c579-5
SDIKELSASIVKLIYLRYLDLSNTKMNDGYLDLSNTEMNDLPNSICKLYNLQTLRFYSNYFLRKLPEEMANMISL
RHIC                1912
RH77023 c671             SGIKELPAKIGKLIYLRYLDLS--------------
NTRITALPNSICKLYNLQTLRFYSINYPLGKLPEEMANMISLRHIC        1894
RH77023 c706-3           SGIKELSASIGKLVHLRYLDLS--------------
YSGIKALPNSICKLYSNQTIRVS-KCPLLKELPDEMANMISLRHYY        1900
RH77023 c706-4           SGIPGLSDKIGKLIYLRYLDIS--------------
STEITALPHSICKLYNLQTFRVN-YCYSLKEFPYEMGMMISLRHIY        1912
ph2 candidate            SGIKELSAKISKLIFLRYLDIS--------------
DTRIEDFPDSICKLYNLQTFRVN-DCSSLRKLPEEMANMISLRHIY        629

Majority
YTSVDETSGHMGGWCLRNEHFQIPLNMGQLTSLQTLRFFKVGLEKGRQIEELGHLKNLRGELTINGLQLVCDKEEA
RTAY

*****----*-------*---*---*-----*-----*----*----------
                                                            730       740       750       760
770        780        790        800
                                         *****----*---*-------*---*---*-----*-----*----*----------
*----*----*----*-----*
94-2031_L4_L7_L8
YTSVDETSGHWGGWCLRNEHFQIPLNMGQLTSLQTLRFFKVGLEKGRQIEELGRLKNLRGELTINGLQLVCDKEEA
QTAY       2275
334-2_J1_J3_J8
YTSVDETSGHWGGWCLHNEHFQIPLNMGQLTSLQTLRFFKVGLEKGRQIEELGRLKNLXGELTINGLQLVCDKEEA
XTAY       2275
334-2_J2_J5_J6
YTSIDETSGHWGGWCLHNEHFQIPLNMGQLTSLQTLRFFKVGLEKGRQIEELGRLKNLGGELTINGLQLVCDKEEA
RTAY       2275
487-1_I4_I6_I8
YTSVDERNEHWGGWCILNERFQMSLRMRQLTCLQTLRFFKIGLEKGRQIEELGRLKNLRGELTINGLQLVCDKEEA
RTAY       2275
493-5_F1_F5_F7
YTSIDETSGHWGGWCLHNEHFQIPLNMGQLTSLQTLRFFKVGLEKGRQIEELGRLKNLGGELTINGLQLVCDKEEA
RTAY       2275
493-7_G2
YTSIDETSGHWGGWCLHNEHFQIPLNMGQLTSLQTLRFFKVGLEKGRQIEELGRLKNLGGELTINGLQLVCDKEEA
RTAY       2275
493-7_G10
YTSVDERNEHWGGWCILNERFQMPLRMRQLTCLQTLRFFKIGLEKGRQIEELGRLKNLRGELTINGLQLVCDKREA
RTAY       2275
```

FIG. 14P

```
493-7_G12
YTSIDETSGHWGGWCLHNEHFQIPLNWGQLTSLQTLKFFKVGLEKGRQIEELGRLKNLGGELTINGLQLVCDKEEA
RTAY          2275
493-7_G14_G22
YTSVDETSGHWGGWCLHNEHFQIPLNWGQLTSLQTLKFFKVGLEKGRQIEELGHLKNLRGELTINGLQLVCDKEEA
QTAY          2275
493-7_G18
YTSVDETSGHWGGWCLHNEHFQIPLNWGQLTSLQTLKFFKVGLEKGRQIEELGHLKNLRGELTINGLQLVCDKEEA
QTAY          2275
493-7_G21
YTSVDETSGHWGGWCLHNEHFQIPLNWGQLTSLQTLKFFKVGLEKGRQIEELGHLKNLRGELTINGLQLVCDKEEA
QTAY          2275
493-9_H5_H30
YTSVDETSGHWGGWCLHNEHFQIPLNWGQLTSLQTLKFFKVGLEKGRQIEELGHLKNLRGELTINGLQLVCDKEEA
QTAY          2275
493-9_H11_H19_H27
YTSIDETSGHWGGWCLHNEHFQIPLNWGQLTSLQTLKFFKVGLEKGRQIEELGHLKNLGGELTINGLQLVCDKEEA
RTAY          2275
543-5_C2
YTSIDETSGHWGGWCLHNEHFQIPLNWGQLTSLQTLKFFKVGLEKGRQIEELGHLKNLGGELTINGLQLVCDKEEA
RTAY          2275
561-2_K4_K14_K22
YTSVDETSGHWGGWCLHNEHFQIPLNWGQLTSLQTLKFFKVGLEKGRQIEELGHLKNLRGELTINGLQLVCDKEEA
QTAY          2275
561-2_K5_K30_K31
YTSVDETSGHWGGWCLHNEHFQIPLNWGQLTSLQTLKFFKVGLEKGRQIEELGHLKNLRGELTINGLQLVCDKEEA
QTAY          2275
849-1_M8_M18_M20
YTSVDKRTLHWGGWCLHNEHFQIPLNWGQLTSLQTLKFFKVGLEKGRQIEELGHLKNLRGELTINGLQLVCDKEEA
RTAY          2275
852-5_B14_B23
YTSVDETSGHWGGWCLHNEHFQIPLNWGQLTSLQTLKFFKVGLEKGRQIEELGHLKNLRGELTINGLQLVCDKEEA
QTAY          2275
852-5_B28
YTSVDETSGHWGGWCLHNEHFQIPLNWGQLTSLQTLKFFKVGLEKGRQIEELGHLKNLRGELTINGLQLVCDKEEA
QTAY          2275
852-5_B30
YTSVDETSGHWGGWCLHNEHFQIPLNWGQLTSLQTLKFFKVGLEKGRQIEELGHLKNLRGELTINGLQLVCDKEEA
.TAY          2275
RH_D3_D4_D7
YTSVDETSGHWGGWCLHNEHFQIPLNWGQLTSLQTLKFFKVGLEKGRQIEELGHLKNLRGELTINGLQLVCDKEEA
RTAY          2275
Rp1-chc1_ORF
YTSVDETSGHWGGWCLHNEHFQIPLNWGQLTSLQTLKFFKVGLEKGRQIEELGHLKNLRGELTINGLQLVCDKEEA
QTAY          2275
chc1_BAC_B07-1C18
YTFVDETSGHWGGWCIRNEHFQMPLNWGQLTSLQTLQFFKVGLQKGRQIEELGHLKNLRGELRINGLQLVCDKEEA
RTAY          2149
chc2_BAC_B07-1C18
YSSINKRNRHNGGWCIRNEHFQMPLNWGQLTCLQTLQFFKVGLEKGHQIEELGHLKNLRGKLRINGLQFVCDKEEA
RTAY          2149
chc_RGC1_BAC_2D06-3D21
YTSVDKGRQHWGGWCILNEHFQMPLNWGQLTSLQTLQFFKVGLEKGRQIEELGHLKNLRGELRINGLQLVCDKEEA
RTTY          2149
chc_RGC2_BAC_2D06-3D21
FTSVDKRTLHNGAWCIRYNMFQMPLNWGQLTSLQTLQFFKVGLEKGRQIEELGHLKNLRGELRFKGLQLVCDKEEA
RTAY          1819
RH122B15 d247                    CYQFFE-SD-----------
FQMPLNWGQLTSLQTLPFFYVGREKGRRIEELGCLKNLRGELFIERLQLVGNKEEARTAY          3128
RH122B15 c85-5
YTSADETNGHLGEWCIRNEHFQMPLKSRQLTCLQTLQFFKVGVAKGRQIEELGHLKNLRGELTINGLQLVCDREEA
RTAN          2095
```

FIG. 14Q

```
RH137D14 c13-1
YTFVDKTSGHWGWCIRNEHFQMPLNMGQLTSLQTLQFFKVGLEKGRQIEELGHLKNLRGELRINGLQLVCDKEEA
RTAY        2344
RH137D14 c13-2
YTSVDKTSGHWGGWCLRNEHPQIPLNMGQLTSLQTLNFFKVGLEKGRQIEELGHLKNLRGELTINGLQLVCDKEEA
RTAY        2275
RH77O23 c579-4              FYSSSQ-----------------
MPLNLGQLTCLQTLQYPNVGLEKGRRIEELGCLKNLRGRLRINELSLVESREDALTAY           2104
RH77O23 c579-5              CYNFFE-SD---------------
FQMPLNMGQLTSLQTLPFFYVGSEKGRRIEELGCLKNLRGELTIERLQLVGNKEEARTAY         2116
RH77O23 c671                CYRFFS-SD---------------
SQMPLNMGQLTSLQTLQPFYVGLKKGRRIEELGCLKNLRGELTIKRLQLVGNKEEARTAY         2088
RH77O23 c706-3              YNS----------------
LCMDNKHFQMFFNMGKLTCLQTLQFFKVGSEKGRRIEEIGHLKNLRGELTIEELQLVCNREEARTAY
2115
RH77O23 c706-4              FYSSSQ------------------
MPLRLGQLTCLQTLQYPNVGLEKGRRIEELGRLKNLRGKLRINGLQLVRDREEARTAC           2104
ph2 candidate               CN----G-SD--------------
MQTPLNMGQLTSLQTLRVPYIGEEKGRRIKELGRLKNLRGKLTINHLQLVBNKEEACTAY         694

Majority
LHDKPNICKLAYLNSHDESEGCEINDEHVLDGLQPHPNLKTLAVVDYLGTKFPSWFSEESLPNLVKLKLGGSKRCK
SIPS 810        820        830        840
850       860        870        880

94-3031_L6_L7_L8
LHDKPNICKLAYLNSHDESEGCEINDEHVLDGLQPHPNLKTLAVVDYLGTKFPSWFSEESLPNLVKLKLGGSKRCK
SIPS       2515
324-2_J1_J3_J8
LHDKPNICKLAYLNSHDESEGCEINDEHVLDGLQPHPNLKTLAVVDYLGTKFPSWFSEESLPNLVELKLGGSKRCK
SIPS       2515
324-2_J2_J3_J8
LHDKPNICKLAYLNSHDESEGCVINDEHVLDGLQPHPNLKTLAVVDYLGTKFPSWFSEESLPNLVKLKLGGSKRCK
SIPS       2515
487-1_I6_I6_I8
LHDKPNICKLAFLNSHDESGSEINDEHVLDGLQPHPNLKTLAVVDYLGTKFPSWFEEESLPNLVKLKLGGSKRCK
SIPS       2515
493-5_F1_F5_F7
LHDKPNICKLAYLNSHDESEGCVINDEHVLDGLQPHPNLKTLAVVDYLGTKFPSWFSEESLPNLVKLKLGGSKRCK
SIPS       2515
493-7_G2
LHDKPNICKLAYLNSHDESEGCVINDEHVLDGLQPHPNLKTLAVVDYLGTKFPSWFSEESLPNLVKLKLGGSKRCK
SIPS       2515
493-7_G10
LHDKPNIFKLAFLNSHDESEGCEINDEHVLDGLQPHPNLKTLAVVDYLGTKFPSWFSRRSLPNLVKLKLGGSKRCK
SIPS       2515
493-7_G12
LHDKPNICKLAYLNSHDESEGCVINDEHVLDGLQPHPNLKTLAVVDYLGTKFPSWFSREESLPNLVKLKLGGSKRCK
SIPS       2515
493-7_G14_G22
LHDKPNICKLAYLNSHDESEGCEINDEHVLDGLQPHPNLKTLAVVDYLGTKFPSWFSEESLPNLVKLKLGGSKRCK
SIPS       2515
493-7_G15
LHDKPNICKLAYLNSHDESEGCEINDEHVLDGLQPHPNLKTLAVVDYLGTKFPSWFSEESLPNLVKLKLGGSKRCK
SIPS       2515
493-7_G23
LHDKPNICKLAYLNSHDESEGCEINDEHVLDGLQPHPNLKTLAVVDYLGTKFPSWFSEESLPNLVKLKLGGSKRCK
SIPS       2515
```

FIG. 14R

```
493-9_H5_H30
LHDKPNICKLAYLWSHDESEGCRINDEHVLDGLQPHPNLKTLAVVDYLGTKPPSWFSEESLPNLVKLKLSGSKRCK
EIPS        2515
493-9_H11_H19_H27
LHDKPNICKLAYLWSHDKSEGCVINDEHVLDGLQPHPNLKTLAVVDYLGTKPPSWFSEESLPNLVKLKLSGSKRCK
EIPS        2515
543-5_C3
LHDKPNICKLAYLWSHDESEGCEINDEHVLDGLQPHPNLKTLAVVDYLGTKPPSWFSEESLPNLVKLKLSGSKRCK
EIPS        2515
561-2_K4_K14_K23
LHDKPNICKLAYLWSHDESEGCEINDEHVLDGLQPHPNLKTLAVVDYLGTKPPSWFSEESLPNLVELKLSGSKRCK
EIPS        2515
561-2_K6_K30_K31
LHDKPNICKLAYLWSHDESEGCEINDEHVLDGLQPHPNLKTLAVVDYLGTKPPSWFSEESLPNLVKLKLSGSKRCK
EIPS        2515
849-1_M8_M18_M20
LHDKPNICKLAYLWSHDESEGCEINDEHVLDGLQPHPNLKTLAVVDYLGTKPPSWPREESLPNLVKLKLSGSKRCK
EIPS        2515
852-5_E14_E23
LHDKPNICKLAYLWSHDESEGCEINDEHVLDGLQPHPNLKTLAVVDYLGTKPPSWFSEESLPNLVKLELSGSKRCK
EIPS        2515
852-5_E28
LHDKPNICKLAYLWSHDESEGCEINDEHVLDGLQPHPNLKTLAVVDYLGTKPPSWFSEESLPNLVKLKLSGSKRCK
EIPS        2515
852-5_E30
LHDKPNICKLAYLWSHDESEGCEINDEHVLDGLQPHPNLKTIAVVDYLGTKPPSWFREESLPNLVKLKLSGSKRCK
EIPS        2515
BN_D3_D4_D7
LHDKPNICKLAYLWSHDESEGCEINDEHVLDGLQPHPNLKTLAVVDYLGTKPPSWPREESLPNLVKLKLSGSKRCK
EIPS        2515
Rp1-chc1_ORF
LHDKPNICKLAYLWSHDESEGCEINDEHVLDGLQPHPNLKTLAVVDYLGTKPPSWFSEESLPNLVKLKLSGSKRCK
EIPS        2515
chc1_BAC_B07-1C15
LQEKPNICKLAYLWSHDESEGCEINDEHVLDGLQPHPNLKTLEVNNYLGTKPPSWFSEELIPNLVKLILSGCKRCK
EIPS        2369
chc2_BAC_B07-1C15
LQEKPNICKLVYLNSHVESEGCEINDEHVLDGLQPHPNLKTLAVGNYLGTKPPSWFSESLPNLVKLKLIGCKRCK
EIPS        2369
chc_BGC1_BAC_2D06-3D21
LQEKPNICKLAYLWSHDDSSGREINDEPVLDGLQPHPNLKTLSVVNYLGTKPPSWPSEVSLPNIVKLKLSGSKRCK
EIPS        2369
chc_BGC2_BAC_2D06-3D21
LQEKPNICKLAYLWSHDELSGCEINDEHVLDGLQPHPNLKSLAVVGFLGTKPPSWPIEESLPNLVKLKLSGCKRCK
EIPS        2057
RH122B15 c347
LQEKPNIYKLVYSNSHDEPEGCEINDEHVLDGLQPHPNLKTLEVVDYLGTKFASWFSEKMLPNLVMLALSGCKRCK
EIPS        2368
RH122B15 c88-5
LQEKSNIYKLAFVWSHDESEGCETNDEYVLDGLQPHPNLKTLAVVGYLGTKPPSWFREDLLPNLVKLKLSGCKRCK
EIPS        2335
RH137D14 c13-1
LQEKPNICKLAYLNSHDESEGCEINDEHVLDGLQPHPNLKTLEVWNYLGTKPPSWFSEELIPNLVKLILSGCKRCK
EIPS        2584
RH137D14 c13-2
LHDKPNICKLAYLWSHDESEGCEINDEHVLDGLQPHPNLKTIAVVDYLGTKPPSWFREESLPNLVKLKLSGSKRCK
EIPS        2515
RH77O23 c579-4
LQEKSNIYKLVYLWSHQESEGCEINAEHVLDGLQPHPYLKTFEVVRYLGTRPPSWFNEESLPNLVKLKLSNCSSCK
EIPS        2344
RH77O23 c579-5
LQEKPNIYKLVYSWSHDEPEGCEINKEHVLDGLQPHPNLKTLEVVDYLGTKFASWFSEKMLENLVKLALSGCKRCK
EIPS        2356
```

FIG. 14S

```
RH77023 c671
LQEKPNIYKLVYSWSHDESEGCEINNEHVLDGLQPHPNLYTLEVVDYLGTKFASWPSEKMLPNLVKLRLSGCKRCK
SIPS      2338
RH77023 c706-3
LQEKPIYKLEYVWSHDEPEGCETSDEHVLDGLQPHPNLKTLAVVSYMQTRPPSWPSEEPLSWLVRLRLSGCKRCK
GIPS      2350
RH77023 c706-4
LREKLNIYKLAYLMSHEESEGCEINDEHVLDGLQPHPNLKTFEVKNYLQTRPPSWPSEESLPNLVELRLSGCKRCK
SIPS      2344
ph2 candidate
LQEKPNIYKLVYSWSHDESEGCEINDEHVLDGLQPHPNLKALSVVDYLGTKLPSWPSEELIPNLVELKLSGCKRCT
SIPS      774

Majority    LGQLKFLRHLELIGPHELSCIGPAFYGVSIRRIGSNSI---
IQVFPSLKELVLEDMRSLIEWKGDS------VG-----V 890        900       910        920
        930       940       950       960

94-2931_L4_L7_L8       LGQLKFLRHLELVGPHELSCIGPAFYGVEMRNIGSNSI---
IQVFPSLKKLVLKDMRSLIENKGDS------VG-----V      2713
324-2_J1_J3_J8         LGQLKFLRHLELVGPHELSCIGPAFYGVEMRNIGSNSI---
IQVFPSLKELVLKDMRSLIENKGDS------VG-----V      2713
324-2_J2_J5_J6         LGQLKFLRHLELIGPHELSCIGPALYGVEIRNTGSNSN---
IQVFPSLKELVLEDMRSLIENKGDS------VG-----V      2713
487-1_I4_I6_I8         LGQLKFLRHLELIGPHELSCIGPAFYGVEIRNIGSRNI---
IQVFPSLKELVLEDMRSLIENKGDS------VG-----V      2713
483-5_F1_F5_F7         LGQLKFLRHLELIGPHELSCIGPALYGVEIRNTGSNSN---
IQVFPSLKELVLEDMRSLIENKGDS------VG-----V      2713
493-7_G2               LGQLKFLRHLELIGPHELSCIGPALYGVEIRNTGSNSN---
IQVFPSLKELVLEDMRSLIENKGDS------VG-----V      2713
493-7_G10              LGQLKFLRHLELIGPHELSCIGPALYGVEIRNIGSNSI---
IQVFPSLKELVLEDMRSLIENKGDS------VG-----V      2713
493-7_G12              LGQLKFLRHLELIGPHELSCIGPALYGVEIRNTGSNSN---
IQVFPSLKELVLEDMRSLIENKGDS------VG-----V      2713
493-7_G14_G23          LGQLKFLRHLELIGPHELSCIGPAFYGVEIRNIGSNSI---
IQVFPSLKKLVLTDMRSLIENKGDS------VG-----V      2713
493-7_G19              LGQLKFLRHLELIGPHELSCIGPALYGVEIRNTGSNSN---
IQVFPSLKELVLEDMRSLIENKGDS------VG-----V      2713
493-7_G21              LGQLKFLRHLELIGPHELSCIGPAFYGVEIRNIGSNSI---
IQVFPSLKKLVLTDMRSLIENKGDS------VG-----V      2713
493-9_H5_H30           LGQLKFLRHLELIGPHELSCIGPAFYGVEMRNIGSNSI---
IQVFPSLKKLVLKDMRSLIENKGDS------VG-----V      2713
493-9_B11_H19_H27      LGQLKFLRHLELIGPHELSCIGPALYGVEIRNTGSNSN---
IQVFPSLKELVLEDMRSLIENKGDS------VG-----V      2713
543-5_C2               LGQLKFLRHLELIGPHELSCIGPALYGVEIRNTGSNGN---
IQVFPSLKELVLEDMRSLIENKGDS------VG-----V      2713
561-3_K4_K14_K32       LGQLKFLRHLELVGPHELSCIGPAFYGVEMRNIGSNSI---
IQVFPSLKKLVLKDMRSLIENKGDS------VG-----V      2713
561-2_K6_K30_K31       LGQLKFLRHLELIGPHELSCIGPAFYGVEIRNIGSNSI---
IQVFPSLKKLVLTDMRSLIENKGDS------VG-----V      2713
849-1_M8_M18_M20       LGQLKFLRHLELIGPHELSCIGPAFYGVEIRNIGSNSI---
IQVFPSLKELVLEDMRSLIENKGDS------VG-----V      2713
852-5_E14_E23          LGQLKFLRHLELIGPHELSCIGPAFYGVEMRNIGSNSI---
IQVFPSLKKLVLKDMRSLIENKGDS------VG-----V      2716
852-5_E28              LGQLKFLRHLELIGPHELSCIGPAFYGVEMRNIGSNSI---
IQVFPSLKELVLEDMRSLIENKGDS------VG-----V      2713
852-5_E30              LGQLKFLRHLELIGPHELSCIGPAFYGVEIRNIGSNSI---
IQVFPSLKELVLEDMRSLIENKGDS------VG-----V      2716
```

FIG. 14T

FIG. 14U

```
493-7_G10
RMSPGLEKLRITDCPLLKSTPSQFESLRELDIVTVGEMPLLNLCSNLTSLVKLSVEAVKELTCLPDEMLRNNVSL
QQIT         2953
493-7_G12
RMSPGLEKLRITDCPLLKSIPNQFEILCELSIRGVDSEMPLLNLCSNLTSLVKLSVYDMKELTCLPDSILRNNVSL
QQIT         2953
493-7_G14_G22
RMSPGLEKLRITDCPLLKSIPNQFEILRQLDIRGVDSSIPLLNLCSNLTSLVKLSVYDMKELTCLPDEMLRNNVSL
QQIM         2953
493-7_G19
RMSTGLEKLRITDCPLLKSIPNQFEILCELSIRGVDSEMPLLNLCSNLTSLVKLSVYDMKELTCLPDEILRNNVSL
QQIT         2953
493-7_G21
RMSPGLEKLRITDCPLLKSIPNQFEILRQLDIRGVDSEIPLLNLCSNLTSLVKLSVYDMKELTCLPDEMLRNNVSL
QQIM         2953
493-9_H3_H30
RMSPGLEKLRITDCPLLKSIPNQFEILRQLDIRGVDSEMPLLNLCSNLTSLVKLSVYDMKELTCLPDEILRNNVSL
QQIT         2953
493-9_H11_H19_H27
RMSPGLEKLRITDCPLLKSIPNQFEILCELSIRGVDSEMPLLNLCSNLTSLVKLSVYDMKELTCLPDEILRNNVSL
QQIT         2953
543-5_C2
RMSPGLEKLRITDCPLLKSIPNQFEILAELSIRGVDSEMPLLNLCSNLTSLVKLSVYDMKELTCLPDEILRNNVSL
QQIT         2953
861-2_K4_K14_K22
RMSPGLEKLRITDCPLLKSIPNQFEILRQLKITGVDSEMPLLNLCSNLTSLVKLRVYDMKELTCLPDEMLRNNVSL
QQII         2953
861-2_K6_K30_K31
RMSPGLEKLRITDCPLLKSIPNQFEILRQLDIRGVDSEIPLLNLCSNLTSLVKLSVYDMKELTCLPDEMLRNNVSL
QQIM         2953
949-1_N8_M18_M20
RMSPGLEKLRITDCPLLKSIPNQFEILRELSIRGVDSEMPLLNLCSNLTSLVKLSVYDMKELTCLPDEILCNNISL
QQIT         2953
853-5_E14_E23
RMSPGLEKLRITDCPLLKSIPNQFEILRQLRITGVDSEMPLLNLCSNLTSLVKLRVYDMKELTCLPDEMLRNNVSL
QQII         2956
853-5_E28
RMSPGLEKLRITDCPLLKSIPNQFEILRQLRITGVDSEMPLLNLCSNLTSLVKLRVYDMKELTCLPDEMLRNNVSL
QQII         2953
853-5_E30
RMSPGLEKLRITDCPLLKSIPNQFEILRELSIRGVDSEMPLLNLCSNLTSLVKLSVYDMKELTCLPDEILRNNISL
QQIT         2956
RH_D3_D4_D7
RMSPGLEKLRITDCPLLKSIPNQFEILRELSIRGVDSEMPLLNLCSNLTSLVKLSVYDMKELTCLPDEILRNNISL
QQIT         2953
Rpi-chc1_ORF
RMSPGLEKLRITDCPLLKSIPNQFEILRQLKITGVDSEMPLLNLCSNLTSLVKLRVYDMKELTCLPDEMLRNNVSL
QQII         2953
chc1_BAC_B07-1C15
RMSPGLEKLRITDCPLLKSIPNQFEILRELRITGVDSEMPLLNLCSNLTSLVMLSVEFVKELTCLPDEMLRSNVSL
QRLS         2827
chc2_BAC_B07-1C15
RMSPGLEKLRITDCPLLKSIPNQFEILRDLEIRGVDSEMPLLNLCSNLTSLVSLDVCRVKELTFLPDEMLRNNVSL
QRLS         2827
chc_BGC1_BAC_2D06-3D21
RMSAXGLEKLRITDCPLLKSIPNQFEILRDLEITGVDSEMPLLNLCSNLTSLVYLEVCRVKELTCLPDEMLRNNVSL
QQIL         2827
chc_BGC2_BAC_2D06-3D31
RMSPGLEKLRITDCPLLKSIPNQFEILRELSITGVDSEMPLFNLCSNLTSLVRLSVCNVKELTCLPDEMLRNNVSL
QYLS         2497
RH122815_c247
RMSPRLEKLTISNCPLLKSTPNQFEILSELNIARVDSEMPLANLCINLPSLVRLSVYEKELTCLPDERLRNNVGL
QRLM         2806
```

FIG. 14V

```
RH132815 c89-5
RMFPPLEKLTITNCPLLKSTPSQFEILRELRIVIVDGEMPLLNLCSNLTSLVELRVSDMKELTCLPDEILRNNVSL
QRLS      2764
RH137D14 c13-1
RMSPQLEKLRTTNCPLLKSIPNQFEILRELSIEGVDSEMPLLSLCSNLTSLVFLAVSTVKRLTCLPDEMLRSNVSL
QRLG      3022
RH137D14 c13-2
RMSPQLEKLRITDCPLLKSIPNQFEILRELSIRGVDSEMPLLSLCSNLTSLVRLSVYDMKELTCLPDEILRNNISL
QQIT      2953
RH77O23 c579-4
RMFPVLEKLRIRYCPLLKSTPKQLSILRELSIRRVDGENPLLNLCSNLTSLVRFSVSFVKELTCFPDEKLRSNVSL
QRLS      2806
RH77O23 c579-5
RMFPRLEKLTISNCPLLKSTPNQFEILRELEIVNVDSEMPLLNLCSRLTSLVQLSVHELKRLTCFPDSKLRNKVSL
QRLV      2794
RH77O23 c671
RMFPRLEKLTIRNCPLLKSTPNQFEILSELVIVRVDSEMPLLNLCSRLPSLVELRVEDMKELTCLPDSKLRSNVSL
QRIS      2776
RH77O23 c706-3
RMFPVLKKLTIRNCPLLKSTPNQPEILRELSIEGVDSSIPLLNLCSNLTSLVMLIIRDVKQLTCLTDEILRSNFSL
QHLL      2821
RH77O23 c706-4
RMFPQLEKLRISNCPLLKSIPNQFEILRSLSIERVDSEMPLLRLFSNLTSLLKLRVYDVKELTCLPDEMLRSNLSL
QHLS      2803
ph3 candidate
RMFLRLEKLRISNCPLLKSTPSQFEILHELITEGVDSEMPLLNLCSNLTSLVKLDVDNVKELTCLSDVMLRNNVSL
QYIS      920

Majority
IPNCGEFRELPQSLYNLHSLKRLDIYNCTNFSSLPVPNGDNYLTSLQFFFLYNCNGLISIPIGMLDQCRSLEFLRV
SCCN
                                      +---------+---------+---------+---------+---------
+---------+---------+---------+---------+
                                          1050      1060      1070      1080
       1090      1100      1110      1120
                                      ---------+---------+---------+---------+---------
+---------+---------+---------+
84-2031_L4_L7_L8
IPNCGEFRELPQSLYNLHSLRRLDIYNCTNFSSLPVPNGDNYLTSLEFFCLYNCNGLISIPIGMLDQCR-
LVFLNVSCCN       3190
324-2_J1_J3_J8
IPNCGEFRELPQSLYNLHSLRRLDIYNCTNFSSLPVPNGDNYLTSLEFFCLYNCNGLISIPIGMLDQCR-
LVFLNVSCCN       3190
324-2_J2_J5_J6
IPNCGEFRELPQSLYNLHSLKRLDIYNCTNFSSLPVPNGDNYLTSLEFFFLYNCNGLISIPIGMLDQCRSLEFLRV
SCCN       3193
487-1_I4_I6_I8
IPNCGEFRELPQSLYNLHSLKRLDIYNCTNFSSLPVPNGDNYLTSLEFFFLHNCNGLISIPIGMLDQCRSLEYLRV
SCCN       3193
493-5_F1_F5_F7
IPNCGEFRELPQSLYNLHSLKRLDIYNCTNFSSLPVPNGDNYLTSLEFFFLYNCNGLISIPIGMLDQCRSLEFLRV
SCCN       3193
493-7_G2
IPNCGEFRELPQSLYNLHSLKRLDIYNCTNFSSLPVPNGDNYLTSLEFFFLYNCNGLISIPIGMLDQCRSLEFLRV
SCCN       3193
493-7_G10
IPNCGEFRELPQSLYNLHSLKRLDIYNCTNFSSLPVPNGDNYLTSLQLFFLYNCNGLISIPIGMLDQCRSLEFLRV
SCCN       3193
493-7_G13
IPNCGEFRELPQSLYNLHSLKRLDIYNCTNFSSLPVPNGDNYLTSLEFFFLYNCNGLISIPIGMLDQCRSLEFLRV
SCCN       3193
```

FIG. 14W

```
493-7_G14_G22
IFDCGEFRELPQSLYNLHFLKRLETYNCTNFSSLPVPNGDNYLTSLQFFQLYNCDGLISLPIGMLDQCRSLSCLSV
SCCN      3193
493-7_G19
IFNCGEFRELPQSLYNLHSLKRLDIYNCTNFSSLPVPNGDNYLTSLEFFLYNCNGLISIPIGMLDQCRSLEYLRV
SCCN      3193
493-7_G21
IFDCGEFRELPQSLYNLHFLKRLETYNCTNFSSLPVPNGDNYLTSLQFFQLYNCDGLISLPIGMLDQCRSLSCLSV
SCCN      3193
493-3_H5_H30
IFNCGEFRELPQSLYNLHSLKRLDIYNCTNFSSLPVPNGDNYLTSLEFFYLYNCNGLISIPIGMLDQCR-
LVFLNVSCCN  3190
493-9_H11_H18_H27
IFNCGEFRELPQSLYNLHSLKRLDIYNCTNFSSLPVPNGDNYLTSLEFFLYNCNGLISIPIGMLDQCRSLEFLRV
SCCN      3193
543-5_C2
IFNCGEFRELPQSLYNLHSLKRLDIYNCTNFSSLPVPNGDNYLTSLEFFKLYNCNGLISIPIGMLDQCRSLEFLRV
SCCN      3193
561-2_K4_K14_K22
IFNCGEFRELPQSLYNLHSLKRLDIYNCTNFSSLPVPNGDNYLTSLEFFCLYNCNGLISIPIGMLDQCR-
LVFLNVSCCN  3190
561-2_K6_K30_K31
IFNCGEFRELPQSLYNLHFLKRLETYNCTNFSSLPVPNGDNYLTSLQFFQLYNCDGLISLPIGMLDQCRSLSCLSV
SCCN      3193
848-1_M8_M18_M30
IFECGEFRELPQSLYNLHSLYRLDIYNCTNFSSLPVPKGDNYLTSLIFFLNCNGLISIPIGMLDQCRSLEYLRV
SCCN      3193
852-5_H14_H23
IFNCGEFRELPQSLYNLHSLRRLDIYNCTNFSSLPVPNGDNYLTSLEFFCLRNCNGLISIPVGMLDQCR-
LVFLNVSCCN  3193
852-5_H28
IFNCGEFRELPQSLYNLHSLRRLDIYNCTNFSSLPVPNGDNYLTSLEFFCLRNCNGLISIPVGMLDQCR-
LVFLNVSCCN  3190
852-5_H30
IPKCGEFRELPQSLYNLHSLYRLDIYNCTNFSSLPVPKGDNYLTSLIFFLRNCNGLISIPIGMLDQCRSLEYLRV
SCCN      3196
RH_D3_D4_D7
IFNCGEFRELPQSLYNLHSLYRLDIYNCTNFSSLPVPKGDNYLTSLIFFLRNCNGLISIPIGMLDQCRSLEYLRV
SCCN      3193
Rpi-chc1_ORF
IFNCGEFRELPQSLYNLHSLKRLDIYNCTNFSSLPVPNGDNYLTSLEFFCLRNCNGLISIPIGMLDQCR-
LVFLNVSCCN  3190
chc1_BAC_B07-1C18
VFDCGEFRELPQSLYNLHSLKRLVTACCTNFSSLPVPSGDNMLTSLQLLQLWNCDGLISLPIGMLDQCRSLKFLSV
RCCN      3067
chc2_BAC_B07-1C15
VFNCGEFRELPQSLYNLHSLKILVIINCTSPSSLPVPKGDNYLTSLQLFQLYNCDGLISLPIGMLDQCRSLDFFSV
RCCN      3067
chc_RGC1_BAC_2D05-3D21
IFDCGKFRELPQSLYNLHSLRILSIYQCTNFSSLPVPCGDNYLTSLQIFQLTDCDGLISLPIGMLDQCRSLELLNV
TCCD      3067
chc_RGC2_BAC_2D06-3D21
VFDCGEFRELPQSLYNLHSLKRLRIHSCTNFSSLPVPNGDNYLTSLQLLRLCNCDGLISLPIGMLDQCRSLEILSV
SCCD      2737
RH122B18 c247            VSGCGEFRELPQSVYNLHSLKRLTIERCTNFSSFPVPSSENYLTSLQDLR.
3959
RH122B18 c68-5
VFDCGEFRELPQSLYNLHSLKTLRISNCANFSSFPVPSGDNYLTSLQSLQLFDCDGLTSLPSGVLRNCRSLRSLVV
LYCN      3004
RH137D14 c13-1
VFNCGEFRELPQSLYNLHSLRRLVIAQCTNFSSLPVPNGDNWLTSLKLLQLWNCDGLISLPIGMLDQCRSLKVLTV
RCCN      3252
```

FIG. 14X

```
RH137D14 c13-2
IFECGEFRELPQSLYRLDIYNCTNFSSLPVPKSDMYLTSLIFFFLRNCRGLISIPIQWLDQCRSLEYLRV
SCCN      3193
RH77023 c579-4
VTNCREFRELPQSLYNLHSLKSLWIEYCTNFSSPPVPSGENYLTSLQNLQLWSCRGLASLPSGMLEKCRSLQWLRV
NYCN      3046
RH77023 c579-5
VSGCGEFHELPQSLYNLHSLKTLKITRCANFNSFPVPSGENYLTSLQHLQLRDCRGLSSLPSGMLEHCRSLETLSV
SCCD      3034
RH77023 c671
VSDCREFHELPQSLYNLHSLKRLTIDNCTNFSSFPVPSEKNYLTSLQELRLLDCDGLSSLPSGMLEHCRSLETLSV
SCCD      3016
RH77023 c706-3
VLNCGEFRELPQSLYNLRSLKSLGIGDCTNFSSIPVSRGENHLTSLLKLRLYNCDGLTSLGSGLLEHCRSLESLSV
RKCN      3061
RH77023 c706-4
VSYCGEFRELPQSLYNLRSLRSLRIDNCTNFNFFPVPKGENYLTSLQSLSLCYCDGLTSLPSGILEHCRSLESLSV
RNCN      3043
ph2 candidate
VVDCCGEFREFPQSLYNLHSLESLRIQHCPNPSSFIVPCGERYLTSLQNFELQQCNGLTSLPSGMLEQCRSLKNLSV
SNCD      1000

Majority
NLVSFPLRVWEMPSLSYLDISECPKLISVPKVGLHHLTGLLRLGIGPFSEMVDFDAFQLIFNGIQQLLSLRDLEVY
GRGH
                                              1130      1140      1150      1160

1170      1180      1190      1200

94-2031_L4_L7_L8
NLVSFPVHVWEMPSLSYLVISECPKLISVPKVGLHHLTGLVRLGIGPFSEMVDFDAFQLIFNGIQQLLSLRDLEVY
GRGH      3430
324-2_J1_J3_J9
NLVSFPVHVWEMPSLSYLVISECPKLISVPKVGLHHLTGLVRLGIGPFSEMVDFDAFQLIFNGIQQLLSLRDLEVY
GRGH      3430
324-2_J2_J5_J6
NLVSFPLRVWEMPSPSFLDIRECPKLISVPKVGLHHLTGLLSLGIGPFSEMVDFDAFQLIFNGIQQLLSLRDLEVY
GRGH      3433
687-1_I4_I6_I8
NLVSFPLRVWSIPSFSVLRITECPKLISVPSVGLHHLTGLLRLGIGPFSEMVDFDAFQLIFNGIQKLLSLRDLEVY
GRGH      3433
493-5_F1_F5_F7
NLVSFPLRVWEMPSPSPLDIRECPKLISVPKVGLHHLTGLLSLGIGPFSEMVDFDAFQLIFNGIQQLLSLRDLEVY
GRGH      3433
493-7_G2
NLVSFPLRVWEMPSPDPLDIRECPKLISVPKVGLHHLTGLLSLGIGPFSEMVDFDAFQLIFNGIQQLLSLRDLEVY
GRGH      3433
493-7_G10
NLVSFPLRVWEMPSLLPLDITECPKLISVPKVGLHHLGLLSLGIGPFSEMVDFDAFQLIFNGIQQLLSLRDLEVY
SRGH      3433
493-7_G12
NLVSFPLHVWEMPSFSFLDIRECPKLISVPKVGLHHLTGLLSLGIGPFSEMVDFDAFQLIFNGIQQLLSLRDLEVY
GRGH      3433
493-7_G14_G22
NLVSFPLHVWEMPSLSYLVISECPKLISVPRVGLHHLTGLLRLGIGPFSEMVDFDAFQLIFNGIQQLLSLRDLEVY
GRGH      3433
493-7_G19
NLVSFPLHVWEMPSPSFLDIRECPKLISVPKVGLHHLTGLLSLGIGPFSEMVDFDAFQLIFNGIQQLLSLRDLEVY
GRGH      3433
```

FIG. 14Y

```
493-7_G21
NLVSFPLRVWEMPSLSYLVISECPKLISVPEVGLHRLTGLLRLGIGPFSEMVDFDAPQLIFNGIQQLLSLRDLEVY
GRGH         3433
493-9_H5_H30
NLVSFPLRVWEMPSPSVLRIESCPKLISVPRVGLHRITGLVRLGIGPFSEMVDFDAPQLIFNGIQQLS-
LRDLEVYGRGH  3427
493-9_H11_H19_H27
NLVSFPLRVWEMPSPLDIRECPKLISVPKVGLHRLTGLLRLGIGPFSEMVDFDAPQLIFNGIQQLLSLRDLEVY
GRGH         3433
543-5_C2
NLVSFPLRVWEMPSPSPLDIRECPKLISVPKVGLHRLTGLLSLAIGPFSEMVDFDAPQLIFNGIQQLLSLRDLAVY
GRGH         3433
561-2_K8_K14_K22
NLVSFPVRVWEMPSLSYLVISECPKLISVPKVGLHRLTGLVRLGIGPFSEMVDFDAPQLIFNGIQQLLSLRDLEVY
GRGH         3430
561-2_K6_K30_K31
NLVSFPLRVWEMPSLSYLVISECPKLISVPSVGLHRLTGLLRLGIGPFSEMVDFDAPQLIFNGIQQLLSLRDLEVY
GRGH         3433
849-1_M8_M19_M20
NLVSFPLRVWEIPSFSVLRITECPKLISVPSVGLHRLTGLLRLGIGPFSEMVDFDAPQLIFNGIQKLLSLRDLEVY
GRGH         3433
852-5_E14_E23
NLVSFPVRVWEMPSLSYLVISECPKLISVPKVGLHRLTGLVRLGIGPFSEMVDFDAPQLIFNGIQQLLSLRDLEVY
GRGH         3433
852-5_E28
NLVSFPVRVWEMPSLSYLVISECPKLISVPKVGLHRLTGLVRLGIGPFSEMVDFDAPQLIFNGIQQLLSLRDLEVY
GRGH         3430
853-5_E30
NLVSFPLRVWDIPSFSVLRITECPKLISVPSVGLHRLTGLLRLGIGPFSEMVDFDAPQLIFNGIQKLLSLRDLEVY
GRGH         3436
RH_D3_D4_D7
NLVSFPLRVWEIPSFSVLRITECPKLISVPSVGLHRLTGLLRLGIGPFSEMVDFDAPQLIFNGIQKLLSLRDLEVY
GRGH         3433
Rpi-chc1_ORF
NLVSFPVRVWEMPSLSYLLISECPKLISVPKVGLHRLTGLVRLGIGPFSEMVDFDAPQLIFNGIQQLLSLRDLEVY
GRGH         3430
chc1_BAC_807-1C15
NLVSFPLRVWEMPSLSRLCISLCPKLISVPEVGLHRLTGLWGLSIGPFSEMVDFDAPQLIFNGIQQLLSLRALTVY
GHGH         3307
chc2_BAC_807-1C15
NFVSFPLRVWEMPSLSYFDISQCPKLISVPEVGLHRLTGLMYLGIGPFSEMVERDAPQLIFNGIQQLLSLRDLAVY
GRGH         3307
chc_RGC1_BAC_2006-3D21
NLVSLPLRVWEMPSLSRLNISQCPKLISVPEVGLHRFAGLQTLKIGPFSEML------------LS-
LCDLAVYGRGH  3262
chc_RGC2_BAC_2006-3D21
NLVSFPLRVWEMPSLLYLEISRCPKLISVPEVGLHRLTGLWKLEIGPFSEMVDFDAPQLIFNGIQQLLSLRDLEVY
GRGH         2877
RH122B15_c247
2959
RH122B15_c95-5
NLLSLPLRVWEMPSLSYLGLSECPKLISVPSGLHRLTGLRALEIGPFSEMVDFSAPQLIFNGIQQLLSLRNVGVY
GRGH         3244
RH137D14_c13-1
NLVSFPLRVWEMRLLRLCISLCPKLISVPRVGLHRLTGLWGLSIGPFSEMVDFDAPQLIFNGIQQLLSLRDLTVY
GHGH         3502
RH137D14_c13-2
NLVSFPLRVNEIPSFSVLEITECPKLISVPEVGLHRLTGLLRLGIGPFSEMVDFDAPQLIFNGIQKLLSLRDLEVY
GRGH         3433
RH77023_c578-4
NLVSFPLRVGDMPSLSYLSIAHCPKLDSVPTGGLHRLFRLRELSIGPVSEMVDFSAPQLIFNGIQQLLSLRTLLVF
GRLH         3286
```

FIG. 14Z

RH77O23 c579-5
NLVSFPLHVGKMPSLSYINTSRCPKLISLPSGGIDHLTELSELKIGPFSEMVDPEAPQLIFNGIQQLLSLRTLTVY
GHGH        3274
RH77O23 c671
NLVSFPLHVGKMPSLSYLXISQCPKLISLPSGGIHHLTELSELRIGPFSEMVDPEAPQLIFNGIQQLLSLRTLWVY
GHGH        3256
RH77O23 c706-3
NLVSLPLHVGMPSLSYLNTSKCPKLSVPAGSLHRLTGLATLNTGPFSELVDFEAPQLIFNGIQQLSSLCVLWVY
GHAH        3301
RH77O23 c706-4
NLVSFPLHVGQMPSLSYLGLSQCPKLISVPSQGLHRLTRLRESHIGPPSEMVDFEAPQLMFNGIRQLSSLRTLRVW
GHLH        3263
ph2 candidate
NLVSFPLHECEMPSLSWLDISQCPKLISVSTGCLHRLTGLIVLGIGPFSEKVDFEVPQLIFSGVQQLFSLRSLRVY
GHLH        1080

Majority
NDSLPYQLMQLSDLREITIADFGIEALPPRLDNLTSLESLTLVRCKRLQHLNFSDAMPKLRLLWISDCPLLEALSD
GLGN 1210      1220      1230      1240
1250      1260      1270      1280
94-2031_L4_L7_L8
NDSLPYQLMQLSDLREITIADFGIEALPPTLDNLTSLESLTLVRCKQLQHLNFSDAMPKLRLLWIRDCPLLEALSD
GLGN        3670
324-2_J1_J3_J8
NDSLPYQLMQLSDLREITIADFGIEALPPTLDNLTSLESLTLVRCKQLQHLNFSDAMPELRLLWIRDCPLLEALSD
GLGN        3670
324-2_J3_J5_J6
NDSLPYQLMQLSNLREITIADFGIEALPPRLDNLTSLESLTLDRCKRLQHLNFSDAMPKLRLLWISDCPLVEALSD
GLGN        3673
487-1_I4_I5_I8
NDSLPYQLMQLSNLRKITIADFGIEALPPRLDNLTSLESLTLSRCKRLQHLNFSDAMPKLRLLWISDCPLLEALSD
GLGN        3673
493-5_F1_F5_F7
NDSLPYQLMQLSNLREITIADFGIEALPPRLDNLTSLESLTLDRCKRLQHLNFSDAMPKLRLLWISDCPLVEALSD
GLGN        3673
493-7_G2
NDSLPYQLMQLSNLREITIADFGIEALPPRLDNLTSLESLTLDRCKRLQHLNFSDAMPKLRLLWISDCPLVEALSD
493-7_G10
NDSLPYQIMQLSDLREITIADFGIEALPPRLDNLTSLESLTLVRCKRLQHLNFSDAMPKLRLLWTRDFPLLEALSD
GLGN        3673
493-7_G12
NDSLPYQLMQLSNLREITIADFGIEALPPRLDNLTSLESLTLDRCKRLQHLNFSDAMPKLRLLWISDCPLVEALSD
GLGN        3673
493-7_G14_G23
NDSLPYQLMQLEDLREIQIADFGIEALPPRLDNLTSLESLTLVRCKRLQHLNFSDAMPSLRLLWINDCPLLEALSD
DLGN        3673
493-7_G19
NDSLPYQLMQLSNLREITIADFGIEALPPRLDNLTSLESLTLDRCKRLQHLNFSDAMPKLRLLWISDCPLVEALSD
GLGN        3673
493-7_G21
NDSLPYQLMQLSDLREIQIADFGIEALPPRLDNLTSLESLTLVRCKRLQHLNFSDAMPSLRLLWIRDCPLLEALSD
DLGN        3673
493-9_H5_H30
NDSLPYQLMQLSDLREITIADFGIEALPPTLDNLTSLESLTLVRCKQLQHLNFSDAMPKLRLLWIRDCPLLEALSD
GLGN        3667

FIG. 14AA

FIG. 14AB

```
RH77023 c706-4
WDSLPYQLMQLSALKEIKIYGFGIEALPHRPQNLTSLEELHLVQCNRLQRVDPSDKPKIQLLWIQDCLLLRDLSN
GLGN     3523
pb2 candidate
WDSLPYQIMQLSALRKLSTDDPGIEALPHRFDNLTSLETLSLKRCKKLRRVDPSDAITKLRNLWIQDCFLLEKLSD
GLGN     1168

Majority        LVSLEELYLQDCEKLELLPSRDAMRRLTKLWNMGIKG-
CPKLEESPTNYS----QWSKISHISNIELGGWR------RTA 1290       1300       1310       1320
       1330       1340       1350       1360

94-2931_L4_L7_L8            LVSLEELYLHDCEKLEHLPSRDAMRRLTKLRNMRIKG-
CPKLEESPTNYS----QWSKISHISNIELGGWR------RTA       3877
324-2_J1_J3_J8              LVSLEELYLHDCEKLEHLPSRDAMRRLTKLWNMRIKG-
CPKLEESPTNYS----QWSKISHISNIELGGWR------RTA       3877
324-2_J2_J5_J6              LVSLEELYLQDCEKLELLPSRDAMRRLTKLWNMGIKG-
CPKLEESPTNYS----QWSKISHISNIELGGWR------RTA       3880
487-3_I4_I6_I8              LVSLEELYLQDCEKLERLPSRDAMRRLTKLWNMRIKG-
CPKLEESPTNYS----QWSKISHISNIELGGWR------RTA       3880
493-5_F1_F5_F7              LVSLEELYLQDCEKLELLPSRDAMRRLTKLWNMGIKG-
CPKLEESPTNYS----QWSKISHISNIELGGWR------RTA       3880
493-7_G2                    LVSLEELYLQDCEKLELLPSRDAMRRLTKLWNMGIKG-
CPKLEESPTNYS----QWSKISHISNIELGGWR------RTA       3880
493-7_G10                   LVSLEELYLHDCEKLEHLPSRDAMRCLTKLWNMGIKG-
CPKLEESYTNYS----QWSKISHISNIELGGWR------RTA       3880
493-7_G12                   LVSLEELYLQDCEKLELLPSRDAMRRLTKLWNMGIKG-
CPKLEESPTNYS----QWSKISHISNIELGGWR------RTA       3880
493-7_G14_G22               LVSLEELYLLDCKKLEGLPSRDAMRRLTKLWNLGIKG-CPKLKET-----
-----WSKISHIPRIEFGGWII------KDT       3865
493-7_G19                   LVSLEELYLQDCEKLELLPSRDAMRRLTKLWNMGIKG-
CPKLEESPTNYS----QWSKISHISNIELGGWR------RTA       3880
493-7_G21                   LVSLEELYLLDCKKLEGLPSRDAMRRLTKLWNLGIKG-CPKLKET-----
-----WSKISHIPRIEFGGWII------KDT       3865
493-9_H8_H30                LVSLEELYLHDCEKLEHLPSRDAMRRLTKLWNMGIKG-
CPKLEESPTNYS----QWSKISHISVIELGGWR------RTT       3874
493-9_H11_H19_H27           LVSLEELYLQDCEKLELLPSRDAMRRLTKLWNMGIKG-
CPKLEESPTNYS----QWSKISHISNIELGGWR------RTA       3880
543-5_C3                    LVSLEELYLHDCEKLELLPSRDAMRRLTKLWNMGIKG-
CPKLEESPTNYS----QWSKISHISNIELGGWR------RTA       3880
561-2_K4_K14_K22            LVSLEELYLHDCEKLEHLPSRDAMRRLTKLWNMRIKG-
CPKLEESPTNYS----QWSKISHISNIELGGWR-------RTA      3877
561-2_K8_K30_K31            LVSLEELYLLDCKKLEGLPSRDAMRRLTKLWNLGIKG-CPKLKET-----
-----WSKISHIPRIEFGGWII------KDT       3865
849-1_M9_M18_M20            LVSLEELYLQDCEKLELLPSRDAMRRLTKLWNMRIKG-
CPKLEESPTNYS----QWSKISHISNIELGGWR------RTT       3880
852-5_E14_E23               LVSLEELYLHDCEKLEHLPSRDAMRRLTKLWNMRIKG-
CPKLEESPTNYS----QWSKISHISNIELGGWR------RTA       3880
853-5_E28                   LVSLEELYLHDCEKLEHLPSRDAMRRLTKLWNMRIKG-
CPKLEESPTNYS----QWSKISHISNIELGGWR-------RTA      3877
852-5_E30                   LVSLEELYLQDCEKLELLPSRDAMRRLTKLWNMRIKG-
CPKLEESPTNYS----QWSKISHISNIELGGWR------RTT       3883
R3_D3_D4_D7                 LVSLEELYLQDCEKLEHLPSRDAMRRLTKLWNMRIKG-
CPKLEESPTNYS----QWSKISHISNIELGGWR------RTT       3880
Rpi-chc1_ORF                LVSLEELYLHDCEKLEHLPSRDAMRRLTKLWNMRIKG-
CPKLEESPTNYS----QWSKISHISNIELGGWR------RTA       3877
chc1_BAC_B07-1C15           LVSLQELHLQDCEKLEHLPSRDAMRRLTKLWNLQTRG-CPKLGRNCTS--
S-----QRSKISHISNIEVGGRII------DDR       3754
```

FIG. 14AC

```
chc3_BAC_B07-1C15          LVSLEELYLQDCEKLEHLPSREAMRRLTKLMRLEIKG-CPKLEESCTN-
S----QMSKISHISNIEVGGRII-----KDR          3764
chc_RGC1_BAC_2D06-3D21     LVSLQELYLQNCEKLEHLPSRDAMRRLTKLRNLRIIEGCPKLEESCTN-
S----QMSKISHISNIEVGGRII-----KDR          3713
chc_RGC2_BAC_2D06-3D21     PVSLEELYLQDCERLEHLPSRDAIRRLTKLMRLGIKG-CPKLEENCIN-
S----QMSKISHIRRIEVGGRII-----KDR          3424
RH122B15 c247                                                                                 3959
RH122B15 c88-5             LVSLEELTLRNCEKLEHLPSQDAMRHLTKLQRLKIRG-
CPKLEESCTNRSGPNSQMSNISHIPKVKVGRSII-----QDL     3706
RH137D14 c13-1             LVSLQELHLQSCEKLEHLPSRDAMRRLTKLMRLEIIG-CPKLEESCTN-
S----QRSKISHISYIEVGGMII-----NDR          3949
RH137D14 c13-2             IVSLEELYLQDCEKLEHLPSRDAMRRLTKLANMRIKG-
CPKLEESFTNYS-----QMSKISHISNIELGGWR-----NTT     3860
RH77023 c579-4             LVSLEELRLENCEKLEHLPSREAMRRLTKLMYLKIKG-
CPKLEESCMNRGQPNTQMSNISHIPKVKVGGSII-----QDL     3746
RH77023 c379-5             LVTLELLHLENCEKLEYLPSRDTMRHLRKLQSLQING-
CPKLEESCTNRSGPNSQMSNISSIQRIEVGRIP-----LYQC     3736
RH77023 c671                                                                                  3358
RH77023 c706-3             LVSLVELSLSNCKNLQHLPSRDAMRRLTKLRRLEIKG-
CPQLEESCTNRSQPNSQMSKISHIPQISVRFTT-----IQDL     3703
RH77023 c706-4             LVTLQQLTLRRSKKLEHLPC.                                 3586
ph2 candidate              LASLEQLILILNCKKLEHLPSRDAMRRLTKLSILRIVS-
CPQLEESCTRQSGPNSQMSKISHIPDIEVGAPPKITEAMRL     1239

Majority      ISLGPSPTP--------------------------------------
---------------------------------------
------------------------------------------
                                           1370      1380      1390      2400
1410      1420      1430      1440
-----------------------------------------
94-2031_L4_L7_L8           ISLGPSPTP.
3907
324-2_J1_J3_J8             ISLGPSPTP.
3907
324-2_J2_J5_J6             ISLGPSPTP.
3910
487-1_I4_I6_I8             ISLGPSPTP.
3910
493-5_F1_F5_F7             ISLGPSPTP.
3910
493-7_G3                   ISLGPSPTP.
3910
493-7_G10                  VSLGPSPTP.
3910
493-7_G12                  ISLGPSPTP.
3910
493-7_G14_G22              CKCNFLSNFLN
3898
493-7_G19                  ISLGPSPTP.
3910
493-7_G21                  CKCNFLSNFLN
3898
493-8_H5_H20               VSLGPSPTP.
3904
493-9_H11_H19_H27          ISLGPSPTP.
3910
```

FIG. 14AD

```
543-5_C2                ISLGPSFTF.
3910
561-2_K4_K14_K22        ISLGPSFTF.
3907
561-2_K5_K30_K31        XKCWFLFHFLN
3896
849-1_M6_M18_M20        ISLGPSFTF.
3910
852-5_E14_E23           ISLGPSFTF.
3910
852-5_E28               ISLGPSFTF.
3907
852-5_E30               ISLGPSFTF.
3913
RH_D3_D4_D7             ISLGPSFTF.
3910
Rpi-cbc1_ORF            ISLGPSFTF.
3907
cbc1_BAC_B07-1C15
QYYFPRVPEKKPCTWVHGTIWNVVDIGAVGDSGCTRLSNSSPINETTVCIDGPCRDVPGNVRCNFIPYYFRKIVHA
NVYP    3994
cbc2_BAC_B07-1C15       CRDNKIHG--------------------------------------------
---------------------   3778
cbc_RGC1_BAC_2D06-3D21  RTTT--VHS-----------------------IMD------------------
---------------------   3742
cbc_RGC2_BAC_2D06-3D21  HYQS--------------------------------------------------
---------------------   3436
RH122B15 c247
2959
RH122B15 c86-5          PQTPSGPTNIS-------------------------------------------
---------------------   3739
RH137D14 c13-1          QYYFPRVPEK--------------K-----------------------------
---------------------   3992
RH137D14 c13-2          ISLGPSFTF.
3910
RH77O23 c579-4          HXSHF.
2766
RH77O23 c579-5          LSKSLFLFQFFSRIF.
3784
RH77O23 c671
3358
RH77O23 c706-3          RKFLFLFSFQSFSN----------------------------------------
---------------------   3749
RH77O23 c706-4
3986
ph2 candidate           ISSTLEVTEPFHRKFQARQIFFGTSI
1289

Majority    ------------------------------------------------------
-------------------------------------
------------------------+------------+------------+
                                      1450         1460         1470         1480
1490        1500        1510        1520
------------------------+------------+------------+
------------+------------+
94-2031_L4_L7_L6
3907
324-2_J1_J3_J6
3907
324-2_J2_J5_J6
3910
```

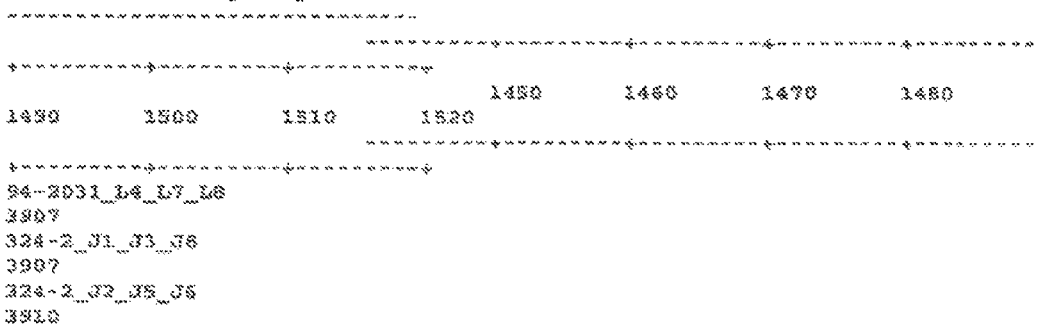

FIG. 14AE

```
487-1_I4_I6_I8
3910
493-5_F1_F5_F7
3910
493-7_G2
3910
493-7_G10
3910
493-7_G12
3910
493-7_G14_G22
3898
493-7_G19
3910
493-7_G21
3898
493-8_H8_H30
3904
493-9_H11_H19_H27
3910
543-5_C9
3910
561-2_K4_K14_K22
3907
561-2_K6_K30_K31
3898
645-1_M9_M18_M30
3910
852-5_E14_E23
3910
852-5_E28
3907
852-5_E30
3913
RX_D3_D4_D7
3910
Rpi-che1_ORF
3907
che1_BAC_B07-1C15
GLEKLRITDCPLLKSIPNQFEILRELAISGVDSEMLLLNLCSHLTSLVHLAVSNVRELTCLFDENLRNNVSLQNIP
IFHC     4234
che2_BAC_B07-1C15                                                         QIAT
                                3790
che_ROC1_BAC_2006-3D21                                                    TPMG
                                3784
che_ROC3_BAC_2006-3D21                                                    IAS
                                3445
RH122B15 c247
3969
RH122B15 c88-5
                                3739
RH137D14 c13-1              -FY-                                          ICS
                                3997
RH137D14 c13-2
3910
RH77023 c379-4
3766
RH77023 c379-5
3784
RH77023 c671
3358
RH77023 c706-3
                                3748
```

FIG. 14AF

```
              Majority      ------------------------------------------
----------------------------------
------+---------+---------+---------+
                                     1530      1540      1550      1560
  1570      1580      1590      1600
------+---------+---------+---------+

86-2031_L4_L7_L8
3907
324-2_J1_J3_J6
3907
324-2_J2_J5_J6
3910
487-1_I4_I6_I9
3910
493-5_F1_F5_F7
3910
493-7_G2
3910
493-7_G10
3910
493-7_G12
3910
493-7_G14_G22
3898
493-7_G19
3910
493-7_G21
3898
493-9_H5_H20
3904
493-9_H11_H19_H27
3910
543-8_C2
3910
561-2_K4_K14_K33
3907
561-2_K6_K30_K31
3898
849-1_M8_M18_M30
3910
852-5_N14_N33
3910
852-5_N28
3907
852-5_N38
3913
RM_D3_D4_D7
3910
Rp1-chc1_C8F
3907
chc1_BAC_B07-1C15
GRFRELPQSLYNLHSLERLETSSCINFSSFPVRRQDNYLTSLQLFNLCVPFVGIHRLTGLAGLEIGFFSRVDFDA
PQLI       4474
chc2_BAC_B07-1C15       ----------------------------------
----------------------------   3790
```

FIG. 14AG

```
chc_RGC1_BAC_2D06-3D21    ----------------------------------------
----------------------    3754
chc_RGC3_BAC_2D06-3D21    ----------------------------------------
----------------------    3445
RH122B15 c247
2999
RH122B15 c88-5           ----------------------------------------
----------------------    3739
RH137D14 c13-1           ----------------------------------------V-
----------------------    4009
RH137D14 c13-2
3910
RH77O23 c573-4
3766
RH77O23 c579-5
3784
RH77O23 c671
3356
RH77O23 c706-3           ----------------------------------------
----------------------    3748
RH77O23 c706-4
3586
ph2 candidate
1365

Majority    ----------------------------------------
----------------------
+----------+----------+----------}
                              1610      1620      1630      1640
1650      1660      1670      1680
+----------+----------+----------+----------+----------+----------}

94-2031_L4_L7_L8
3907
324-2_J1_J3_J8
3907
324-2_J2_J5_J6
3910
487-1_J4_J6_J8
3910
493-5_F1_F5_F7
3910
493-7_G2
3910
493-7_G10
3910
493-7_G12
3910
493-7_G14_G22
3898
493-7_G19
3910
493-7_G21
3898
493-9_H5_H30
3904
493-9_H11_H19_H27
3910
543-5_C2
3910
```

FIG. 14AH

```
493-5_F1_F6_F7
3910
493-7_G3
3910
493-7_G10
3910
493-7_G12
3910
493-7_G14_G22
3898
493-7_G19
3910
493-7_G21
3898
493-9_H5_H30
3904
493-9_H11_H19_H27
3910
543-5_C3
3910
561-2_K4_K14_K22
3907
561-2_K6_K30_K31
3898
849-1_M6_M18_M20
3910
852-5_E14_E23
3910
852-5_E28
3907
852-5_E30
3913
RH_D3_D4_D7
3910
Rpi-chc1_ORF
3907
chc1_BAC_B07-1C15
MLLNISDCPLLEALSDQLQRLVSLEDLYIQNCRNLRHLPSRDAMQHLTKLRNLRISGCPKLSSNCTNSQWSKISRI
PRIN       4954
chc2_BAC_B07-1C15                  -------------------------------------------
-------------------------------    3798
chc_RGC1_BAC_2D06-3D21             -------------------------------------------
-------------------------------    3754
chc_RGC2_BAC_2D06-3D21             -------------------------------------------
-------------------------------    3445
RH122B15 c247
3959
RH123B15 c98-5                     -------------------
------------------------------     3739
RH137D14 c13-1                     -------------------------------------------
------------------------------     4000
RH137D14 c13-2
3910
RH77023 c579-4
3766
RH77023 c579-5
3784
RH77023 c671
3358
RH77023 c706-3                     -------------------------------------------
------------------------------     3748
RH77023 c706-4
3586
```

FIG. 14AJ

```
ph3 candidate
1265

Majority    --------------------------------------------
-----------------------------------
------------------------------------                1770      1780      1790      1800
    1810      1820      1830      1840
                                        ----------------------------------------------
------------------------+----------+
94-2031_L4_L7_L8
3907
324-2_J1_J3_J8
3907
324-2_J2_J5_J6
3910
487-1_I4_I6_I8
3910
493-5_F1_F6_F7
3910
493-7_G2
3910
493-7_G10
3910
493-7_G13
3910
493-7_G14_G22
3898
493-7_G19
3910
493-7_G21
3898
493-9_H5_H30
3904
493-9_H11_H15_H27
3910
543-9_C2
3910
561-2_K4_K14_K22
3907
561-2_K6_K30_K31
3898
849-1_M8_M13_M20
3910
852-5_E14_E23
3910
852-5_E28
3907
852-5_E30
3913
RN_D3_D4_D7
3910
Rpi-chc1_ORF
3907
chc1_BAC_B07-1C15
VDGRITKDRHYQSVLCPQHFACPLELNCSSSNSSSMVAGSKBLCGKSSQIVTRGTTSVILYEEQHSTVDSLWDTLM
SIWV     5194
chc2_BAC_B07-1C15            ----------FCPSSDCG------------------------
----------------------------- 3814
chc_BGC1_BAC_2D06-3D21       ----------INVLSNLPG------------------------
----------------------------- 3781
```

FIG. 14AK

```
chr_RSV2_BAC_2D06-3D31              ------------MLCFQHSACP------------------------
                                    3476
RH132B15 c347
2959
RH132B15 c86-5                      ------------------------------------------------
                                    3739
RH137D14 c13-1                      -----------------VD-----------------------------
F--R------------------------        4013
RH137D14 c13-2
3910
RH77O23 c579-4
3766
RH77O23 c579-5
3784
RH77O23 c671
3358
RH77O23 c706-3                      ------------------------------------------------
                                    3748
RH77O23 c706-4
3586
ph3 candidate
1265

Majority               ------------------------------------------------
-------------------------------     ----------+---------+---------+---------+------
                                    1850      1860      1870      1880
1890      1900      1910      1920
                                    ----------+---------+---------+---------+------
94-2031_L4_L7_L8
3907
324-2_J1_J3_J8
3907
324-2_J2_J5_J6
3910
487-1_I4_I6_I8
3910
493-5_F1_F5_F7
3910
493-7_G2
3910
493-7_G10
3910
493-7_G12
3910
493-7_G14_G22
3898
493-7_G19
3910
493-7_G21
3898
493-8_H8_H10
3904
493-8_H11_H18_H27
3910
543-5_C3
3910
561-2_K4_K14_K22
3907
```

FIG. 14AL

```
493-5_F1_F6_F7
3910
493-7_G2
3910
493-7_G10
3910
493-7_G12
3910
493-7_G14_G22
3898
493-7_G19
3910
493-7_G21
3898
493-9_H5_H30
3904
493-9_H11_H19_H27
3910
543-5_C2
3910
561-2_K4_K14_K22
3907
561-3_K6_K30_K31
3898
849-1_M8_M18_M28
3910
852-5_B14_B23
3910
852-5_B26
3907
852-5_B30
3913
RH_D3_D4_D7
3910
Kpl-chc1_ORF
3907
chc1_BAC_BG7-1C15
CFSGDCGCTKLESSSNAPCVGCVSVSSLABSIAICKLICIHQFVBRRSRKGSRBQLLPVTLLQFSTMYMGRIGTPC
ISGA         5611
chc2_BAC_BG7-1C15          ----TPICSRSQSQN---------RHIK-----------------
--------------NKKRHGLRFDITFQGA        4021
chc_RGC1_BAC_2D06-3D21      CFSGDCGCTKLESLSMGLVBNQLSDLRBIRIADFQIRAFPPRLDN-----
-------LISLRRITLVRCKRLGHIBFSDA        4297
chc_RGC2_BAC_2D06-3D31      ----SRQCGNSS.
3565
RH122B15 c247
2959
RH122B15 c85-5           FNIFRCSCTPNBQDVDIPVRFYKRHKFYMHNT.
4306
RH137D14 c13-1           ----DSQCTKLENSR---------------------
---------------TISP------FIKTSA    4147
RH137D14 c13-2
3910
RH77O23 c679-4
3786
RH77O23 c679-5
3784
RH77O23 c671
3359
RH77O23 c706-3
3832
RH77O23 c706-4
3586
```

FIG. 14AN

```
ph2 candidate
1263

Majority    --------------------------------------------------
--------------------------------
                                    ---------+---------+---------+---------+----------
+---------+---------+---------+
                                              2010      2020      2030      2040
         2050      2060      2070      2080
                                    ---------+---------+---------+---------+----------
+---------+---------+---------+
94-2031_L4_L7_L8
3907
324-2_J1_J3_J8
3907
324-2_J2_J5_J6
3910
487-1_J4_J6_J8
3910
493-5_F1_F5_F7
3910
493-7_G2
3910
493-7_G10
3910
493-7_G13
3910
493-7_G14_G22
3898
493-7_G19
3910
493-7_G21
3898
493-9_H5_H30
3904
493-9_H11_H19_H27
3910
543-5_C2
3910
561-2_K4_K14_K22
3907
561-2_K6_K10_K11
3898
649-1_M8_M18_M20
3910
852-5_E14_E23
3910
852-5_E28
3907
852-5_E30
3913
RH_D3_D4_D7
3910
Rpi-chc1_ORF
3907
chc1_BAC_B07-1C15
FGDLGYIIKWAGSAKMVTBQLQQEVTIPGSIKFFKFRFFFQESTLPIAPIGVHQSLKKTCATTLRRLSKGAHTT
5836
chc2_BAC_B07-1C15           AN------
NMPTSWRRATPPLVQESSLENGRPETAKKSKFIPRVKDDVPYFTTQSLSRFRTFVVLEDKRNL..
4216
```

FIG. 14AO

```
chr_RGC1_BAC_2006-3021
MPKLQDLWINDCPLLKALLDGLRWLVSLQSLWLANYEKLSHLPSEDAMRRLTKLWKLDITGCPKLQESCTNSQWSR
ISHI        4447
chr_RGC2_BAC_2006-3021
3555
RH122B15 c247
2959
RH133B15 c85-5
4006
RH137D14 c12-1                    N----------------BGLQQR.
4171
RH137D14 c13-2
3910
RH77O23 c579-4
3766
RH77O23 c579-5
3784
RH77O23 c671
3358
RH77O23 c706-3
3832
RH77O23 c706-4
3586
ph2 candidate
1265

Majority      ----------
                          ----------+
                                  2090
                          ----------#
94-2931_L4_L7_L8
3907
324-2_J1_J3_J8
3907
324-2_J2_J5_J6
3910
487-1_I4_I6_I8
3910
493-6_F1_F5_F7
3910
493-7_G2
3910
493-7_G10
3910
493-7_G13
3910
493-7_G14_G22
3898
493-7_G19
3910
493-7_G21
3898
493-9_H5_H30
3904
493-9_H11_H19_H27
3910
543-6_C2
3910
561-2_K4_K14_K22
3907
561-2_K6_K30_K31
3898
```

FIG. 14AP

```
649-1_M8_M18_N20
3910
852-5_E14_E23
3910
852-5_E28
3907
852-5_E36
3913
RH_D3_D4_D7
3910
Rpi-chc1_ORF
3907
chc1_BAC_B07-1C18
5836
chc2_BAC_B07-1C18
6215
chc_RGC1_BAC_2D06-3D21    PRISVVLNK,
4477
chc_RGC2_BAC_2D06-3D21
3565
RH122815 c247
2989
RH122815 c88-5
4006
RH137D14 c13-1
4171
RH137D14 c13-3
3910
RH77O23 c879-4
3766
RH77O23 c879-5
3784
RH77O23 c671
3358
RH77O23 c706-3
3832
RH77O23 c706-4
3586
ph2 candidate
1265
```

FIG. 14AQ

CLONING AND EXPLOITATION OF A FUNCTIONAL R-GENE FROM *SOLANUM CHACOENSE*

CROSS-REFERENCE TO RELATED APPLICATION

This application is a continuation of U.S. Ser. No. 13/496,845 having an international filing date of 20 Sep. 2010 (now allowed), which is the national phase of PCT application PCT/NL2010/050612 having an international filing date of 20 Sep. 2010, which claims benefit of European patent application No. 09170769.5 filed 18 Sep. 2009. The contents of the above patent applications are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 313632013301_SeqList.txt, date recorded: Jan. 31, 2017 size: 900,735 bytes).

FIELD OF THE INVENTION

The invention relates to a resistance gene isolated from *S. chacoense*. Moreover, the invention relates to the use of said resistance gene, for example to clone functional homologues, and the use of said resistance gene(s) in a method to increase or confer at least partial resistance to an oomycete infection in a plant. More in specific the invention provides a resistance gene that is capable of increasing or conferring at least partial resistance to *Phytophthora* sp. (for example *Phytophthora infestans*) through genetic engineering techniques or through marker assisted breeding techniques.

BACKGROUND

Late blight, caused by the oomycete *Phytophthora infestans*, is one of the most serious diseases in worldwide potato production. It was responsible for the Irish potato famine of the mid-19th century, resulting in the death of one million people. Although a lot of effort has been invested in controlling the pathogen, chemical control of *P. infestans* is still the main crop management strategy, but environmental safety is becoming more important and the pathogen is sometimes able to evolve resistance to the fungicide treatment. Therefore, introduction of resistance into modern potato varieties is the most durable strategy to control the disease.

In the last century, *Solanum demissum*, which is a hexaploid Mexican species, was extensively used in breeding for late-blight resistance in potato. Initially, a series of 11 R genes derived from *S. demissum* was described. Of these, R1, R2, R3a/b, R6, and R7 have been localized on the genetic maps of potato (*Solanum tuberosum*). However, these R genes confer pathovar-specific resistance and those that were introgressed into potato varieties, mainly R1, R2, R3, R4, and R10, were quickly overcome by the pathogen. Hence, new sources for resistance are required, and currently, several other wild *Solanum* species have been reported as being potential sources of resistance, many of which have been genetically characterized (Table 6).

Recent efforts to identify late blight resistance have focused on major R genes conferring broad-spectrum resistance derived from diverse wild *Solanum* species. Beside *S. demissum*, other wild *Solanum* species such as *S. acaule, S. chacoense, S. berthaultii, S. brevidens, S. bulbocastanum, S. microdontum, S. sparsipilum, S. spegazzinii, S., stoloniferum, S. sucrense, S. toralapanum, S. vernei* and *S. verrucosum* have been reported as new sources for resistance to late blight (reviewed by (Jansky, 2000)).

*S. chacoense*, is a self-incompatible diploid species from South America, and is thought to be a source for late-blight resistance. A recent taxonomic rearrangement of the section Petota revealed its relationship with species like *S. berthaultii* and *S. tarijense*. Several accessions of *S. chacoense* (CHC543-1), *S. berthaultii* (BER481-3, BER94-2031) and *S. tarijense* (TAR852-5) have been tested in detached leaf assays (DLA) with multiple isolates (Table 5) and in repeated field trials with isolate IPO-C. In all tests CHC543-5, BER94-2031, BER481-3 and TAR852-2 remained unaffected, underscoring the relevance of the expressed R genes for resistance breeding.

Molecular cloning of the genes responsible for resistance and subsequent introduction of the genes into potato varieties is a third method that circumvents many of the problems encountered in the previous two strategies.

To date, multiple late blight R-genes have been cloned, like the allelic genes RB and Rpi-blb1 on chromosome 8 and Rpi-blb2 on chromosome 6 (Table 6). Recently, also an Rpi-blb3 resistance gene has been isolated (WO 2008/091153). Although the initial results obtained with RB and Rpi-blb1, -2 and -3 are promising, there is a further need for additional R-genes.

SUMMARY OF THE INVENTION

Figure 7A:
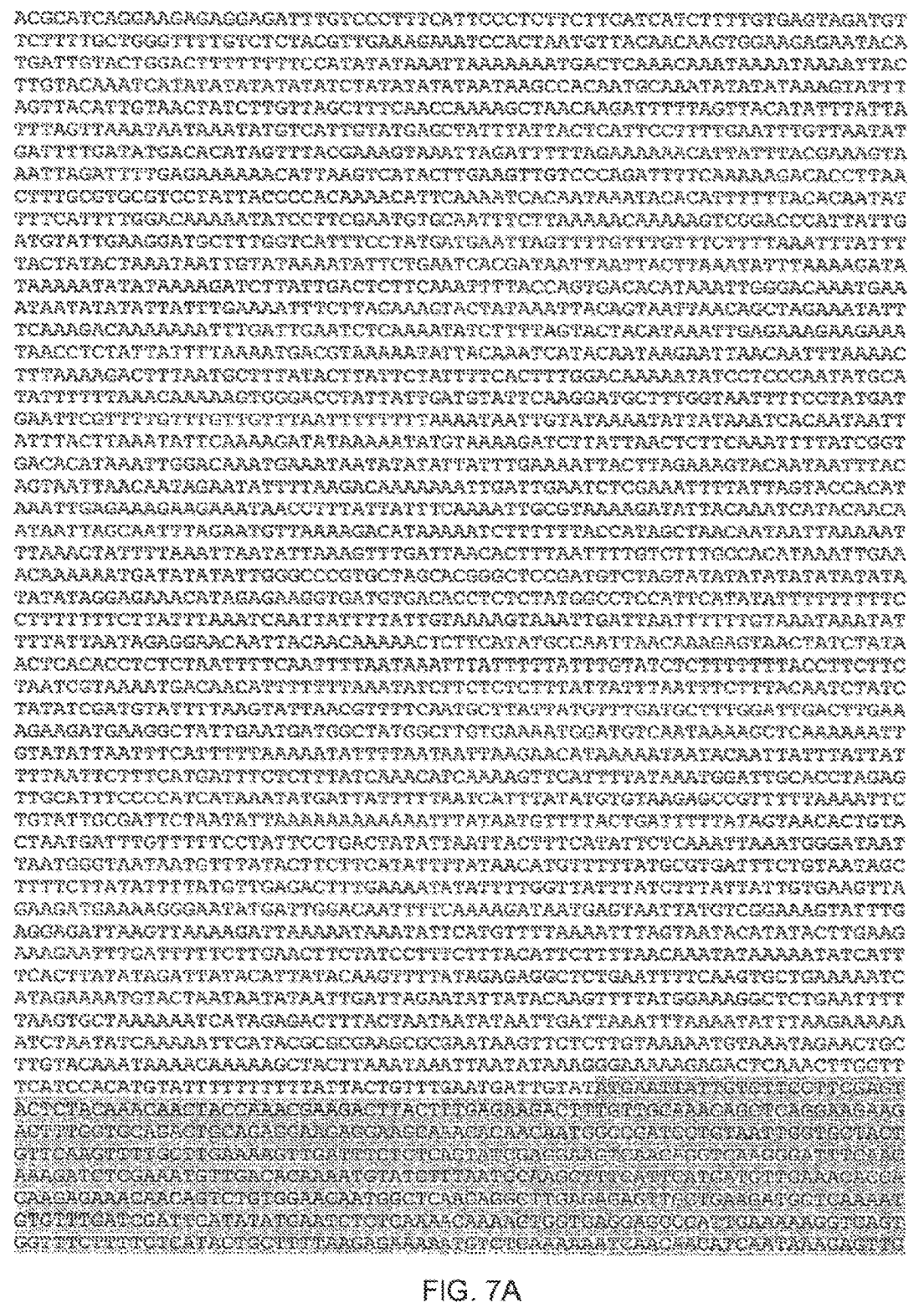
Figure 7B:
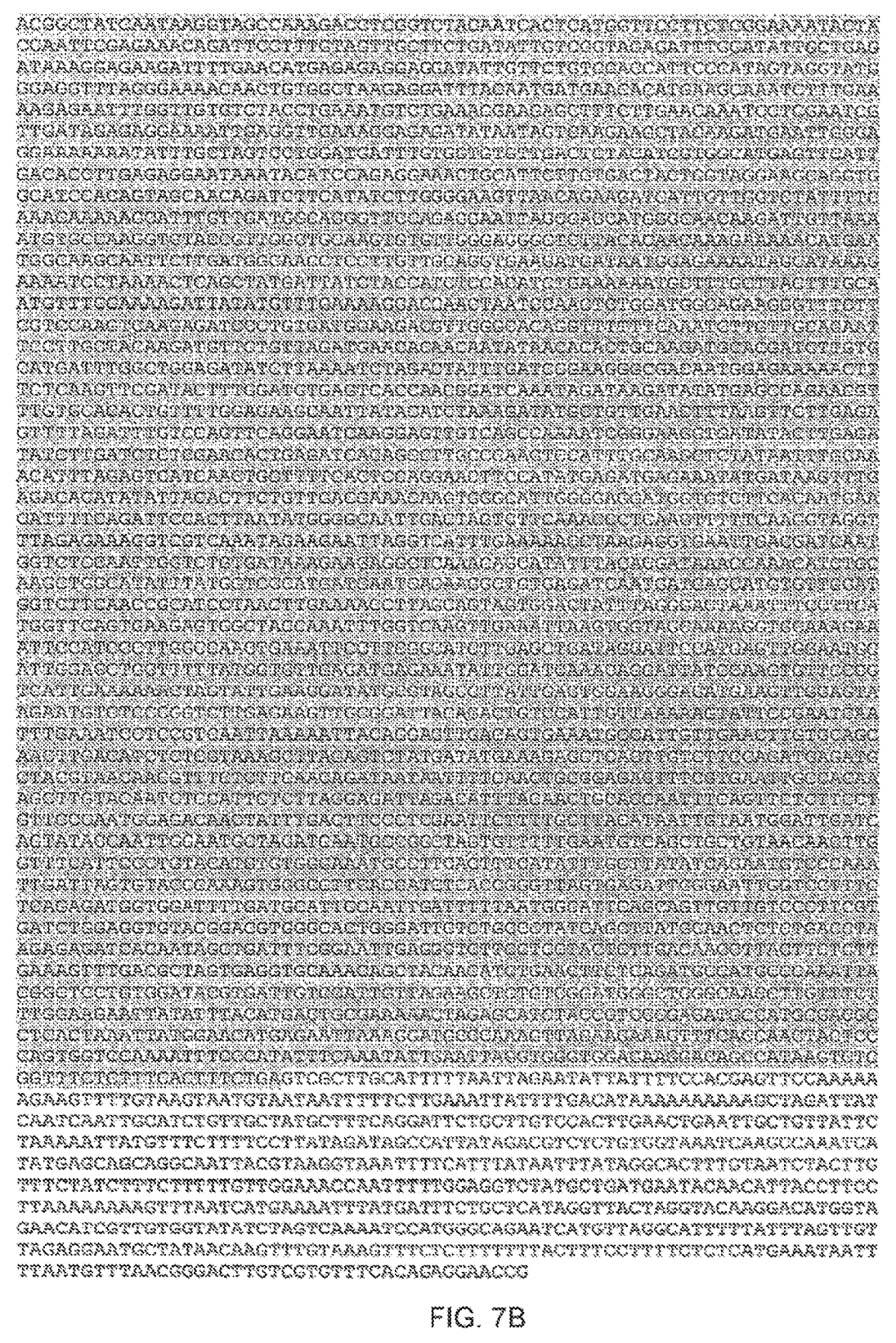
Figure 13C:
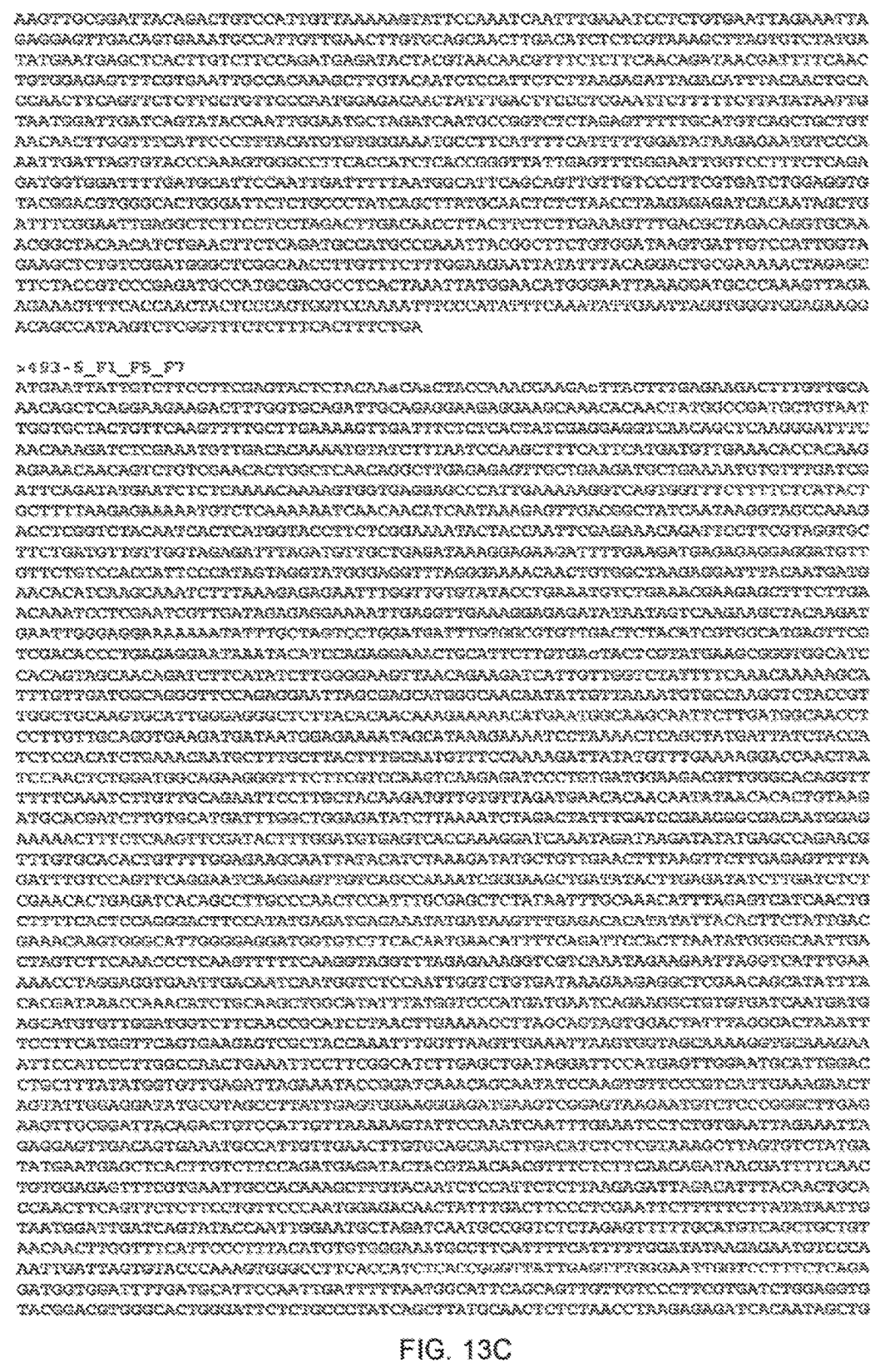
Figure 13D:
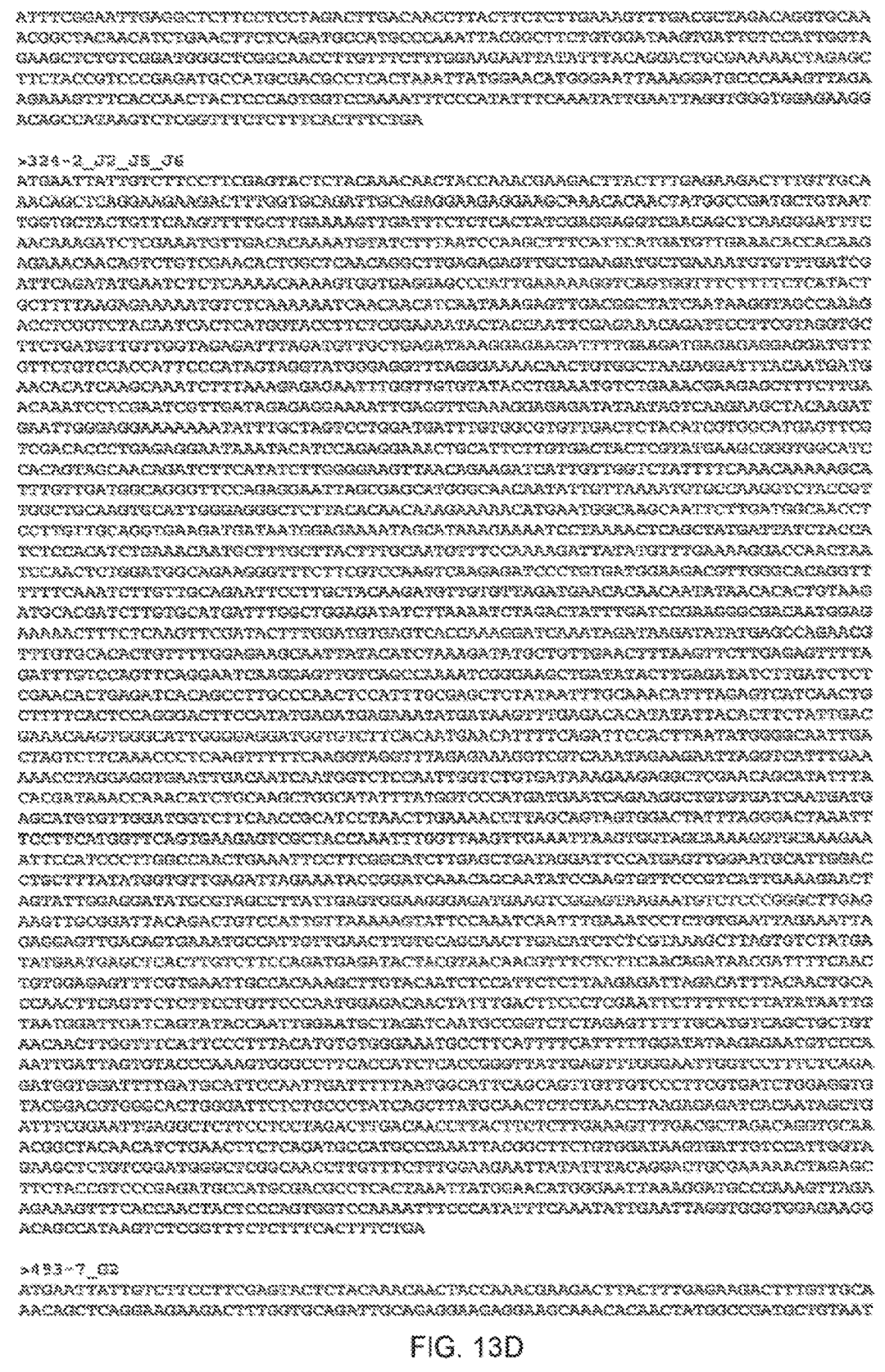
Figure 13E:
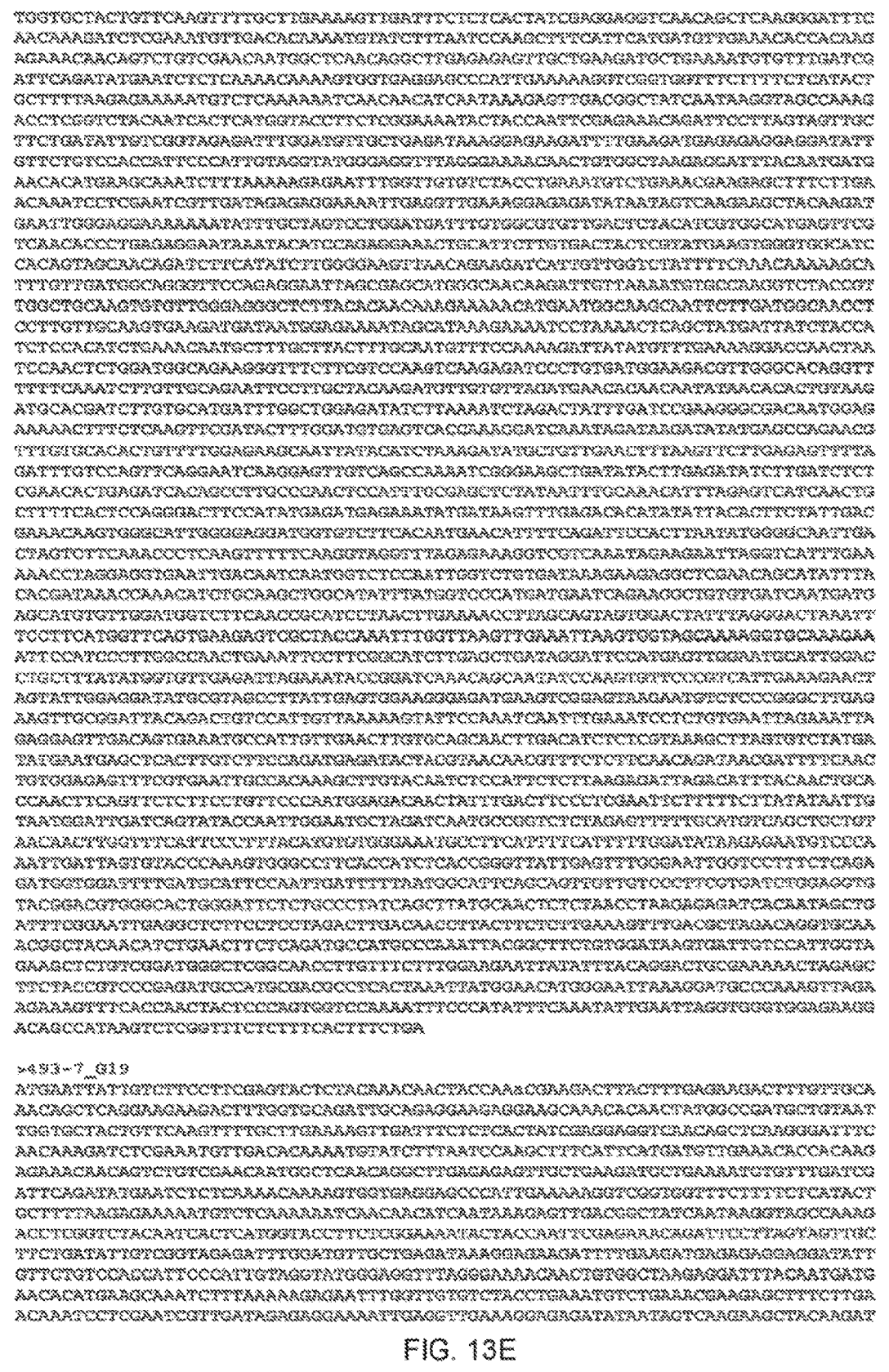
Figure 13F:
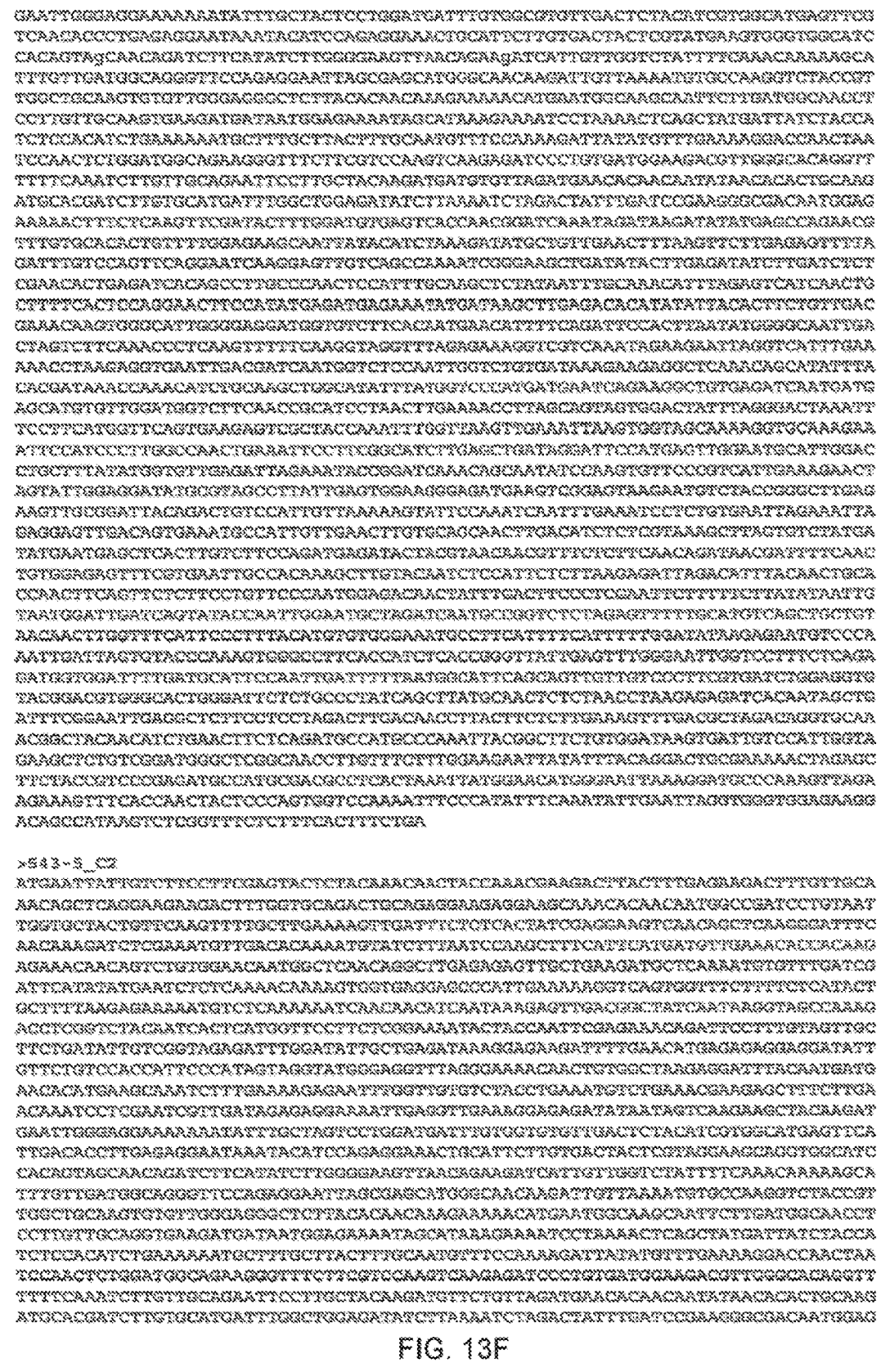
Figure 13G:
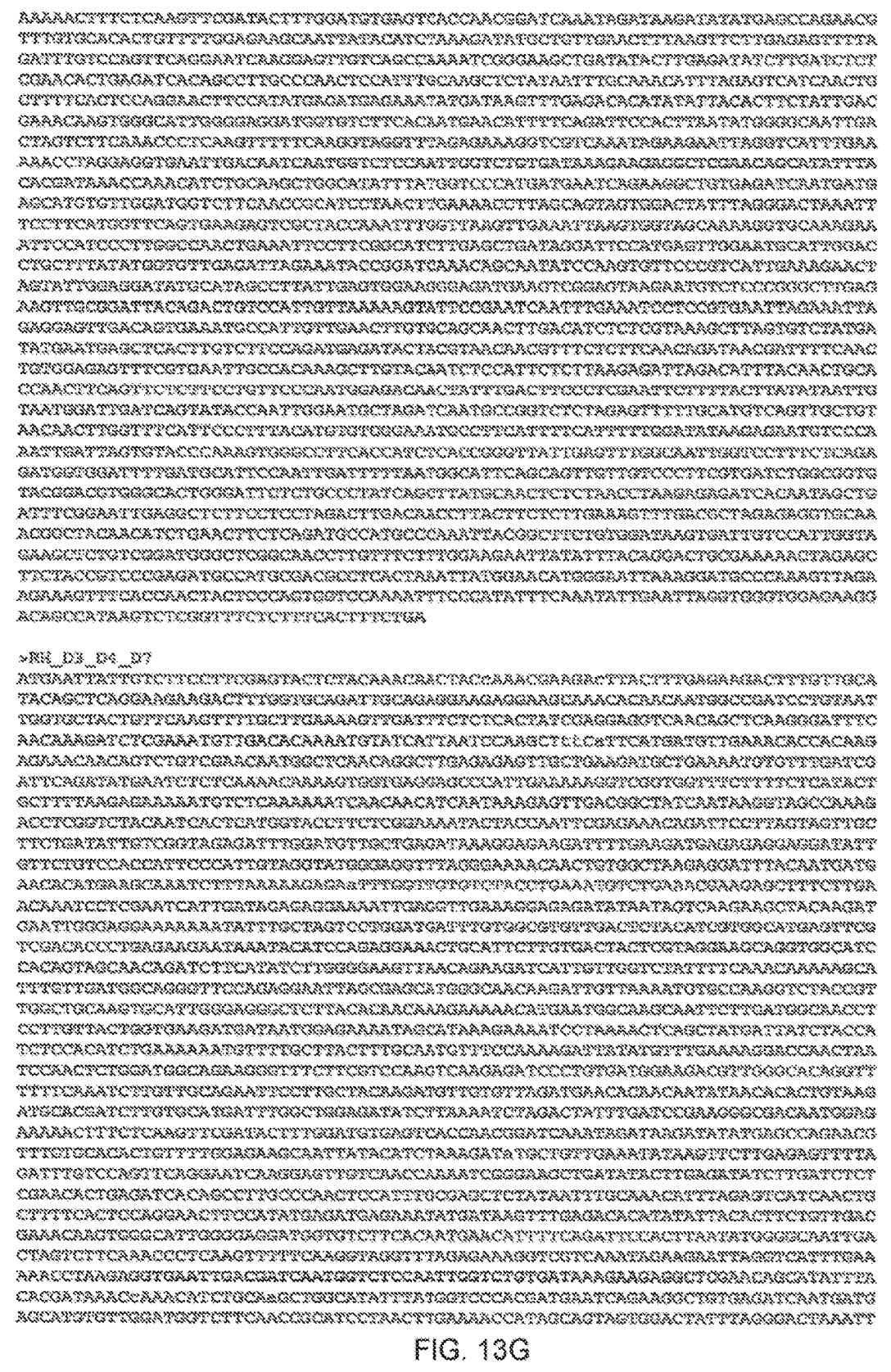
Figure 13H:
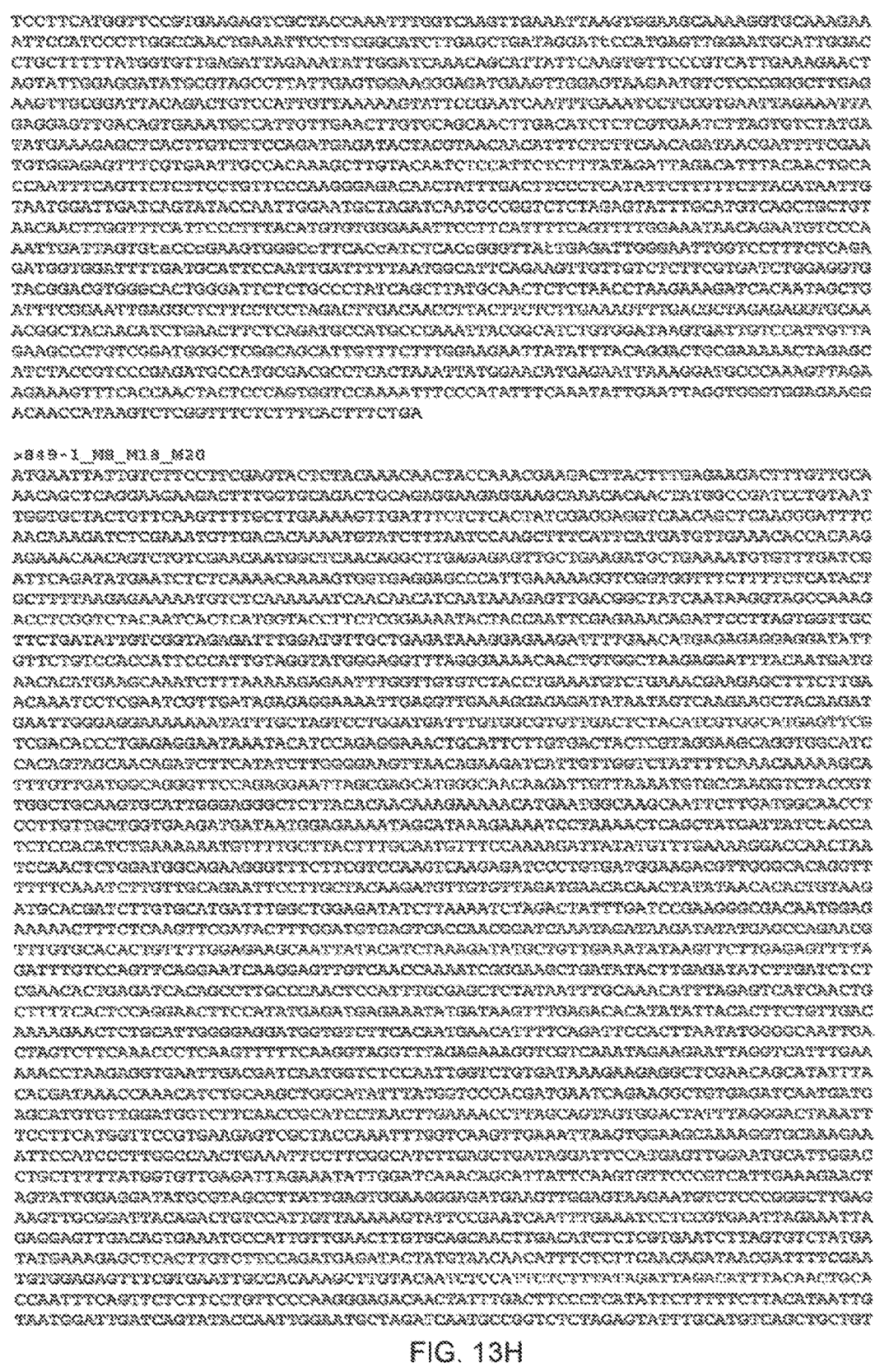
Figure 13I:
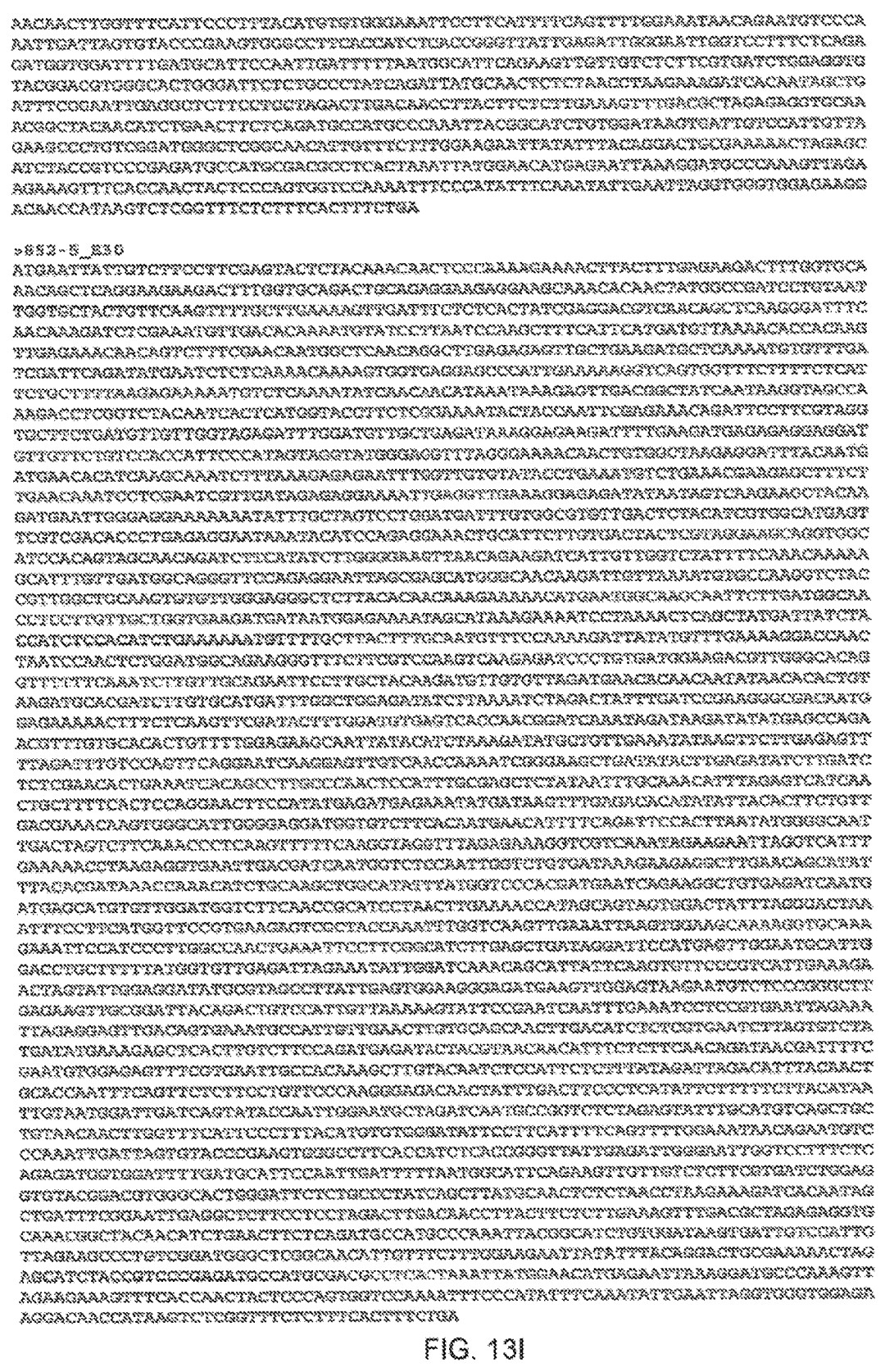
Figure 13J:
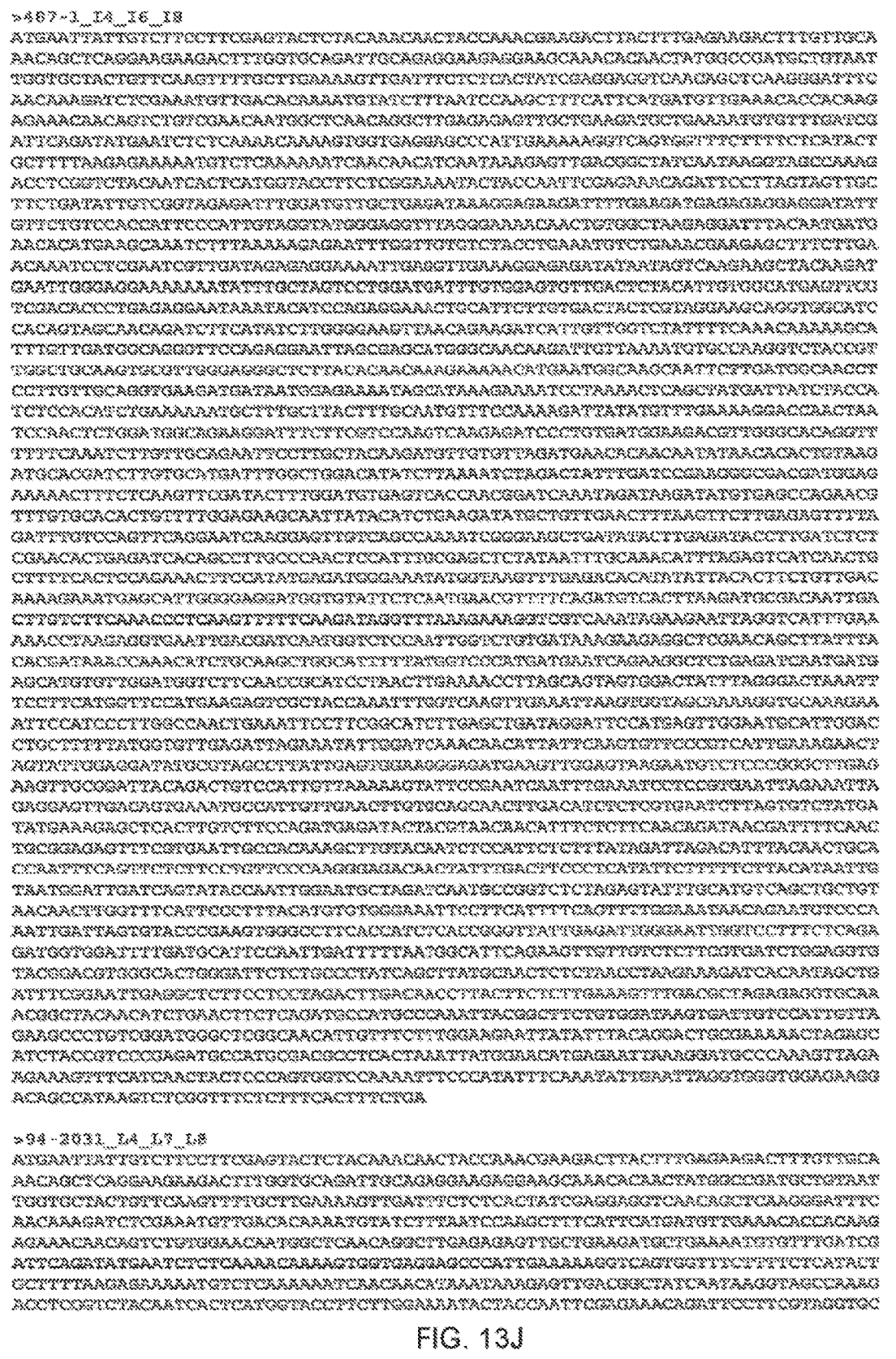
Figure 13K:
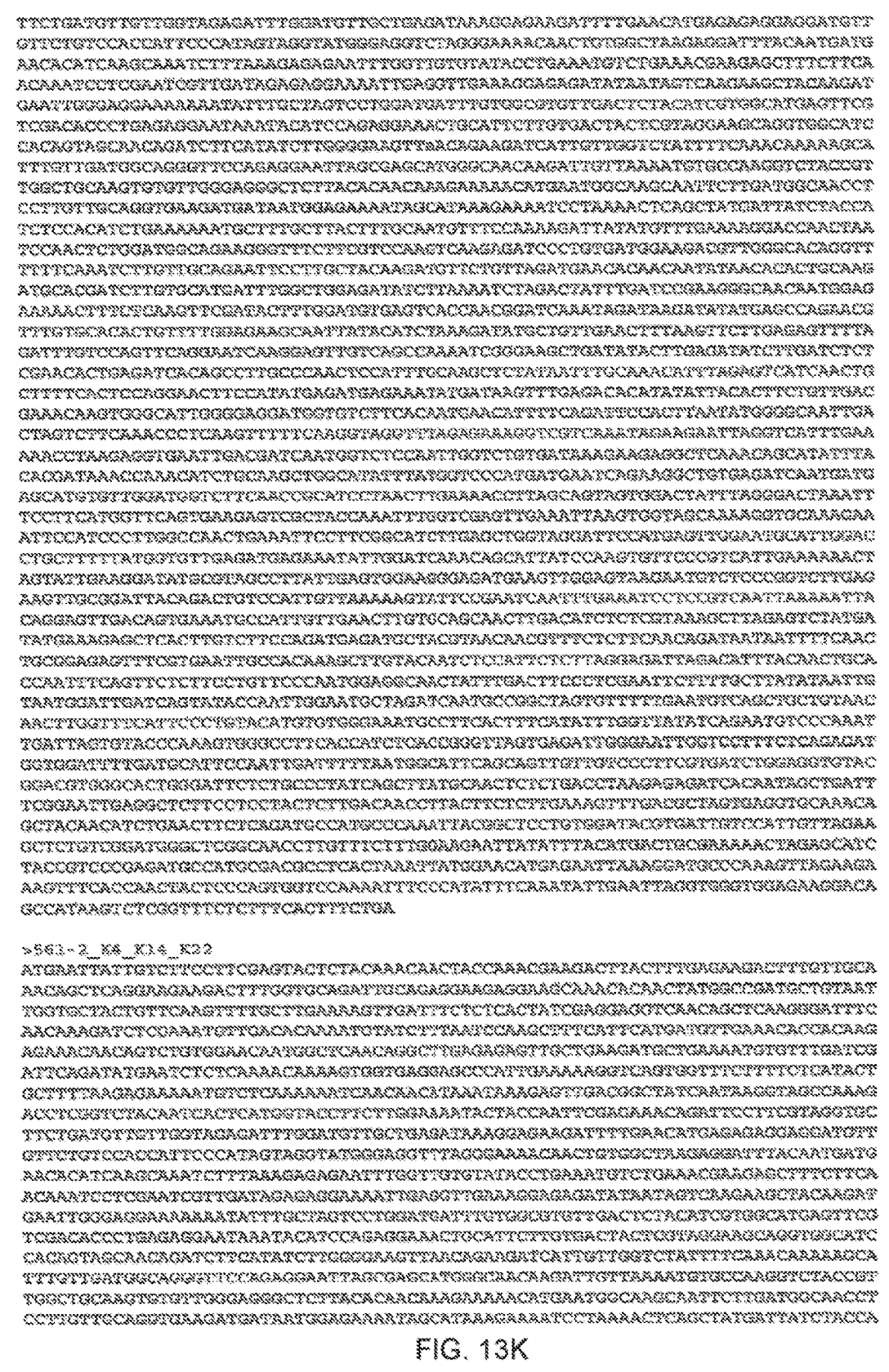
Figure 13M:
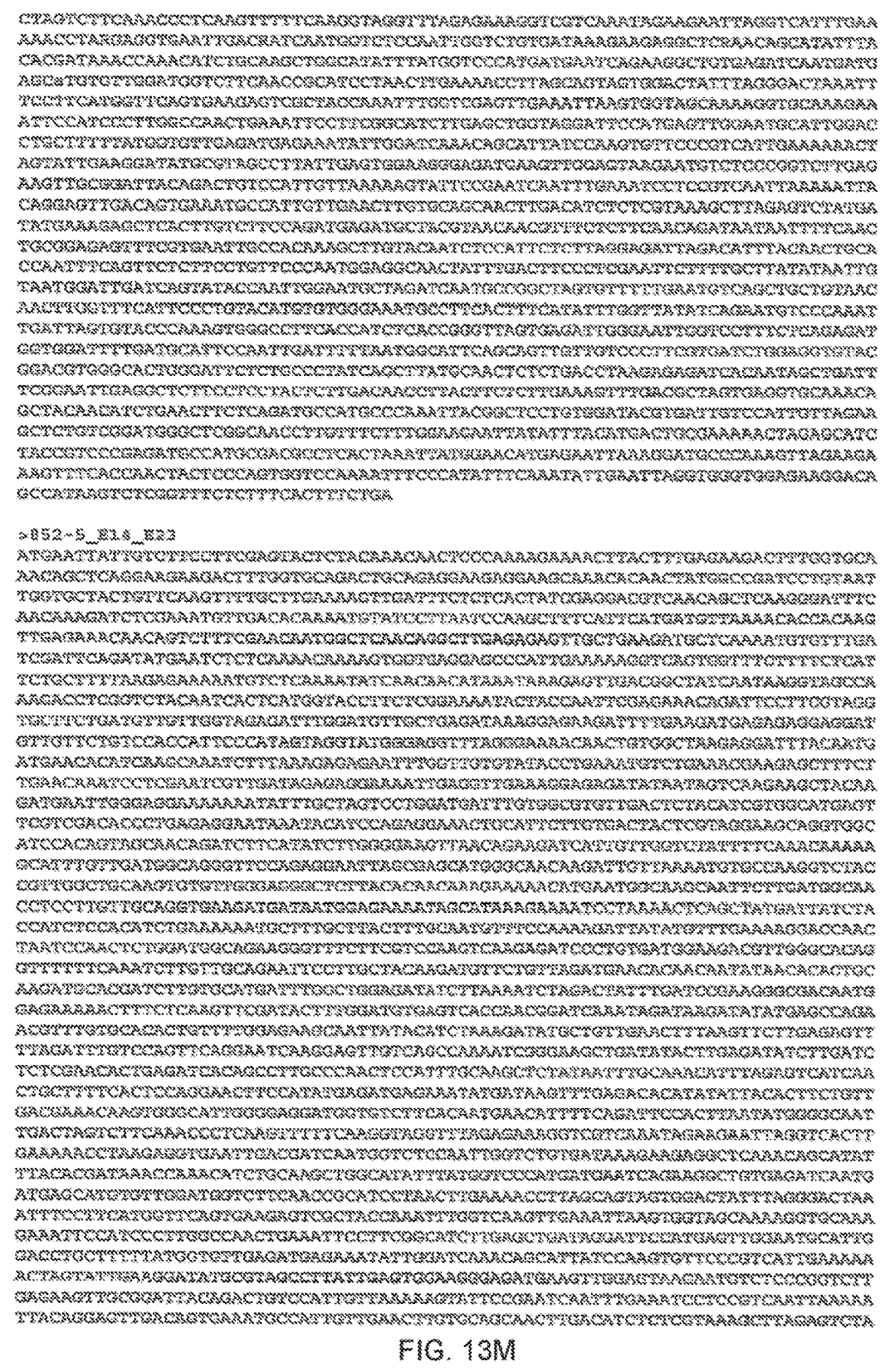
Figure 13N:
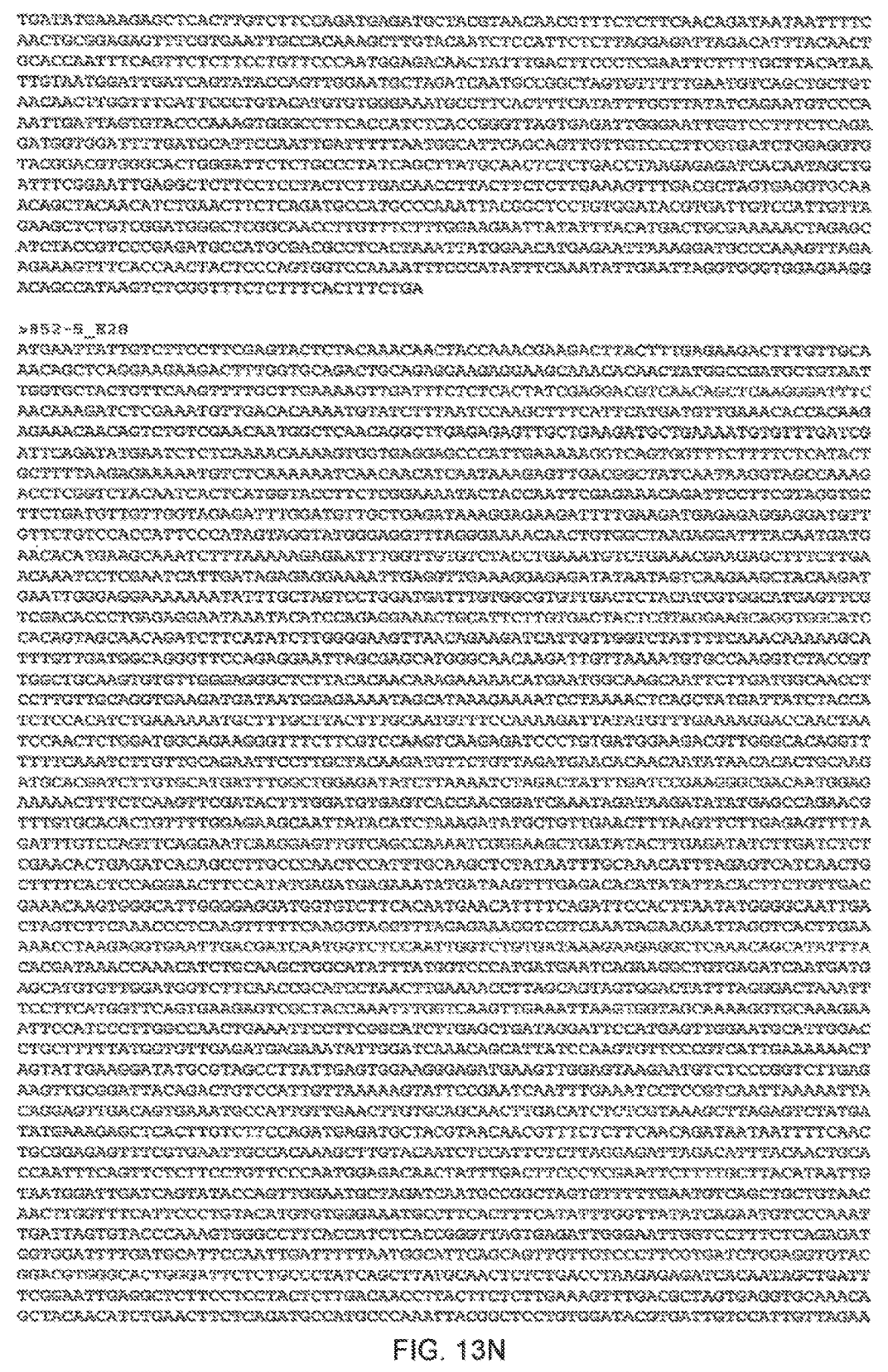
Figure 13P:
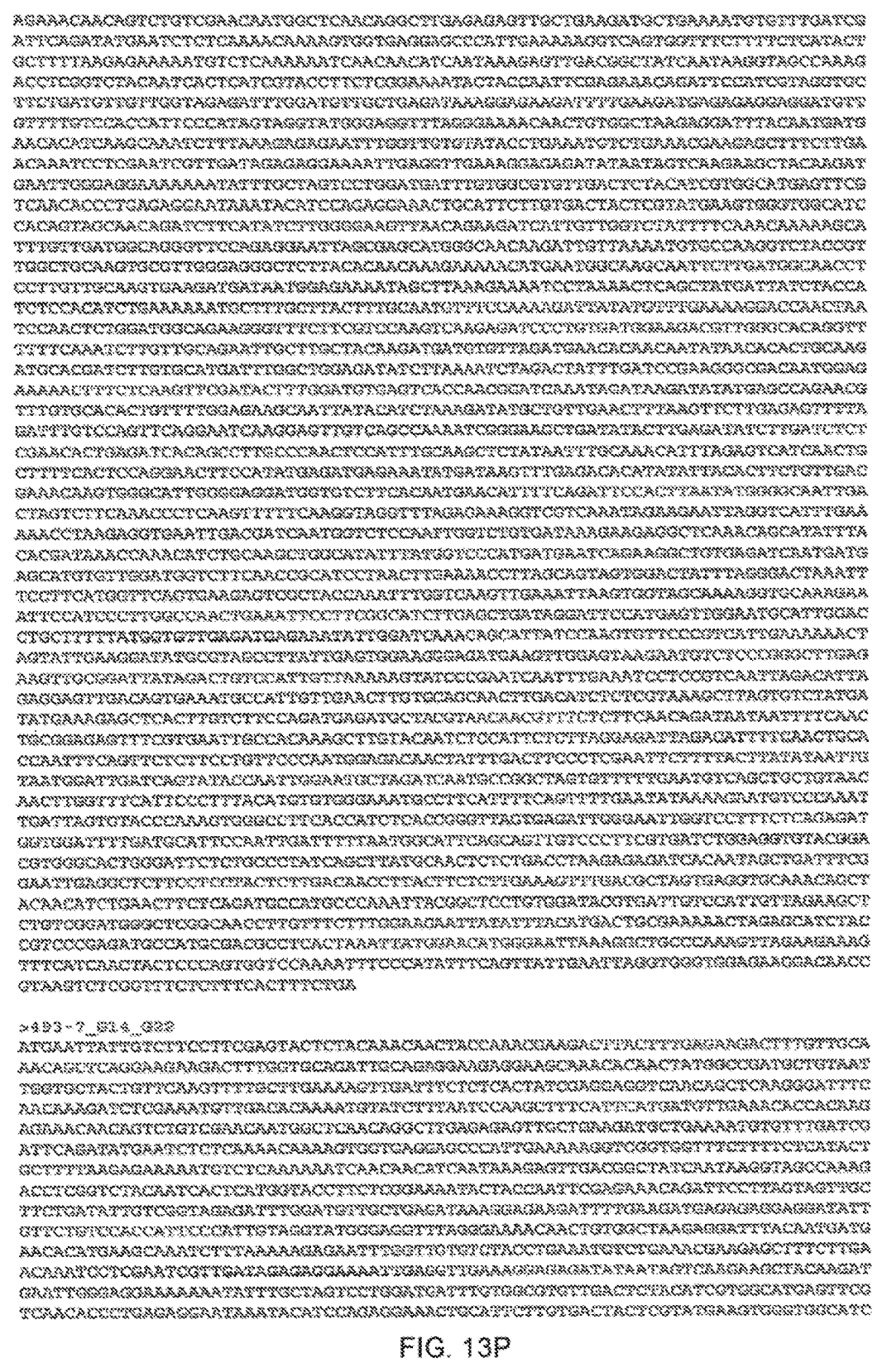
Figure 13Q:
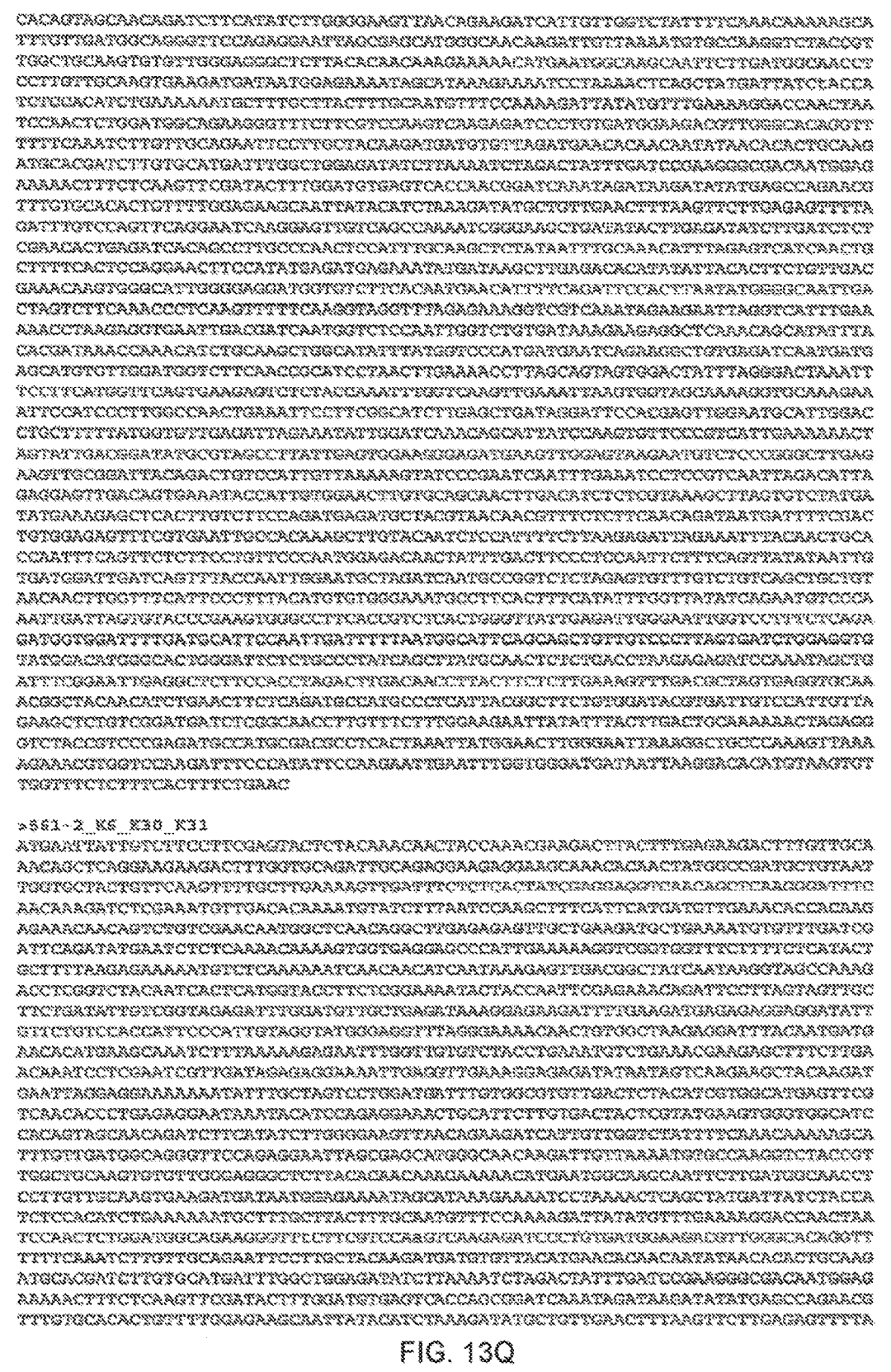
Figure 13R:
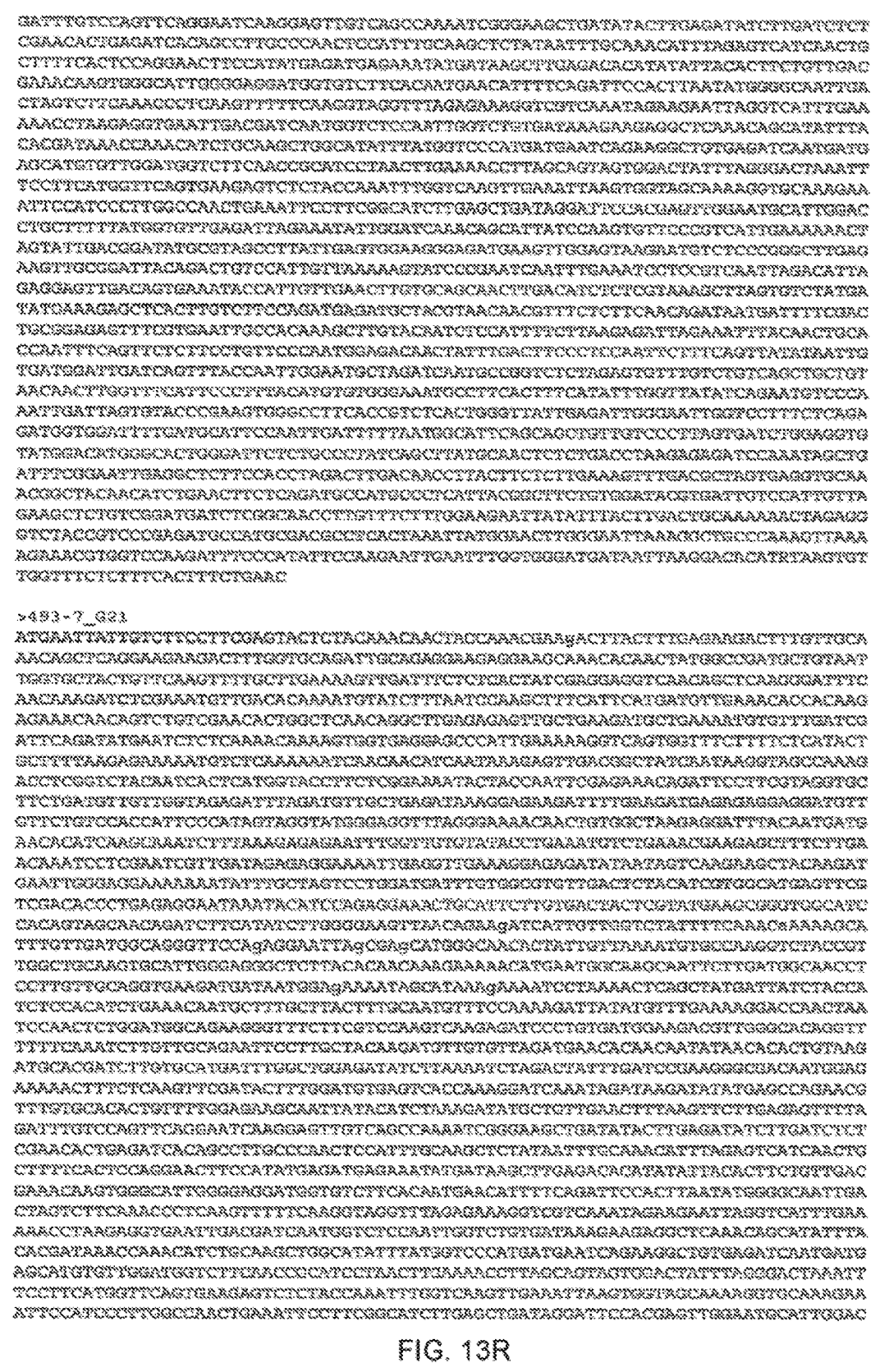

The invention now relates to a method for providing at least partial resistance or increasing resistance in a plant against an oomycete infection comprising providing a plant or a part thereof with a nucleic acid encoding the amino acid sequence Rpi-chc1 of FIG. 4A-K or a functional fragment or a functional homologue thereof, preferably wherein said plant is a plant from the Solanaceae family, more preferably *Solanum tuberosum*. Preferably said oomycete comprises *Phytophthora*, more preferably *Phytophthora infestans*. In a specific embodiment, the above mentioned functional homologue is selected from the group of amino acid sequences consisting of 493-7_G12, 543-5_C2, 849-1_M8_M18_M20, 487-1_I4_I6_I8, 94-2031_L4_L7_18, 561-2_K4_K14_K22, 324-2_J1_J3_J8, 852-5_E14_E23, 852-5_E28, 493-9_H5_H30, 493-7_G14_G22, 561-2_K6_K30_K31 and 493-7_G21. In a further specific embodiment the nucleic acid sequence as defined above comprises a nucleic acid sequence as depicted in FIG. 7A-B or a nucleic acid sequence encoding the amino acid sequences 493-7_G12, 543-5_C2, 849-1_M8_M18_M20, 487-1_I4_I6_I8, 94-2031_L4_L7_18, 561-2_K4_K14_K22, 324-2_J1_J3_J8, 852-5_E14_E23, 852-5_E28, 493-9_H5_H30, 493-7_G14_G22, 561-2_K6_K30_K31 and 493-7_G21 as depicted in FIG. 13A-T.

The invention further comprises a method for breeding an oomycete, preferably a Phytopthora resistant tetraploid plant, comprising
a. increasing the ploidy level of the gametes of a diploid plant that already contains a nucleic acid sequence as defined above;
b. using said gametes in a cross with gametes of a tetraploid plant; and
c. selecting the offspring of said cross for the presence of said nucleic acid sequence.

Preferably in such a method the diploid plant of step a) is plant from the genus *S. chocaense, S. berthaultii, S. sucrense,* or *S. tarijense.*

The invention also relates to a method for selecting a plant or plant material or progeny thereof for its susceptibility or resistance to an oomycete infection, said method comprising the steps of testing at least part of said plant or plant material or progeny thereof for the presence or absence of a nucleic acid as defined above. Specifically in such a method the testing involves detecting the presence of one or more of the markers of Table 2 and 8 and it is performed with a primer or a probe that specifically binds to said nucleic acid.

Hence, the invention also relates to a marker for marker assisted selection in plant breeding to obtain resistance against oomycetes, wherein said marker is chosen from the markers presented in Table 2 and 8.

In another embodiment, the invention also relates to an isolated or recombinant nucleic acid sequence comprising a nucleic acid sequence encoding the amino acid sequence Rpi-chc1 of FIG. 4A-K or a functional fragment thereof, or a nucleic acid encoding the amino acid sequence of 493-7_G12, 543-5_C2, 849-1_M8_M18_M20, 487-1_I4_I6_I8, 94-2031_L4_L7_18, 561-2_K4_K14_K22, 324-2_J1_J3_J8, 852-5_E14_E23, 852-5_E28, 493-9_H5_H30, 493-7_G14_G22, 561-2_K6_K30_K31 and 493-7_G21 or a functional fragment thereof. Preferably said fragment comprises at least the LRR domain of the amino acid sequence. It is further a preferred embodiment where the isolated or recombinant nucleic acid sequence comprises a nucleic acid sequence as depicted in FIG. 7A-B or in FIG. 13A-T.

The invention further relates to a transgenic or tetraploid cell comprising a nucleic acid according to the invention.

Also part of the invention is a vector comprising a nucleic acid sequence according to the invention. Preferably said vector further comprises the promoter and/or terminator to which the gene is naturally associated, more preferably a truncated promoter having less than 1000 nucleotides upstream of the gene sequence.

The invention also is related to a transgenic or tetraploid host cell comprising a nucleic acid according to the invention or a vector according to the invention, preferably wherein such a host cell is an *Agrobacterium* cell or a plant cell.

The invention also relates to a transgenic or tetraploid plant cell comprising a nucleic acid according to the invention or a vector according to the invention, preferably wherein said plant cell is a cell from a Solanaceae, more preferably *Solanum tuberosum*, more preferably a tetraploid *Solanum tuberosum*. In a further embodiment the invention comprises a transgenic or tetraploid plant comprising such a cell and also a part derived from such a plant, preferably wherein said part is a tuber.

Also comprised in the current invention is a protein encoded by an isolated or recombinant nucleic acid according to the invention or a functional fragment thereof, preferably wherein said protein has the amino acid sequence of Rpi-chc1 as depicted in FIG. 4A-K. The invention also relates to an antibody that (specifically) binds to said protein.

LEGENDS TO THE FIGURES

Figure 1B:
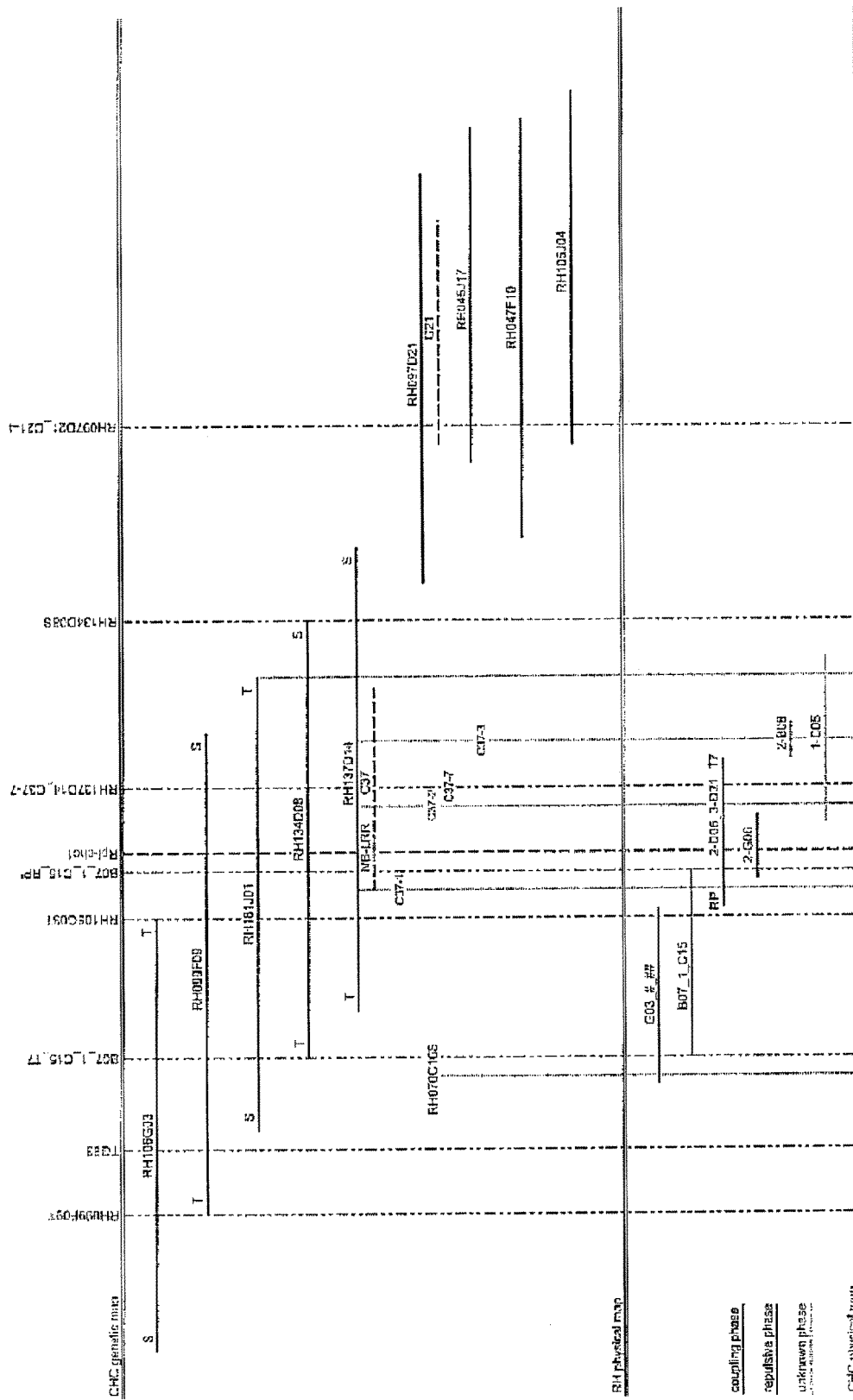
Figure 4A:
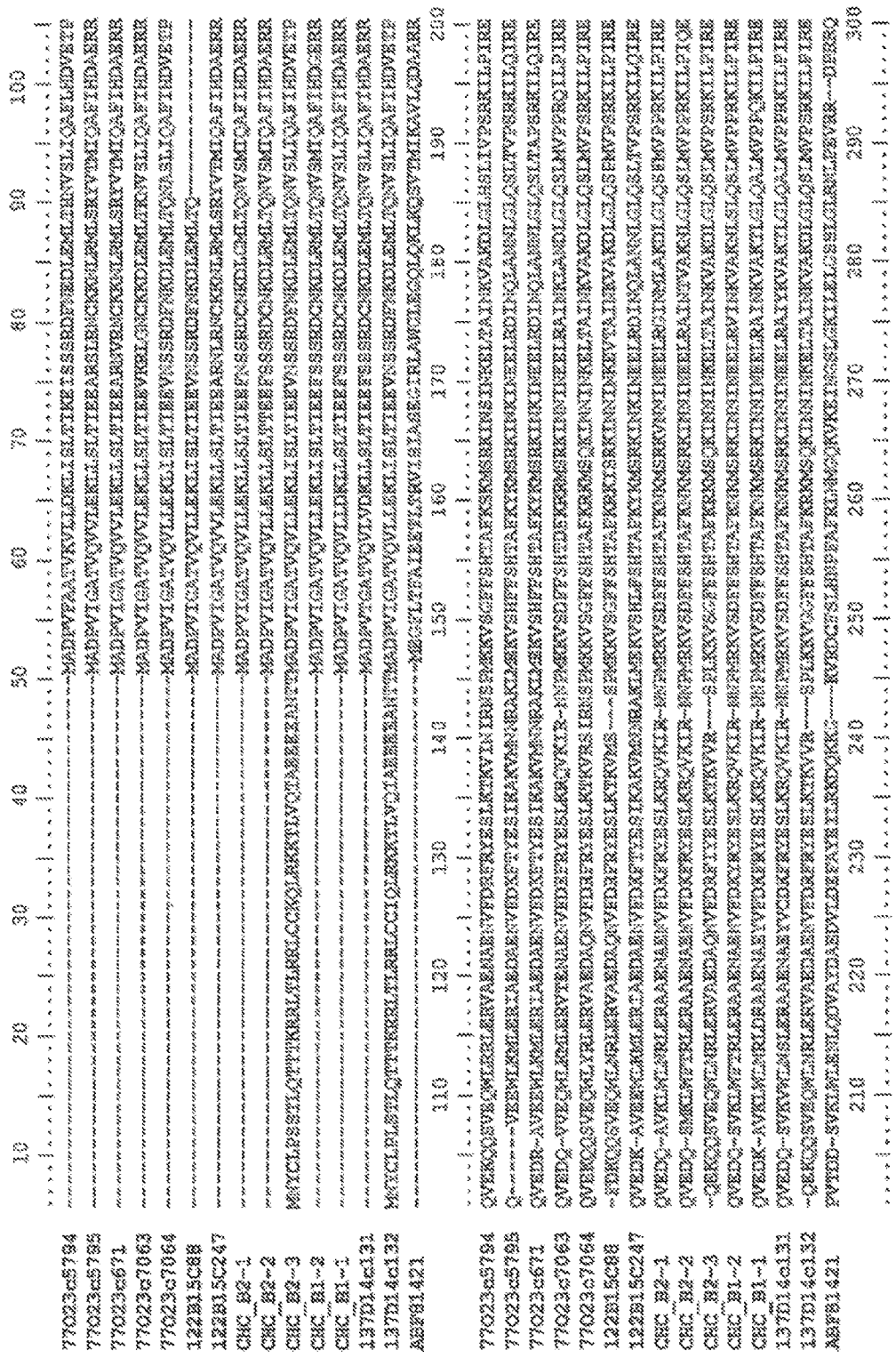
Figure 4E:
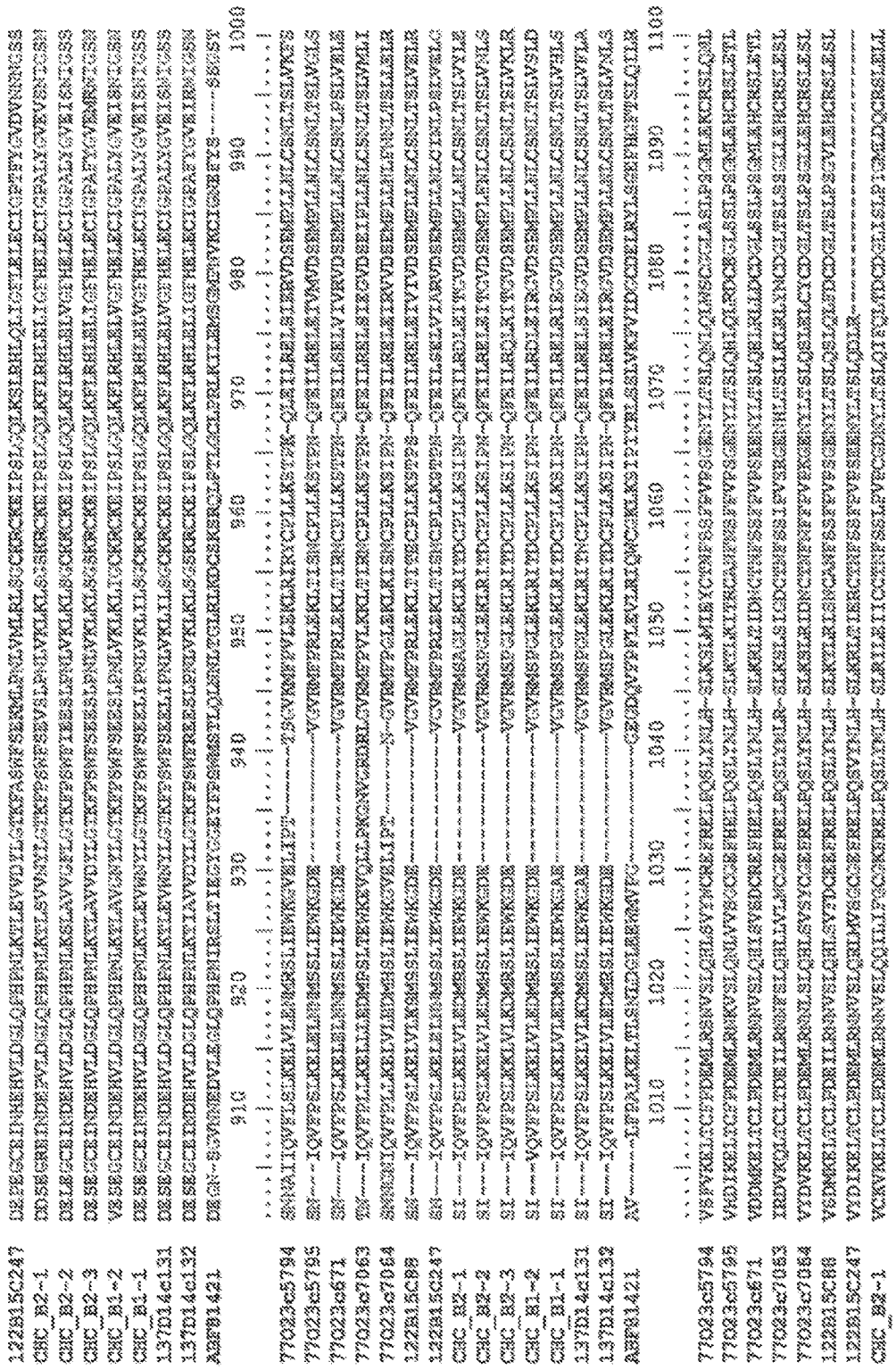
Figure 4H:
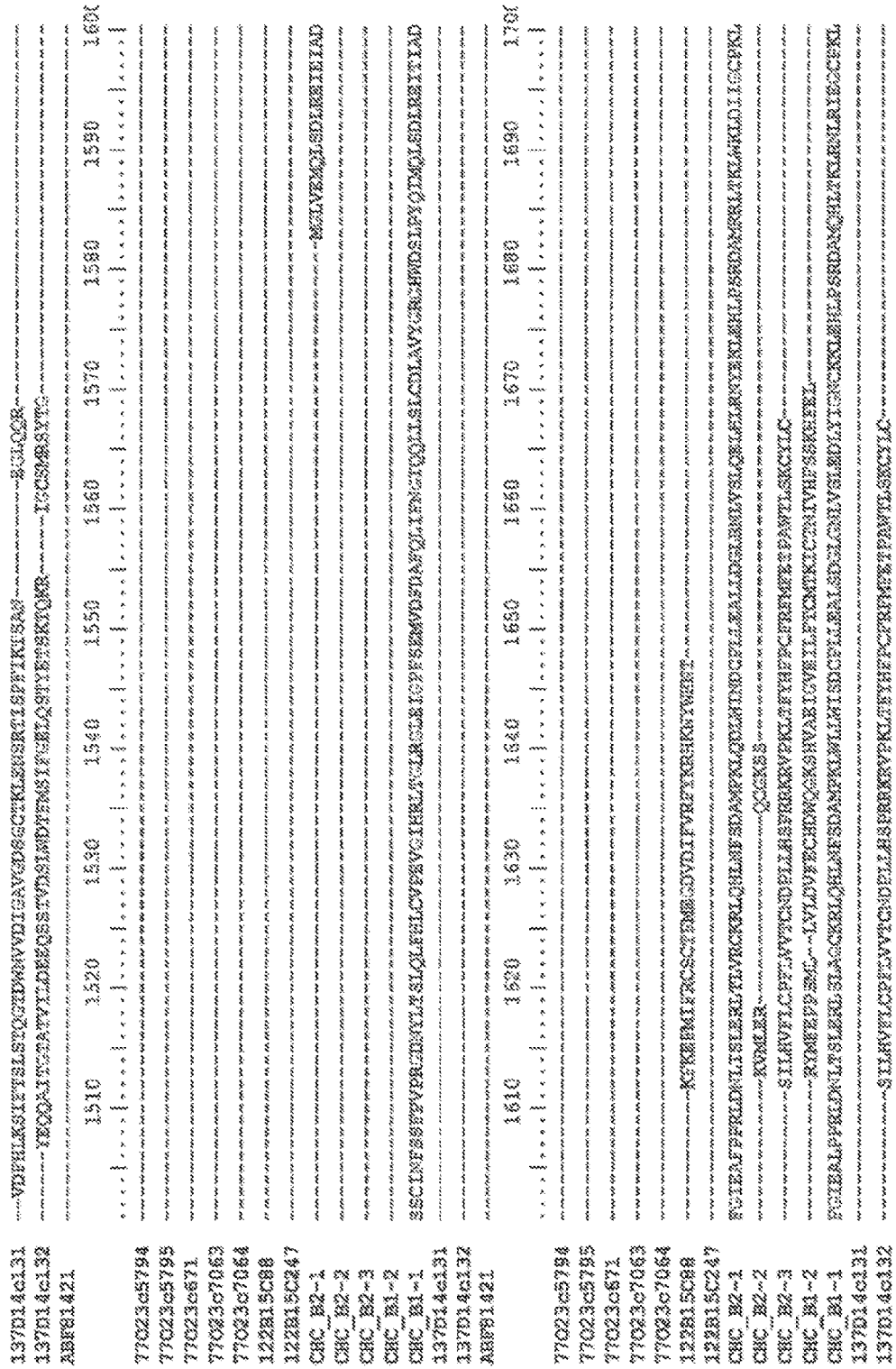

FIG. 1A-B. Genetic and physical maps of the Rpi-chc1 (A) and Rpi-ber (B) loci (7650 and 06-882 populations respectively). Indicated are the relative positions of markers, the number of recombinants identified between markers, overlapping BAC clones that span the R-loci, and the relative positions of RGAs in the CHC543-5 and RH89-039-16 physical maps.

FIG. 2A-G. Chr10 BAC sequence annotation.

Two tiling paths consisting of 3 and 4 overlapping BACs from RH89-039-16 (RH106G038, RH137D014, RH009D021 and RH122B15, RH77O23, RH04G12, RH199E15) and two overlapping BACs from CHC543-5 were sequenced and annotated. Positions of markers and BAC end sequences from overlapping BACs are indicated by arrow heads. Positions of sequence contigs are indicated by horizontal arrows. Positions of genes, as predicted by the FGENESH algorithm, are indicated by colored boxes. Protein sequence homology, as found by BlastP search against the NR database is indicated by vertical arrows. RGAs are numbered by underlined figures and their gene structure are numbered correspondingly
A: RH106G03, B: RH137D14, C: RH97D21, D: RH122B15, E: RH77O23, F: CHC B1 (B07-1-05), G: CHC B2 (2-D06_3-D21).

FIG. 3. Transient complementation of *Phytophthora* susceptibility in *Nicotiana benthamiana* leaves. Two days after agro-infiltration the leaves were challenged by the inoculation with a zoospore suspension of *P. infestans* isolate 90128 (avirulent on CHC543-5) in a detached leaf assay. Typical disease phenotypes developed 6 days after inoculation of control plants that had been agro-infiltrated with pBINplus without an insert. Full resistance was observed in control plants agroinfiltrated with pBINplus:Rpi-blb1. Agroinfiltration of pBINplus:CHCB2-3, one of three RGAs from the Rpi-chc1 mapping interval, also conferred full resistance to infection by *P. infestans*, while pBINplus:CHCB2-1 and pBINplus:CHCB2-2 infiltrated leaves remained susceptible.

Figure 4B:
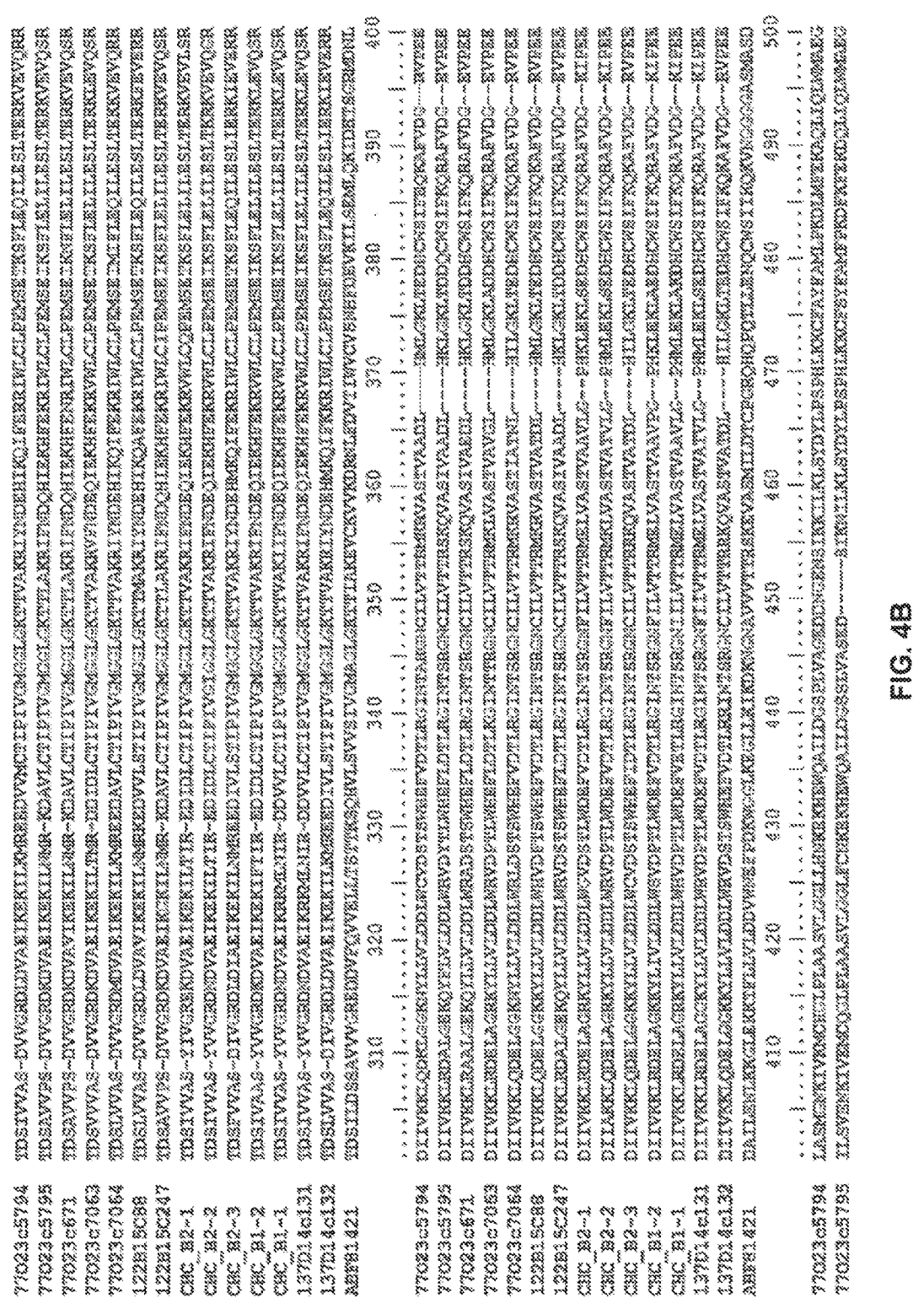
Figure 4C:
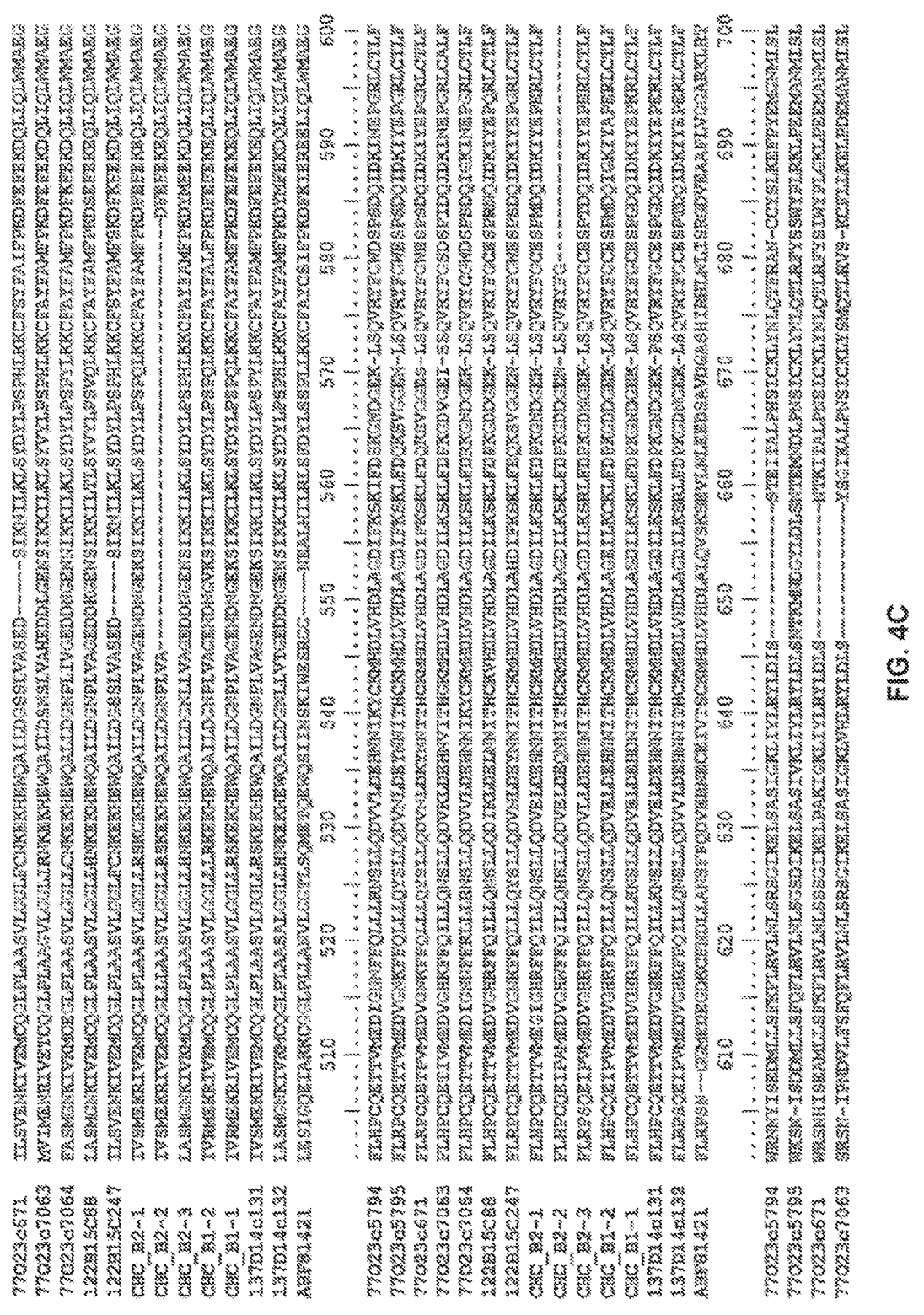
Figure 4D:
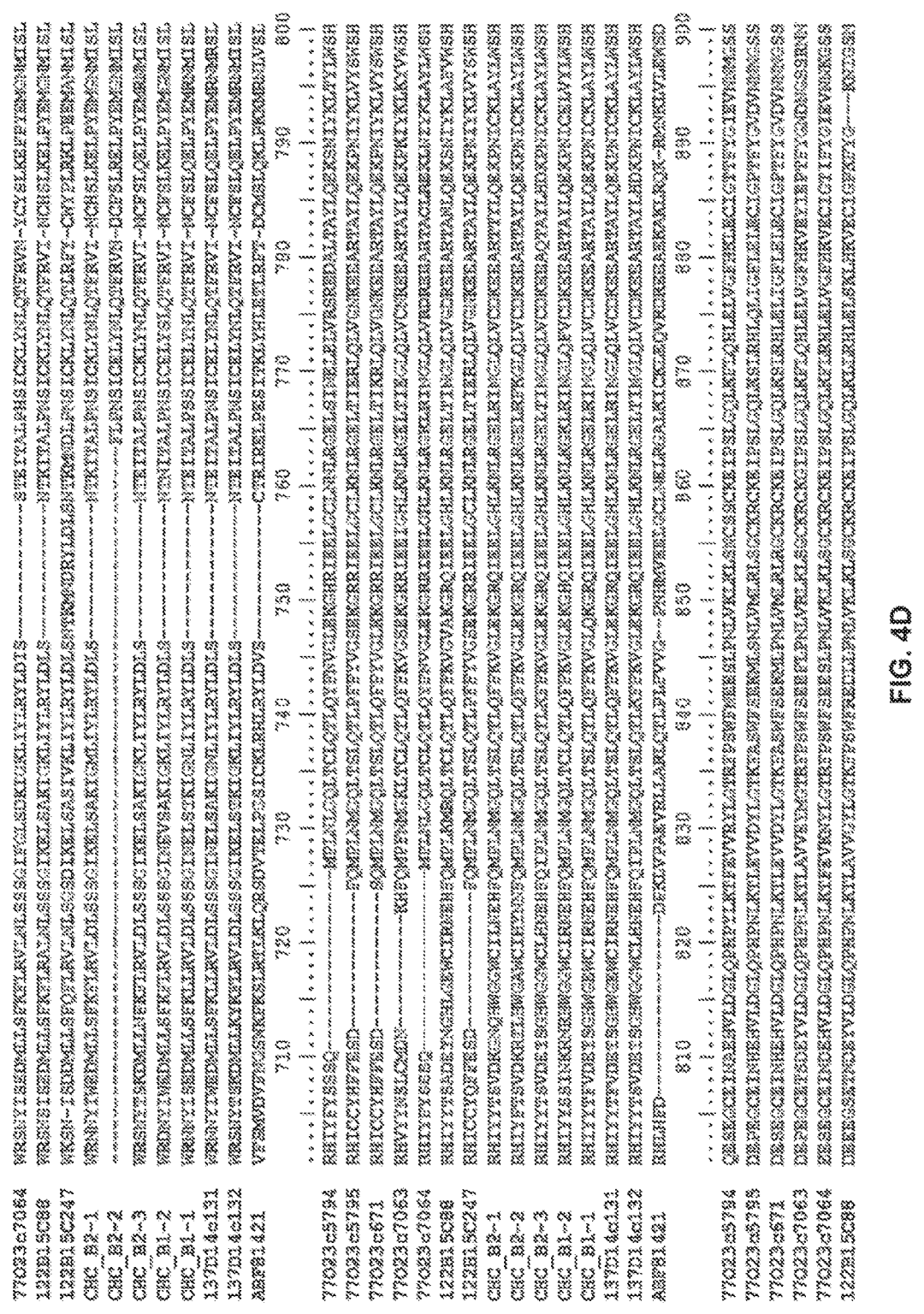
Figure 4F:
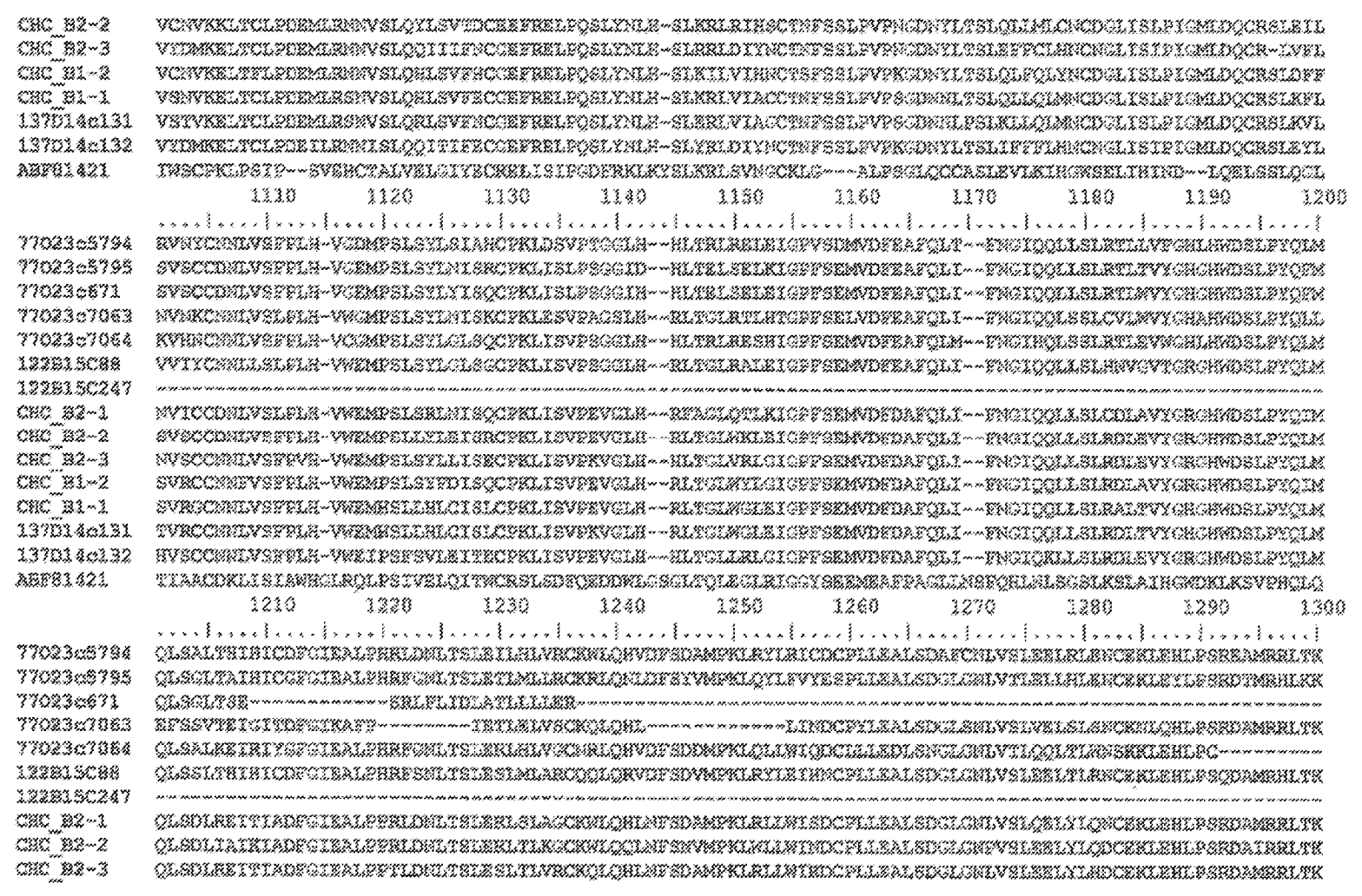
Figure 4G:
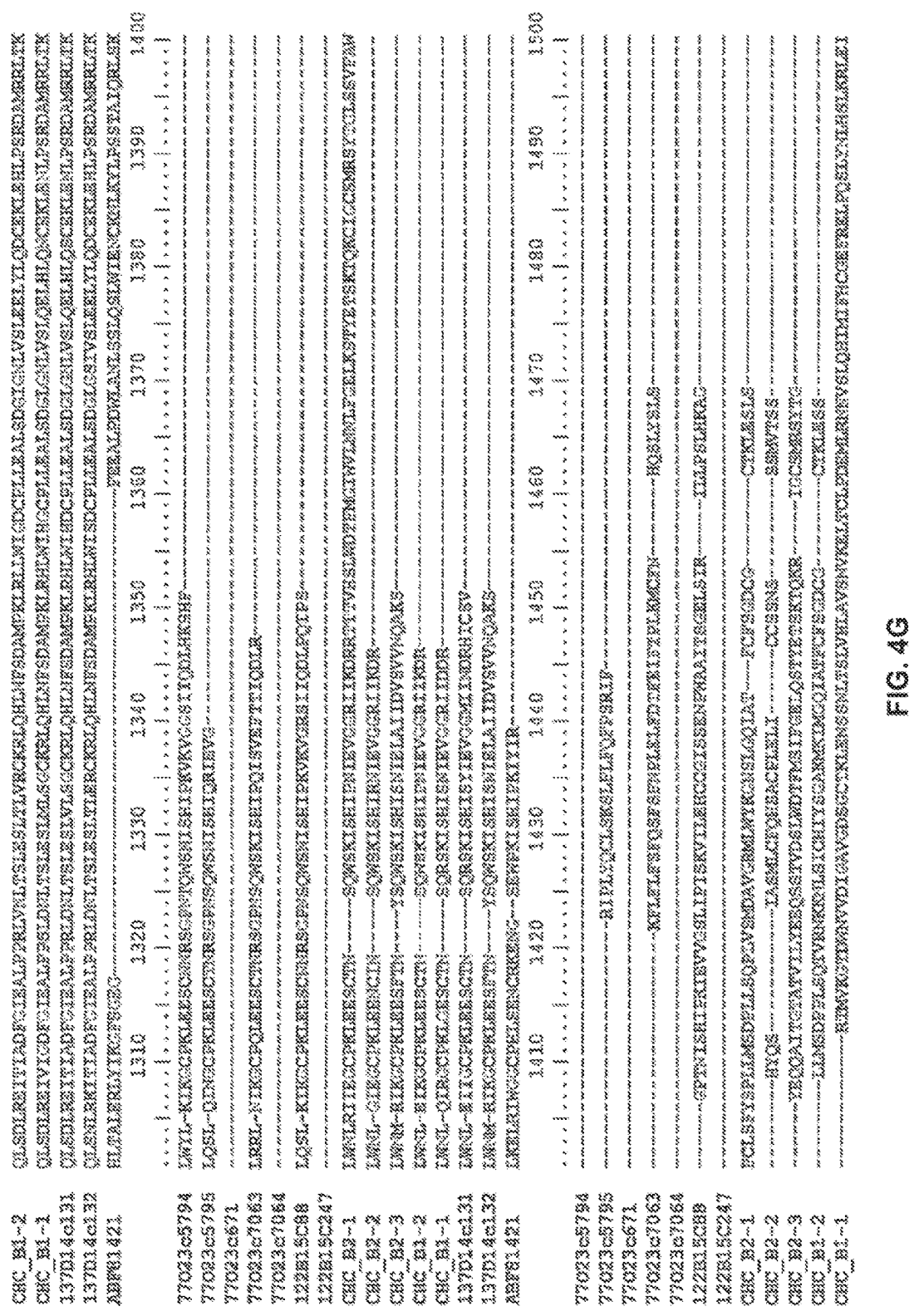
Figure 4I:
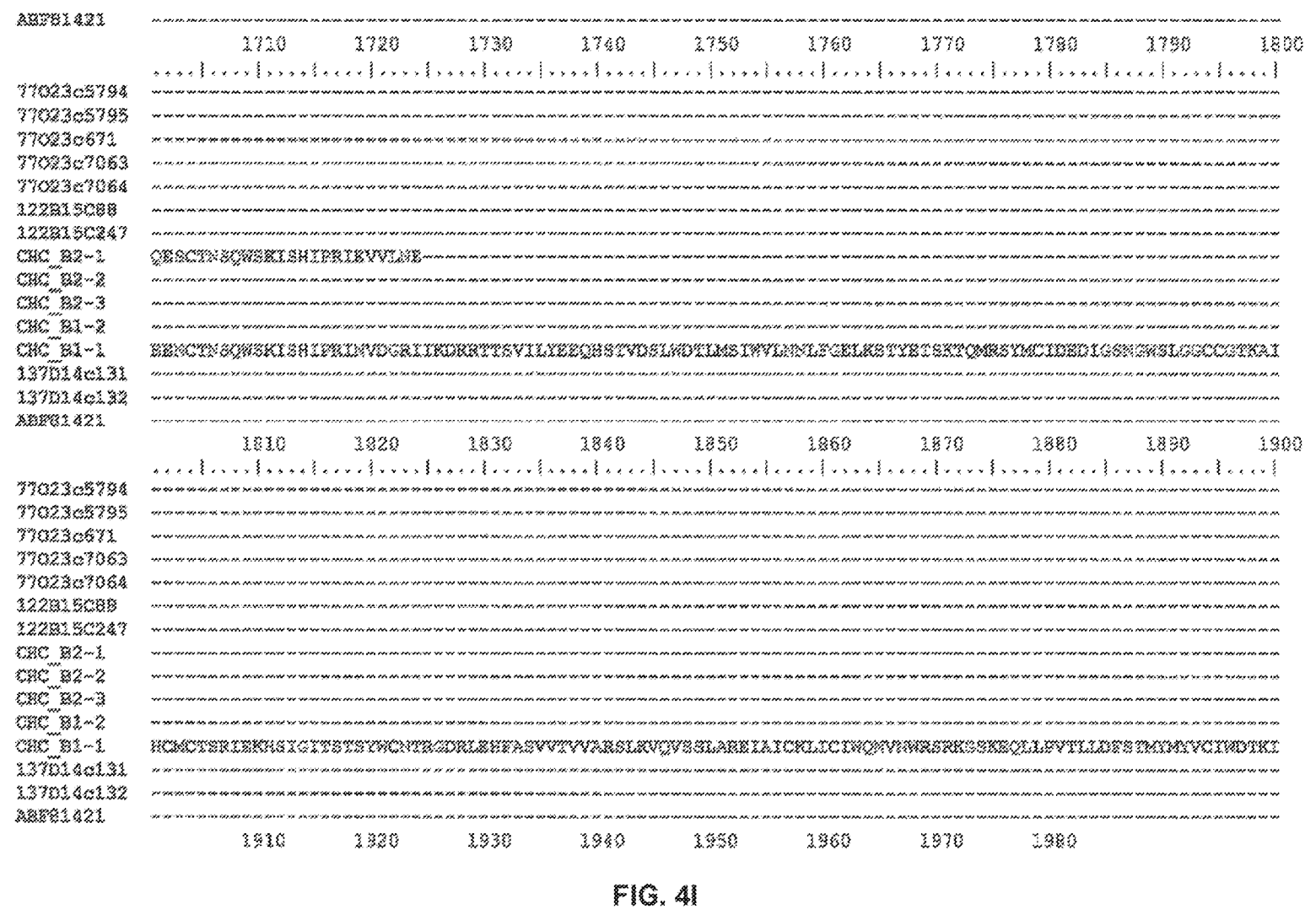
Figure 4J:
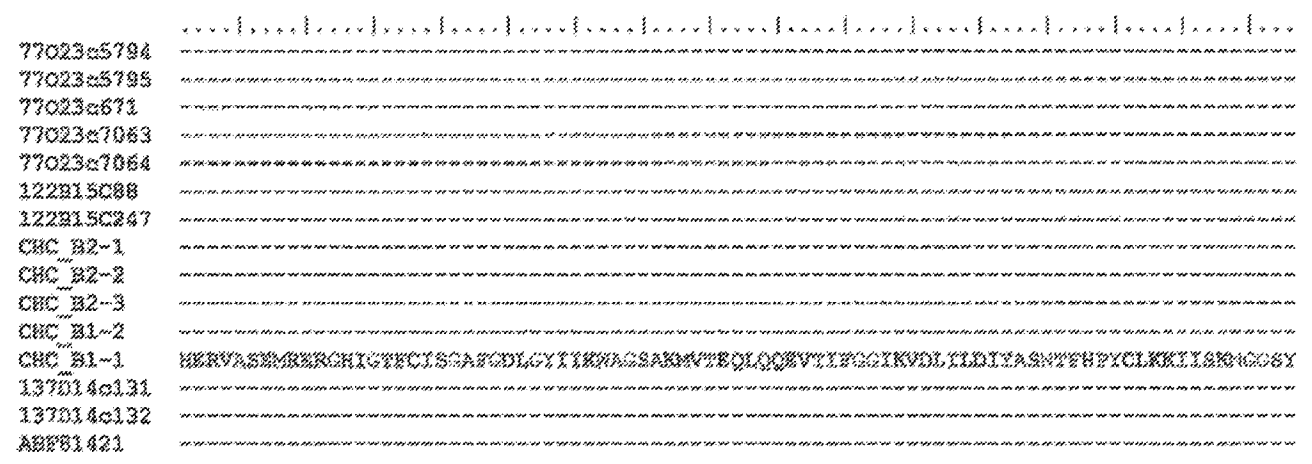

FIG. 4A-K. Amino acid sequence alignment of RGAs from *S. chacoense* (CHC B1-1, CHC B1-2, CHC B2-1, CHC B2-2, and CHC B2-3=Rpi-chc1) and from related sequences deriving from *S. tuberosum* accession RH89-039-16 (77O23c5794, 77O23c5795, 77O23c671, 77O23c7063, 77O23c7064, 122B15C88, 122B15C247, 137D14c131, and 137D14c132).

The protein with unknown function, ABF81421, is encoded by a gene from *Populus trichocarpa*.

FIG. 5. Rpi-chc1 protein domain organization.

The N-terminal CC-domain comprises amino acids 1-231. The amino acids depicted in shading are predicted to fold into a coiled structure using the "COIL" algorithm with window size 14. The central domain NB-ARC domain comprises amino acids 232-557. Domains in shading show similarity to the previously described Kinase 1a, Kinase 2, kinase 3a, GLPL, RNBS-D and MHD domains, respectively. The C-terminal LRR-domain consists of 29 imperfect leucine rich repeats. Conserved hydrophobic amino acids (A, V, L, and F) herein are marked by shading. The consensus is shown at the bottom.

Figure 6:
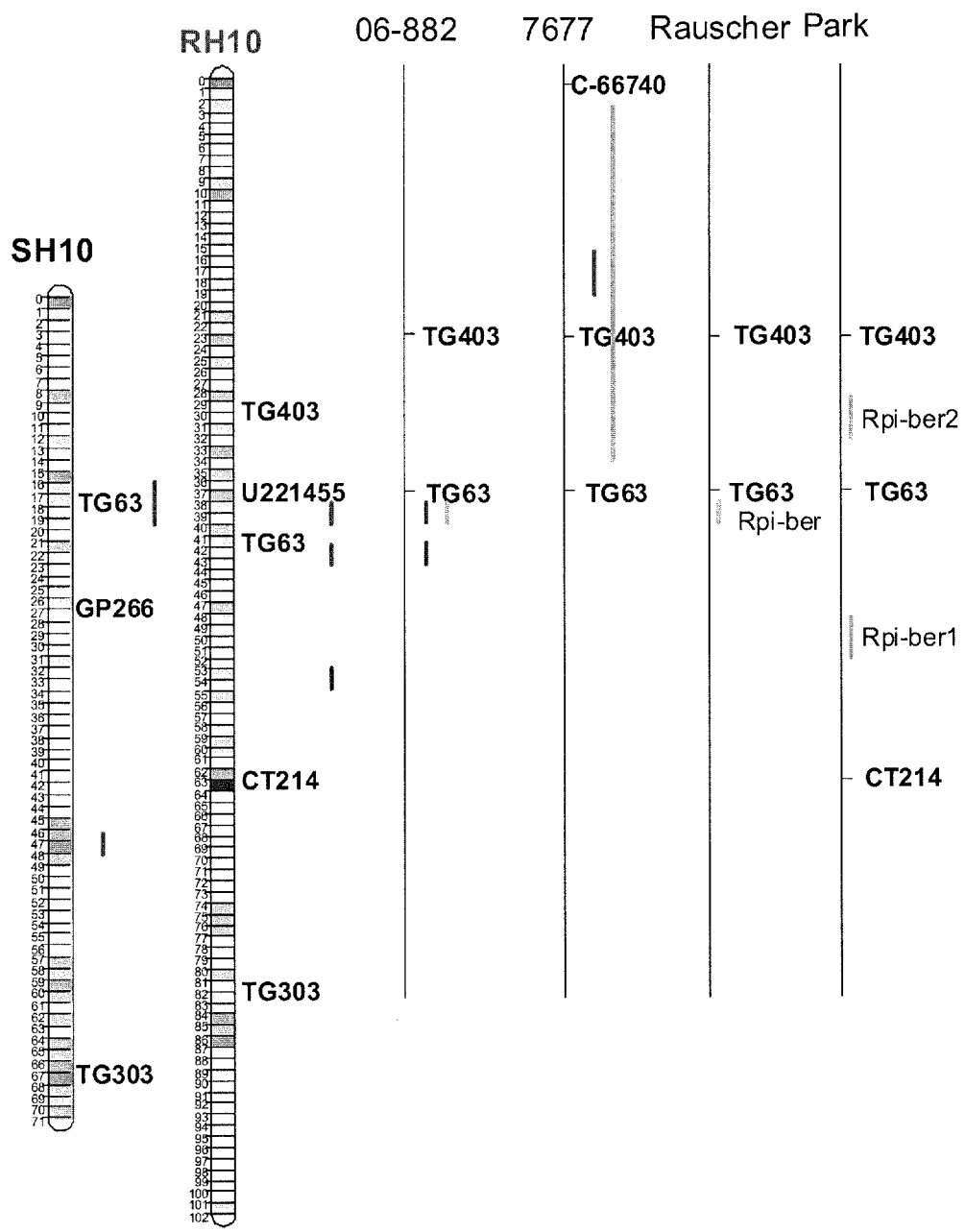

FIG. 6. Map positions of Rpi-chc1 related sequences and late blight resistance genes on chromosome 10.

The UHD maps of the SH and RH chromosomes are shown on left (van Os et al., 2006). 06-882 and 7677, as produced in this study, are shown in the middle. The positions of Rpi-ber (Rauscher et al., 2006), Rpi-ber1 and Rpi-ber2 (Park et al., 2008) are shown on the right. Red lines indicate the location of Rpi-chc1 related sequences. Green lines indicate the location of late blight resistance genes.

FIG. 7A-B. Nucleotide sequence of clone CHC B2-3 (7907 bp) containing the Rpi-chc1 coding- and regulatory sequences. The Rpi-chc1 coding region of 4550 bp is highlighted by shading (3358-7266). The upstream 3357 nucleotides (1-3357) and the downstream 641 nucleotides (7267-7907) harbour the regulatory sequences.

FIG. 8. Functional complementation of *Phytophthora infestans* (Pi) susceptibility in transgenic Desiree plants. Cv Desiree transformed with Rpi-chc1 candidate genes (RGC-1, -2 and -3) were challenged with Pi isolate 90128 in a detached leaf assay. Pictures were taken 6 days post inoculation. Only in transgenics containing RGC-3 resistance was observed.

FIG. 9A-C. Screening of PEX set using co-infiltration. PEX clones were infiltrated in the leafs of *N. benthamiana* alone or co-infiltrated with Rpi-chc1. One week after infiltration pictures were taken. Leaf A, PEX1=RD31, PEX2=RD36. Leaf B PEX1=RD12-1, PEX2=RD12-2. Leaf C PEX1=INF1, PEX2=pGR106. In each leaf the bottom left spot was infiltrated with R3a+avr3a. The bottom right spots were infiltrated with Rpi-chc1. Leaf A shows no identification of a responding effector. B shows necrosis for the interaction of Rpi-chc1 and RD12. C shows autonecrosis for INF1.

FIG. 10. Regulatory elements driving Rpi-chc1 expression.

The Rpi-chc1 ORF was cloned in between one of four promoter/terminator sequences; its own 3 kb promotor and 0.5 kb terminator (p-chc1-long), 0.9 kb of its own promoter and 0.5 kb terminator (p-chc1-short), the double 35S promoter in pMDC32 or the Rpi-blb3 promoter/terminator combination (Lokossou et al., 2009). Co-agro-infiltration with PEX-RD12 was performed at five serial dilutions (OD600=2.0, 1.0, 0.5, 0.2, 0.1), as indicated. R3a mixed with Avr3a was used as positive control (+) and Rpi-chc1 was used as a negative control (−). Pictures were taken 6 days post infiltration.

FIG. 11A-B. Selection of Rpi-chc1 specific primer pairs, used for germplasm screening.

A. Selection of Rpi-chc1 specific primer pairs. Primer combinations a: 581+582, b: 585+587, c: 585+589, d: 586+587, e: 586+589, f: 588+589 refer to Table 8. Templates used were 1: chc543-5 (donor plant for Rpi-chc1), 2: chc544-5 (susceptible parent of mapping population, 3: RH89-39-16 (susceptible plant, donor of Rpi-chc1 homologous sequences, 4: CHC BAC-1 (BAC clone containing three inactive RGA's), 5: CHC BAC-2 (BAC clone containing Rpi-chc1), 6: MQ.

B. 225 genotypes from taxonomic groups 10-12 till 10-17, listed in Table 7 were screened with primer combination D. White arrowheads indicate the fragments of the expected size in 6 genotypes.

FIG. 12. Fylogenetic analysis of Rpi-chc1 homologs.
green: Sequences isolated by Rpi-chc1 homolog PCR (Example 2)
black: Rpi-chc1 homologs identified during map based cloning (Example 1)

FIG. 13A-T. Nucleic acid sequences of 21 mined Rpi-chc1 homologs.

Figure 14E:
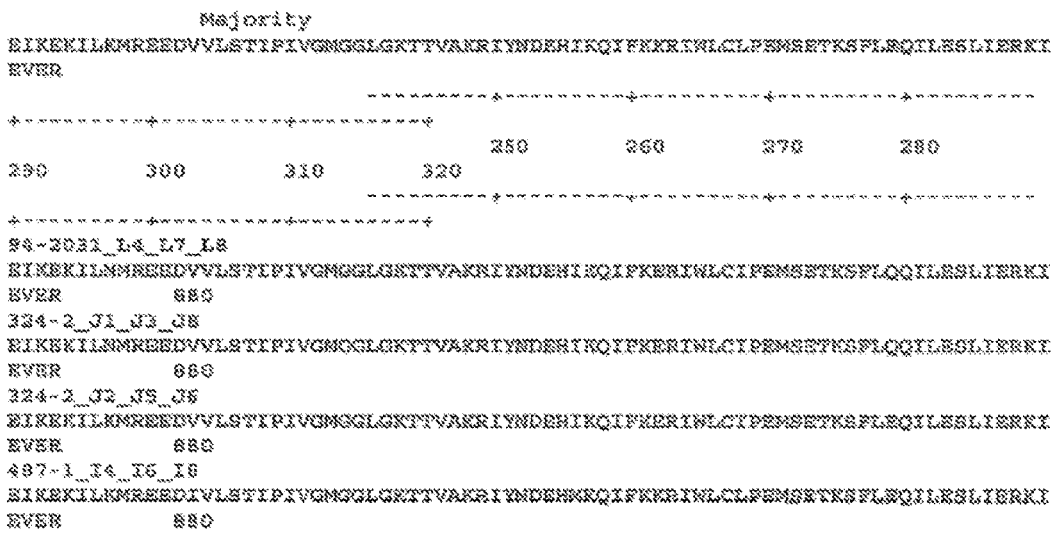
Figure 14A:
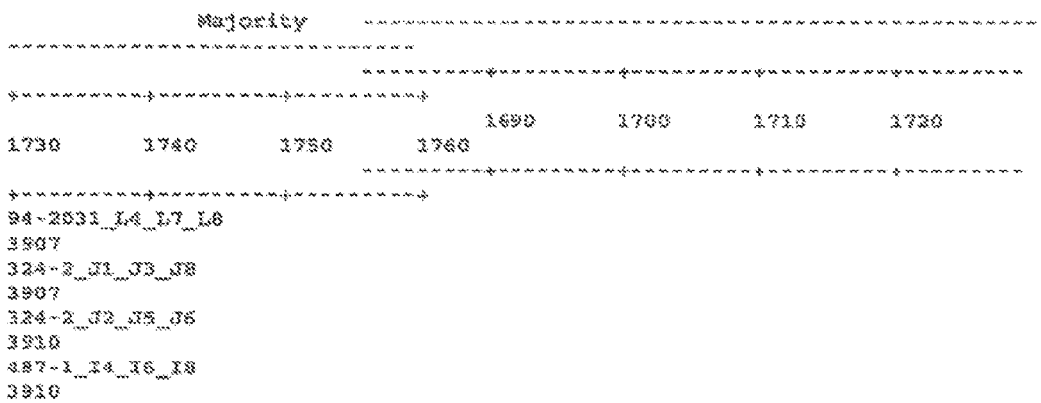
Figure 14A:
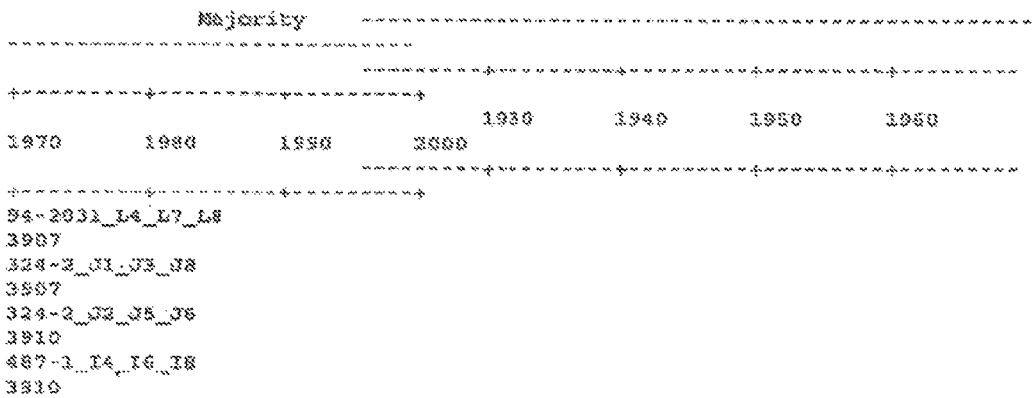

FIG. 14A-AQ. Clustal W alignment of proteins sequences encoded by Rpi-chc1 homologs of FIG. 11 and Rpi-chc1 homologous sequences described in Example 1.

DETAILED DESCRIPTION

As used herein, the term "plant or part thereof" means any complete or partial plant, single cells and cell tissues such as plant cells that are intact in plants, cell clumps and tissue cultures from which potato plants can be regenerated. Examples of plant parts include, but are not limited to, single cells and tissues from pollen, ovules, leaves, embryos, roots, root tips, anthers, flowers, fruits, stems shoots, tubers, including potato tubers for consumption or 'seed tubers' for cultivation or clonal propagation, and seeds; as well as pollen, ovules, leaves, embryos, roots, root tips, anthers, flowers, fruits, stems, shoots, scions, rootstocks, seeds, protoplasts, calli, and the like.

As used herein, the term "population" means a genetically heterogeneous collection of plants sharing a common genetic derivation.

As used herein, the term "variety" is as defined in the UPOV treaty and refers to any plant grouping within a single botanical taxon of the lowest known rank, which grouping can be: (a) defined by the expression of the characteristics that results from a given genotype or combination of genotypes, (b) distinguished from any other plant grouping by the expression of at least one of the said characteristics, and (c) considered as a unit with regard to its suitability for being propagated unchanged.

The term "cultivar" (for cultivated variety) as used herein is defined as a variety that is not normally found in nature but that has been cultivated by humans, i.e. having a biological status other than a "wild" status, which "wild" status indicates the original non-cultivated, or natural state of a plant or accession. The term "cultivar" specifically relates to a potatoplant having a ploidy level that is tetraploid. The term "cultivar" further includes, but is not limited to, semi-natural, semi-wild, weedy, traditional cultivar, landrace, breeding material, research material, breeder's line, synthetic population, hybrid, founder stock/base population, inbred line (parent of hybrid cultivar), segregating population, mutant/genetic stock, and advanced/improved cultivar.

As used herein, "crossing" means the fertilization of female plants (or gametes) by male plants (or gametes). The term "gamete" refers to the haploid or diploid reproductive cell (egg or sperm) produced in plants by meiosis, or by first or second restitution, or double reduction from a gametophyte and involved in sexual reproduction, during which two gametes of opposite sex fuse to form a diploid or polyploid zygote. The term generally includes reference to a pollen (including the sperm cell) and an ovule (including the ovum). "Crossing" therefore generally refers to the fertilization of ovules of one individual with pollen from another individual, whereas "selfing" refers to the fertilization of ovules of an individual with pollen from genetically the same individual.

The term "backcrossing" as used herein means the process wherein the plant resulting from a cross between two parental lines is crossed with one of its parental lines, wherein the parental line used in the backcross is referred to as the recurrent parent. Repeated backcrossing results in the genome becoming more and more similar to the recurrent parent, as far as this can be achieved given the level of homo- or heterozygosity of said parent.

As used herein, "selfing" is defined as refers to the process of self-fertilization wherein an individual is pollinated or fertilized with its own pollen.

The term "marker" as used herein means any indicator that is used in methods for inferring differences in characteristics of genomic sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location.

As used herein, "locus" is defined as the genetic or physical position that a given gene occupies on a chromosome of a plant.

The term "allele(s)" as used herein means any of one or more alternative forms of a gene, all of which alleles relate to the presence or absence of a particular phenotypic trait or characteristic in a plant. In a diploid cell or organism, the two alleles of a given gene occupy corresponding loci on a pair of homologous chromosomes. It is in some instance more accurate to refer to "haplotypes" (i.e. an allele of a chromosomal segment) instead of "allele", however, in these instances, the term "allele" should be understood to comprise the term "haplotype".

The term "heterozygous" as used herein, and confined to diploids, means a genetic condition existing when different alleles reside at corresponding loci on homologous chromosomes.

As used herein, and confined to diploids, "homozygous" is defined as a genetic condition existing when identical alleles reside at corresponding loci on homologous chromosomes.

As used herein, and confined to tetraploids, the term "nulliplex", "simplex", "duplex", "triplex" and "quadruplex", is defined as a genetic condition existing when a specific allele at a corresponding locus on corresponding homologous chromosomes is present 0, 1, 2, 3 or 4 times, respectively. At the tetraploid level the phenotypic effect associated with a recessive allele is only observed when the allele is present in quadruplex condition, whereas the phenotypic effect associated with a dominant allele is already observed when the allele is present in a simplex or higher condition.

The terms "haploid", "diploid" and "tetraploid" as used herein are defined as having respectively one, two and four pairs of each chromosome in each cell (excluding reproductive cells).

The term "haplotype" as used herein means a combination of alleles at multiple loci that are transmitted together on the same chromosome. This includes haplotypes referring to as few as two loci, and haplotypes referring to an entire chromosome depending on the number of recombination events that have occurred between a given set of loci.

As used herein, the term "infer" or "inferring", when used in reference to assessing the presence of the fungal resistance as related to the expression of the Rpi-chc1 gene, means drawing a conclusion about the presence of said gene in a plant or part thereof using a process of analyzing individually or in combination nucleotide occurrence(s) of said gene in a nucleic acid sample of the plant or part thereof. As disclosed herein, the nucleotide occurrence(s) can be identified directly by examining the qualitative differences or quantitative differences in expression levels of nucleic acid molecules, or indirectly by examining (the expression level of) the Rpi-chc1 protein.

The term "primer" as used herein refers to an oligonucleotide which is capable of annealing to the amplification target allowing a DNA polymerase to attach thereby serving as a point of initiation of DNA synthesis when placed under conditions in which synthesis of primer extension product which is complementary to a nucleic acid strand is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and source of primer. A "pair of bi-directional primers" as used herein refers to one forward and one reverse primer as commonly used in the art of DNA amplification such as in PCR amplification.

As used herein, the term "probe" means a single-stranded oligonucleotide sequence that will recognize and form a hydrogen-bonded duplex with a complementary sequence in a target nucleic acid sequence analyte or its cDNA derivative.

The terms "stringency" or "stringent hybridization conditions" refer to hybridization conditions that affect the stability of hybrids, e.g., temperature, salt concentration, pH, formamide concentration and the like. These conditions are empirically optimised to maximize specific binding and minimize non-specific binding of primer or probe to its target nucleic acid sequence. The terms as used include reference to conditions under which a probe or primer will hybridise to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridises to a perfectly matched probe or primer.

Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1 M NaCl, 1% SDS at 37° C., and a wash in 0.1×SSC at 60° C. Hybridization procedures are well known in the art and are described in e.g. Ausubel, F. M., Brent, R., Kingston, R. E., Moore, D. D., Seidman, J. G., Smith, J. A., Struhl, K. eds. (1998) Current protocols in molecular biology. V. B. Chanda, series ed. New York: John Wiley & Sons.

The present invention describes the cloning of the Rpi-chc1 gene. Rpi-chc1 was mapped to a new R gene locus on chromosome 10 using a *S. chacoense* mapping population. Markers highly linked to Rpi-chc1 were used to generate a physical map of the R locus. Three R gene analogs (RGA) present on one of two BAC clones that encompassed the Rpi-chc1 locus were targeted for complementation analysis, one of which turned out to be the functional Rpi-chc1 gene. Outside the R-gene clusters described in this invention, Rpi-chc1 shares the highest amino acid sequence identity (40%) to a protein encoded by a gene with unknown function, designated ABF81421, from poplar (*Populus trichocarpa*). Lower percentages of homology (<30%) were found with R proteins previously identified within the Solanaceae (Table 3).

In a first embodiment, the invention provides an isolated or recombinant nucleic acid sequence comprising a nucleic acid sequence encoding the amino acid sequence Rpi-chc1 (=CHC_B2-3) as presented in FIG. 4A-K or a functional fragment or a functional homologue thereof, i.e. a functional fragment or a functional homologue of the amino sequence as shown in FIG. 4A-K.

The term "nucleic acid" means a single or double stranded DNA or RNA molecule.

Also included are the complementary sequences of the herein described nucleotide sequences.

The term "functional fragment thereof" is typically used to refer to a fragment of the Rpi-chc1 protein that is capable of providing at least partial resistance or increasing resistance in a plant of the Solanaceae family against an oomycete infection. Such a fragment is, for example, a truncated version of the Rpi-chc1 protein as presented in FIG. 4A-K. A truncated version/fragment of the Rpi-chc1 protein is a fragment that is smaller than 1302 amino acids and preferably comprises part of the LRR domain (i.e. part of the leucine-rich repeats domain which stretches from about amino acid 557 to amino acid 1302 of Rpi-chc1) and/or the N-terminal parts of the Rpi-chc1 protein.

The term "functional homologue" is typically used to refer to a protein sequence that is highly homologous to or has a high identity with the herein described Rpi-chc1 protein, which protein is capable of providing at least partial resistance or increasing resistance in a plant of the Solanaceae family against an oomycete infection. Included are artificial changes or amino acid residue substitutions that at least partly maintain the effect of the Rpi-chc1 protein. For example, certain amino acid residues can conventionally be replaced by others of comparable nature, e.g. a basic residue by another basic residue, an acidic residue by another acidic residue, a hydrophobic residue by another hydrophobic residue, and so on. Examples of hydrophobic amino acids are valine, leucine and isoleucine. Phenylalanine, tyrosine and tryptophan are examples of amino acids with an aromatic side chain and cysteine as well as methionine are examples of amino acids with sulphur-containing side chains. Serine and threonine contain aliphatic hydroxyl groups and are considered to be hydrophilic. Aspartic acid and glutamic acid are examples of amino acids with an acidic side chain. In short, the term "functional homologue thereof" includes variants of the Rpi-chc1 protein in which amino acids have been inserted, replaced or deleted and which at least partly maintain the effect of the Rpi-chc1 protein (i.e. at least partly providing or increasing resistance in a plant of the Solanaceae family against an oomycete infection). Preferred variants are variants which only contain conventional amino acid replacements as described above. A high identity in the definition as mentioned above means an identity of at least 80, 85 or 90%. Even more preferred are amino acids that have an identity of 91, 92, 93, 94 or 95%. Most preferred are amino acids that have an identity of 96, 97, 98 or 99% with the amino acid sequence of Rpi-chc1. Homologous proteins are for example the sequences aligned with CHC_B2-3 in FIG. 5 and with the Rpi-chc1 ORF in FIG. 14A-AQ.

A functional homologous nucleic acid sequence is a nucleic acid sequence that encodes a functional homologous protein as described above.

Homology and/or identity percentages can for example be determined by using computer programs such as BLAST, ClustalW or ClustalX.

Many nucleic acid sequences code for a protein that is 100% identical to the Rpi-chc1 protein as presented in FIG. 4A-K. This is because nucleotides in a nucleotide triplet may vary without changing the corresponding amino acid (wobble in the nucleotide triplets). Thus, without having an effect on the amino acid sequence of a protein the nucleotide sequence coding for this protein can be varied. However, in a preferred embodiment, the invention provides an isolated or recombinant nucleic acid sequence as depicted in FIG. 7A-B. In a preferred embodiment, the invention provides an isolated, synthetic, or recombinant nucleic acid that represents the coding sequence (CDS) of the Rpi-chc1 protein, i.e. nucleotides 3358-7266 of FIG. 7A-B (shaded) or a functional fragment or a functional homologue thereof. The nucleotide sequences of homologues with a high identity are represented in FIG. 13A-T, and the corresponding amino acid sequences are given in the alignment of FIG. 14A-AQ.

Fragments as well as homologues of the herein described Rpi-chc1 gene and protein can for example be tested for their functionality by using an *Agrobacterium tumefaciens* transient transformation assays (agro-infiltration) and/or by using a detached leaf assay.

The experimental part for example describes a functional screen for testing candidate genes using agro-infiltration, whereby 4 week old wild type *Nicotiana benthamiana* plants are infiltrated with *Agrobacterium* strains containing the candidate Rpi-chc1 homologues. The infiltrated leaves are subsequently challenged one day after infiltration with a *P. infestans* strain that is virulent on *N. benthamiana*, for example IPO-C or 90128, in detached leaf assays. This system is equally suitable for testing candidate homologous fragments of Rpi-chc1. A person skilled in the art thus can easily determine whether or not an Rpi-chc1 homolog or fragment can be considered to be a functional homolog or fragment.

Transient gene expression, as is achieved through agro-infiltration, is a fast, flexible and reproducible approach to high-level expression of useful proteins. In plants, recombinant strains of *Agrobacterium tumefaciens* can be used for transient expression of genes that have been inserted into the T-DNA region of the bacterial Ti plasmid. A bacterial culture is infiltrated into leaves, and upon T-DNA transfer, there is ectopic expression of the gene of interest in the plant cells. However, the utility of the system is limited because the ectopic RNA expression ceases after 2-3 days. It is shown that post-transcriptional gene silencing (PTGS) is a major cause for this lack of efficiency. A system based on co-expression of a viral-encoded suppressor of gene silencing, the p19 protein of tomato bushy stunt virus (TBSV), prevents the onset of PTGS in the infiltrated tissues and allows high level of transient expression. Expression of a range of proteins was enhanced 50-fold or more in the presence of p19 so that protein purification could be achieved from as little as 100 mg of infiltrated leaf material. Although it is clear that the use of p19 has advantages, an agroinfiltration without p19 can also be used to test the functionality of candidate fragments and functional homologues.

Alternatively, each candidate gene (for example being a fragment or homologue) construct is targeted for transformation to a susceptible potato cultivar, for example Desiree. Primary transformants are challenged in detached leaf assays using for example isolates IPO-0, IPO-C or 90128. Transformants that are resistant to these isolates harbour for example functional fragments or homologues of Rpi-chc1.

In yet another embodiment, the invention provides a vector comprising a nucleic acid as provided herein, i.e. a nucleic acid capable of providing at least partial resistance or increasing resistance in a plant of the Solanaceae family against an oomycete infection. More particularly, the invention provides a vector comprising an isolated, synthetic or recombinant nucleic acid sequence comprising a nucleic acid sequence encoding the amino acid sequence Rpi-chc1 of FIG. 4A-K or a functional fragment or a functional homologue thereof. The invention also provides a vector comprising a nucleic acid sequence as depicted in FIG. 7A-B.

Examples of a suitable vector are pBeloBACII, pBINplus, pKGW-MG or any commercially available cloning vector.

As will be outlined below there are multiple ways in which a nucleic acid of the invention can be transferred to a plant. One suitable means of transfer is mediated by *Agrobacterium* in which the nucleic acid to be transferred is part of a binary vector and hence it is preferred that the above described vector is a binary vector. Another suitable means is by crossing a plant which contains the gene encoding Rpi-chc1 to a plant that does not contain the gene and to identify those progeny of the cross that have inherited the Rpi-chc1 gene.

The invention further provides a host cell comprising a nucleic acid as described herein or a vector as described herein. Examples of a preferred host cell are an *E. coli* cell suitable for BAC clones (e.g. DH10B) or an *Agrobacterium* (host) cell. In another embodiment, said host cell comprises a plant cell. A preferred plant cell is a cell derived from a member of the Solanaceae family and even more preferred said plant cell comprises a cell from *Solanum tuberosum, Solanum lycopersicum*, formerly known as *Lycopersicon esculentum*, pepper and eggplant. From such a cell, a transgenic or genetically modified plant (for example a potato or tomato plant) can be obtained by methods known by the skilled person (for example regeneration protocols).

The invention further provides a leaf, tuber, fruit or seed or part or progeny of a genetically modified plant as described herein.

In yet another embodiment, the invention provides a protein encoded by the herein described isolated or recombinant nucleic acid or a functional fragment or a functional homologue thereof. In a preferred embodiment, the invention provides a protein encoded by a nucleic acid sequence as depicted in FIG. 7A-B. In yet another preferred embodiment, the invention provides a protein comprising the amino acid sequence of FIG. 4A-K or a functional fragment or a functional homologue thereof. Further preferred are the functional (active) proteins depicted in FIG. 14A-AQ, more specifically the proteins designated as 493-7_G12, 543-5_C2, 849-1_M8_M18_M20, 487-1_I4_I6_I8, 94-2031_L4_L7_18, 561-2_K4_K14_K22, 324-2_J1_J3_J8, 852-5_E14_E23, 852-5_E28, 493-9_H5_H30, 493-7_G14_G22, 561-2_K6_K30_K31 and 493-7_G21.

The herein described Rpi-chc1 protein comprises 1302 amino acids and the LRR domains of Rpi-chc1 consist of 29 imperfect repeats (FIG. 5). Interestingly Rpi-chc1 shares the highest homology (75-98%) with other RGAs from the Rpi-chc1 gene cluster from *S. chacoense* and with genes from synhenic clusters on chromosome 10 from *S. tuberosum* (Table 3). A lower (40%), but significant, extent of homology was found with a protein encoded by a gene with unknown function from poplar (accession number ABF81421, Table 3). The different domains of Rpi-chc1 share varying degrees of homology with corresponding domains of the poplar protein encoded by ABF81421. The NBS domain is most conserved (48% aa identity), followed by the CC domain (34% aa identity). The LRR domain is least conserved (21% aa identity). Overall homologies of lower than 33% are found with the FOM2 protein from cucumber, which confers resistance to fungal pathogen *Fusarium oxysporum*, Rpi-blb1 from *S. bulbocastanum*, R3a from *S. demissum*, and RPS1 from soybean (*Glycine max*), which confer resistance to *Phytophthora* sp. These sequence homologies show that Rpi-chc1 is a member of an ancient R-gene family that has not been characterised before in Solanaceae As already described, a functional fragment or a functional homologue thereof of Rpi-chc1 is a fragment or homologue that is capable of providing at least partial resistance or increasing resistance in a plant of the Solanaceae family against an oomycete infection.

Means to test the functionality of a functional fragment or a functional homologue of Rpi-chc1 have been provided above.

Based on the herein described nucleic acid sequences, the invention also provides probes and primers (i.e. oligonucleotide sequences complementary to one of the (complementary) DNA strands as described herein). Probes are for example useful in Southern or northern analysis and primers are for example useful in PCR analysis. Primers based on the herein described nucleic acid sequences are very useful to assist plant breeders active in the field of classical breeding and/or breeding by genetic modification of the nucleic acid content of a plant (preferably said plant is a *Solanum tuberosum, Solanum lycopersicum*, formerly known as *Lycopersicon esculentum*), pepper or eggplant in selecting a plant that is capable of expressing for example Rpi-chc1 or a functional fragment or functional homolog thereof.

Hence, in a further embodiment, the invention provides a binding molecule capable of binding to a nucleic acid encoding Rpi-chc1 or a functional fragment or functional homolog thereof as described herein or its complementary nucleic acid. In a preferred embodiment, said binding molecule is a primer or a probe. As mentioned, such a binding molecule is very useful for plant breeders and hence the invention further provides a method for selecting a plant or plant material or progeny thereof for its susceptibility or resistance to an oomycete infection. Preferably, the nucleic acid of a plant to be tested is isolated from said plant and the obtained isolated nucleic acid is brought in contact with one or multiple (preferably different) binding molecule(s). One can for example use a PCR analysis to test plants for the presence of absence of Rpi-chc1 in the plant genome. Such a method would be especially preferable in marker-free transformation protocols, such as described in WO 03/010319.

The herein described Rpi-chc1 protein can also be used to elicit antibodies by means known to the skilled person. The invention thus also provides an antibody that (specifically) binds to the protein encoded by the herein described isolated or recombinant nucleic acid (for example the nucleic acid sequence of FIG. 7A-B) or an antibody that (specifically) binds to a protein as depicted in FIG. 4A-K or a functional fragment or a functional homolog thereof. Such an antibody is for example useful in protein analysis methods such as Western blotting or ELISA, and hence can be used in selecting plants that successfully express the Rpi-chc1 gene.

Based on the herein provided nucleic acid sequences, the invention also provides the means to introduce or increase resistance against an oomycete infection in a plant. The invention therefore also provides a method for providing at least partial resistance or increasing resistance in a plant against an oomycete infection comprising providing a plant or a part thereof with:

an isolated or recombinant nucleic acid sequence comprising a nucleic acid sequence encoding the Rpi-chc1 amino acid sequence of FIG. 4A-K or a functional fragment or a functional homologue thereof, or an isolated or recombinant nucleic acid sequence as depicted in FIG. 7A-B, or a vector comprising the herein described nucleic acid sequences, or a host cell as described herein.

Such a method for providing at least partial resistance or increasing resistance in a plant against an oomycete infection may be based on classical breeding, departing from a parent plant that already contains the Rp1-chc1 gene or a functional homolog thereof, or it involves the transfer of DNA into a plant, i.e., involves a method for transforming a plant cell comprising providing said plant cell with a nucleic acid as described herein or a vector as described herein or a host cell as described herein.

There are multiple ways in which a recombinant nucleic acid can be transferred to a plant cell, for example *Agrobacterium* mediated transformation. However, besides by *Agrobacterium* infection, there are other means to effectively deliver DNA to recipient plant cells when one wishes to practice the invention. Suitable methods for delivering DNA to plant cells are believed to include virtually any method by which DNA can be introduced into a cell, such as by direct delivery of DNA such as by PEG-mediated transformation of protoplasts, by desiccation/inhibition-mediated DNA uptake (Potrykus et al., Mol. Gen. Genet., 199:183-188, 1985), by electroporation (U.S. Pat. No. 5,384,253), by agitation with silicon carbide fibers (Kaeppler et al., 1990; U.S. Pat. Nos. 5,302,523; and 5,464,765), and by acceleration of DNA coated particles (U.S. Pat. Nos. 5,550,318; 5,538,877; and 5,538,880). Through the application of techniques such as these, cells from virtually any plant species may be stably transformed, and these cells may be developed into transgenic plants.

In case *Agrobacterium* mediated transfer is used, it is preferred to use a substantially virulent *Agrobacterium* such as *A. tumefaciens*, as exemplified by strain A281 or a strain derived thereof or another virulent strain available in the art. These *Agrobacterium* strains carry a DNA region originating from the virulence region of the Ti plasmid pTiBo542, which coordinates the processing of the T-DNA and its transfer into plant cells. *Agrobacterium*-based plant transformation is well known in the art (as e.g. described in, for example by Komari, T. et al.: Plant Transformation Technology: *Agrobacterium*-Mediated Transformation, in: Handbook of Plant Biotechnology, Eds. Christou, P. and Klee, H., John Wiley & Sons, Ltd, Chichester, UK 2004, pp. 233-262). Preferably a marker-free transformation protocol is used, such as described in WO 03/010319.

Alternatively, the nucleic acid of the Rpi-chc1 gene or a functional homolog thereof may be introduced into a plant by crossing. Such a crossing scheme starts off with the selection of a suitable parent plant. This may for instance be an original *Solanum chacoense* variety (such as accession CHC543-5), an original *S. tarijense* variety (such as accession TAR852-5), an original *S. sucrense* variety (such as accession SUC849-2) or an original *S. berthaultii* variety (such as accession BER481-3 or BER94-2031) or a plant that has obtained the desired nucleic acid by genetic engineering as described above.

Any suitable method known in the art for crossing selected plants may be applied in the method according to the invention. This includes both in vivo and in vitro methods. A person skilled in the art will appreciate that in vitro techniques such as protoplast fusion or embryo rescue may be applied when deemed suitable.

Selected plants that are used for crossing purposes in the methods according to the invention may have any type of ploidy. For example, selected plants may be haploid, diploid or tetraploid. However, crossing diploid plants, such as *S. chacoense, S. tarijense* and *S. berthaultii*, will only provide diploid offspring. Crossing a diploid plant with a tetraploid plant will result in triploid offspring that is sterile.

Thus, when plants are selected that are diploid, their ploidy must be increased to tetraploid level before they can be crossed with another tetraploid plant in the methods according to the invention. Methods for increasing the ploidy of a plant are well known in the art and can be readily applied by a person skilled in the art. For example, ploidy of a diploid plant for crossing purposes can be increased by using 2N gametes of said diploid plant. Ploidy can also be increased by inhibiting chromosome segregation during meiosis, for example by treating a diploid plant with colchicine. By applying such methods on a diploid plant, embryos or gametes are obtained that comprise double the usual number of chromosomes. Such embryos or gametes can then be used for crossing purposes. For potatoes a resistant tetraploid plant is preferred, since tetraploid plants are known to have higher yields of tubers.

Since the resistance characteristic has appeared to be a dominant trait, it is sufficient if only one allele with the functional gene is present.

Preferably, selected plants are crossed with each other using classical in vivo crossing methods that comprise one or more crossing steps including selfing. By applying such classical crossing steps characteristics of both the parents can be combined in the progeny. For example, a plant that provides a high yield can be crossed with a plant that contains large amounts of a certain nutrient. Such a crossing would provide progeny comprising both characteristics, i.e. plants that not only comprise large amounts of the nutrient but also provide high yields.

When applying backcrossing, F1 progeny is crossed with one of its high-yielding parents P to ensure that the characteristics of the F2 progeny resemble those of the high-yielding parent. For example, a selected diploid potato with oomycete resistance is made tetraploid by using colchicine and then crossed with a selected high-yielding tetraploid potato cultivar, with the purpose of ultimately providing a high-yielding tetraploid progeny having oomycete resistance. Also selfing may be applied. Selected plants, either parent or progeny, are then crossed with themselves to produce inbred varieties for breeding. For example, selected specimens from the above mentioned F1 progeny are crossed with themselves to provide an F2 progeny from which specimens can be selected that have an increased level of resistance.

After transfer of a nucleic acid into a plant or plant cell, it must be determined which plants or plant cells have been provided with said nucleic acid. When selecting and crossing a parental genotype in a method according to the invention, a marker is used to assist selection in at least one selection step. It is known in the art that markers, indicative for a certain trait or condition, can be found in vivo and in vitro at different biological levels. For example, markers can be found at peptide level or at gene level. At gene level, a marker can be detected at RNA level or DNA level. Preferably, in the present invention the presence of such a marker is detected at DNA level, using the above described primers and/or probes. Alternatively, proper expression of the Rpi-chc1 protein or a functional homolog thereof can be assessed in plant parts by performing an immunoassay with an antibody that specifically binds the protein. Next to the primers and probes according to the invention, use can also be made of specific markers that are to be found in the vicinity of the coding sequence. Such markers are indicated in the experimental part below and comprise the markers as indicated in Table. 2. Markers are derived from accompanying BAC sequences.

In case of transgenic approaches selecting a transformed plant may be accomplished by using a selectable marker or a reporter gene. Among the selective markers or selection genes that are most widely used in plant transformation are the bacterial neomycin phosphotransferase genes (nptI, nptII and nptIII genes) conferring resistance to the selective agent kanamycin, suggested in EP131623 and the bacterial aphIV gene suggested in EP186425 conferring resistance to hygromycin. EP 275957 discloses the use of an acetyl transferase gene from *Streptomyces viridochromogenes* that confers resistance to the herbicide phosphinotricin. Plant genes conferring relative resistance to the herbicide glyphosate are suggested in EP218571. Suitable examples of reporter genes are beta-glucuronidase (GUS), beta-galactosidase, luciferase and green fluorescent protein (GFP).

TABLE 2

Primer sequences for amplification of specific (parts of) nucleotide sequences according to the invention.

| marker | Forward | F primer sequence 5'-3' | Reverse | R primer sequence 5'-3' | target(s) | polymorphism |
|---|---|---|---|---|---|---|
| 2D06_3D21_C27-1 | MN469 | TGTTTGATCTCCTCACCCATC | MN470 | GTTCCCCTCTTCTCCCTCTCC | 7650 | CAPS, enzyme NlaIII |
| 2D06_3D21_C27-7 | MN491 | TGAGAATTTACAGTGGTTTGTTGC | MN492 | GATCAATCAATCCATCATAACGTC | 7650 | CAPS, enzyme RsaI |
| CHC_B07_1_C15_RP' | MN396 | CGACCCCACCCCTCATCCTT | MN397 | CGCCAACATATTCGTGCTTCA | 7650 | CAPS, MnlI |
| CHC_B07_1_C15_T7 | MN382 | CGTGAGCTAAGCATGAACACC | MN383 | GCACGTTTCTCATAATCCCATC | 7650 | CAPS, enzyme HinfI |
| COS6740 | JV57 | ATGTGACTCCGCATTGCAGCTC | JV58 | ATCTCATCTTATTAATCTGATTCAAAGC | 7650 | CAPS, enzyme FspBI |
| CT214 | JV117 | GAACCGAAAGAGTCTGATAG | JV118 | CCCGCTGCCTATGGAGAGT | 06-882 | CAPS, enzyme DdeI |
| RH036A10S | MN161 | GTGCATTACCCGTGTTATTTTGC | MN162 | TGGGTCTTTGGAAGACAGGTG | 7650 | CAPS, enzyme DdeI |
| RH046C09T | MN257 | GGCCACGTATTAACAATTTTGAG | MN258 | GCATAGCAATTGAAAGCCTAAAC | 06-882 | CAPS, enzyme HpyCH4IV |
| RH070C16S | MN300 | TGTTTGACATCCTCCAGCAG | MN301 | CTCAGCTTGGGTTTGTTTC | 06-882 | CAPS, enzyme AluI |
| RH077O23S | MN263 | ACATTAAGGCTGCCCACAG | MN264 | GCAGTTGCACAATTTTACGTC | 06-882 | CAPS, enzyme SduI |
| RH092A09S | MN151 | TCAAGGTGGCATTCTTCAAC | MN152 | AAGCAAGACTTTGCGATTC | 7650 | CAPS, enzyme NlaIII |
| RH097D21_C21-4 | MN406 | TTGCTTTGAGTTGTTGCCTG | MN407 | TATGCATCATCATCGCGAAC | 06-882 | CAPS, enzyme HpyCH4IV |
| RH099F09T | MN292 | TGTTTGATGCTTGGGTAGTG | MN293 | CAGCGTTGAACACTCAAAATC | 7650 | CAPS, enzyme SsiI |
| RH106G03S | MN296 | TGGCCTAAAGTTGGCTGTTG | MN297 | TCCAACCAAAACATGAGACG | 06-882 | CAPS, enzyme Bsh1236I |
| RH106G03T | MN294 | CCCCGAATGATAAGTCCAAC | MN295 | TGAGGCATAGAGAACAATCTTTG | 7650 | CAPS, enzyme MseI |
| RH106G03T | MN294 | CCCCGAATGATAAGTCCAAC | MN295 | TGAGGCATAGAGAGAACAATCTTTG | 06-882, 06-882, RH | CAPS, enzyme RsaI |
| RH137D14_C37-2 | JV233 | TTTCTCTACTGTCTGGCTTGCTTGGGGATAC | JV234 | GAGCTGCTTCTTTGGACTTTCTTCTGACCT | BAC(s) | CAPS, enzyme XapI |
| RH137D14_C37-7 | MN429 | AAAATTGCTCGCCAAAGAAGC | MN430 | AGTCCGATACGCCAACCTAC | 7650 | CAPS, enzyme XapI |
| RH173M16T | MN165 | TCTTTGCTAGTCGTTGGTTGAG | MN166 | TGGGTTTCCCAAGTTGAAAG | 7650 | CAPS, enzyme Bme1390I |
| RH173M16T | MN165 | TCTTTGCTAGTCGTTGGTTGAG | MN166 | TGGGTTTCCCAAGTTGAAAG | 06-882 | CAPS, enzyme HpyF1oVI |
| RH198E12T | MA78 | GACTCTGCCGTGATTGCTGAA | MA79 | CACCGGGAAGACGCTGTTT | 06-882 | CAPS, enzyme RsaI |
| RH19E15S | MN177 | ACTTGGGAAACCCAGGAGAG | MN178 | TTTATGGTCCTGGGTCTTGG | RHxSH | CAPS, enzyme Bme1390I |
| RH19E15S | MN177 | ACTTGGGAAACCCAGGAGAG | MN178 | TTTATGGTCCTGGGTCTTGG | 06-882 | CAPS, enzyme HpyCH4IV |

TABLE 2-continued

Primer sequences for amplification of specific (parts of) nucleotide sequences according to the invention.

| marker | Forward | F primer sequence 5'-3' | Reverse | R primer sequence 5'-3' | target(s) | polymorphism |
|---|---|---|---|---|---|---|
| RH19E15S | MN177 | ACTTGGGAAACCCAGGAGAG | MN178 | TTTATGGTCCTGGGTCTTGG | 7650 | CAPS, enzyme MnII |
| RH19E15T | MN173 | GATGCATATCATCAAATTCAATCTC | MN174 | CTCCGGTGTTATCGACGTG | 06-882 | CAPS, enzyme HinI II |
| RH19E15T | MN173 | GATGCATATCATCAAATTCAATCTC | MN174 | CTCCGGTGTTATCGACGTG | 7650 | CAPS, enzyme XapI |
| TG233 | JV95.2 | CATGCCTTTTTCTTGGGATG | JV96 | TGGAACCCCTTTAACTGTGC | 06-882 | CAPS, enzyme AluI |
| TG63 | JV23 | TCCAATTGCCAGACGAA | JV24 | TAGAGAAGGCCCTTGTAAGTTT | 06-882 | CAPS, enzyme Bsh1236I |
| TG63 | JV23 | TCCAATTGCCAGACGAA | JV24 | TAGAGAAGGCCCTTGTAAGTTT | 7650 | CAPS, enzyme HhaI |
| TG63 | JV80 | CTGCATCAACTGGATATTCC | JV81 | GTTGAGCAGTGCAATGTAC | RHxSH | CAPS, enzyme SsiI |
| U221455 | JV82 | AGGGCTTCTTATTATCTTTCTC | JV83 | ACCACAAGCAATCATTCTACACC | 7650 | CAPS, enzyme AluI |
| Rpi-chc1 locus directed profiling F1 | JV 162 | ctaatycaactytgatggcwgaagg | adaptor | ACTCGATTCTCAACCCGAAAG | SHxRH, 06-882 | MDP |
| Rpi-chc1 locus directed profiling F2 | JV 163 | ctaccamkycgasaracagattcc | | | SHxRH, 06-882 | MDP |
| Rpi-chc1 locus directed profiling R1 | JV 164 | tggmckragaaamccttcwgccatc | | ACTCGATTCTCAACCCGAAAG | SHxRH, 06-882 | MDP |
| Rpi-chc1 locus directed profiling R2 | JV 165 | ccwarrccwsccatwccyactat | | ACTCGATTCTCAACCCGAAAG | SHxRH, 06-882 | MDP |
| RH099F09S | MN290 | CATGAGAAATGAACCCCTCAC | MN291 | AACGTGCAGAGGTATTTTGG | 7650 | SCAR |
| RH134D08S | MN286 | TTTTCCACAAGAATAGCCAAGAC | MN287 | ATCTGGGCTCATCCGAATC | 06-882 | SCAR |
| RH056H18S | MN320 | GGCCATTGTTTGTGAAACTG | MN321 | CGTCGGGAAGTTCACATTGC | 7650 | SCAR |
| RH40G17T | MN251 | TAGGGGGGTGTCAAAATGAGC | MN252 | GCTGGAACTTCACAGTAAAACC | 7650 | SCAR |
| RH40G17T | MN251 | TAGGGGGGTGTCAAAATGAGC | MN252 | GCTGGAACTTCACAGTAAAACC | 06-882 | SCAR |
| RH19E15T | MN173 | GATGCATATCATCAAATTCAATCTC | MN174 | CTCCGGTGTTATCGACGTG | RHxSH | SCAR |
| RH092A09S | MN151 | TCAAGGTGGCATTCTTCAAC | MN152 | AAGCAAGGACTTTGCGATTC | RHxSH | SCAR |
| E39/M56_GW fragment | MN113 | CTAAGGGTTCCTCTCCGCAAG | MN114 | CAAATTGGACCGAACCTTTG | 7650 | SCAR |
| RH091C10T | MN304 | CCCGAGATCCAGTGAAATTG | MN305 | GGTTCTGAACTTCATCCTATTCCTC | 06-882 | SCAR |
| RH046C09S | MN253 | TAGGGGGGTGTCAAAATGAGC | MN254 | ATGGCAAAACGGAGTTAGGG | 06-882 | SCAR |
| RH047F10S | MA92 | TTGTGTACATTCTATCCCCCG | MA93 | TGGCGTATGCATCAATGG | 06-882 | SCAR |

TABLE 2-continued

Primer sequences for amplification of specific (parts of) nucleotide sequences according to the invention.

| marker | Forward | F primer sequence 5'-3' | Reverse | R primer sequence 5'-3' | target(s) | polymorphism |
|---|---|---|---|---|---|---|
| RH106G03T | MN294 | CCCCGAATGATAAGTCCAAC | MN295 | TGAGGCATAGAGAACAATCTTTG | 543-5 BAC(s) | |
| CHC_B07_1_C15_T7 | MN382 | CGTGAGCTAAGCATGAACACC | MN383 | GCACGTTTCTCATAATCCCATC | RH BAC(s) 543-5 | |
| CHC_B07_1_C15_RP | MN396 | CGACCCCACCCCTCATCCTT | MN397 | CGCCAACATATTCGTGCTTCA | BAC(s) 543-5 | |
| RH137D14 C37-7 | MN429 MN38 | AAAATTGCTGCCAAAGAAGC CGAACTCTGAGATTGGGACTATG | MN430 MN39 | AGTCCGATACGCCAACCTAC CACGAATAGAACAATAATAGAAAAAG | BAC(s) RH BAC | |
| E46-M48c | | | | | library | |
| RH099F09S | MN290 | CATGAGAAATGAACCCCTCAC | MN291 | AACGTGCAGAGGTATTTTTGG | RH BAC(s) | |
| RH134D08S | MN286 | TTTTCCACAAGAATAGCCAAGAC | MN287 | ATCTGGGCTCATCCGAATC | RH BAC(s) | |
| RH40G17T | MN251 | TAGGGGGTGTCAAAATGAGC | MN252 | GCTGGAACTTCACAGTAAAACC | RH BAC(s) | |
| RH199E15T | MN173 | GATGCATATCATCAAATTCAATCTC | MN174 | CTCCGGTGTTATCGACGTG | RH BAC(s) | |
| RH137D14T | MA74 | CTACAAATGATAAATAAGCAAACT | MA75 | AATAGGTGGAGGGAGGAC | RH BAC(s) | |
| RH137D14S | MA72 | GAAGCAAACATCAATAATA | MA73 | TTCCCCTCAAATCATAG | RH BAC(s) | |
| RH184J01T | MN288 | CCGATTTACTATTGGTTCATGC | MN289 | TCAAATTTCGATTGGCTTGC | RH BAC(s) 543-5 | |
| RH184J01T | MN288 | CCGATTTACTATTGGTTCATGC | MN289 | TCAAATTTCGATTGGCTTGC | BAC(s) | |
| RH070C16S | MN300 | TGTTTGACATCCTCCAGCAG | MN301 | CTCAGCTTGGGCTTTGTTTC | BAC(s) | |

In a preferred embodiment, the invention provides a method for providing at least partial resistance or increasing resistance in a plant against an oomycete infection comprising providing a plant or a part thereof with:

an isolated or recombinant nucleic acid sequence comprising a nucleic acid sequence encoding the Rpi-chc1 amino acid sequence of FIG. 4A-K or a functional fragment or a functional homologue thereof, or an isolated or recombinant nucleic acid sequence as depicted in FIG. 7A-B, or an isolated or recombinant nucleic acid sequence encoding a protein selected from the group of 493-7_G12, 543-5_C2, 849-1_M8_M18_M20, 487-1_I4_I6_I8, 94-2031_L4_L7_18, 561-2_K4_K14_K22, 324-2_J1_J3_J8, 852-5_E14_E23, 852-5_E28, 493-9_H5_H30, 493-7_G14_G22, 561-2_K6_K30_K31 and 493-7_G21 as depicted in FIG. 13A-T, a vector comprising the herein described nucleic acid sequences, or a host cell as described herein, wherein said oomycete comprises *Phytophthora*, preferably *Phytophthora infestans* and/or wherein said plant comprises a plant from the Solanaceae family, preferably a potato or tomato plant, more preferably a tetraploid potato plant.

The invention also provides a plant that is obtainable by using a method for providing at least partial resistance or increasing resistance in a plant against an oomycete infection as described above. A preferred plant is a plant from the Solanaceae family and even more preferred said plant is a *Solanum tuberosum* or a *Solanum lycopersicum*, formerly known as *Lycopersicon esculentum, Solanum melononga, Capsicum* spp., such as *C. annuum, C. baccatum, C. chinense, C. frutescens* and *C. pubescens*. The invention thus also provides a plant that has been provided with a nucleic acid encoding a Rpi-chc1 protein or a functional fragment or a functional homologue thereof.

The invention further provides a plant part or progeny of a plant according to the invention comprising a nucleic acid encoding the Rpi-chc1 amino acid sequence of FIG. 4A-K or a functional fragment or a functional homologue thereof.

In a preferred embodiment, the herein described nucleic acid is transferred to a *Solanum* variety other than *Solanum chacoense*, i.e. the herein described nucleic acid is preferably provided to a non-*chacoense* background, preferably *S. lycopersicon* or *S. tuberosum*. Of the latter most preferred is a tetraploid variety and more preferably to a commercial interesting variety such as Bintje, Desiree or Premiere, Spunta, Nicola, Favorit, Russet Burbank, Aveka or Lady Rosetta.

It is also possible to provide the resistance according to the invention to a plant that is already partially resistant to an oomycete infection, wherein said plant is provided with a nucleic acid encoding a further resistance gene, such as Rpi-blb1, -2, -3, Rpi-vnt1 or Rpi-mcq1.

The invention further provides use of an isolated or recombinant nucleic acid sequence comprising a nucleic acid sequence encoding the Rpi-chc1 amino acid sequence of FIG. 4A-K or a functional fragment or a functional homologue thereof or use of an isolated or recombinant nucleic acid sequence as depicted in FIG. 7A-B or use of a vector comprising any of said nucleic acid sequences or use of a host cell comprising any of said nucleic acid sequences or said vector for providing a plant with at least partial resistance against an oomycete infection. In a preferred embodiment, said oomycete comprises *Phytophthora* and even more preferably *Phytophthora infestans*. In yet another preferred embodiment said plant comprises *Solanum tuberosum* or *Solanum lycopersicum*, formerly known as *Lycopersicon esculentum*.

In yet another embodiment, the invention provides a method for producing Rpi-chc1 protein or a functional fragment or a functional homologue thereof comprising functionally linking a nucleic acid as described herein to a regulatory sequence and allowing said nucleic acid to be expressed in a host cell. Examples of a regulatory sequence are a promoter and/or terminator sequence. Further, as will become clear from Example 2, it is preferred that the Rpi-chc1 sequence is expressed under control of its own promoter and terminator. Therefore, the invention further provides the promoter and/or terminator sequences of Rpi-chc1 (FIG. 7A-B). FIG. 7A-B show the nucleotide sequence of clone CHC B2-3 (7907 bp) containing the Rpi-chc1 gene and regulatory sequences. The Rpi-chc1 coding region of 4550 bp is highlighted in shading (nt 3358-7266). The upstream 3357 nucleotides (nt 1-3357) and the downstream 641 nucleotides (nt 7267-7907) harbour the regulatory sequences that ensure correct expression of the gene. The skilled person is very well capable of cloning (part of) said regulatory sequences and testing their efficiency in transcription. It has further been found that even a better expression is obtained with a truncated promoter, i.e. a promoter containing less than 1000, preferably not more than 900 base pairs upstream of the gene sequence.

The invention will be explained in more detail in the following, non-limiting examples.

EXPERIMENTAL PART

Example 1: Population Development

A recent taxonomic regrouping of the *Solanum* section Petota revealed the lack of species structure in this section (Jacobs et al., 2008). In order to identify late blight resistance traits from the taxonomic group 10-14 (Jacobs et al., 2008) we selected several accessions and tested their resistance levels to *Phytophthora infestans* in field trials. Five accessions, that were previously determined as *S. tarijense* (TAR), *S. berthaultii* (BER), and *S. chacoense* (CHC), with high resistance levels were selected (TAR852-5, BER94-2031-01, BER481-3, BER493-7, CHC543-5). In order to study the genetic basis of these resistances, crosses were generated using BER493-7, CHC543-5, BER94-2031-01 as resistant parents. The resulting F1 populations were tested for the segregation of resistance to *P. infestans* in a detached leaf assay (Table 1).

TABLE 1 population analysis

| pop number | R-parent | S-parent | Individuals | DLA R:S:Q | isolate |
|---|---|---|---|---|---|
| 06-882 | 94-2031-01 | G254 | 94 | 1:1:0 | IPO-C |
| 7677 | BER 493-7 | RH 89-039-16 | 71 | 3:3:1 | 90128 |
| 7650 | CHC 543-5 | CHC 544-5 | 212 | 1:1:0 | 90128 |

Detached leaf assays were performed in the offspring of the indicated crosses. Segregation ratios of plants with R(esistant), S(usceptible) or Q(uestionable) phenotypes were determined.

In populations 7650 and 06-882 a clear 1:1 segregation was found, a hallmark for the segregation of a single dominant resistance gene. In population 7767 also a 1:1 segregation was found, however, also a group of 10 plants with intermediate (Q) resistance levels was found.

Map Positions of Rpi-chc1 and Rpi-ber

From literature it was known that a late blight resistance gene from *S. berthaultii* (Rpi-ber) was closely linked to TG63 on the long arm of chromosome 10 (Rauscher et al., 2006), a region to which also the tomato Ph-2 QTL from *S. pimpenellifolium* mapped (Moreau et al., 1998). We therefore developed CAPS markers in TG63 in the three populations. Using the polymorphism described in Table 2, it was found that the resistances in 06-882 and 7650 were closely linked to TG63 since one and two recombinants were found respectively. Also the resistance in 7677 was linked to TG63 albeit a higher recombination frequency (15 recombinations) was observed. It is concluded that this area on chromosome 10 is very important for resistance to late blight. Therefore, we set out to exploit the well characterised RH89-039-16 physical map in order to generate a reference map of the TG63 locus. Using the polymorphism described in Table 2, TG63 was mapped to RH10B41. At this map-position the contig 6701 was anchored. BAC end sequences in this contig were used to generate markers suitable for mapping in population 7650. RH199E15S (Table 2) was found to co-segregate with resistance in 7650 and 06-882, indicating that 6710 from RH89-039-16 was in a locus synthenic with the Rpi-chc1 and Rpi ber locus.

Besides anchoring TG63 genetically, it was also located in the physical map of RH89-039-16 by PCR screening the RH BAC library. A positive contig, 2203, was found. Remarkably, contig 2203 was anchored to RH10B38 using two independent markers (Jan de Boer, PGSC). CAPS markers were developed based on BAC end sequences in contig 2203 and mapped in the 06-882 and 7650 populations. Also these markers were closely linked to resistance, indicating that also this contig is in a locus synthenic with the Rpi-chc1 and Rpi-ber locus.

Using BAC-end sequences, three additional RH BAC contigs flanking contigs 2203 and 6701 were identified (FIG. 1A). In order to generate sufficient sequence information for finemapping two tiling paths consisting of 3 and 4 overlapping BACs (106G038, 137D014, 009D021 and 122B15, 77O23, 04G12, 199E15) were composed and sequenced. Annotation of the RH BAC sequence (FIG. 2) revealed the presence of two RGAs in the first tiling path (that mapped to RH10B38) and 7 RGAs in the second tiling path (that mapped to RH10B41, 42), indicated as arrowheads in FIG. 1A. Several markers deriving from these and other chromosome 10 sequences were mapped in the *S. chacoense* population 7650 (FIG. 1B) and in the *S. berthaultii* population 06-882 (FIG. 1A). The sizes of these populations were increased to 2357 and 2532 respectively. Recombinants in the relevant genomic area were screened for using markers RH099F09T and RH092A09S in population 7650 en markers RH91C10T and RH199 E15 S in population 06-882. Markers that were derived from the same RH BAC (RH137D14), 137D14-C37-7 and 137D14-C37-2 are only 15 kb apart in RH89-039-16 and co-segregate in the 7650 population (two recombinants) and in the 06-882 population (no recombinants), respectively. This strongly suggests that Rpi-chc1 and Rpi-ber are in synthenic gene clusters and that there might be an allelic relationship between the genes.

Cloning of Rpi-chc1

In order to clone Rpi-chc1, two BAC libraries were constructed using DNA derived from the resistant clone CHC543-5. The first library was constructed in the pCC1BAC BAC vector and contained approximately 22.000 clones with an average insert size of ~70 Kbp, corresponding to 1 genome equivalent. A second library was constructed in the pIndigoBAC-5 BAC vector and contained approximately 110.000 clones with an average insert size of ~45 Kbp, corresponding to 3 genome equivalents. The first library was screened with marker RH106G03T (Table 2, FIG. 1B), which cosegregated with resistance in the 7650 population with only three recombination events. In this way BAC clones CHC B1 was identified. Both BAC ends of CHC B1 (B07_1_C15) were mapped and the RP end (marker B07_1_C15_RP'), which showed only one recombination event with the Rpi-chc1 resistance gene, was used to screen the second BAC library and identified CHC B2 (2-D06_3-D21) (FIG. 1B). CHC B2 turned out to contain the RH137D14 C37-7 marker. Two recombination events were found with RH137D14 C37-7, on the other site of the Rpi-chc1 resistance gene. It was therefore concluded that the Rpi-chc1 locus was delimited to a 0.2 cM (5/2357 recombinants) interval that is physically spanned by the two partially overlapping BAC clones CHC B1 and CHC B2 (FIG. 1B).

By sequencing these two BACs, it was found that CHC B1 contained two RGAs and CHC B2 contained three RGAs, which were named CHC B1-1, CHC B1-2, CHC B2-1, CHC B2-2, and CHC B2-3 respectively (FIG. 2). The latter three RGAs were within mapping interval delimited by B07_1_C15_RP" and RH137D14 C37-7. Therefore, the three genes were subcloned into pBINplus vector under the control of their native regulatory elements by longrange PCR using the high fidelity polymerase Phusion®. The resulting subclones were completely sequenced and were found to be identical to their BAC template sequences.

Complementation analysis was carried out in *Nicotiana benthamiana* using the *Agrobacterium tumefaciens* transient assay (agroinfiltration) whereby 4-week old wild type *N. benthamiana* plants were infiltrated with the *Agrobacterium* strain AGL1+virG containing pBINplus:CHC B2-1, pBINplus:CHC B2-2, and pBINplus:CHC B2-3 respectively. As controls we used pBINplus without an insert and pBINplus:Rpi-blb1. Infiltrated leaves were challenged after two days with *P. infestans* strain 90128 in detached leaf assays (DLA). Leaves infiltrated with pBINplus:CHC B2-3 and pBINplus:Rpi-blb1 showed resistance to infection, while pBINplus:CHC B2-1, pBINplus:CHC B2-2 and pBINplus without an insert were colonized by Phytophtora as was apparent from the sporulating lesions (FIG. 3). This experiment clearly showed that CHC B2-3 is an active resistance gene against *P. infestans*. Since none of the other genes present in the genetic mapping interval of Rpi-chc1 shows activity, it can be concluded that CHC B2-3 is the Rpi-chc1 gene.

Rpi-chc1 Homology and Structure

Interestingly, Rpi-chc1 shares the highest homology (75-98%) with other RGAs from the Rpi-chc1 gene cluster from *S. chacoense* and with genes from synthenic clusters on chromosome 10 from *S. tuberosum* clone RH89-039-16 (Table 3, FIG. 4A-K). A lower (40%), but significant, extent of homology was found with a protein encoded by a gene with unknown function from poplar (accession number ABF81421, Table 3, FIG. 4A-K). The different domains of Rpi-chc1 protein share varying degrees of homology with corresponding domains of the poplar protein encoded by ABF81421. The NBS domain is most conserved (48% aa identity), followed by the CC domain (34% aa identity). The LRR domain is least conserved (21% aa identity). Overall homologies of lower than 33% are found with the FOM2 protein from cucumber (Joobeur et al., 2004), which confers resistance to fungal pathogen *Fusarium oxysporum*, Rpi-blb1 from *S. bulbocastanum* (Song et al., 2003; van der Vossen et al., 2003), R3a from *S. demissum* (Huang et al., 2005), and RPS1-k from soybean (*Glycine max*) (Gao et al., 2005), which confer resistance to *Phytophthora* sp.

Rpi-chc1 comprises an ORFs of 3909 nucleotides (nt) that encode a protein of 1302 amino acids harboring all sequences characteristic of a CC-NB-LRR R-proteins (FIG. 5). In the N terminus 5 stretches of amino acids can be distinguished with the potential to fold into a coiled coil structure. The central NB-ARC domain contains stretches of amino acids which show similarity with the Kinase 1a, Kinase 2, Kinase 3a, GLPL, RNBS-D and MHD subdomains (Bendahmane et al., 2002; van der Biezen and Jones, 1998). In contrast to many other NB-LRR proteins, the Rpi-chc1 protein is characterized by the absence of an obvious RNBS-A sub-domain and the presence of a double MHD sub-domain. The C-terminal domain contains 29 imperfect leucine rich repeats (LRRs). Both LRR 3 and 4 contain the characteristic LDL signature, which often present in LRR3. Both the MHD and the LRR3 have been implicated in activity regulation and putative intra-molecular interactions (Bendahmane et al., 2002; Tameling et al., 2006). Duplication of both of these subdomains might hint to a common regulatory mechanism.

Rpi-chc1 Homologous Loci in the Genome; Locus Directed Profiling

In order to identify positions in the genome that contain Rpi-chc1 related nucleotide sequences a new technique was developed that is derived from the NBS profiling (Brugmans et al., 2008; van der Linden et al., 2004) and will be referred to as "locus directed profiling". Instead of the primers that were used previously, which target domains that are generally present in all R-genes, we now used primers that are conserved within the family of Rpi-chc1 sequences (Table 2). This way only Rpi-chc1 related genes are expected to be targeted. Genomic DNA from parents and offspring from different populations (SHxRH, 06-882) was digested with either RsaI, HaeIII, AluI or MseI. An adaptor was ligated to the digestion products and using an adaptor primer combined with the Rpi-chc1 family specific primer, multiple fragments of varying molecular weight were created in a PCR reaction. Polymorphic bands were detected in the two populations using the Licor polyacrylamide gelsystem. Polymorphic bands were scored in 40 offspring plants from the SHxRH population and successively the marker segregation patterns were fitted to the UHD map (van Os et al., 2006). 73% of the markers mapped to the long arm of chromosome 10 where the Rpi-chc1 gene is located. Also sequence analysis of the isolated marker fragments showed strong homology to the Rpi-chc1 gene family (Table 4b). Altogether these data show that "locus directed profiling" was a successful approach to generate markers in a specified genomic area. On chromosome 10 three different loci were tagged with high frequency (Table 4A). Interestingly, the first two loci coincided with the map positions of contigs 2203 and 6701, which map to RH10B38-39 and RH10B41-42 respectively. A third group of markers mapped to RH10B54. Interestingly, the

TABLE 3

Sequence distance table derived from alignment Rpi-chc1
with related RGAs from publically accessible databases
Percent Similarity in upper triangle
Percent Divergence in lower triangle

|  | ABF81420 populus2.pro | ABF81421 populus.pro | BAB44079 oryza.pro | CAO40742 vitis.pro | CHC B2-1.pro | CHC B2-3.pro | FOM2 Cucumis melo.pro |
|---|---|---|---|---|---|---|---|
| ABF81420 populus2.pro | *** | 34.4 | 42.2 | 40.5 | 31.5 | 27.8 | 32.4 |
| ABF81421 populus.pro | 141.4 | *** | 38.8 | 39.7 | 42.2 | 40.3 | 43.5 |
| BAB44079 oryza.pro | 114.8 | 140.4 | *** | 50.4 | 34.9 | 31.2 | 39.7 |
| CAO40742 vitis.pro | 120.6 | 133.5 | 124.8 | *** | 37.1 | 32.5 | 41.3 |
| CHC B2-1.pro | 150.4 | 126.4 | 153.9 | 132.8 | *** | 78.1 | 36.7 |
| CHC B2-3.pro | 154.9 | 125.9 | 150.8 | 135.3 | 17.9 | *** | 33.2 |
| FOM2 Cucumis melo.pro | 151.5 | 122 | 160.6 | 144.8 | 137.9 | 136.5 | *** |
| Gpa2.pro | 233 | 240 | 229 | 220 | 253 | 250 | 262 |
| AAR29073 blb1.pro | 126.8 | 141.8 | 130.9 | 104.3 | 147.5 | 149.3 | 144.6 |
| AAX89383 RPS! glycine max.pro | 102.5 | 146 | 126.6 | 133.2 | 156 | 160.2 | 158.8 |
| R3a.pro | 99.3 | 158 | 121.6 | 139 | 171.9 | 169.7 | 175.5 |
|  | ABF81420 populus2.pro | ABF81421 populus.pro | BAB44079 oryza.pro | CAO40742 vitis.pro | CHC B2-1.pro | CHC B2-3.pro | FOM2 Cucumis melo.pro |

|  | Gpa2.pro | AAR29073 blb1.pro | AAX89383 RPS! glycine max.pro | R3a.pro |  |
|---|---|---|---|---|---|
| ABF81420 populus2.pro | 25.6 | 36.5 | 47 | 45.2 | ABF81420 populus2.pro |
| ABF81421 populus.pro | 30.4 | 38.4 | 34.1 | 33.1 | ABF81421 populus.pro |
| BAB44079 oryza.pro | 35.6 | 47.1 | 41.4 | 40.3 | BAB44079 oryza.pro |

TABLE 3-continued

Sequence distance table derived from alignment Rpi-chc1
with related RGAs from publically accessible databases
Percent Similarity in upper triangle
Percent Divergence in lower triangle

| CAO40742 vitis.pro | 37.1 | 52.7 | 39.7 | 37 | CAO40742 vitis.pro |
|---|---|---|---|---|---|
| CHC B2-1.pro | 25.9 | 34.4 | 31.9 | 29.8 | CHC B2-1.pro |
| CHC B2-3.pro | 22.8 | 30 | 27.7 | 26.2 | CHC B2-3.pro |
| FOM2 Cucumis melo.pro | 33.7 | 42.9 | 33.6 | 29.4 | FOM2 Cucumis melo.pro |
| Gpa2.pro | *** | 41.5 | 26.5 | 23.9 | Gpa2.pro |
| AAR29073 blb1.pro | 244 | *** | 37.5 | 33.4 | AAR29073 blb1.pro |
| AAX89383 RPS! glycine max.pro | 230 | 134.4 | *** | 40.4 | AAX89383 RPS! glycine max.pro |
| R3a.pro | 234 | 148 | 124.8 | *** | R3a.pro |
| | Gpa2.pro | AAR29073 blb1.pro | AAX89383 RPS! glycine max.pro | R3a.pro | |

Rpi-ber1 gene (Park et al., 2008) is in the same marker interval as the RH10B54 cluster. In order to test whether the Rpi-ber gene was potentially a Rpi-chc1 homolog, in population 06-882, 58 Rpi-chc1 locus directed profiling markers were developed. 34 of these markers derived from the resistant parent. 28 of them were linked to resistance (9 in coupling phase, 19 in repulsion phase). 2 coupling phase markers and 7 repulsion phase markers were completely linked to resistance in the first 1771 individuals of the population. This strongly suggests that Rpi-ber is a Rpi-chc1 homolog. Within the 28 linked Rpi-chc1 locus directed profiling markers, four groups of recombination patterns could be distinguished, each group is marked by the name of a representative marker in FIG. 1A. Three marker groups match the RH10B38-39 cluster, one marker group matches the RH10B41-42 cluster. This result confirms our finding from the SHxRH population, that the family of Rpi-chc1 related sequences on chromosome 10 is located in at least two closely linked clusters.

TABLE 4a

Map positions in SH and RH genomes of Rpi-chc1 locus directed profiling markers

| MarkerName | SHPosition | SHRecFreq | RHPosition | RHRecFreq | LOD |
|---|---|---|---|---|---|
| R1A2 | SH10B016-020 | 0.894737 | | | 5.885886 |
| R2R13 | SH10B016-020 | 0.897436 | | | 6.139272 |
| R2R14 | SH10B016-020 | 0.897436 | | | 6.139272 |
| F2A4 | SH10B016-020 | 0.974359 | | | 9.720427 |
| R2A6 | SH10B016-020 | 0.974359 | | | 9.720427 |
| F2M2 | SH10B016-020 | 0.974359 | | | 9.720427 |
| F2M3 | SH10B016-020 | 0.974359 | | | 9.720427 |
| F2M9 | SH10B016-020 | 0.974359 | | | 9.720427 |
| R1M4 | SH10B016-020 | 0.974359 | | | 9.720427 |
| R1M10 | SH10B016-020 | 0.974359 | | | 9.720427 |
| R1M11 | SH10B016-020 | 0.974359 | | | 9.720427 |
| R1M12 | SH10B016-020 | 0.974359 | | | 9.720427 |
| R2M2 | SH10B016-020 | 0.974359 | | | 9.720427 |
| R2M4 | SH10B016-020 | 0.974359 | | | 9.720427 |
| R2R9 | SH10B016-020 | 0.974359 | | | 9.720427 |
| R1R8 | SH10B016-020 | 1 | | | 11.43914 |
| R2A8 | SH10B016-020 | 0.047985 | RH10B022-026 | 0.951954 | 6.746727 |
| R1A4 | SH10B022-027 | 0.087129 | RH10B027-041 | 1 | 8.351405 |
| R2H5 | SH10B016-020 | 0 | RH10B027-048 | 0.952381 | 8.250089 |
| F2A1 | SH10B016-020 | 0 | RH10B027-048 | 0.954545 | 8.831465 |
| F2A5 | SH10B016-020 | 0 | RH10B027-048 | 0.954545 | 8.831465 |
| F2A6 | SH10B016-020 | 0 | RH10B027-048 | 0.954545 | 8.831465 |
| F2A7 | SH10B016-020 | 0 | RH10B027-048 | 0.954545 | 8.831465 |
| F2A8 | SH10B016-020 | 0 | RH10B027-048 | 0.954545 | 8.831465 |
| F2A9 | SH10B016-020 | 0 | RH10B027-048 | 0.954545 | 8.831465 |
| F2A10 | SH10B016-020 | 0 | RH10B027-048 | 0.954545 | 8.831465 |
| R2A3 | SH10B016-020 | 0 | RH10B027-048 | 0.954545 | 8.831465 |
| F2M4 | SH10B016-020 | 0 | RH10B027-048 | 0.954545 | 8.831465 |
| F2M8 | SH10B016-020 | 0 | RH10B027-048 | 0.954545 | 8.831465 |
| R1M7 | SH10B016-020 | 0 | RH10B027-048 | 0.954545 | 8.831465 |
| R1M8 | SH10B016-020 | 0 | RH10B027-048 | 0.954545 | 8.831465 |
| R2M3 | SH10B016-020 | 0 | RH10B027-048 | 0.954545 | 8.831465 |
| R2M9 | SH10B016-020 | 0 | RH10B027-048 | 0.954545 | 8.831465 |
| R2M11 | SH10B016-020 | 0 | RH10B027-048 | 0.954545 | 8.831465 |
| R2M16 | SH10B016-020 | 0 | RH10B027-048 | 0.954545 | 8.831465 |

TABLE 4a-continued

Map positions in SH and RH genomes of Rpi-chc1 locus directed profiling markers

| MarkerName | SHPosition | SHRecFreq | RHPosition | RHRecFreq | LOD |
|---|---|---|---|---|---|
| F2R1 | SH10B016-020 | 0 | RH10B027-048 | 0.954545 | 8.831465 |
| R1R1 | SH10B016-020 | 0 | RH10B027-048 | 0.954545 | 8.831465 |
| R1R2 | SH10B016-020 | 0 | RH10B027-048 | 0.954545 | 8.831465 |
| R2R5 | SH10B016-020 | 0 | RH10B027-048 | 0.954545 | 8.831465 |
| R2R10 | SH10B016-020 | 0 | RH10B027-048 | 0.954545 | 8.831465 |
| R1M6 | SH10B025-027 | 0 | RH10B027-048 | 0.954545 | 9.308586 |
| F2R4 | SH10B032-034 | 0 | RH10B027-048 | 0.857143 | 5.903571 |
| R1A3 | | | RH10B038-039 | 0.114286 | 5.134121 |
| R2H3 | | | RH10B038-039 | 0.128205 | 5.253783 |
| R1M3 | | | RH10B038-039 | 0.078947 | 6.881108 |
| R1M5 | | | RH10B038-039 | 0.078947 | 6.881108 |
| F2A3 | | | RH10B038-039 | 0.076923 | 7.146904 |
| R2A2 | | | RH10B038-039 | 0.076923 | 7.146904 |
| R2A7 | | | RH10B038-039 | 0.076923 | 7.146904 |
| R1H1 | | | RH10B038-039 | 0.076923 | 7.146904 |
| R2H4 | | | RH10B038-039 | 0.076923 | 7.146904 |
| R2M12 | | | RH10B038-039 | 0.076923 | 7.146904 |
| R2M13 | | | RH10B038-039 | 0.076923 | 7.146904 |
| R1R9 | | | RH10B038-039 | 0.076923 | 7.146904 |
| R2R1 | | | RH10B038-039 | 0.076923 | 7.146904 |
| R2R3 | | | RH10B038-039 | 0.076923 | 7.146904 |
| R2R2 | | | RH10B041 | 0.102564 | 6.139272 |
| R2M7 | | | RH10B041 | 0.076923 | 7.146904 |
| R2R8 | | | RH10B041 | 0.076923 | 7.146904 |
| F2A14 | | | RH10B042-048 | 0.076923 | 7.146904 |
| R2M8 | | | RH10B042-048 | 0.076923 | 7.146904 |
| R1R4 | | | RH10B042-048 | 0.076923 | 7.146904 |
| R1R5 | | | RH10B042-048 | 0.076923 | 7.146904 |
| R1R6 | | | RH10B042-048 | 0.076923 | 7.146904 |
| R2R12 | | | RH10B042-048 | 0.076923 | 7.146904 |
| R2R15 | | | RH10B042-048 | 0.076923 | 7.146904 |
| R1A5 | | | RH10B042-048 | 0.054054 | 7.759088 |
| F2M7 | SH10B047-049 | 1 | RH10B054 | 0.125 | 5.821641 |
| F2A11 | SH10B047-049 | 1 | RH10B054 | 0.055556 | 6.535189 |
| F2M5 | SH10B047-049 | 1 | RH10B054 | 0.055556 | 6.535189 |
| R1R7 | SH10B047-049 | 1 | RH10B054 | 0.055556 | 6.535189 |
| R2R7 | SH10B047-049 | 1 | RH10B054 | 0.055556 | 6.535189 |
| F2A12 | SH10B047-049 | 0.128205 | | | 5.253783 |
| R1M1 | | | RH02B023-025 | 0.921053 | 6.881108 |
| R1M2 | | | RH02B023-025 | 0.078947 | 6.881108 |
| R1R3 | | | RH04B014-020 | 0.076923 | 7.146904 |
| F1R3 | | | RH04B033-039 | 0.868421 | 5.013173 |
| R2M14 | | | RH04B033-039 | 0.974359 | 9.720427 |
| F2A2 | | | RH07B068-069 | 0.897436 | 6.139272 |
| R2A4 | SH12B051-058 | 0.896552 | RH12B047-051 | 1 | 5.807144 |
| R2R11 | SH12B051-058 | 0.931034 | RH12B047-051 | 1 | 6.35823 |
| F2H3 | SH12B051-058 | 0.933333 | RH12B047-051 | 1 | 6.452677 |
| F2M6 | SH12B051-058 | 0.933333 | RH12B047-051 | 1 | 6.452677 |
| R2M6 | SH12B051-058 | 0.933333 | RH12B047-051 | 1 | 6.452677 |
| F1R2 | SH01B033-034 | 0.897436 | | | 6.139272 |
| F1H5 | SH01B033-034 | 0.078947 | | | 6.881108 |
| F1R4 | SH01B033-034 | 0.941176 | | | 6.931596 |
| F1H3 | SH01B033-034 | 0.948718 | | | 8.314174 |
| F1H4 | SH04B024-030 | 0.102564 | | | 6.139272 |
| R2M15 | SH04B031-032 | 0.128205 | | | 5.253783 |
| R2A1 | SH04B031-032 | 0.102564 | | | 6.139272 |
| R2M1 | SH04B031-032 | 0.102564 | | | 6.139272 |
| R2R6 | SH07B048-057 | 0.078947 | | | 6.881108 |
| R2M5 | SH07B048-057 | 0.076923 | | | 7.146904 |
| F2M1 | SH09B049-054 | 0.897436 | | | 6.139272 |
| F2R2 | SH09B049-054 | 0.897436 | | | 6.139272 |

TABLE 4b

Sequence homology of Rpi-chc1 locus directed profiling markers derived from SHxRH population

| markername | Seq. length | blastx hit |
|---|---|---|
| F1R5 | 180 | |
| F1R6 | 185 | |

TABLE 4b-continued

Sequence homology of Rpi-chc1 locus directed profiling markers derived from SHxRH population

| markername | Seq. length | blastx hit |
|---|---|---|
| F1R7 | | |
| F1R8 | 225 | ref|YP_514854.1 ribosomal protein S4 type |
| F1R9 | 230 | NBS-LRR type |
| F2A1 | 180 | gb|ABB91438.1| R-FOM-2 (*Cucumis melo*), NBS-LRR type |
| F2A2 | 225 | gb|ABB91438.1| R-FOM-2 (*Cucumis melo*), NBS-LRR type |
| F2A3 | 119 | |
| F2R1 | | |
| F2R2 | | |
| F2R4 | 145 | |
| F2R6 | 424 | NBS-LRR type |
| F2R7 | | |
| R1A1 | 305 | gb|ABB91438.1| R-FOM-2 (*Cucumis melo*), NBS-LRR type |
| R1A2 | 495 | No significant similarity found |
| R1R10 | 700 | gb|AAS80152.1| FOM-2 (*Cucumis melo*), NBS-LRR type |
| R1R11 | 461 | NBS domain resistance protein |
| R1R2 | | |
| R1R3 | | |
| R1R5 | 515 | emb|CAD29726.1| hero resist. Prot. 2 homologue NBS-LRR type |
| R1R6 | 510 | emb|CAD29726.1| hero resist. Prot. 2 homologue NBS-LRR type |
| R1R7 | 570 | No significant similarity found |
| R1R8 | 700 | gb|AAS80152.1| FOM-2 (*Cucumis melo*), NBS-LRR type |
| R2A1 | | |
| R2A2 | | |
| R2A3 | | emb|CAN82053.1| hypothetical protein (*Vitis vinifera*), NBS-LRR type |
| R2A4 | | dbj|BAB44079.1| putative NBS-LRR type (*Oryza sativa*), NBS-LRR type |
| R2R10 | | |
| R2R12 | | dbj|BAB44079.1| putative NBS-LRR type (*Oryza sativa*), NBS-LRR type |
| R2R13 | | dbj|BAB44079.1| putative NBS-LRR type (*Oryza sativa*), NBS-LRR type |
| R2R14 | | dbj|BAB44079.1| putative NBS-LRR type (*Oryza sativa*), NBS-LRR type |
| R2R15 | | emb|CAN82053.1| hypothetical protein (*Vitis vinifera*), NBS-LRR type |
| R2R16 | | No significant similarity found |
| R2R17 | | emb|CAN82053.1| hypothetical protein (*Vitis vinifera*), NBS-LRR type |
| R2R2 | | emb|CAN82053.1| hypothetical protein (*Vitis vinifera*), NBS-LRR type |
| R2R3 | | emb|CAN82053.1| hypothetical protein (*Vitis vinifera*), NBS-LRR type |
| R2R4 | | emb|CAN82053.1| hypothetical protein (*Vitis vinifera*), NBS-LRR type |
| R2R5 | | emb|CAN82053.1| hypothetical protein (*Vitis vinifera*), NBS-LRR type |
| R2R6 | | emb|CAN82053.1| hypothetical protein (*Vitis vinifera*), NBS-LRR type |
| R2R7 | | emb|CAN82053.1| hypothetical protein (*Vitis vinifera*), NBS-LRR type |
| R2R9 | | emb|CAN82053.1| hypothetical protein (*Vitis vinifera*), NBS-LRR type |

In a different population (7677) deriving from *S. berthaultii* accession 493-7 an NBS profile marker generated with the previously described NBS5a6 primer was found to be closely linked to *Phytophthora* resistance in this population. It mapped to the telomeric site relative to TG403 on the long arm of chromosome 10 (FIG. 6). Sequence analysis of this fragment revealed high homology to members of the Rpi-chc1 family. All together these results show that at least four, genetically different, Rpi-chc1 like clusters are present on chromosome 10. This is similar to the situation on the long arm of chromosome 9, where three different Tm2-2 related clusters were identified (Foster et al., 2009; Pel et al., 2009).

Plant Material and *Phytophthora infestans* Isolates

In this study we used four late blight resistant clones TAR852-5 (deriving from CGN22729), BER94-2031-01 (deriving from PI473331), BER481-3 (deriving from CGN18190) BER493-7 (deriving from CGN17823), CHC543-5 (deriving from BGRC63055). CHC543-5 was crossed with CHC544-5 to produce population 7650. BER94-2031-01 was crossed with the susceptible clone G254 to generate population 06-882. BER493-7 was crossed with RH89-039-16 to produce population 7677. Potato cultivar Desiree was used for transformation. Wild-type *Nicotiana benthamiana* plants were used for transient complementation assays.

Characteristics and origin of *P. infestans* isolates used in this study are indicated in Table 5.

BAC Library Construction

Clone CHC543-5 was used as a DNA source for the construction of the BAC libraries. High-molecular weight DNA preparation and BAC library construction were carried out as described by (Rouppe van der Voort et al., 1999). For the first library pCC1BAC backbone was used. For the second library pIndigoBAC-5 was used, both from Epicenter. Approximately 22.000 clones with an average insert size of ~70 Kbp, corresponding to 1 genome equivalents, were obtained for library 1, and approximately 110.000 clones with an average insert size of ~45 Kbp, corresponding to 3 genome equivalents, were obtained for library 2. The BAC clones were stored as bacterial pools containing approximately 700 to 1000 white colonies. These were generated by scraping the colonies from the agar plates and successive resuspension into LB medium containing 18% glycerol and 12.5 µg ml$^{-1}$ chloramphenicol using a sterile glass spreader. These so-called super pools were stored at −80° C. Marker screening of the BAC libraries was done, first by isolating plasmid DNA from each pool using the standard alkaline lysis protocol and PCR was carried out to identify positive pools. Bacteria corresponding to positive pools were diluted and plated on LB agar plate containing chloramphenicol (12.5 µg ml$^{-1}$). Individual white colonies were picked into 384-well microtitre plates and single positive BAC clones were subsequently identified by marker screening as described by (Rouppe van der Voort et al., 1999). Names of BAC clones isolated from the super pools carry the prefix CHC and are extended with a number (B1 and B2), corresponding to the order in which they were identified.
Subcloning of Candidate Genes
Longrange PCR Candidate RGAs were subcloned from BAC clone CHC B2 as follows. Primers were designed approximately 3 kb upstream of the predicted start codon and approximately 700 bp downstream of the predicted stop codon. (CHC B2-1F=MN459:

```
tgaccctgcaggGGACCCCTTAACAAGTGATGTG,

CHC B2-1R = MN462:
tgacggcgcgccAAAAAGTCCCGCTTTGATACC,

CHC B2-2F = MN483:
tgaccctgcaggCCCCTTAACAAGTGATGTGATG,

CHC B2-2R = MN484:
tgacggcgcgccTCAGGTTCCCTTACAAGATTCC,

CHC B2-3F = MN479:
tgaccctgcaggACGCATCAGGAAGAGAGGAG,

CHC B2-3R = MN480:
tgacggcgcgccGCGGTTCCTCTGTGAAACAC)
```

DNA Sequencing and Computer Analysis

BAC clone sequencing was performed using a shotgun cloning strategy of 2 kb and 6 kb libraries and was carried out by Macrogen (South-Korea). Sequencing reactions were performed using the dye terminator principle. Sequence contigs were assembled by Macrogen. Gap closing was done using primer walking on shotgun clones or directly on the BAC.

The contig sequences were analyzed using the web-based application FGENESH (Softberry) in order to predict gene structure. RGAs and RGAs from publically accessible databases were aligned for homology and distance analysis using the DNA star software package (Lasergene). Conserved domains were identified using the web-based application SMART (EMBL)
Resistance Assay Detached leaf assays were used to determine the resistance phenotypes of primary transformants and N. benthamiana leaves. For the phenotyping of the CHC population isolate 90128 was used. For the phenotyping of the ber population, isolate IPO-C was used. The resistance spectra of the resistant parents was determined using the isolates described in Table 5. Inoculum preparation and inoculation were performed as described by (Vleeshouwers et al., 1999). Six days after inoculation, plant phenotypes were determined. Leaves showing no symptoms or a localized necrosis at the point of inoculation were scored as resistant and those with clear sporulating lesions as susceptible.
Transient Complementation in N. benthamiana Agrobacterium transient transformation assays (agro-infiltration) were carried out on N. benthamiana. Recombinant A. tumefaciens AGL1+ cultures were grown in LB medium (10 gram bacteriological peptone, 10 gram NaCl and 5 gram yeast extract in 1 liter MQ water) supplemented with 5 mg/l Tetracycline and 50 mg/l Kanamycin for the pBINplus constructs. After one or two days a calculated amount of culture (according to OD 0.5 at 600 nm) was transferred to YEB medium (5 gram beef extract, 5 gram bacteriological peptone, 5 gram sucrose, 1 gram yeast extract, 2 ml 1 M MgSO4 in 1 liter MQ water) supplemented with Kanamycin for all strains. After 1 day overnight cells were centrifuged at 3500 rpm and re-suspended in MMA medium (20 gram sucrose, 5 gram MS salts and 1.95 gram MES) supplemented with 1 ml 200 mM acetosyringone to a final OD of 0.2 and infiltrated into 4 weeks old plants with a 3 ml syringe. Infiltrated leaves were subsequently challenged after two days with P. infestans strain 90128 in detached leaf assays (DLA). Hypersensitive response (HR) or P. infestans sporulation were scored from 5 to 7 days post inoculation.

Example 2 Rpi-chc1 is a Functional Resistance Gene Against Phytophthora infestans Methods
Plant Material and Phytophthora infestans Isolates In this study we used 225 Solanum plants, their names as used in this study and accession numbers are listed in Table 7. Nine late blight resistant plants were used for the isolation of functional homologs of Rpi-chc1 (tar852-5, ber94-2031-01 which derives from PI473331, ber481-3, ber493-5, -7, -9, chc543-5, ber324-2, ber487-1, ber561-2, and scr849-1). CHC543-5 was crossed with CHC544-5 to produce population 7650. BER94-2031-01 was crossed with the susceptible clone G254 to generate population 06-882. BER493-7 was crossed with RH89-039-16 to produce population 7677. Potato cultivar Desiree was used for transformation. Wild-type Nicotiana benthamiana plants were used for transient complementation assays.

Characteristics and origin of P. infestans isolates used in this study are indicated in Table 5.
Cloning of Candidate Genes Rpi-chc1 homologs were PCR amplified using the long range high fidelity thermostable DNA polymerase Phusion® according to the manufacturer's instructions (New England Biolabs). Primers were designed, overlapping the start and stop codons of Rpi-chc1 and contained AttB1 and AttB2 extensions (MN595 and MN597, Table 8). PCR products were recombined into pDONR221 using BP Clonase® according to manufacturer's instructions (InVitroGen). DNA sequencing was performed at Baseclear (The Netherlands) using standard and custom primers (MN622-MN650, Table 8). Sequences were analyzed and aligned for homology and phylogeny analysis using the DNA star software package (Lasergene).
Promoter Terminator Constructs In order to produce clones containing the promoter and terminator of Rpi-chc1 for construction of triple point gateway application mediated expression constructs, specific primers were designed (MN598, MN599, MN600, MN601, MN670; Table 8) matching the Rpi-chc1 promoter and terminator sequences, to which AttB4, AttB1 and AttB2, AttB3 recombination sites were added, respectively. PCR products were generated using the long range high fidelity thermostable DNA polymerase Phusion® according to the manufacturer's instructions. PCR products were recombined using BP Clonase®. The occurrence of PCR errors was ruled out using sequence analysis of the resulting clones using primers MN651 and 652 as listed in Table 8. Triple point gateway reactions were performed using these constructs and ORF sequences in pDONR221 by LR clonase.
Resistance Assay Detached leaf assays were used to determine the resistance phenotypes of primary transformants and N. benthamiana leaves. For the phenotyping of the CHC transgenics isolate 90128 was used. For the phenotyping of the Rpi-chc1 homologs in *N. benthamiana*, isolate IPO-C was used. Inoculum preparation and inoculation were performed as described by Vleeshouwers et al., 1999. Six days after inoculation, plant phenotypes were determined. Leaves showing no symptoms or a localized necrosis at the point of inoculation were scored as resistant and those with clear sporulating lesions as susceptible.

Transient Complementation in *N. benthamiana*

*Agrobacterium* transient transformation assays (agro-infiltration) were carried out on *N. benthamiana*. Recombinant *A. tumefaciens* COR308 cultures were grown in LB medium (10 gram bacteriological peptone, 10 gram NaCl and 5 gram yeast extract in 1 liter MQ water) supplemented with 5 mg/l tetracycline and 50 mg/l kanamycin for the pBINplus constructs. After one or two days a calculated amount of culture (according to OD 0.5 at 600 nm) was transferred to YEB medium (5 gram beef extract, 5 gram bacteriological peptone, 5 gram sucrose, 1 gram yeast extract, 2 ml 1 M $MgSO_4$ in 1 liter MQ water) supplemented with kanamycin for all strains. After 1 day overnight cells were centrifuged at 3500 rpm and re-suspended in MMA medium (20 gram sucrose, 5 gram MS salts and 1.95 gram MES) supplemented with 1 ml 200 mM acetosyringone to a final OD of 0.2 and infiltrated into 4 weeks old plants with a 3 ml syringe. Infiltrated leaves were subsequently challenged after two days with *P. infestans* strain 90128 in detached leaf assays (DLA). Hypersensitive response (HR) or *P. infestans* sporulation were scored from 5 to 7 days post inoculation.

Co-Infiltration

A set of 90 effectors was present in *Agrobacterium tumefaciens* COR308 in a PVX plasmid (PEX set). The binary plasmids contain an effector from Pi cloned inside the PVX genome. Upon agro-infiltration both effector and PVX will be expressed. Within the time course of the experiment PVX cannot spread systemically and we are only interested in the local expression of the effector. Upon recognition of the encoded effector by the R-gene, an HR can be observed between 3 and 5 dpi. PVX symptoms are visible after 6 days and are generally first observed in non-infiltrated leaves.

As a positive control we used R3a and Avr3a-KI, an R-gene—Avr-gene combination which is known to give a strong response (Armstrong et al., 2005). Screening with the Rpi-chc1 candidate showed necrotic spots with two potential effectors genes RD12-1 and RD12-2 (FIG. 8).

In the previous example we described the map based cloning of the Rpi-chc1 gene from *Solanum chacoense* accession 543-5. Rpi-chc1 is the founder of a previously undescribed R gene family of the CC-NB-LRR class and is located on chromosome 10 near marker TG63. The gene was present in a gene cluster with five homologs. Genetic analysis revealed that only three of these homologs (CHC B2-1, CHC B2-2, and CHC B2-3 could potentially encode Rpi-chc1. Transient complementation analysis in *N. benthamiana* suggested that CHC B2-3 was the active copy.

In this experiment we show by stable transformation of the susceptible cv. Desiree that indeed CHC B2-3 could complement the *Phytophthora infestans* (Pi) susceptibility (FIG. 8). This result supports our previous suggestion that CHC B2-3 is Rpi-chc1. Also this result shows that Rpi-chc1 can be functional in a broad spectrum of *Solanaceous* species, such as *S. chacoense* and *N. benthamiana* but also in *S. tuberosum*.

Rpi-chc1 Specifically Recognizes an RXLR Effector Protein.

In order to understand the activity spectrum of Rpi-chc1, it was investigated which component of Pi was recognized. Until now all Pi components being recognized by host R-proteins are effectors of the RXLR class. Pi isolate T30-4 is a-virulent on plants expressing Rpi-chc1 and therefore the cognate component must be expressed in this isolate. Recently the genome of T30-4 was sequenced and its genome appears to encode hundreds of RXLR effectors (Haas et al., 2009). Sixty-five RXLR effectors comprising all known Avr's (Avr1, Avr2, Avr3a, Arv4, Avr-blb1, Avr-blb2) and also a few non RXLR effectors (Infl, PiNIP) effectors were cloned into the plant expression vector pGR106 and are referred to as the PEX set (Vleeshouwers et al., 2008). The PEX set was screened by co-agro-infiltration with Rpi-chc1 in *N. benthamiana*. This way both the selected effector and the Rpi-chc1 gene are expressed in the same cells. In case the effector is recognized by Rpi-chc1 it will induce a hypersensitive response (HR) and will result in a necrotic lesion in the infiltrated area of the leaf. This phenomenon was well described for the co-infiltration of R3a and Avr3a (Armstrong et al., 2005) which was included in our experiments as a positive control (FIG. 9). Leaf areas that were agro-infiltrated with Rpi-chc1 alone remained green which showed that Rpi-chc1 in itself did not induce cell death. Also co-infiltration with the previously described Avr's (Avr1, Avr2, Avr3a, Arv4, Avr-blb1, Avr-blb2) did not induce HR, which showed that Rpi-chc1 recognizes a new component of Pi and that it has a unique way of inducing resistance. On the other hand some effectors in the PEX set produced an Rpi-chc1 independent hypersensitive response (FIG. 9 leaf C). There were, however also two clones in the PEX set that only showed an Rpi-chc1 dependent cell death (FIG. 9 leaf B). Both clones (RD12-1 and RD12-2) were highly homologous to each other and in fact encoded identical proteins. RD31, that encodes a protein with 60% identity to RD12 was not recognized (FIG. 9 leaf A), showing that recognition by Rpi-chc1 was quite specific. In order to test the specificity of recognition on the R-gene side, RD12 was co-infiltrated with Rpi-blb1, Rpi-blb3 and R3a. Also the Rpi-chc1 paralogs CHC B2-1 and CHC B2-2 (see Example 1), which showed 78% and 83% identity, respectively, at the amino acid level to Rpi-chc1, were tested by co-infiltration. None of these R-genes or R-gene paralogs produced a hypersensitive response upon co-infiltration with RD12 (data not shown). These results clearly showed that Rpi-chc1 could specifically recognize Pi component RD12. RD12 (=PITG_16245 has several paralogs in the Pi genome (PITG_16418, PITG_16427, PITG_16233, PITG_16240, PITG_20934, PITG_20936, PITG_20336, and PITG_23230), of which the sequences are given below.

```
PITG_16245   MATATVLVQSPASGLTTTVADTAQTATSILTPVLAGEP

KNHVTTRSLRTHPIADSDDGEERLLNGMTDFVKYHAGK

MNPEQLYKYLKLQGRGQEAYKHKNYASYIKKSKKWWK

PITG_16418   MATATVLVQSPASGLTTTVADTAQTATSILTPVLAGEP

NKHVTTRSLRTHPIADSDDGEERLLNGMTDFVKYHAGK

MNPEQLYKYLKLQGRGQEAYKHKNYASYIKKSKKWWKN

Q

PITG_16427   MRVLCLALMATATVLVPSPASGLTTTVADTAQTATSIL

TPVLAGEPNKHVTTRSLRTHPIADSDDGEERLLNGMTD

FVKYHAGKMNPEQLYKYLKLQGRGQEAYKHKNYASYIK

KSKKWWKNQ
```

-continued

```
PITG_16233   MRVLCLALMATATVLVQSPASGLTTTVADTAQTATSIL
             TPVLAGEPNKHVATRSLRTHPIDDSDDGEERLLNGMTD
             FFKYHAGKMSPEQLYKYLNLKGLGQEAYKHKNYASYIK
             KSKKWWKNQ

PITG_16240   MRVLCLALMATATVLVQSPASGLTTTVADTAQTATSIL
             TPVLAGEPNKHVATRSLRTHPIDDSDDGEERLLNGMTD
             FFKYHAGKMSPEQLYKYLNLKGLGQEAYKHKNYASYIK
             KSKKWWKNQ

PITG_20934   MRVLCLALMATATVLVPSPASGLTTTVADTAQTATSIL
             TPVLAGEPNKHVATRSLRTHPIDDSDDGEERLLNGMTD
             FFKYHAGKMSPEQLYKYLNLKGLGQEAYKHKNYASYIK
             KSKKWWKNQ

PITG_20936   MRVLCLALMATATVLVPSPASGLTTTVADTAQTATSIL
             TPVLAGEPNKHVATRSLRTHPIDDSDDGEERLLNGMTD
             FFKYHAGKMSPEQLYKYLNLKGLGQEAYKHKNYASYIK
             KSKKWWKNQ

PITG_20336   MRVLCLALMATATVLVPSPASGLTTTVADTAQTATSIL
             TPVLAGEPNKHVATRSLRTHPIDDSDDGEERLLNGMTD
             FFKYHAGK

PITG_23230   MRVLCLALMATATVLVPSPASGLTTTVADTAQTATSIL
             TPVLAGEPNKHVATRSLRTHPIDDSDDGEERL
```

It cannot be excluded that also these paralogs are recognized by Rpi-chc1 in the interaction with Pi. Neither can it be ruled out that additional unrelated Pi components can be recognized since dual specificity R-genes have been described (Jones and Dangl, 2006).

Promotor Requirement for Rpi-chc1 Expression

In order to determine which regulatory sequences were most suited to drive the expression of the open reading frames of Rpi-chc1, we used the strategy described before (Lokossou et al., 2009) in which the candidate ORFs are cloned in between the desired promoters and terminators using a triple point gateway strategy. The Rpi-chc1 ORF was cloned in between its own 3 kb promoter and 0.5 kb terminator (p-chc1-long) which were also present in the initial complementation analyses as presented in FIG. 8. In addition, Rpi-chc1 ORF was cloned in between three alternative promoter/terminator combinations. A shorter version (0.8 kb) of its own promoter and its own 0.6 kb terminator (p-chc1-short); the double 35S promoter in pMDC32, and the Rpi-blb3 promoter/terminator combination (Lokossou et al., 2009). In order to test which was the optimal promoter terminator combination, the four Rpi-chc1 constructs were transformed to AGL-1+virG, cultures were mixed 1:1 with *A. tumefaciens* COR308 containing PEX-RD12. Serial dilutions in MMA medium were infiltrated in the leaves of *N. benthamiana* (FIG. 10). The p-chc1-long construct induced HR in mixtures with RD12 of $OD_{600}$ 2.0 and 1.0. The p-chc1-short construct also expressed HR in a two fold lower concentration ($OD_{600}$=0.5). Remarkably, the 35S and Rpi-blb3 promoter/terminator constructs were not suitable for functional expression of the Rpi-chc1 gene. These results show that the promoter of Rpi-chc1 is functionally distinct from the other promoters tested. Furthermore, it is concluded that sequences upstream (<−900 bp) in the Rpi-chc1 promoter contain inhibitory elements for expression.

Germplasm Screen for Rpi-chc1 Like Sequences

To further support the suggestion that Rpi-chc1 can be active in a wide range of *Solanum* species and also study divergence of the Rpi-chc1 allele sequence and activity in the germplasm we screened 225 genotypes (Table 7) from our germplasm collection for the presence of Rpi-chc1 related sequences using a sequence alignment of the active Rpi-chc1 and several related sequences identified in the initial application that were derived from RH89-039-16 and from the inactive paralogs in chc543-5. Primer pairs (Table 8) were designed in such a way that only the active copy was predicted to be amplified by PCR. As shown in FIG. 11A, primer combinations D and E were highly specific since PCR products were observed only in reactions that contained the Rpi-chc1 template and no amplification was found from the templates that contained closely related sequences. Primer combinations D and E were used to screen the recombinants in the finemapping population (n=2400) of *S. chacoense* and *S. berthaultii* (n=2600; Rpi-ber; accession P1265858; 94-2031*G254) in which Pi resistance is segregating. No recombinants were found between the marker and the resistance in either population (data not shown). This showed that both markers are highly specific. Also this showed that the Rpi-ber gene is related to Rpi-chc1 and that Rpi-chc1 derived molecular markers can be used to tag these resistance genes.

Genotype chc543-5, from which Rpi-chc1 was isolated, is located in taxonomic group 10-14 (Jacobs et al., 2008). In order to screen for other Rpi-chc1 homologous sequences, 225 genotypes in our germplasm collection (Table 7) located in taxonomic groups 10-12 till 10-17 were selected. DNA integrity was confirmed using Ef1-α PCR (data not shown) and successively primer combination D was used to screen for Rpi-chc1 related sequences. Six genotypes were found to be positive in this screen (FIG. 11B). First of all chc543-5 was found, which confirmed the robustness of the screen. Besides, five other genotypes were identified amongst which *S. berthaultii* plants 324-2, 481-3 and 561-2, confirming the previous suggestion that Rpi-chc1 and Rpi-ber are very related. Also two other species were tagged, *S. tarijense* (852-5) and *S. sucrense* (849-1).

Rpi-chc1 Homolog Mining

In order to further characterize functional and sequence conservation or divergence of Rpi-chc1 we set out to clone the open reading frames from the plants that were positive in the germplasm screen and in addition from plants known to contain resistance genes on chromosome 10 (described in FIG. 6). Primers overlapping the start- and the stopcodon of Rpi-chc1 were designed and attB1 and AttB2 extensions were added for BP cloning into pDONR221. PCR reactions using the proofreading polymerase Phusion® resulted in specific products for all selected genotypes. These PCR fragments were cloned and for each genotype six colonies were selected and end sequenced. Some genotypes produced only one sequence type and for those genotypes we concluded that only one target gene was amplified. For genotypes with two or more sequence types an additional 16 colonies were end sequenced and grouped. From each sequence group three clones were fully sequenced using Rpi-chc1 derived internal primers. This resulted in the identification of 21 new Rpi-chc1 like sequences (FIG. 13A-T). The encoded protein sequences were aligned using clustal-W together with previously identified Rpi-chc1 homologs (FIG. 14A-AQ). This resulted in the phylogenetic tree as presented in FIG. 12. From chc543-5 we isolated two sequence types. The first type was identical to Rpi-chc1. The second sequence type located in a different clade (clade 1 in FIG. 12) with multiple sequences, all deriving from *S. berthaultii* plants, showing that this approach was successful in identifying Rpi-chc1 homologs. Four genotypes yielded only one sequence type 849-1, RH89-39-16, 487-1 and 94-2031-1. The first three located to the same clade (clade 2 in FIG. 12). RH89-39-16 sequences RH_D3, D4, and D7 were identical to each other and showed two nucleotide mismatches with RH137D14 c13-2, a sequence that was generated during construction of the RH physical map in the initial application. Both sequences located to clade 2 which also contained *S. sucrense* sequences 849-1_M8, M18, and M20, and also *S. berthaultii* sequences 487-1, 14, 16 and I8 was M20. In addition *S. tarijense* 852-5_E3 was present in clade 2. Because RH89-39-16 is susceptible to Pi infection, it is suggested that these sequences represent inactive homologs. Two other sequences isolated from *S. tarijense* 852-5 located in clade 3 which also harboured the Rpi-chc1 gene. Furthermore, three sequences from *S. berthaultii* plants 94-2031-1, 561-2, 324-2 were found in this clade which showed only minor sequence deviation and encoded identical aminoacid sequences. Clade 4 contained only sequences from *S. berthaultii* plants. Clade 5 contained only sequences that were identified before as also was the case in the remaining group, referred to as group 6. Clades 1 till 4 had a 45 a.a. N-terminal extension of the encoded protein as compared to proteins in clade 5 and group 6. Sequences in clade 2, 3 and 5 mapped to the R-gene cluster within 0.1 cM to TG63. No sequences in clades 1 and 4 have been genetically mapped. Comparison with the newly available *S. phureja* genome sequence revealed that sequences from clade 1 till 5 had closest homologs in the TG63 cluster. Comparison to the tomato genome revealed that also here an Rpi-chc1 cluster near TG63 existed. As shown before, at this genetic location the Pi resistance gene Ph-2 was mapped. Some tomato plants, that were sequenced did not carry the Ph-2 resistance gene but a potential inactive allele could be present (FIG. 13A-T). Group 6 sequences had closest homology to a related R-gene cluster near TG403 on chromosome 10, an area where we also mapped Pi resistance (see FIG. 6), showing that also Rpi-chc1 homologous sequences from this cluster potentially encode Pi resistance.

Functional Analysis of Rpi-chc1 Homologs

Now we have identified 21 new Rpi-chc1 homologs and we have shown sequence diversification, the question arises if functionality is conserved or diversified among those sequences. All identified sequences, which are ORFs, were subcloned using triple point gateway recombination under the control of the Rpi-chc1-short promoter and the Rpi-chc1 terminator in the binary vector pDEST236. Based on the results in FIG. 10, this was considered the best constellation to drive the expression of the mined Rpi-chc1 homologs. Successively, the constructs were transformed into *A. tumefaciens* strain COR308 for transient complementation assays in *N. benthamiana*. Alternatively, for co-expression with the cognate Pi effector RD12, the Rpi-chc1 homologs were transformed into *A. tumefaciens* strain AGL1+virG. Both experiments are complementary since the transient complementation assay could show whether a Rpi-chc1 could induce resistance, the co-infiltration could indicate the recognition specificity of the gene. All experiments were repeated at least twice and the results are summarized in Table 9. Several combinations of RD12 responsiveness and IPO-C resistance can be observed. Two clear groups can be distinguished. A first group is not responsive to RD12 and is susceptible to IPO-C (group 1; Table 9). These sequences are inactive homologs and mainly locate in phylogenetic clade 1 (FIG. 12). The second group (group 2; Table 9) are functional homologs of Rpi-chc1 since they are actively inducing resistance against Pi and they recognize the same Pi component (RD12). The sequences of this group are also clearly distinct from the other sequences since they all locate in clade 3 (FIG. 12). *S. tarijense* 852-5 clone E28 induces HR in the absence of RD12 and is in that sense unique in its activity pattern and constitutes activity group 3. Since it does not induce resistance it is most likely an inactive allele. Another allele from the same plant (clone E14) does not recognize RD12 but does induce strong resistance. Activity group 4 is therefore distinct from group 2 because it most likely recognizes a different component from Pi. Activity group 5 is quite similar to group 4; the only difference is that disease resistance is not that strong. This suggests that also group 5 recognizes different components from Pi and will have a different resistance spectrum. The last group (Group 6) is distinct because RD12 is only weakly recognised and also resistance is weak. Summarising, these data show that the closest related Rpi-chc1 homologs have a conserved resistance mechanism, while less related sequences have a more diversified resistance mechanism. Altogether, these data show that multiple members of the Rpi-chc1 gene family, with different extents of similarity, are functional in providing resistance again Pi.

TABLE 5

Characteristics of *P. infestans* isolates used in this study, and their interaction with chc, ber and tar accessions.

| Isolate ID | Collection | Country of origin | Race | Phenotype 543-5 | Phenotype 481-3 | Phenotype 94-2031 | Phenotype 852-5 |
|---|---|---|---|---|---|---|---|
| EC1[a] | | Ecuador | 3.4.7.11 | R | R | R | R |
| 3128-A | SCRI | | | R | R | nd | R |
| 51368 | PHYTO | | | R | R | R | R |
| 80029 | PHYTO | | | R | R | nd | R |
| 88069 | SCRI | | | R | R | R | R |
| 88133 | PHYTO | | | R | R | R | R |
| 89094 | PHYTO | | | R | R | R | R |
| 91011 | PHYTO | | | R | R | R | R |
| 99177 | Kessel, PRI, WUR (Flier et al., 2002) | 1999, Metepec, Mexico | 2.7 | R | R | R | R |
| 99183 | Kessel, PRI, WUR (Flier et al., 2002) | 1999, Metepec, Mexico | 1.3.7 | R | R | S | R |

TABLE 5-continued

Characteristics of P. infestans isolates used in this study, and their interaction with chc, ber and tar accessions.

| Isolate ID | Collection | Country of origin | Race | Phenotype 543-5 | Phenotype 481-3 | Phenotype 94-2031 | Phenotype 852-5 |
|---|---|---|---|---|---|---|---|
| 99189 | Kessel, PRI, WUR (Flier et al., 2002) | 1999, Metepec, Mexico | 1.3.4.7.8.10 | R | R | nd | R |
| CA-65 | SCRI | | | R | R | nd | R |
| EC3364 | PHYTO | | | R | R | R | R |
| EC3425 | PBR | | | R | R | R | R |
| IPO-0(87000) | Kessel, PRI, WUR | Netherlands | 0 | R | R | R | R |
| NL05-194 | PHYTO | | | R | nd | S | S |
| SC95.173.2 | SCRI | | | R | R | R | R |
| SC96.9.5.1 | SCRI | | | R | R | R | R |
| UK7818 | PHYTO | | | R | R | R | R |
| UK7824 | PHYTO | | | R | R | R | R |
| US580 | PHYTO | | | R | R | R | R |
| 90128[a,b] | PHYTO | 1990, Geldrop, The Netherlands | 1.3.4.7.8.11 | R | R | R | R |
| H30P04[a] | | The Netherlands | 7 | R | R | R | R |
| IPO-C[a] | Kessel, PRI, WUR | 1990, Belgium | 1.2.3.4.6.7.10.11 | R | R | R | R |

[a] host potato,
[b] mating type A1
R is resitant, S is susceptible, nd is not determined

TABLE 6

R-genes and quantitative trait loci for late blight resistance reported for wild Solanum species

| Wild species | Locus type or name | Also known as | Chromosome | cloned | Reference |
|---|---|---|---|---|---|
| S. berthaultii | QTLs (4) | | I, III, VII and XI | | |
| | Rpi-ber | | X | | (Rauscher et al., 2006) |
| | Rpi-ber1 | | X | | (Park et al.) |
| | Rpi-ber2 | | X | | (Park et al.) |
| S. bulbocastanum | RB/Rpi-blb1 | RB | VIII | yes | (Song et al., 2003; van der Vossen et al., 2003) |
| | Rpi-blb2 | | VI | yes | Van der Vossen et al. 2005 |
| | Rpi-blb3 | | IV | yes | (Park et al., 2005a) |
| S. caripense | QTL (2) | | unassigned | | |
| S. demissum | R1 | | V | yes | (Ballvora et al., 2002) |
| | R2 | | IV | yes | (Park et al., 2005b) |
| | R3, R6, R7 | | XI | | |
| | R3a | | XI | yes | (Huang et al., 2005) |
| | R3b | | XI | | |
| | R5-R11 | | XI | | |
| | R10, R11 | | XI | | (Bradshaw et al., 2006) |
| S. microdontum | QTLs (3) | | IV, V and X | | (Tan et al., 2008) |
| | QTL | | Unassigned | | |
| S. mochiquense | Rpi-mcq1 | (Rpi-moc1) | IX | yes | |
| S. papita | Rpi-pta1 | | VIII | yes | (Vleeshouwers et al., 2008) |
| S. paucissectum | QTLs (3) | | X, XI and XII | | |
| S. phureja | Rpi-phu1 | | IX | | |
| S. pinnatisectum | Rpi-pnt1 | (Rpi1) | VII | | (Kuhl et al., 2001) |
| S. stoloniferum | Rpi-sto1 | | VIII | yes | (Wang et al., 2008) |
| S. venturii | Rpi-vnt1.1 | Rpi-phu1 | IX | yes | Foster et al. 2009 |
| | Rpi-vnt1.3 | | IX | yes | Pel et al. 2009 |
| S. vernei | QTLs (several) | | VI, VIII, IX | | |
| Hybrids with S. tuberosum | Rpi-abpt | | IV | yes | Lokosou et al. 2009 |
| | R2-like | | IV | yes | (Park et al., 2005b) |

TABLE 7

Genotypes screened for Rpi-chc1 related sequences. Taxonomic groups refer to regrouping of Solanum section petota by (Jacobs el al., 2008)

| GENOTYPE code | tree main group | tree sub group | species, accesssion nr |
|---|---|---|---|
| 4-11 | 10 | 12 | arnezii PI545880 |
| 98-1 | 10 | 12 | yungasense PI614703 |
| 109-1 | 10 | 16 | aracc-papa GLKS82 |
| 110-1 | 10 | 16 | aracc-papa GLKS81 |
| 110-4 | 10 | 16 | |
| 111-1 | 10 | 12 | arnezii GLKS2832 |
| 114-5 | 10 | 16 | astleyi GLKS2836 |
| 123-2 | 10 | 16 | candolleanum GLKS2175 |
| 142-4 | 10 | 17 | curtilobum GLKS5346 |
| 144-3 | 10 | 16 | doddsii GLKS2882 |
| 144-5 | 10 | 16 | doddsii GLKS2882 |
| 165-2 | 10 | 16 | species GLKS1512 |
| 171-2 | 10 | 16 | |
| 187-2 | 10 | 17 | morelliforme BGRC7200 |
| 194-1 | 10 | 17 | ochranthum BGRC53684 |
| 194-3 | 10 | 17 | ochranthum BGRC53684 |
| 194-22 | 10 | 17 | species BGRC53684 |
| 194-23 | 10 | 17 | species BGRC53684 |
| 194-25 | 10 | 17 | species BGRC53684 |
| 200-4 | 10 | 17 | phureja GLKS1467 |
| 201-3 | 10 | 17 | phureja BGRC15481 |
| 203-2 | 10 | 17 | phureja GLKS1455 |
| 220-2 | 10 | 17 | stenotomum goniocalyx GLKS2703 |
| 224-1 | 10 | 14 | tarijense BGRC18324 |
| 235-1 | 10 | 17 | tuberosum andigena GLKS5027 |
| 240-2 | 10 | 17 | tuberosum andigena CPC3121E |
| 243-1 | 10 | 17 | tuberosum andigena GLKS4737 |
| 246-3 | 10 | 12 | tundalomense GLKS2343 |
| 248-5 | 10 | 16 | ugentii GLKS2887 |
| 257-3 | 10 | 14 | alandiae BGRC10057 |
| 263-1 | 10 | 12 | chacoense CPC5901 |
| 270-1 | 10 | 14 | gandarillasii CPC7044 |
| 280-1 | 10 | 12 | neocardenasii CPC7208 |
| 280-4 | 10 | 12 | |
| 281-1 | 10 | 16 | neorossii CPC6047 |
| 281-2 | 10 | 16 | |
| 296-1 | 10 | 17 | stenotomum CPC4741 |
| 322-3 | 10 | 14 | berthaultii CGN20644 |
| 322-5 | 10 | 14 | berthaultii CGN20644 |
| 322-6 | 10 | 14 | berthaultii CGN20644 |
| 323-2 | 10 | 14 | berthaultii CGN20650 |
| 323-3 | 10 | 14 | berthaultii CGN20650 |
| 324-2 | 10 | 14 | berthaultii CGN18042 |
| 338-1 | 10 | 14 | chacoense CGN18248 |
| 338-2 | 10 | 14 | chacoense CGN18248 |
| 346-2 | 10 | 14 | gandarillasii CGN20560 |
| 347-2 | 10 | 13 | gourlayi CGN17851 |
| 347-9 | 10 | 13 | gourlayi CGN17851 |
| 351-8 | 10 | 16 | hondelmannii CGN18106 |
| 352-2 | 10 | 16 | hondelmannii CGN18182 |
| 352-6 | 10 | 16 | hondelmannii CGN18182 |
| 352-8 | 10 | 16 | hondelmannii CGN18182 |
| 357-5 | 10 | 16 | leptophyes CGN18140 |
| 357-6 | 10 | 16 | leptophyes CGN18140 |
| 356-8 | 10 | 16 | leptophyes CGN18174 |
| 371-1 | 10 | 17 | phureja CGN17667 |
| 371-7 | 10 | 17 | phureja CGN17667 |
| 372-8 | 10 | 17 | phureja CGN18301 |
| 381-4 | 10 | 16 | raphanifolium CGN17753 |
| 384-2 | 10 | 16 | sparsipilum CGN18154 |
| 384-5 | 10 | 16 | sparsipilum CGN18154 |
| 382-2 | 10 | 16 | sparsipilum CGN18225 |
| 382-5 | 10 | 16 | sparsipilum CGN18225 |
| 383-2 | 10 | 16 | sparsipilum CGN18230 |
| 383-3 | 10 | 16 | sparsipilum CGN18230 |
| 383-4 | 10 | 16 | sparsipilum CGN18230 |
| 383-5 | 10 | 16 | |
| 391-1 | 10 | 16 | sucrense CGN18205 |
| 391-3 | 10 | 16 | sucrense CGN18205 |
| 391-6 | 10 | 16 | sucrense CGN18205 |
| 392-1 | 10 | 12 | tarijense CGN17861 |
| 392-6 | 10 | 12 | tarijense CGN17861 |
| 392-8 | 10 | 12 | tarijense CGN17861 |
| 416-1 | 10 | 16 | species CGN20580 |
| 454-3 | 10 | 17 | ajanhuiri CGN22389 |
| 455-1 | 10 | 16 | alandiae CGN22349 |
| 457-5 | 10 | 14 | alandiae BGRC28490 |
| 458-1 | 10 | 14 | alandiae CGN20651 |
| 458-5 | 10 | 14 | alandiae CGN20651 |
| 470-1 | 10 | 17 | andreanum CGN17679 |
| 470-3 | 10 | 17 | chacoense CGN17679 |
| 471-1 | 10 | 12 | arnezii BGRC27309 |
| 472-3 | 10 | 16 | astleyi CGN18207 |
| 475-4 | 10 | 16 | astleyi CGN18211 |
| 475-22 | 10 | 16 | astleyi CGN18211 |
| 478-25 | 10 | 16 | avilesii CGN18256 |
| 477-1 | 10 | 16 | avilesii CGN18255 |
| 477-4 | 10 | 16 | avilesii CGN18255 |
| 477-5 | 10 | 16 | brevicaule |
| 478-2 | 10 | 16 | avilesii CGN18256 |
| 494-3 | 10 | 14 | berthaultii CGN18118 |
| 481-3 | 10 | 14 | berthaultii CGN18190 |
| 483-2 | 10 | 14 | berthaultii CGN20636 |
| 483-3 | 10 | 14 | berthaultii CGN20636 |
| 486-2 | 10 | 14 | berthaultii CGN22716 |
| 486-3 | 10 | 14 | berthaultii CGN22716 |
| 487-1 | 10 | 14 | berthaultii CGN20645 |
| 487-8 | 10 | 14 | berthaultii CGN20645 |
| 488-1 | 10 | 14 | berthaultii CGN18246 |
| 488-2 | 10 | 14 | berthaultii CGN18246 |
| 489-1 | 10 | 14 | berthaultii BGRC28496 |
| 491-1 | 10 | 14 | berthaultii CGN22727 |
| 493-5 | 10 | 14 | berthaultii CGN17823 |
| 493-7 | 10 | 14 | berthaultii CGN17823 |
| 493-9 | 10 | 14 | |
| 496-1 | 10 | 16 | |
| 505-4 | 10 | 16 | brevicaule CGN17841 |
| 509-1 | 10 | 16 | brevicaule CGN22321 |
| 509-2 | 10 | 16 | brevicaule CGN22321 |
| 544-11 | 10 | 14 | chacoense CGN18365 |
| 550-3 | 10 | 12 | chacoense BGRC24528 |
| 550-4 | 10 | 12 | chacoense BGRC24528 |
| 543-1 | 10 | 14 | chacoense BGRC63055 |
| 543-5 | 10 | 14 | |
| 545-1 | 10 | 12 | chacoense CGN17702 |
| 547-1 | 10 | 12 | |
| 548-1 | 10 | 12 | chacoense CGN18294 |
| 548-2 | 10 | 12 | chacoense CGN18294 |
| 544-1 | 10 | 14 | chacoense CGN18365 |
| 544-5 | 10 | 14 | |
| 561-2 | 10 | 14 | berthaultii BGRC55178 |
| 561-3 | 10 | 14 | chomatophilum BGRC55178 |
| 601-2 | 10 | 14 | species BGRC55186 |
| 605-1 | 10 | 13 | gourlayi CGN17591 |
| 606-1 | 10 | 13 | gourlayi CGN18039 |
| 608-1 | 10 | 13 | gourlayi BGRC17316 |
| 609-1 | 10 | 13 | gourlayi CGN17592 |
| 609-5 | 10 | 13 | gourlayi CGN17592 |
| 610-4 | 10 | 13 | gourlayi CGN22336 |
| 611-1 | 10 | 13 | gourlayi CGN21335 |
| 613-1 | 10 | 13 | gourlayi pachytrichum CGN18176 |
| 613-2 | 10 | 13 | gourlayi pachytrichum CGN18176 |
| 614-1 | 10 | 16 | gourlayi pachytrichum BGRC27294 |
| 616-2 | 10 | 13 | |
| 616-4 | 10 | 13 | gourlayi pachytrichum CGN18188 |
| 617-1 | 10 | 16 | gourlayi pachytrichum BGRC7231 |
| 618-1 | 10 | 16 | gourlayi pachytrichum BGRC28084 |
| 619-5 | 10 | 13 | gourlayi vidaurrei CGN17848 |
| 620-1 | 10 | 13 | gourlayi vidaurrei CGN17849 |
| 620-3 | 10 | 13 | gourlayi vidaurrei CGN17849 |
| 622-1 | 10 | 13 | gourlayi vidaurrei CGN17850 |
| 622-5 | 10 | 13 | gourlayi vidaurrei CGN17850 |
| 624-1 | 10 | 16 | gourlayi vidaurrei CGN17864 |
| 625-2 | 10 | 16 | gourlayi vidaurrei CGN23024 |

TABLE 7-continued

Genotypes screened for Rpi-chc1 related sequences. Taxonomic groups refer to regrouping of Solanum section petota by (Jacobs el al., 2008)

| GENOTYPE code | tree main group | tree sub group | species, accesssion nr |
|---|---|---|---|
| 626-2 | 10 | 16 | gourlayi vidaurrei CGN23045 |
| 634-4 | 10 | 13 | hawkesianum CGN17888 |
| 635-3 | 10 | 13 | hawkesianum CGN17889 |
| 646-3 | 10 | 16 | hondelmannii CGN18192 |
| 646-4 | 10 | 16 | hondelmannii CGN18192 |
| 650-1 | 10 | 13 | hoopesii CGN18363 |
| 650-3 | 10 | 13 | hoopesii CGN18363 |
| 652-3 | 10 | 13 | hoopesii CGN18368 |
| 653-5 | 10 | 13 | hoopesii CGN18372 |
| 658-1 | 10 | 13 | incamayoense CGN21320 |
| 658-4 | 10 | 13 | incamayoense CGN21320 |
| 659-3 | 10 | 13 | incamayoense CGN17874 |
| 660-1 | 10 | 13 | incamayoense CGN17875 |
| 660-5 | 10 | 13 | incamayoense CGN17875 |
| 661-1 | 10 | 13 | incamayoense CGN17968 |
| 661-4 | 10 | 13 | incamayoense CGN17968 |
| 662-1 | 10 | 13 | incamayoense BGRC17334 |
| 664-1 | 10 | 13 | infundibuliforme CGN17720 |
| 664-4 | 10 | 13 | infundibuliforme CGN17720 |
| 665-4 | 10 | 16 | infundibuliforme CGN23063 |
| 666-1 | 10 | 16 | infundibuliforme CGN22334 |
| 666-4 | 10 | 16 | infundibuliforme CGN22334 |
| 667-4 | 10 | 13 | brevicaule |
| 682-5 | 10 | 16 | leptophyes CGN18167 |
| 683-5 | 10 | 16 | leptophyes CGN20611 |
| 735-1 | 10 | 16 | |
| 735-2 | 10 | 16 | neorossii CGN18280 |
| 735-4 | 10 | 16 | neorossii CGN18280 |
| 742-1 | 10 | 15 | okadae BGRC27158 |
| 747-1 | 10 | 16 | oplocense CGN23049 |
| 750-1 | 10 | 16 | oplocense CGN21352 |
| 750-2 | 10 | 16 | |
| 753-1 | 10 | 16 | oplocense CGN21319 |
| 754-2 | 10 | 16 | oplocense CGN17871 |
| 755-1 | 10 | 16 | oplocense CGN18086 |
| 802-1 | 10 | 12 | ruiz-lealii CGN18117 |
| 816-3 | 10 | 16 | sparsipilum CGN18096 |
| 816-5 | 10 | 16 | sparsipilum CGN18096 |
| 818-8 | 10 | 16 | sparsipilum CGN18221 |
| 819-2 | 10 | 16 | sparsipilum CGN20653 |
| 819-4 | 10 | 16 | sparsipilum CGN20653 |
| 821-1 | 10 | 16 | sparsipilum CGN20602 |
| 821-3 | 10 | 16 | sparsipilum CGN20602 |
| 821-4 | 10 | 16 | sparsipilum CGN20602 |
| 827-1 | 10 | 16 | spegazzinii CGN23015 |
| 829-3 | 10 | 17 | stenotomum CGN18161 |
| 829-9 | 10 | 17 | stenotomum CGN18161 |
| 843-4 | 10 | 16 | sucrense CGN20628 |
| 844-1 | 10 | 16 | sucrense CGN20630 |
| 844-3 | 10 | 16 | sucrense CGN20630 |
| 843-5 | 10 | 16 | sucrense CGN20628 |
| 844-7 | 10 | 16 | sucrense CGN20630 |
| 845-6 | 10 | 16 | sucrense CGN20631 |
| 846-1 | 10 | 16 | sucrense CGN18187 |
| 846-6 | 10 | 16 | sucrense CGN18187 |
| 849-1 | 10 | 16 | sucrense CGN18206 |
| 849-2 | 10 | 16 | sucrense CGN18206 |
| 849-6 | 10 | 16 | sucrense CGN18206 |
| 852-5 | 10 | 14 | tarijense CGN22729 |
| 853-4 | 10 | 14 | tarijense BGRC27348 |
| 855-8 | 10 | 14 | tarijense CGN18198 |
| 855-10 | 10 | 14 | tarijense CGN18198 |
| 856-5 | 10 | 14 | tarijense BGRC8232 |
| 859-3 | 10 | 14 | tarijense CGN17975 |
| 863-2 | 10 | 14 | tarijense BGRC18609 |
| 864-3 | 10 | 14 | tarijense BGRC18610 |
| 864-21 | 10 | 14 | tarijense BGRC18610 |
| 868-9 | 10 | 12 | tarijense CGN18107 |
| 869-3 | 10 | 12 | tarijense BGRC17022 |
| 870-3 | 10 | 14 | tarijense CGN17978 |
| 876-1 | 10 | 14 | tarijense BGRC17438 |
| 887-1 | 10 | 17 | tuberosum andigena CGN20614 |
| 891-1 | 10 | 16 | ugentii CGN18364 |
| 927-1 | 10 | 16 | virgultorum BGRC31203 |
| 928-1 | 10 | 16 | virgultorum CGN17775 |
| 928-3 | 10 | 16 | virgultorum CGN17775 |
| 987-3 | 10 | 16 | |

TABLE 8

Primers used in this study

| primer code | Application | sequence | orientation | Tm |
|---|---|---|---|---|
| MN581 | Marker germplasm screen | GCGGAGAGTTTCGTGAATTG | F | 61 |
| MN582 | Marker germplasm screen | CCCACACATGTACAGGGAATG | R | 61 |
| MN585 | Marker germplasm screen | ACATCTCTCGTAAAGCTTAGAG | F | 55 |
| MN586 | Marker germplasm screen | ACAGATAATAATTTTCAACTGC | F | 55 |
| MN587 | Marker germplasm screen | ATTTGGGACATTCTGATATAAG | R | 55 |
| MN588 | Marker germplasm screen | CACTTTCATATTTGCTTATATC | F | 55 |
| MN589 | Marker germplasm screen | GACAATCACGTATCCACAGGAG GGGGACAAGTTTGTACAAAAAAGCAG GCT | R | 55 |
| MN595 | Rpi-chc 1 homolog mining | ATGAATTATTGTCTTCCTTCGAGTAC GGGGACCACTTTGTACAAGAAAGCTGG GT | F | |
| MN597 | Rpi-chc 1 homolog mining | TCAGAAAGTGAAAGAGAAACCGAG | R | |

TABLE 8-continued

Primers used in this study

| primer code | Application | sequence | orientation | Tm |
|---|---|---|---|---|
| MN598 | Rpi-chc1 promoter construction | GGGGACAACTTTGTATAGAAAAGTTG ACGCATCAGGAAGAGAGGAG | F | |
| MN599 | Rpi-chc1 promoter construction | GGGGACTGCTTTTTTGTACAAACTTG ATACAATCATTCAAACAGTAAT | R | |
| MN600 | Rpi-chc1 terminator construction | GGGGACAGCTTTCTTGTACAAAGTGG GTCGCTTGCATTTTTAATTAG | F | |
| MN601 | Rpi-chc1 terminator construction | GGGGACAACTTTGTATAATAAAGTTG GCGGTTCCTCTGTGAAACAC | R | |
| MN670 | Rpi-chc1 promoter construction | GGGGACAACTTTGTATAGAAAAGTTG TGATTTGTTTTTCCTATTCCTGAC | F | 59 |
| MN622 | Rpi-chc1 homolog sequencing | atgaattattgtcttccttc | | |
| MN623 | Rpi-chc1 homolog sequencing | acacaaaatgtatctttaatcc | | |
| MN624 | Rpi-chc1 homolog sequencing | agagttgacggctatcaataag | | |
| MN625 | Rpi-chc1 homolog sequencing | ttacaatgatgaacacatgaag | | |
| MN626 | Rpi-chc1 homolog sequencing | gaggaataaatacatccagagg | | |
| MN627 | Rpi-chc1 homolog sequencing | acaaagaaaaacatgaatggc | | |
| MN628 | Rpi-chc1 homolog sequencing | gaagacgttgggcacaggt | | |
| MN629 | Rpi-chc1 homolog sequencing | ttgtgcacactgttttggag | | |
| MN630 | Rpi-chc1 homolog sequencing | tgagatgagaaatatgataag | | |
| MN631 | Rpi-chc1 homolog sequencing | tgataaagaagaggctcaaac | | |
| MN632 | Rpi-chc1 homolog sequencing | gcaaagaaattccatcccttg | | |
| MN633 | Rpi-chc1 homolog sequencing | cagactgtccattgttaaaaag | | |
| MN634 | Rpi-chc1 homolog sequencing | aatctccattctcttaggag | | |
| MN635 | Rpi-chc1 homolog sequencing | atatcagaatgtcccaaattg | | |
| MN636 | Rpi-chc1 homolog sequencing | aattgaggctcttcctcctac | | |
| MN637 | Rpi-chc1 homolog sequencing | cctcactaaattatggaacatg | | |
| MN638 | Rpi-chc1 homolog sequencing | TGCAGGACGCATCAGGAAGAG | | |
| MN639 | Rpi-chc1 homolog sequencing | ATAAGCCACAATGCAAATATAT | | |
| MN640 | Rpi-chc1 homolog sequencing | ATTTAGTTACATTGTAACTATC | | |
| MN641 | Rpi-chc1 homolog sequencing | GAGAAAAAACATTAAGTCATAC | | |

TABLE 8-continued

Primers used in this study

| primer code | Application | sequence | orientation | Tm |
|---|---|---|---|---|
| MN642 | Rpi-chc1 homolog sequencing | TCTTTTAAATTTATTTTACTATAC | | |
| MN643 | Rpi-chc1 homolog sequencing | CAAAATATCTTTTAGTACTAC | | |
| MN644 | Rpi-chc1 homolog sequencing | TATGATGAATTCGTTTTGTTTG | | |
| MN645 | Rpi-chc1 homolog sequencing | CTCGAAATTTTATTAGTACC | | |
| MN646 | Rpi-chc1 homolog sequencing | TGATATATATTGGGCCCGTG | | |
| MN647 | Rpi-chc1 homolog sequencing | ATCTATAACTCACACCTCTC | | |
| MN648 | Rpi-chc1 homolog sequencing | TTGAATGATGGCTATGGCTTG | | |
| MN649 | Rpi-chc1 homolog sequencing | GTTTTTAAAATTCTGTATTGCG | | |
| MN650 | Rpi-chc1 homolog sequencing | TTATTATTGTGAAGTTAGAAG | | |
| MN651 | Rpi-chc1 promoter sequencing | AGTTTTATAGAGAGGCTCTG | | |
| MN652 | Rpi-chc1 promoter sequencing | AAGCGCGAATAAGTTCTCTTG | | |

TABLE 9

Functional analysis of newly identified Rpi-chc1 homologs.

| clone | genotype | RD12 Responsiveness | IPO-C Resistance | Activity group |
|---|---|---|---|---|
| J2 | 324-2 | N | S | 1 |
| J8 | 324-2 | R | R | 2 |
| I6 | 487-1 | N | r | 5 |
| F1 | 493-5 | N | S | 1 |
| G2 | 493-7 | N | S | 1 |
| G19 | 493-7 | r | r | 6 |
| G10 | 493-7 | N | S | 1 |
| G12 | 493-7 | N | S | 1 |
| G14 | 493-7 | nd | r | |
| H11 | 493-9 | N | S | 1 |
| H5 | 493-9 | r | R | 2 |
| C2 | 543-5 | N | r | 5 |
| K30 | 561-2 | N | r | 5 |
| K4 | 561-2 | R | R | 2 |
| M8 | 849-1 | r | r | 6 |
| E30 | 852-5 | N | S | 1 |
| E28 | 852-5 | R* | S | 3 |
| E14 | 852-5 | N | R | 4 |
| L4 | 94-2031 | R | R | 2 |

In the column with RD12 responsiveness R means responsive, N means Non responsive, * means autoactivating, r means weak response. In the column with IPO-C resistance, R means strong resistance, r means weak resistance, S means susceptible.

REFERENCES

Armstrong, M. R., Whisson, S. C., Pritchard, L., Bos, J. I. B., Venter, E., Avrova, A. O., Rehmany, A. P., Böhme, U., Brooks, K., Cherevach, I., Hamlin, N., White, B., Fraser, A., Lord, A., Quail, M. A., Churcher, C., Hall, N., Berriman, M., Huang, S., Kamoun, S., Beynon, J. L. and Birch, P. R. J. (2005) An ancestral oomycete locus contains late blight avirulence gene Avr3a, encoding a protein that is recognized in the host cytoplasm. *Proceedings of the National Academy of Sciences of the United States of America,* 102, 7766-7771.

Ballvora, A., Ercolano, M. R., Weiss, J., Meksem, K., Bormann, C. A., Oberhagemann, P., Salamini, F. and Gebhardt, C. (2002) The R1 gene for potato resistance to late blight (*Phytophthora infestans*) belongs to the leucine zipper/NBS/LRR class of plant resistance genes. *Plant J.,* 30, 361-371.

Bendahmane, A., Farnham, G., Moffett, P. and Baulcombe, D. C. (2002) Constitutive gain-of-function mutants in a nucleotide binding site-leucine rich repeat protein encoded at the Rx locus of potato. *Plant J.,* 32, 195-204.

Bradshaw, J. E., Bryan, G. J., Lees, A. K., McLean, K. and Solomon-Blackburn, R. M. (2006) Mapping the R10 and R11 genes for resistance to late blight (*Phytophthora infestans*) present in the potato (*Solanum tuberosum*) R-gene differentials of Black *Theor. Appl. Genet.,* 112, 744-751.

Brugmans, B., Wouters, D., van Os, H., Hutten, R. C. B., van der Linden, G., Visser, R. G. F., van Eck, H. J. and van der Vossen, E. A. G. (2008) Genetic mapping and transcription analyses of resistance gene loci in potato using NBS profiling. *Theor Appl Genet,* 117, 1379-1388.

Foster, S. J., Park, T. H., Pel, M., Brigneti, G., Sliwka, J., Jagger, L., van der Vossen, E. A. G. and Jones, J. D. (2009) Rpi-vnt1.1, a Tm-2(2) Homolog from *Solanum* venturii, Confers Resistance to Potato Late Blight. *Mol. Plant Microbe Interact.,* 22, 589-600.

Gao, H., Narayanan, N. N., Ellison, L. and Bhattacharyya, M. K. (2005) Two Classes of Highly Similar Coiled Coil-Nucleotide Binding-Leucine Rich Repeat Genes Isolated from the Rps1-k Locus Encode *Phytophthora* Resistance in Soybean. *Mol. Plant Microbe Interact.,* 18, 1035-1045.

Haas, B. J., Kamoun, S., Zody, M. C., Jiang, R. H., Handsaker, R. E., Cano, L. M., Grabherr, M., Kodira, C. D., Raffaele, S., Torto-Alalibo, T., Bozkurt, T. O., Ah-Fong, A. M., Alvarado, L., Anderson, V. L., Armstrong, M. R., Avrova, A., Baxter, L., Beynon, J., Boevink, P. C., Bollmann, S. R., Bos, J. I., Bulone, V., Cai, G., Cakir, C., Carrington, J. C., Chawner, M., Conti, L., Costanzo, S., Ewan, R., Fahlgren, N., Fischbach, M. A., Fugelstad, J., Gilroy, E. M., Gnerre, S., Green, P. J., Grenville-Briggs, L. J., Griffith, J., Grunwald, N. J., Horn, K., Horner, N. R., Hu, C. H., Huitema, E., Jeong, D. H., Jones, A. M., Jones, J. D., Jones, R. W., Karlsson, E. K., Kunjeti, S. G., Lamour, K., Liu, Z., Ma, L., Maclean, D., Chibucos, M. C., McDonald, H., McWalters, J., Meijer, H. J., Morgan, W., Morris, P. F., Munro, C. A., O'Neill, K., Ospina-Giraldo, M., Pinzon, A., Pritchard, L., Ramsahoye, B., Ren, Q., Restrepo, S., Roy, S., Sadanandom, A., Savidor, A., Schornack, S., Schwartz, D. C., Schumann, U. D., Schwessinger, B., Seyer, L., Sharpe, T., Silvar, C., Song, J., Studholme, D. J., Sykes, S., Thines, M., van de Vondervoort, P. J., Phuntumart, V., Wawra, S., Weide, R., Win, J., Young, C., Zhou, S., Fry, W., Meyers, B. C., van West, P., Ristaino, J., Govers, F., Birch, P. R., Whisson, S. C., Judelson, H. S. and Nusbaum, C. (2009) Genome sequence and analysis of the Irish potato famine pathogen *Phytophthora infestans. Nature,* 461, 393-398.

Huang, S., van der Vossen, E. A. G., Kuang, H., Vleeshouwers, V. G. A. A., Zhang, N., Borm, T. J., van Eck, H. J., Baker, B., Jacobsen, E. and Visser, R. G. F. (2005) Comparative genomics enabled the isolation of the R3a late blight resistance gene in potato. *Plant J.,* 42, 251-261.

Jacobs, M. M., van den Berg, R. G., Vleeshouwers, V. G., Visser, M., Mank, R., Sengers, M., Hoekstra, R. and Vosman, B. (2008) AFLP analysis reveals a lack of phylogenetic structure within *Solanum* section Petota. BMC evolutionary biology, 8, 145.

Jansky, S. (2000) Breeding for disease resistance in potato. *Plant Breeding Rev.,* 19, 69-155.

Jones, J. D. and Dangl, J. L. (2006) The plant immune system. *Nature,* 444, 323-329.

Joobeur, T., King, J. J., Nolin, S. J., Thomas, C. E. and Dean, R. A. (2004) The *Fusarium* wilt resistance locus Fom-2 of melon contains a single resistance gene with complex features. *Plant J.,* 39, 283-297.

Kuhl, J. C., Hanneman, R. E., Jr. and Havey, M. J. (2001) Characterization and mapping of Rpi1, a late-blight resistance locus from diploid (1EBN) Mexican *Solanum pinnatisectum. Mol. Genet. Genomics,* 265, 977-985.

Lokossou, A. A., Park, T. H., van Arkel, G., Arens, M., Ruyter-Spira, C., Morales, J., Whisson, S. C., Birch, P. R., Visser, R. G., Jacobsen, E. and van der Vossen, E. A. (2009) Exploiting knowledge of R/Avr genes to rapidly clone a new LZ-NBS-LRR family of late blight resistance genes from potato linkage group IV. *Mol. Plant Microbe Interact.,* 22, 630-641.

Moreau, P., Thoquet, P., Olivier, J., Laterrot, H. and Grimsley, N. (1998) Genetic Mapping of Ph-2, a Single Locus Controlling Partial Resistance to *Phytophthora infestans* in Tomato. *Mol. Plant Microbe Interact.,* 11, 259-269.

Park, T. H., Foster, S. J., Brigneti, G. and Jones, J. D. G. (2008) Two distinct potato late blight resistance genes from *Solanum berthaultii* are located on chromosome 10. *Euphytica.*

Park, T. H., Gros, J., Sikkema, A., Vleeshouwers, V. G. A. A., Muskens, M., Allefs, S., Jacobsen, E., Visser, R. G. F. and van der Vossen, E. A. G. (2005a) The late blight resistance locus Rpi-bib3 from *Solanum bulbocastanum* belongs to a major late blight R gene cluster on chromosome 4 of potato. *Mol. Plant Microbe Interact.,* 18, 722-729.

Park, T. H., Vleeshouwers, V. G. A. A., Huigen, D. J., van der Vossen, E. A. G., van Eck, H. J. and Visser, R. G. F. (2005b) Characterization and high-resolution mapping of a late blight resistance locus similar to R2 in potato. *TAG. Theoretical and applied genetics,* 111, 591-597.

Pel, M. A., Foster, S. J., Park, T. H., Rietman, H., van Arkel, G., Jones, J. D., Van Eck, H. J., Jacobsen, E., Visser, R. G. F. and Van der Vossen, E. A. G. (2009) Mapping and Cloning of Late Blight Resistance Genes from *Solanum venturii* Using an Interspecific Candidate Gene Approach. *Mol. Plant Microbe Interact.,* 22, 601-615.

Rauscher, G. M., Smart, C. D., Simko, I., Bonierbale, M., Mayton, H., Greenland, A. and Fry, W. E. (2006) Characterization and mapping of RPi-ber, a novel potato late blight resistance gene from *Solanum berthaultii. Theor. Appl. Genet.,* 112, 674-687.

Rouppe van der Voort, J. N. A. M., Kanyuka, K., van der Vossen, E. A. G., Bendahmane, A., Mooijman, P., Klein-Lankhorst, R. M., Stiekema, W. J., Baulcombe, D. C. and Bakker, J. (1999) Tight physical linkage of the nematode resistance gene Gpa2 and the virus resistance gene Rx on a single segment introgressed from the wild species *Solanum tuberosum* subsp. *andigena* CPC 1673 into cultivated potato. *Mol. Plant Microbe Interact.,* 12, 197-206.

Song, J., Bradeen, J. M., Naess, S. K., Raasch, J. A., Wielgus, S. M., Haberlach, G. T., Liu, J., Kuang, H., Austin-Phillips, S., Buell, C. R., Helgeson, J. P. and Jiang, J. (2003) Gene RB cloned from *Solanum bulbocastanum* confers broad spectrum resistance to potato late blight. *Proc. Natl. Acad. Sci. USA,* 100, 9128-9133.

Tameling, W. I., Vossen, J. H., Albrecht, M., Lengauer, T., Berden, J. A., Haring, M. A., Cornelissen, B. J. and Takken, F. L. (2006) Mutations in the NB-ARC domain of 1-2 that impair ATP hydrolysis cause autoactivation. *Plant Physiol.,* 140, 1233-1245.

Tan, M. Y., Hutten, R. C., Celis, C., Park, T. H., Niks, R. E., Visser, R. G. F. and van Eck, H. J. (2008) The R(Pi-mcd1) locus from *Solanum microdontum* involved in resistance to *Phytophthora infestans,* causing a delay in infection, maps on potato chromosome 4 in a cluster of NBS-LRR genes. *Mol. Plant Microbe Interact.,* 21, 909-918.

van der Biezen, E. A. and Jones, J. D. (1998) The NB-ARC domain: a novel signalling motif shared by plant resistance gene products and regulators of cell death in animals. *Curr. Biol.,* 8, R226-227.

van der Linden, C. G., Wouters, D. C., Mihalka, V., Kochieva, E. Z., Smulders, M. J. and Vosman, B. (2004) Efficient targeting of plant disease resistance loci using NBS profiling. *Theor. Appl. Genet.,* 109, 384-393.

van der Vossen, E. A. G., Sikkema, A., Hekkert, B. L., Gros, J., Stevens, P., Muskens, M., Wouters, D., Pereira, A., Stiekema, W. J. and Allefs, S. (2003) An ancient R gene from the wild potato species *Solanum bulbocastanum* confers broad-spectrum resistance to *Phytophthora infestans* in cultivated potato and tomato. *Plant J.,* 36, 867-882.

van Os, H., Andrzejewski, S., Bakker, E., Barrena, I., Bryan, G. J., Caromel, B., Ghareeb, B., Isidore, E., de Jong, W., van Koert, P., Lefebvre, V., Milbourne, D., Ritter, E., van der Voort, J. N. A. M., Rousselle-Bourgeois, F., van Vliet, J., Waugh, R., Visser, R. G. F., Bakker, J. and van Eck, H. J. (2006) Construction of a 10,000-marker ultradense genetic recombination map of potato: providing a framework for accelerated gene isolation and a genomewide physical map. *Genetics*, 173, 1075-1087.

Vleeshouwers, V. G. A. A., Rietman, H., Krenek, P., Champouret, N., Young, C., Oh, S. K., Wang, M., Bouwmeester, K., Vosman, B., Visser, R. G. F., Jacobsen, E., Govers, F., Kamoun, S. and Van der Vossen, E. A. G. (2008) Effector genomics accelerates discovery and functional profiling of potato disease resistance and *Phytophthora infestans* avirulence genes. *PLoS ONE*, 3, e2875.

Vleeshouwers, V. G. A. A., van Dooijweert, W., Paul Keizer, L. C., Sijpkes, L., Govers, F. and Colon, L. T. (1999) A laboratory assay for *Phytophthora infestans* resistance in various *Solanum* species reflects the field situation. *Eur. J. Plant Pathol.*, 105, 241-250.

Wang, M., Allefs, S., van den Berg, R. G., Vleeshouwers, V. G. A. A., van der Vossen, E. A. G. and Vosman, B. (2008) Allele mining in *Solanum*: conserved homologues of Rpi-blb1 are identified in *Solanum stoloniferum*. *Theor. Appl. Genet.*, 116, 933-943.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10450581B2). An electronic copy of the "Sequence Listing" will also be available from the USPTO upon request and payment of the fee set forth in 37 CFR 1.19(b)(3).

The invention claimed is:

1. A method for increasing resistance in a Solanaceae plant against infection by *Phytophthora infestans*, said method comprising introducing into said plant or a part thereof a nucleic acid that expresses a nucleotide sequence encoding a protein of the amino acid sequence SEQ ID NO:126 or a protein of an amino acid sequence having at least 95% sequence identity thereto and which protein confers resistance to *P. infestans* in Solanaceae in a detached leaf assay, or a nucleic acid expressing a homolog thereof;
    wherein the homolog is a protein having an amino acid sequence selected from the group consisting of SEQ ID NO:194; SEQ ID NO:198; SEQ ID NO:203; SEQ ID NO:205; SEQ ID NO:207; SEQ ID NO:209; SEQ ID NO:211; SEQ ID NO:217; SEQ ID NO:219; SEQ ID NO:221; and SEQ ID NO:223; or is a protein with an amino acid sequence having at least 95% sequence identity thereto and which homolog confers resistance to *P. infestans* in Solanaceae in a detached leaf assay; and wherein said plant exhibits increased resistance to said infection as compared to a plant into which said nucleic acid has not been introduced.

2. The method of claim 1, wherein the encoding nucleotide sequence comprises SEQ ID NO:125; SEQ ID NO:193; SEQ ID NO:197; SEQ ID NO:202; SEQ ID NO:204; SEQ ID NO:206; SEQ ID NO:208; SEQ ID NO:210; SEQ ID NO:216; SEQ ID NO:218; SEQ ID NO:220; or SEQ ID NO:222, or comprises a sequence having at least 95% sequence identity thereto.

3. A method for breeding a *P. infestans*-resistant plant, comprising a) increasing the ploidy level of gametes of a diploid Solanaceae plant that already contains the nucleic acid as it is defined in the method of claim 1;

b) crossing said gametes with gametes of a Solanaceae tetraploid plant; and c) selecting offspring of said cross for the presence of said nucleic acid, wherein offspring that exhibit the presence of said nucleic acid exhibit resistance to *P. infestans* in a detached leaf assay.

4. The method of claim 3, wherein the diploid plant of step a) is *S. chacoense, S. berthaultii, S. sucrense*, or *S. tarijense.*

5. A method for determining whether a Solanaceae plant, plant part, or progeny of a plant is susceptible or resistant to *P. infestans* infection, said method comprising the steps of testing said plant or plant part or progeny for the presence or absence of the nucleic acid as it is defined in the method of claim 1, wherein the presence of said nucleic acid indicates said plant, plant part or progeny is resistant to *P. infestans* infection and the absence of said nucleic acid indicates said plant, plant part or progeny is susceptible to *P. infestans* infection; and wherein said testing comprises detecting the presence of one or more amplification products obtained using a primer pair of Table 2.

6. A recombinant cloning vector that is modified to express an encoding nucleotide sequence encoding the amino acid sequence SEQ ID NO:126 or a protein having an amino acid sequence having at least 95% sequence identity thereto and which protein confers resistance to

*P. infestans* in Solanaceae in a detached leaf assay, or to express an encoding nucleotide sequence encoding a protein having an amino acid sequence selected from the group consisting of:

SEQ ID NO:194; SEQ ID NO:198; SEQ ID NO:203; SEQ ID NO:205; SEQ ID NO:207; SEQ ID NO:209; SEQ ID NO:211; SEQ ID NO:217; SEQ ID NO:219; SEQ ID NO:221; and SEQ ID NO:223, or encoding a protein having an amino acid sequence having at least 95% sequence identity thereto and which protein confers resistance to *P. infestans* in Solanaceae in a detached leaf assay.

7. The recombinant cloning vector of claim 6 wherein said encoding nucleotide sequence is selected from the group consisting of SEQ ID NO:125; SEQ ID NO:193; SEQ ID NO:197; SEQ ID NO:202; SEQ ID NO:204; SEQ ID NO:206; SEQ ID NO:208; SEQ ID NO:210; SEQ ID NO:216; SEQ ID NO:218; SEQ ID NO:220; and SEQ ID NO:222 or the
  encoding nucleotide sequence has at least 95% sequence identity thereto.

8. A transgenic or tetraploid Solanaceae cell comprising the recombinant cloning vector of claim 6.

9. A transgenic or Solanaceae tetraploid plant comprising the cell of claim 8.

10. A plant part obtained from the plant of claim 9 which contains a recombinant cloning vector that is modified to express an encoding nucleotide sequence encoding the amino acid sequence SEQ ID NO:126 or a protein having an amino acid sequence having at least 95% sequence identity thereto and which protein confers resistance to
  *P. infestans* in Solanaceae in a detached leaf assay, or to express an encoding nucleotide sequence encoding a protein having an amino acid sequence selected from the group consisting of:
  SEQ ID NO:194; SEQ ID NO:198; SEQ ID NO:203; SEQ ID NO:205; SEQ ID NO:207; SEQ ID NO:209; SEQ ID NO:211; SEQ ID NO:217; SEQ ID NO:219; SEQ ID NO:221; and
  SEQ ID NO:223, or encoding a protein having an amino acid sequence having at least 95% sequence identity thereto and which protein confers resistance to *P. infestans* in Solanaceae in a detached leaf assay.

11. The cell of claim 8 which is *Solanum tuberosum*.

12. The method of claim 5 which further comprises contacting the amplification product with the corresponding CAPS restriction enzyme set forth in Table 2.

* * * * *